(12) United States Patent
Bregeon et al.

(10) Patent No.: US 9,427,478 B2
(45) Date of Patent: Aug. 30, 2016

(54) ENZYMATIC CONJUGATION OF POLYPEPTIDES

(71) Applicants: Innate Pharma, Marseilles (FR); Paul Scherrer Institut, Villigen PSI (CH)

(72) Inventors: Delphine Bregeon, Marseilles (FR); Patrick Dennler, Wettingen (CH); Christian Belmant, Six-Fours-les-Plages (FR); Laurent Gauthier, Marseilles (FR); François Romagne, Marseilles (FR); Eliane Fischer, Eglisau (CH); Roger Schibli, Baden (CH)

(73) Assignees: Innate Pharma, Marseille (FR); Paul Scherrer Institut, Villigen (CH)

( * ) Notice: Subject to any disclaimer, the term of this patent is extended or adjusted under 35 U.S.C. 154(b) by 0 days.

(21) Appl. No.: 14/582,040

(22) Filed: Dec. 23, 2014

(65) Prior Publication Data
US 2015/0165064 A1    Jun. 18, 2015

Related U.S. Application Data

(63) Continuation-in-part of application No. PCT/EP2014/063064, filed on Jun. 20, 2014.

(60) Provisional application No. 61/837,932, filed on Jun. 21, 2013.

(51) Int. Cl.
| | | |
|---|---|---|
| A61K 47/48 | (2006.01) | |
| C07K 16/00 | (2006.01) | |
| C07K 16/30 | (2006.01) | |
| C07K 19/00 | (2006.01) | |
| A61K 31/5517 | (2006.01) | |

(52) U.S. Cl.
CPC ..... A61K 47/48384 (2013.01); A61K 31/5517 (2013.01)

(58) Field of Classification Search
CPC .............. A61K 47/48384; A61K 47/48623; A61K 47/48215; A61K 47/48369; A61K 47/48376; A61K 31/5517; C07K 16/00; C07K 16/30; C07K 16/3007; C07K 16/28; C07K 19/00; C07K 2317/40
See application file for complete search history.

(56) References Cited

U.S. PATENT DOCUMENTS

| | | |
|---|---|---|
| 4,741,900 A | 5/1988 | Alvarez et al. |
| 4,816,567 A | 3/1989 | Cabilly et al. |
| 5,156,956 A | 10/1992 | Motoki et al. |
| 5,225,539 A | 7/1993 | Winter |
| 5,229,275 A | 7/1993 | Goroff |
| 5,252,469 A | 10/1993 | Andou et al. |
| 5,530,101 A | 6/1996 | Queen et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,693,761 A | 12/1997 | Queen et al. |
| 5,693,762 A | 12/1997 | Queen et al. |
| 5,712,120 A | 1/1998 | Rodriguez et al. |
| 5,714,350 A | 2/1998 | Co et al. |
| 5,731,183 A | 3/1998 | Kobayashi et al. |
| 5,736,356 A | 4/1998 | Sano et al. |
| 5,766,886 A | 6/1998 | Studnicka et al. |
| 5,770,196 A | 6/1998 | Studnicka |
| 5,777,085 A | 7/1998 | Co et al. |
| 5,821,123 A | 10/1998 | Studnicka |
| 5,821,337 A | 10/1998 | Carter et al. |
| 5,869,619 A | 2/1999 | Studnicka |
| 5,877,293 A | 3/1999 | Adair et al. |
| 5,886,152 A | 3/1999 | Nakatani et al. |
| 5,895,205 A | 4/1999 | Werner et al. |
| 5,929,212 A | 7/1999 | Jolliffe et al. |
| 6,054,297 A | 4/2000 | Carter et al. |
| 6,162,963 A | 12/2000 | Kucherlapati et al. |
| 6,180,370 B1 | 1/2001 | Queen et al. |
| 6,204,388 B1 | 3/2001 | Danishefsky et al. |
| 6,380,394 B1 | 4/2002 | Nicolaou et al. |
| 6,387,927 B1 | 5/2002 | Altmann et al. |
| 6,407,213 B1 | 6/2002 | Carter et al. |
| 6,548,640 B1 | 4/2003 | Winter |
| 6,632,927 B2 | 10/2003 | Adair et al. |
| 6,639,055 B1 | 10/2003 | Carter et al. |
| 6,750,325 B1 | 6/2004 | Jolliffe et al. |
| 6,797,492 B2 | 9/2004 | Daugherty et al. |
| 7,087,409 B2 | 8/2006 | Barbas, III et al. |
| 7,090,843 B1 | 8/2006 | Francisco et al. |
| 7,117,096 B2 | 10/2006 | Luo et al. |

(Continued)

FOREIGN PATENT DOCUMENTS

| | | |
|---|---|---|
| DE | 19907588 A1 | 8/2000 |
| EP | 0555649 A2 | 8/1993 |

(Continued)

OTHER PUBLICATIONS

Jubala et al., Vet Pathol 42: 468-476, 2005.*
Golay et al., Archives of Biochemistry and Biophysics 526: 146-153, 2012.*
Jeffrey et al., Bioconjugate Chem 17: 831-840, 2006.*
Hay et al., Nature Biotechnology 32(1): 40-51, Jan. 2014.*
Gregson et al., J. Med Chem 47: 1161-1174, 2004.*
Dosio et al., Toxins 3: 848-883, 2011.*

(Continued)

*Primary Examiner* — Phuong Huynh
(74) *Attorney, Agent, or Firm* — Knobbe Martens Olson & Bear, LLP

(57) ABSTRACT

The present application relates to methods for the enzymatic functionalization of immunoglobulins, in particular with drugs. Also disclosed herein are linking reagents, functionalized antibodies, pharmaceutical compositions, and method of treating disease and/or conditions.

21 Claims, 35 Drawing Sheets

(56) References Cited

U.S. PATENT DOCUMENTS

| | | | |
|---|---|---|---|
| 7,338,933 B2* | 3/2008 | DeFrees | A61K 38/193 514/1.3 |
| 7,498,298 B2 | 3/2009 | Doronina et al. | |
| 7,657,380 B2 | 2/2010 | Lazar et al. | |
| 7,659,241 B2 | 2/2010 | Senter et al. | |
| 7,763,736 B2 | 7/2010 | Sharpless et al. | |
| 7,807,619 B2 | 10/2010 | Bertozzi et al. | |
| 7,981,843 B2 | 7/2011 | Flynn et al. | |
| 8,133,515 B2 | 3/2012 | Boons et al. | |
| 2002/0034765 A1 | 3/2002 | Daugherty et al. | |
| 2002/0052028 A1 | 5/2002 | Santi et al. | |
| 2002/0058286 A1 | 5/2002 | Danishefsky et al. | |
| 2002/0062030 A1 | 5/2002 | White et al. | |
| 2002/0102208 A1 | 8/2002 | Chinn et al. | |
| 2002/0161201 A1 | 10/2002 | Filpula et al. | |
| 2003/0153043 A1 | 8/2003 | Carr et al. | |
| 2004/0253645 A1 | 12/2004 | Daugherty et al. | |
| 2005/0026263 A1 | 2/2005 | Meares et al. | |
| 2005/0238646 A1 | 10/2005 | Ledbetter et al. | |
| 2005/0238649 A1 | 10/2005 | Doronina et al. | |
| 2005/0256030 A1 | 11/2005 | Feng | |
| 2006/0073137 A1 | 4/2006 | Adair et al. | |
| 2008/0038260 A1 | 2/2008 | Ponath et al. | |
| 2010/0004431 A1 | 1/2010 | Bernett et al. | |
| 2011/0184147 A1 | 7/2011 | Kamiya et al. | |
| 2011/0256157 A1* | 10/2011 | Howard | A61K 47/48561 424/181.1 |
| 2011/0305631 A1* | 12/2011 | Govindan et al. | 424/1.49 |
| 2013/0122020 A1 | 5/2013 | Liu et al. | |
| 2013/0189287 A1 | 7/2013 | Bregeon et al. | |
| 2013/0230543 A1 | 9/2013 | Pons et al. | |
| 2014/0088089 A1* | 3/2014 | Chari | 514/220 |
| 2014/0356385 A1 | 12/2014 | Dennler et al. | |
| 2015/0284713 A1 | 10/2015 | Fischer et al. | |
| 2015/0346195 A1 | 12/2015 | Belmant et al. | |
| 2016/0022833 A1 | 1/2016 | Bregeon et al. | |
| 2016/0114056 A1 | 4/2016 | Bregeon et al. | |

FOREIGN PATENT DOCUMENTS

| | | |
|---|---|---|
| EP | 1859811 A1 | 11/2007 |
| JP | 2003199569 A | 7/2003 |
| WO | WO 92/02190 | 1/1992 |
| WO | WO 92/11018 | 7/1992 |
| WO | WO 92/22583 | 12/1992 |
| WO | WO 93/10102 | 5/1993 |
| WO | WO 96/06931 | 3/1996 |
| WO | WO 96/22366 | 7/1996 |
| WO | WO 98/25929 A1 | 6/1998 |
| WO | WO 99/02514 A2 | 1/1999 |
| WO | WO 99/07692 A2 | 2/1999 |
| WO | WO 99/58534 A2 | 11/1999 |
| WO | WO 99/67252 A2 | 12/1999 |
| WO | WO 99/67253 A2 | 12/1999 |
| WO | WO 00/00485 A1 | 1/2000 |
| WO | WO 00/37473 A1 | 6/2000 |
| WO | WO 00/49019 A2 | 8/2000 |
| WO | WO 00/49020 A2 | 8/2000 |
| WO | WO 00/49021 A2 | 8/2000 |
| WO | WO 00/57874 A1 | 10/2000 |
| WO | WO 00/66589 A1 | 11/2000 |
| WO | WO 00/71521 A1 | 11/2000 |
| WO | WO 01/27308 A2 | 4/2001 |
| WO | WO 01/64650 A2 | 9/2001 |
| WO | WO 01/70716 A1 | 9/2001 |
| WO | WO 01/73103 A2 | 10/2001 |
| WO | WO 01/81342 A2 | 11/2001 |
| WO | WO 01/92255 A2 | 12/2001 |
| WO | WO 02/08440 A2 | 1/2002 |
| WO | WO 02/14323 A2 | 2/2002 |
| WO | WO 02/30356 A2 | 4/2002 |
| WO | WO 02/32844 A2 | 4/2002 |
| WO | WO 02/080846 A2 | 10/2002 |
| WO | WO 02/083180 A1 | 10/2002 |
| WO | WO 03/074053 A1 | 9/2003 |
| WO | WO 2004/014919 A1 | 2/2004 |
| WO | WO 2004/043493 A1 | 5/2004 |
| WO | WO 2004/043880 A2 | 5/2004 |
| WO | WO 2005/040219 A1 | 5/2005 |
| WO | WO2005/070468 * | 8/2005 |
| WO | WO 2005/070468 A2 | 8/2005 |
| WO | WO 2005/085251 A1 | 9/2005 |
| WO | WO 2007/008603 A1 | 1/2007 |
| WO | WO 2007/008848 A2 | 1/2007 |
| WO | WO 2007/020290 A1 | 2/2007 |
| WO | WO 2008/017122 A1 | 2/2008 |
| WO | WO 2008/102008 A1 | 8/2008 |
| WO | WO 2009/067663 A1 | 5/2009 |
| WO | WO 2009/105969 A1 | 9/2009 |
| WO | WO 2010/115630 A1 | 10/2010 |
| WO | WO 2010/136598 A1 | 12/2010 |
| WO | WO 2011/023883 A1 | 3/2011 |
| WO | WO 2011/085523 A1 | 7/2011 |
| WO | WO 2011/120053 A1 | 9/2011 |
| WO | WO 2011/130616 A1 | 10/2011 |
| WO | WO2011/013645 * | 11/2011 |
| WO | WO 2012/041504 A1 | 4/2012 |
| WO | WO 2012/059882 A2 | 5/2012 |
| WO | WO2012059882 * | 5/2012 |
| WO | WO 2012/112687 A1 | 8/2012 |
| WO | WO 2013/092983 A2 | 6/2013 |
| WO | WO 2013/092998 A1 | 6/2013 |
| WO | WO 2013/177481 A1 | 11/2013 |
| WO | WO 2014/009426 A1 | 1/2014 |
| WO | WO 2014/072482 A1 | 5/2014 |
| WO | WO 2014/140300 A1 | 9/2014 |
| WO | WO 2014/202773 A1 | 12/2014 |

OTHER PUBLICATIONS

Yu et al., Investigative Ophthalmology & Visual Science 49(2): 522-527, Feb. 2008.*
Kamal et al., Biorganic & Medicinal Chemistry Letters 18: 1468-1473, 2008.*
Hu et al., J Am Chem Soc 125: 14298-14299, 2003.*
Moses et al., Chem Soc Rev 36: 1249-1262, 2007.*
Gregson et al., J. Med Chem 47:1161-1174, 2004.*
Altschul et al., "Gapped BLAST and PSI-BLAST: A new generation of protein database search programs", Nucl Acids Res. (1997) 25(17): 3389-3402.
Altschul et al., "Basic Local Alignment Search Tool", J Mol Biol. (1990) 215:403-410.
Amersham Biosciences, Antibody Purification Handbook, (2002) Publication No. 18-1037-46, Edition AC, 112 pages.
Amsberry et al., "The Lactonization of 2'-Hydroxyhydrocinnamic Acid Amides: A Potential Prodrug for Amines", J. Org Chem (1990) 55:5867-5877.
Ando et al., "Purification and Characteristics of a Novel Transglutaminase Derived from Microorganisms", Agric Biol Chem. (1989) 53(10):2613-2617.
Ausubel et al. (Eds.) Current Protocols in Molecular Biology (1993) John Wiley & Sons, Inc., Table of Contents, 15 pages.
Bernard et al., "Cysteine analogs of recombinant barley ribosome inactivating protein form antibody conjugates with enhanced stability and potency in vitro", Bioconjugate Chem., (1994) 5(2):126-132.
Brabez et al., "Design, synthesis and biological studies of efficient multivalent melanotropin ligands: tools towards melanoma diagnosis and treatment", J Med Chem. (2011) 54(20):7375-7384.
Carillo et al., "The Multiple Sequence Alignment Problem in Biology", Siam J. Appl Math. (1988) 48(5):1073-1082.
Carter et al., "Improved oligonucleotide site-directed mutagenesis using M13 vectors", Nucl Acids Res. (1985) 13(12):4431-4443.
Carter et al., "Humanization of an anti-p185HER2 antibody for human cancer therapy", Proc Natl Acad Sci. USA (1992) 89:4285-4289.
Chapman, Andrew P., "PEGylated antibodies and antibody fragments for improved therapy: a review", Advan Drug Del Rev. (2002) 54:531-545.
Chothia et al., "Canonical Structures for the Hypervariable Regions of Immunoglobulins", J Mol Biol. (1987) 196:901-917.

(56) References Cited

OTHER PUBLICATIONS

Connolly et al., "In Vivo Inhibition of Fas Ligand-Mediated Killing by TR6, a Fas Ligand Decoy Receptor", J Pharmacol Exp Ther. (2001) 298(1):25-33.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody", J Immunol. (2002) 169(6):3076-3084.
Devereux et al., "A comprehensive set of sequence analysis programs for the VAX", Nucl Acids Res. (1984) 12(1):387-395.
Doronina et al., "Development of potent monoclonal antibody Auristatin conjugates for cancer therapy", Nat Biotech. (2003) 21(7):778-784 & Erratum Nat Biotech. (2003) 21(8):941.
Doronina et al., "Enhanced activity of monomethylauristatin F through Monoclonal Antibody Delivery", Bioconjugate Chem. (2006) 17(1):114-124.
Edelman et al., "The Covalent Structure of an Entire γG Immunoglobulin Molecule", Proc Natl Acad. USA, (1969) 63:78-85.
Folk et al., "Polyamines as Physiological Substrates for Transglutaminases", J. Biol. Chem. (1980) 255(8):3695-3700.
Genbank Reference Sequence NM_024003.2; "Homo sapiens L1 cell adhesion molecule (L1CAM), transcript variant 2, mRNA", May 4, 2013; 8 pages.
Genbank Reference Sequence NM_024003.3; "*Homo sapiens* L1 cell adhesion molecule (L1CAM), transcript variant 2, mRNA", May 26, 2013; 10 pages.
Genbank Reference Sequence NM_0764493.1; "Neural cell adhesion molecule L1 isoform 2 precursor [*Homo sapiens*]", May 26, 2014; 6 pages.
Gorman et al., "Transglutaminase Amine Substrates for Photochemical Labeling and Cleavable Cross-linking of Proteins", J Biol Chem. (1980) 255(3):1175-1180.
Green et al., "Antigen-specific human monoclonal antibodies from mice engineered with human Ig heavy and light chain YACs", Nature Gen. (1994) 7:13-21.
Gribskov et al., (Eds.) Sequence Analysis Primer; Stockton Press (1991); Table of Contents, 7 pages.
Griffin et al., (Eds.) Methods in Molecular Biology-24: Computer Analysis of Sequence Data; Part I & II; Humana Press, New Jersey (1994) Tables of Contents, 8 pages.
Griffiths et al., "Human anti-self antibodies with high specificity from phage display libraries", EMBO J. (1993) 12(2):725-734.
Griffiths et al., "Isolation of high affinity human antibodies directly from large synthetic repertoires", EMBO J. (1994) 13(14):3245-3260.
Hamblett et al., "Effects of Drug Loading on the Antitumor Activity of a Monoclonal Antibody Drug Conjugate", Clin Cancer Res. (2004) 10:7063-7070.
Harlow et al., (Eds.), Antibodies—A Laboratory Manual; Table of Contents, Cold Spring Harbor Laboratory Press, Cold Spring Harbor, NY (1988) TOC; 9 pages.
Hay et al., "A 2-nitroimidazole carbamate prodrug of 5-amino-1-(Chloromethyl)-3-[(5,6,7-Trimethoxyindo1-2-YL)Carbony1]-1,2-dihydro-3H-Benz[e]indole (amino-SECO-CBI-TMI) for use with ADEPT and GDEPT", Bioorg Med Chem Lttrs. (1999) 9:2237-2242.
Higuchi, Russell "Recombinant PCR" Chapter 22 in Part II of PCR Protocols, A Guide to Methods and Applications [Innis et al. (Eds.)], Academic Press, (1990) pp. 177-183.
Ho et al. Site-directed Mutagenesis by Overlap Extension Using the Polymerase Chain Reaction. Gene (1989) 77(1):51-59.
Hollinger et al., "Engineered antibody fragments and the rise of single domains", Nature Biotech. (2005) 23(9):1126-1136.
Ill et al., "Design and construction of a hybrid immunoglobulin domain with properties of both heavy and light chain variable regions", Prot Engineer. (1997) 10(8):949-957.
Ito et al A General Method for Introducing a Series of Mutations into Cloned DNA Using the Polymerase Chain Reaction. Gene (1991) 102(1):67-70.
Jakobovits et al., "Germ-line transmission and expression of a human-derived yeast artificial chromosome", Nature (1993) 362:255-258.
Jones et al., "Replacing the complementarity-determining regions in a human antibody with those from a mouse", Nature (1986) 321:522-525.
Josten et al., "Use of microbial transglutaminase for the enzymatic biotinylation of antibodies", J Immunol Meth. (2000) 240:47-54.
Junutula et al., "Site-specific conjugation of a cytotoxic drug to an antibody improves the therapeutic index", Nature Biotech (2008) 26(8):925-932.
Kabat et al., (Eds.) Sequences of Proteins of Immunological Interest, 5th Edition; (1991) Table of Contents; 11 pages.
Kämpfer et al., "A numerical classification of the genera Streptomyces and Streptoverticillium using miniaturized physiological tests", J Gen Microbiol. (1991) 137:1831-1891.
Kajiwara et al., "Expression of L1 Cell Adhesion Molecule and Morphologic Features at the Invasive Front of Colorectal Cancer", Anat Pathol. (2011) 136(1):138-144.
Kamiya et al., "Site-specific cross-linking of functional proteins by transglutamination", Enzy Micro Tech. (2003) 33:492-496.
Kingsbury et al., "A Novel Peptide Delivery System Involving Peptidase Activated Prodrugs as Antimicrobial Agents. Synthesis and Biological Activity of Peptidyl Derivatives of 5-Fluorouracil", J Med Chem. (1984) 27:1447-1451.
Knappik et al., "Fully Synthetic Human Combinatorial Antibody Libraries (HuCAL) Based on Modular Consensus Frameworks and CDRs Randomized with Trinucleotides", J Mol Biol. (2000) 296:57-86.
Knogler et al., "Copper-67 Radioimmunotherapy and Growth Inhibition by Anti-L1-Cell Adhesion Molecule Monoclonal Antibodies in a Therapy Model of Ovarian Cancer Metastasis", Clin Cancer Res (2007) 13(2):603-611.
Kuil et al., "ITAM-derived phosphopeptide-containing dendrimers as multivalent ligands for Syk tandem SH2 domain", Org Biomol Chem. (2009) 7:4088-4094.
Kunkel, Thomas A., "Rapid and efficient site-specific mutagenesis without phenotypic selection", Proc Natl Acad Sci USA (1985) 82:488-492.
Lesk, Arthur M. (Ed.) Computational Molecular Biology, Oxford University Press (1988); Table of Contents; 4 pages.
Lin et al., "Transglutaminase-catalyzed site-specific conjugation of small-molecule probes to proteins in vitro and on the surface of living cells", J Am Chem Soc. (2006) 128(14):4542-4543 (7pages).
Liu et al., "Identification of Active Site Residues in the "GyrA" Half of Yeast DNA Topoisomerase II", J Biol Chem. (1998) 273(32):20252-20260.
Lonberg et al., "Antigen-specific human antibodies from mice comprising four distinct genetic modifications", Nature (1994) 368:856-859.
Lonberg, Nils, "Human antibodies from transgenic animals", Nature Biotech. (2005) 23(9):1117-1125.
Lorand et al., "Specificity of Guinea Pig Liver Transglutaminase for Amine Substrates", Biochem. (1979) 18(9):1756-1765.
Lorand et al., "Transglutaminases: Cross-linking enzymes with pleiotropic functions", Nature (2003) 4:140-156.
Lyon et al., "Conjugation of Anticancer Drugs through Endogenous Monoclonal Antibody Cysteine Residues", Meth Enzymol. (2012) 502:123-138.
Maeda et al., "Susceptibility of human T-cell leukemia virus type I-infected cells to humanized anti-CD30 monoclonal antibodies in vitro and in vivo", Cancer Sci. (2010) 101(1):224-230.
McCafferty et al., "Phage antibodies: Filamentous phage displaying antibody variable domains", Nature (1990) 348:552-554.
Morrison et al., "Chimeric human antibody molecules: Mouse antigen-binding domains with human constant region domains", Proc Natl Acad Sci. USA (1984) 81:6851-6855.
Murthy et al., "Residue Gln-30 of Human Erythrocyte Anion Transporter is a Prime Site for Reaction with Intrinsic Transglutaminase" J Biolog Chem. (1994) 269(36):22907-22911.
Murthy et al., "Selectivity in the Post-Translational, Transglutaminase-dependent Acylation of Lysine Residues", Biochem. (2009) 48:2654-2660.

(56) References Cited

OTHER PUBLICATIONS

Pearson, William R., "Rapid and Sensitive Sequence Comparison with FASTP and FASTA", Meth Enzymol. (1990) 183(5):63-98.
Presta, Leonard G., "Antibody engineering", Curr Opin Struct Biol. (1992) 2:593-596.
Presta et al., "Humanization of an Antibody Directed Against IgE", J Immunol. (1993) 151(5):2623-2632.
Riechmann et al., "Reshaping human antibodies for therapy", Nature (1988) 332:323-327.
Rodrigues et al., "Synthesis and β-lactamase-mediated activation of a cephalosporin-taxol prodrug", Chem Biol. (1995) 2:223-227.
Roguska et al., "Humanization of murine monoclonal antibodies through variable domain resurfacing", Proc Natl Acad Sci. (1994) 91:969-973.
Sambrook et al., (Eds.) Molecular Cloning—A Laboratory Manual, [2nd Edition]; Cold Spring Harbor Laboratory Press, NY; (1989) Table of Contents, 30 pages.
Sambrook et al., (Eds.) Molecular Cloning—A Laboratory Manual, [3rd Edition]; vol. 1; Cold Spring Harbor Laboratory Press, NY; (2001); Table of Contents, 18 pages.
Sazinsky et al., "Aglycosylated immunoglobulin G1 variants productively engage activating Fc receptors", PNAS (2008) 105(51):20167-20172.
Sims et al., "A Humanized CD18 Antibody can block Function without Cell Destruction", J Immunol. (1993) 151:2296-2308.
Smith, Douglas W. (Ed.), Biocomputing—Informatics and Genome Projects, Academic Press, Inc. (1993) Table of Contents, 7 pages.
Suzuki et al., Glycopinion Mini-Review: N-Glycosylation/Deglycosylation as a Mechanism for the Post-Translational Modification/Remodification of Proteins. Glycoconjug J. (1995) 12:183-193.
Takazawa et al., Enzymatic Labeling of a Single Chain Variable Fragment of an Antibody With Alkaline Phosphates by Microbial Transglutaminase. Biotech Engin. (2004) 86(4):399-404.
Tan et al., "Superhumanized" Antibodies: Reduction of Immunogenic Potential by Complementarity-Determining Region Grafting with Human Germline Sequences: Application to an Anti-CD28. J Immunol. (2002) 169:1119-1125.
Tomlinson et al., The Repertoire of Human Germline VH Sequences Reveals about Fifty Groups of VH Segments with Different Hypervariable Loops. J Mol Biol. (1992) 227:776-798.
Vallette et al., Construction of Mutant and Chimeric Genes Using the Polymerase Chain Reaction. Nuc Acids Res. (1989) 17(2):723-733.
Verhoeyen et al., Reshaping Human Antibodies: Grafting an Antilysozyme Activity. Science (1988) 239:1534-1536.
Von Heinje, Gunnar [Ed.] "Sequence Analysis in Molecular Biology—Treasure Trove or Trivial Pursuit", 1987, Academic Press [TOC Only].
Wakankar et al., Analytical Methods for Physicochemical Characterization of Antibody Drug Conjugates. Landes Biosci. (2011) 3(2):161-172.
Wängler et al., "Antibody-Dendrimer Conjugates: The Number, Not the Size of the Dendrimers, Determines the Immunoreactivity" Bioconjugate Chem. (2008) (19)4:813-820.
Ward et al., Binding Activities of a Repertoire of Single Immunoglobulin Variable Domains Secreted From Escherichia coli. Nature (1989) 341:544-546.
Wells et al., Cassette Mutagenesis: An Efficient Method for Generation of Multiple Mutations at Defined Sites. Gene (1985) 34(2-3):315-323.
Xu et al., "Characterization of intact antibodydrug conjugates from plasma/serum in vivo by affinity capture capillary liquid chromatography mass spectrometry", Anal Biochem. (2011) 412(1): 56-66.
Yurkovetskiy et al., Synthesis of a Macromolecular Camptothecin Conjugate with Dual Phase Drug Release. Mol Pharm. (2004) 1(5):375-382.

Zoller et al., "Oligonucleotide-directed mutagenesis using M13-derived vectors: an efficient and general procedure for the production of point mutations in any fragment of DNA", Nucl Acids Res. (1982) 10(20):6487-6500.
Zoller et al., "Oligonucleotide-directed mutagenesis of DNA fragments cloned into M13 vectors", Methods Enzymol. (1983) 100:468-500.
International Search Report mailed Apr. 23, 2013 for International Application No. PCT/EP2012/076631 filed Dec. 21, 2012.
International Search Report mailed Feb. 5, 2014 for International Application No. PCT/EP2012/076606 filed Dec. 21, 2012.
International Search Report mailed Jan. 31, 2014 for International Application No. PCT/EP2013/064605 filed Jul. 10, 2013.
U.S. Appl. No. 61/410,840, filed Nov. 5, 2010.
U.S. Appl. No. 61/553,917, filed Oct. 31, 2011.
U.S. Appl. No. 61/579,908, filed Dec. 23, 2011.
U.S. Appl. No. 61/661,569, filed Jun. 19, 2012.
U.S. Appl. No. 61/671,122, filed Jul. 13, 2012.
U.S. Appl. No. 61/671,128, filed Jul. 13, 2012.
U.S. Appl. No. 61/837,932, filed Jun. 21, 2013.
Dosio et al., "Immunotoxins and Anticancer Drug Conjugate Assemblies: The Role of the Linkage between Components", Toxins (2011) 3:848-883.
Yu et al., "Interaction between Bevacizumab and Murine Vegf-A: a Reassessment", Invest Ophtalmol Vis Sci. (2008 Feb);49(2):522-527. U.S. Office Action dated Feb. 27, 2015 in Application No. 13/725,382, filed Dec. 21, 2012.
U.S. Office Action dated Feb. 27, 2015 in U.S. Appl. No. 13/725,382, filed Dec. 21, 2012.
U.S. Preliminary Amendment dated May 3, 2013 in U.S. Appl. No. 13/883,535, filed May 3, 2013.
U.S. Office Action dated Dec. 19, 2014 in U.S. Appl. No. 13/883,535, filed May 3, 2013.
U.S. Second Preliminary Amendment dated Feb. 17, 2015 in U.S. Appl. No. 13/883,535, filed May 3, 2013.
Baeuerle et al., "Bispecific T-cell engaging antibodies for cancer therapy", Cancer Res. (2009) 69(12):4941-4944.
Dosio et al., "Immunotoxins and Anticancer Drug Conjugate Assemblies: The Role of the Linkage between Components", Toxins (2011) 3:848-883.
Jackman et al., "Development of a two-part strategy to identify a therapeutic human bispecific antibody that inhibits IgE receptor signaling", J Biol Chem. (2010) 285(27):20850-20859.
Kamiya et al., "S-Peptide as a Potent Peptidyl Linker for Protein Cross-Linking by Microbial Transglutaminase from *Streptomyces mobaraensis*", Bioconj Chem. (2003) 14:351-357.
Nilsson et al., A synthetic IgG-binding domain based on stapylococcal protein A. Protein Eng. (1987) 1(2):107-113.
Pearson, William R., "Flexible sequence similarity searching with the FASTA3 program package", Methods Mol Biol. (2000) 132:185-219.
Plagmann et al., "Transglutaminase-catalyzed covalent multimerization of camelidae anti-human TNF single domain antibodies improves neutralizing activity", J Biotech. (2009) 142:170-178.
Strop et al., "Location Matters: Site of Conjugation Modulates Stability and Pharmacokinetics of Antibody Drug Conjugates", Chem Biol. (2013) 20(2):161-167.
Sung et al., "Functional glass surface displaying a glutamyl donor substrate for transglutaminase-mediated protein immobilization", Biotech J. (2010) (5):456-462.
Uhlén et al., Complete Sequence of the Staphylococcal Gene Encoding Protein A—A Gene Evolved Through Multiple Duplications. J Biol Chem. (1984) 259(3):1695-1702.
Yu et al., "Interaction between Bevacizumab and Murine VEGF-A: A Reassessment", Invest Ophtalmol Vis Sci. (Feb. 2008);49(2):522-527.
International Search Report mailed Apr. 15, 2014 for International Application No. PCT/EP2013/073428 filed Nov. 8, 2013.
Dennler et al. 2013. Enzymatic antibody modification by bacterial transglutaminase. *Bioconjugate Chemistry*, 1045:205-215.

(56) References Cited

OTHER PUBLICATIONS

Dennler et al. 2014. Transglutaminase-based chemo-enzymatic conjugation approach yields homogeneous antibody-drug conjugates. *Bioconjugate Chemistry*, 25(3):569-578.

Grünberg et al. 2013. DOTA-functionalized polylysine: A high number of DOTA chelates positively influences the biodistribution of enzymatic conjugated anti-tumor antibody chCE7agl. *PLOS One*, 8(4): e60350.

Jeger et al. 2010. Site-specific and stoichiometric modification of antibodies by bacterial transglutaminase. *Angewandte Chemie International Edition, Wiley VCH*, 49(51):9995-9997.

Jeger et al. 2010. Site-specific and stoichiometric modification of antibodies by bacterial transglutaminase—Supporting Information. *Angewandte Chemie International Edition, Wiley VCH*, 46 pages.

Mindt et al. 2008. Modification of different IgG1 antibodies via glutamine and lysine using bacterial and human tissue transglutaminase. *Bioconjugate Chemistry*, 19(1):271-278.

International Search Report and Written Opinion mailed Sep. 24, 2014 for International Application No. PCT/EP2014/063064 filed Jun. 20, 2014, 16 pages.

Jeger. Site-Specific Conjugation of Tumour-Targeting Antibodies Using Transglutaminase. Dissertation. ETH Zurich: University of Basel (2009) 1-135.

International Search Report mailed Aug. 20, 2014 for International Application No. PCT/EP2014/063061 filed Jun. 20, 2014.

U.S. Response to Office Action filed Dec. 11, 2015 in U.S. Appl. No. 13/725,382, filed Dec. 21, 2012.

U.S. Response dated Nov. 16, 2015 in U.S. Appl. No. 13/883,535, filed May 3, 2013.

Lhospice et al., "Site-specific conjugation of monomethyl auristatin E to Anti-CD30 antibodies improves their pharmacokinetics and therapeutic index in rodent models", Mol Pharmaceutics (2015) 12:1863-1871.

Stancovski et al., "Mechanistic aspects of the opposing effects of monoclonal antibodies to the ERBB2 receptor on tumor growth", Proc Natl Acad Sci USA. (Oct. 1991) 88(19):8691-8695.

International Search Report mailed Jun. 25, 2014 for International Application No. PCT/EP2014/055140 filed Mar. 14, 2014.

U.S. Response to Office Action filed May 28, 2015 in U.S. Appl. No. 13/725,382, filed Dec. 21, 2012.

U.S. Office Action dated Aug. 13, 2015 in U.S. Appl. No. 13/725,382, filed Dec. 21, 2012.

U.S. Office Action dated Sep. 16, 2015 in U.S. Appl. No. 13/883,535, filed May 3, 2013.

Chari, Ravi V.J., "Targeted Cancer Therapy: Conferring Specificity to Cytotoxic Drugs", Acc of Chem Res. (Jan. 2008) 41(1):98-107.

U.S. Office Action dated Feb. 25, 2016 in U.S. Appl. No. 13/725,382, filed Dec. 21, 2012.

U.S. Office Action dated Jan. 29, 2016 in U.S. Appl. No. 14/367,840, filed Jun. 20, 2014.

U.S. Office Action dated Dec. 30, 2015 in U.S. Appl. No. 13/883,535, filed May 3, 2013.

U.S. Response to Office Action filed May 23, 2016 in U.S. Appl. No. 13/725,382, filed Dec. 21, 2012.

U.S. Response to Office Action filed Mar. 25, 2016 in U.S. Appl. No. 14/367,840, filed Jun. 20, 2014.

U.S. Response dated May 2, 2016 in U.S. Appl. No. 13/883,535, filed May 3, 2013.

\* cited by examiner

ENZYMATIC CONJUGATION OF POLYPEPTIDES

CROSS-REFERENCE TO RELATED APPLICATIONS

This application is a continuation-in-part of PCT Application No. PCT/EP2014/063064 filed 20 Jun. 2014, which claims the benefit of U.S. Provisional Application No. 61/837,932 filed 21 Jun. 2013, the disclosures of which are incorporated herein by reference in their entireties including any drawings.

REFERENCE TO SEQUENCE LISTING

The present application is being filed along with a Sequence Listing in electronic format. The Sequence Listing is provided as a file entitled "INNAT-018P1_Substitute_Sequence_Listing.txt", created Jul. 21, 2015, which is 20 KB in size. The information in the electronic format of the Substitute Sequence Listing is incorporated herein by reference in its entirety.

FIELD OF THE INVENTION

The present application relates to the field of chemistry, biochemistry, and medicine. Disclosed herein are methods for the functionalization of immunoglobulins, in particular with drugs. Also disclosed herein are linking reagents, functionalized antibodies, pharmaceutical compositions, and method of treating disease and/or conditions.

BACKGROUND

Immunoglobulins conjugated to a drug of interest, generally known as antibody drug conjugates (ADCs), are a promising area of therapeutic research. Recent developments in ADC technology have focused on linker technology that provides for intracellular cleavage or more recently, non-cleavable linkers that provide greater in vivo stability and reduced toxicity. The feasibility of a non-cleavable linker-based approach, however, may be more dependent on the cellular target than in the case of cleavable linkers. ADCs with noncleavable linkers must be internalized and degraded within the cell, whereas compounds with cleavable linkers may be active against targets that are poorly internalized through extracellular drug release and drug entry into tumor cells. Similarly, killing of bystander antigen-negative cells through targeting of antigen-positive cells (collateral toxicity) is presumably only possible with cleavable linkers. As a consequence, it is generally believed that no general linker design exists for all ADCs and that each antibody must be examined separately. Additionally, the efficacy of a drug linked to a toxin may vary, e.g. depending on the cell type or particular tumor cell, such that it may also be necessary to test a variety of drugs against a given target and further in combination with a particular linker system. Development of ADCs therefore remains an expensive and time-consuming process and there is a need in the field for improved linker systems.

Transglutaminases (TGases) have been exploited for some time in the food industry for their ability to cross-link proteins. Such utilization has avoided the need to cross-link in quantitative or stoichiometric fashion. TGases have been shown to be capable of conjugating glutamine and lysine residues, including on antibodies (see, e.g., Josten et al. (2000) J. Immunol. Methods 240, 47-54; Mindt et al (2008) Bioconjug. Chem. 19, 271-278; Jeger et al (2010) Angew. Chem. Int. Ed. 49: 9995-9997); Kamiya et al (2003) Enzyme. Microb. Technol. 33, 492-496, PCT publication WO2012/059882 and US patent publication no. 2011/0184147. While previous attempts to cross-link proteins have studied protein motifs that gave rise to conjugation and identified peptides that can be conjugated, the rules which govern selection by TGases of glutamine residues for modification are still largely unknown. Additionally, little is known about TGases' ability to take up different substrates, or their effect on the ability to TGases to conjugate in quantitative fashion.

SUMMARY OF THE INVENTION

The present disclosure provides methods using TGase to stoichiometrically functionalize acceptor glutamines on antibodies with difficult substrates (notably large hydrophobic organic molecules). The invention arises from the finding that the environment of acceptor glutamines within antibodies and the nature of the lysine-derivative donor substrates both independently and in combination influence the efficacy of transglutaminase (TGase)-mediated conjugation.

It has been discovered that conjugation of moieties (e.g. chemical entities) to antibodies using TGase in combination with lysine-derivative linkers provides at best only partial conjugation to acceptor glutamines within antibodies. The conjugation appears to be dependent, among other things, on the nature of the substrate: while smaller, uncharged and non-hydrophobic substrates such as biotin can be partially coupled using known methods, some substrates such as charged substrates are not coupled at all. Hydrophobic and/or larger substrates appear to be poorly coupled leading to heterogeneous mixtures of antibodies. Coupling reaction parameters were optimized but could not resolve the problems of low levels of coupling and thus product homogeneity. Large, rigid and/or hydrophobic molecules, particularly those also containing polycycles or macrocycles, (along the lines of common cytotoxic drugs) could not be coupled with a high level of completion.

It was further discovered that strongly improved coupling could be achieved when modified Fc domains were used that avoided a negatively charged aspartic acid group at the +2 position relative to the acceptor glutamine. The Fc domain modifications were designed to abolish heavy chain N297-linked glycosylation, such that no enzymatic (PNGase F) deglycosylation was needed. PNGase F deglycosylation modifies the side chain of the asparagine at position 297 (EU index) which becomes a negatively charged aspartic acid residue. Use of a N297S mutant with one acceptor glutamine per heavy chain (at residue 295 (EU index) yielded an antibody composition with much higher coupling compared to an antibody having a N297D mutation. Furthermore, mutations N297R, N297A and N297S provided improved conjugation.

In further experiments, it was discovered that when hydrophobic and/or larger substrates (auristatins or pyrrolobenzodiazepine drugs) are coupled, residue 297 (EU numbering) may present better accessibility for TGase than the naturally occurring Q295 site. Specifically for larger substrates, accessibility of enzyme and/or linker to the reaction site may become a factor that can limit coupling. could be coupled at high rates (substantially complete coupling) when conjugated to a Q295X+N297Q double mutant with one acceptor glutamine per heavy chain at position 297. The accessibility may be less of a factor for smaller substrates, as cadavarin-dansyl linkers did not show substantial difference between coupling on residue 295 or 297; cadavarin-dansyl showed if anything better coupling onto Q295, e.g. in the context of N297A, N297S and N297R mutants.

Furthermore, the coupling environment is strongly influenced by solvents. As demonstrated in FIGS. 26 and 27, presence of organic solvents in the TGase coupling reaction mixture at above 5% or further 10% strongly inhibits the activity of TGase for coupling onto amino acids in the CH2 domain. Thus in one aspect coupling processes are provided such that linker-drug moieties preparations are adjusted such that solvent concentrations in the TGase coupling reaction mixture is below 10% (v/v), preferably below 5% (v/v) Substantially complete direct coupling using a linker comprising a drug moiety) could be achieved using a process is which solvent concentration was low (1%, for example).

In one embodiment, a smaller linker substrate is coupled to an antibody at residue Q295, wherein the Q295 is flanked at the +2 position (i.e. residue 297) by a non-glycosylated, non-aspartic acid, amino acid residue, optionally wherein the residue is an alanine, serine or arginine. Preferably the coupling is carried out by reacting an antibody comprising having an acceptor glutamine residue with a linking reagent comprising a primary amine, in the presence of a transglutaminase enzyme, wherein solvent (e.g. organic solvent, polar solvent, non-polar solvent, DMSO) is less than 10% (v/v), optionally further less than 5%, 4%, 3% or 2% (v/v).

In one embodiment, a large and/or hydrophobic linker substrate is coupled to an antibody at residue 297, wherein the antibody comprises a N297Q mutations (and optionally further a Q295X mutation. Preferably the coupling is carried out by reacting an antibody comprising having an acceptor glutamine residue with a linking reagent comprising a primary amine, in the presence of a transglutaminase enzyme, wherein solvent (e.g. organic solvent, polar solvent, non-polar solvent, DMSO) is less than 10% (v/v), optionally further less than 5%, 4%, 3% or 2% (v/v).

However, for highly hydrophobic drugs, organic solvent is generally required to maintain solubility and avoid formation of aggregated antibody-drug conjugates, e.g. pyrrolobenzodiazepines require as much as 50% (v/v). Where a hydrophobic linker substrate cannot be solubilized without high concentrations of organic solvent (e.g. linkers comprising pyrrolobenzodiazepine moieties require as much as 50% solvent to permit highly homogenous coupling at a DAR of 2), a multi-step coupling process making use of a linker with a reactive moiety is used. The linker with reactive moiety is coupled to an antibody, e.g. at residue Q295 and/or at residue 297 when the antibody comprises a N297Q mutation. Preferably the coupling is carried out by reacting an antibody comprising having an acceptor glutamine residue with a linking reagent with reactive moiety (R), in the presence of a transglutaminase enzyme, wherein solvent (e.g. organic solvent, polar solvent, non-polar solvent, DMSO) is absent or is less than 10% (v/v), optionally further less than 5%, 4%, 3% or 2% (v/v). The resulting antibody is then reacted with a linker comprising a complementary reactive group (R') and a hydrophobic drug (e.g. a pyrrolobenzodiazepine moiety) to yield an antibody coupled (e.g. via the reaction produce of R and R') to the hydrophobic drug (or other moiety of interest (Z)). The reaction step with linker comprising a complementary reactive group (R') and a hydrophobic drug can be carried out in the presence of solvent (e.g. wherein solvent (e.g. organic solvent, polar solvent, non-polar solvent, DMSO) is present in the reaction mixture, wherein solvent is present is present at more than 2%, 3%, 4%, 5%, 10%, 20%, 40% or 50% (v/v). See e.g., FIG. 10B for an example of a multi-step approach.

In one aspect, present disclosure relates to a method for conjugating a hydrophobic, high molecular weight and/or charged organic compound to an antibody, comprising:
a) providing an antibody having at least one acceptor glutamine residue; and
b) reacting said antibody with a linker comprising a primary amine (a lysine-based linker) comprising a reactive group (R), in the presence of a TGase, under conditions sufficient to obtain an antibody comprising an acceptor glutamine linked (covalently) to a reactive group (R) via said linker, wherein the reaction mixture is free of organic solvent or contains less than 10% (v/v) or contains less than 5%, 4%, 3% or 2% (v/v) organic solvent; and
c): reacting, in the presence of organic solvent (e.g., at least 2%, 3%, 4%, 5%, 10%, 20%, 25%, 40% or 50% (v/v) organic solvent):
(i) an antibody of step (b) comprising an acceptor glutamine linked to a reactive group (R) via a linker comprising a primary amine (a lysine-based linker), with
(ii) a compound comprising a hydrophobic, high molecular weight and/or charged organic compound and a reactive group (R') capable of reacting with reactive group R, under conditions sufficient to obtain an antibody comprising an acceptor glutamine linked to a moiety of interest (Z) via a linker comprising a primary amine (a lysine-based linker).

The process enables the conjugation to antibodies at height rates of completion of pyrrolobenzodiazepines. This class of compounds is highly hydrophobic and requires substantial concentrations of solvent for solubility without aggregation. As shown herein, conjugation in less than 50% solvent resulted in aggregation which prevented TGase from achieving a drug:antibody ratios beyond 1 for an antibody having two acceptor glutamines. Thus, in one aspect, present disclosure relates to a method for conjugating a pyrrolobenzodiazepine to an antibody, comprising:
a) providing an antibody having at least one acceptor glutamine residue; and
b) reacting said antibody with a linker comprising a primary amine (a lysine-based linker) comprising a reactive group (R), in the presence of a TGase, under conditions sufficient to obtain an antibody comprising an acceptor glutamine linked (covalently) to a reactive group (R) via said linker, wherein the reaction mixture is free of organic solvent or contains less than 10% (v/v) or contains less than 5%, 4%, 3% or 2% (v/v) organic solvent; and
c): reacting, in the presence of organic solvent (e.g., at least 25%, 40% or 50% (v/v) organic solvent):
(i) an antibody of step (b) comprising an acceptor glutamine linked to a reactive group (R) via a linker comprising a primary amine (a lysine-based linker), with
(ii) a compound comprising a pyrrolobenzodiazepine and a reactive group (R') capable of reacting with reactive group R,
under conditions sufficient to obtain an antibody comprising an acceptor glutamine linked to a pyrrolobenzodiazepine via a linker comprising a primary amine (a lysine-based linker).

In one embodiment, the pyrrolobenzodiazepine is a pyrrolobenzodiazepine monomer. In one embodiment, the pyrrolobenzodiazepine is a pyrrolobenzodiazepine dimer comprising two pyrrolobenzodiazepine units. In one embodiment, the pyrrolobenzodiazepine is a pyrrolobenzodiazepine trimer comprising three pyrrolobenzodiazepine units. In one embodiment, the pyrrolobenzodiazepine is a pyrrolobenzodiazepinemultimer comprising more than three pyrrolobenzodiazepine units. In one embodiment, the pyrrolobenzodiazepine is a C8/C8'-linked pyrrolobenzodiazepine dimer.

In one aspect of the any of the embodiments herein, a pyrrolobenzodiazepine monomer or unit is a pyrrolo[2,1-c][1,4]benzodiazepine.

In one aspect on the methods, an antibody or composition of Formula IVc is obtained.

In one aspect of the any of the embodiments herein, a pyrrolobenzodiazepine dimer is a C8/C8'-linked pyrrolo[2,1-c][1,4]benzodiazepine dimer.

In one embodiment provided is an antibody or antibody fragment comprising a functionalized acceptor glutamine residue, the functionalized acceptor glutamine residue having Formula IVc, (Q)-NH—C—X-L-RR'-L'-V—Y—Z    Formula IVc or a pharmaceutically acceptable salt or solvate thereof, wherein:

Q is a glutamine residue present in an antibody or antibody fragment;

C is a substituted or unsubstituted alkyl or heteroalkyl chain, optionally wherein any carbon of the chain is substituted with a alkoxy, hydroxyl, alkylcarbonyloxy, alkyl-S—, thiol, alkyl-C(O)S—, amine, alkylamine, amide, or alkylamide, optionally wherein the chain length is between 2 and 20 atoms;

X is NH, O, S, absent, or a bond;

L is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

(RR') is an addition product between a reactive moiety R and a complementary reactive moiety R';

L' is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

V is independently absent, a bond or a continuation of a bond, a non-cleavable moiety or a conditionally-cleavable moiety;

Y is independently absent, a bond or a continuation of a bond, or a spacer system which is comprised of 1 or more spacers;

Z is a pyrrolobenzodiazepine. Optionally, the position of V and Y can be inverted.

In one embodiment, V is a conditionally cleavable moiety, optionally a di- or tri-peptide, optionally a valine-alanine, or optionally a valine-citrulline shown below:

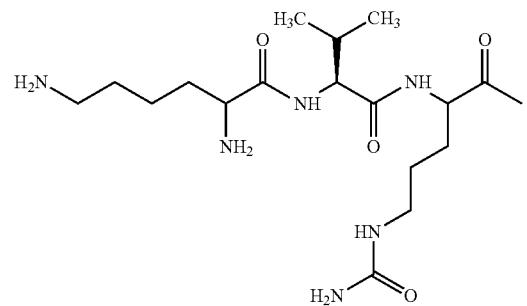 [SMILES: CC(=O)C(CCCNC(N)=O)NC(=O)[C@@H](NC(=O)C(N)CCCCN)C(C)C]

In one embodiment, Z is a pyrrolobenzodiazepine monomer. In one embodiment, Z is a pyrrolobenzodiazepine dimer comprising two pyrrolobenzodiazepine units. In one embodiment, Z is a pyrrolobenzodiazepine trimer comprising three pyrrolobenzodiazepine units. In one embodiment, Z is a pyrrolobenzodiazepinemultimer comprising more than three pyrrolobenzodiazepine units.

In one aspect of the any of the embodiments herein, a pyrrolobenzodiazepine (or a PBD moiety or unity) is a pyrrolo[2,1-c][1,4]benzodiazepine.

In one aspect of the any of the embodiments herein, a pyrrolobenzodiazepine dimer is a C8/C8'-linked pyrrolobenzodiazepine dimer.

One example of a compound of Formula IVc has the structure, where "mAb" indicates ((Q)-NH):

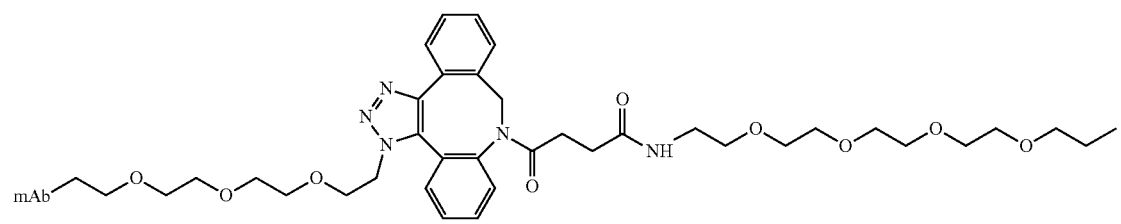

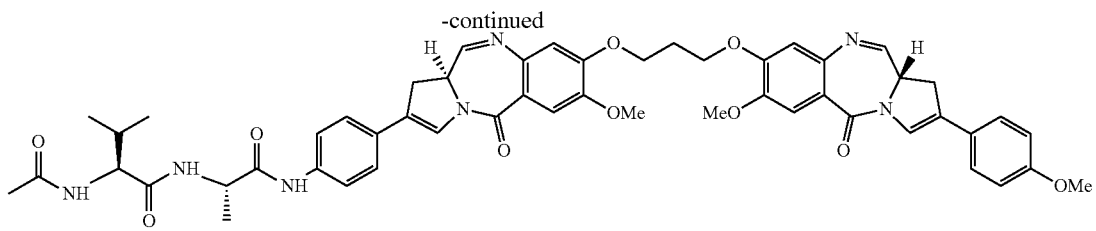

In one embodiment provided is a composition comprising a plurality of antibodies or antibody fragments comprising a functionalized acceptor glutamine residue having Formula IVc as defined above, (Q)-NH—C—X-L-RR'-L'-V—Y—Z    Formula IVc wherein at least 80%, 85%, 90%, 95% of the antibodies or antibody fragments comprise one functionalized acceptor glutamine on each heavy chain; in one embodiment, the antibody is a tetrameric antibody having two heavy chains, wherein each heavy chain comprises one functionalized acceptor glutamine (i.e. the antibody has a DAR of 2).

Optionally, said acceptor glutamine residue of the antibody or antibody fragment is flanked at the +2 position by a non-aspartic acid residue. Optionally, the residue at the +2 position is a non-aspartic acid residue. In one embodiment, the residue at the +2 position is a non-aspartic acid, non-glutamine residue. In one embodiment, the residue at the +2 position is a non-aspartic acid, non-asparagine residue. In one embodiment, the residue at the +2 position is a non-negatively charged amino acid (an amino acid other than an aspartic acid or a glutamic acid). Optionally, the acceptor glutamine is in an Fc domain of an antibody heavy chain, optionally further—within the CH2 domain. Optionally, the antibody is free of heavy chain N297-linked glycosylation. Optionally, the acceptor glutamine is at position 295 and the residue at the +2 position is the residue at position 297 (EU index numbering) of an antibody heavy chain. Optionally, the acceptor glutamine is at position 297 and the antibody comprises a Q295X mutation, wherein X is any amino acid other than glutamine.

The positions (295 or 297) are highly exposed in comparison to existing ADC which conjugate drugs at positions in which they are more protected (e.g. Adcetris™). Nevertheless, linkers tested herein were stable and had lower aggregates in aqueous conditions than Adcetris™, even when conditionally cleavable peptide moieties were included. In one aspect of any of the antibody conjugates compositions herein, a composition is substantially free of aggregates.

The linkers that yielded improved coupling provided a spacer and/or lacked polar and/or polycycles or macrocycles (or generally groups conferring structural rigidity) close to the site of BTG interaction, that is, proximal to the primary amine, and/or provided spacers that distanced the site of BTG interaction from substituents that inhibit BTG-mediated coupling. Such linkers enabled improved coupling of smaller compounds with charges and macrocycles (up to 70% conjugation) onto deglycosylated antibodies. The linker also enabled the design of reactive linkers that enabled a multi-step approach that permitted complete and stoichiometric conjugation of larger molecules.

Examples include linkers of Formulae I, II, III or IV, optionally wherein any of $C_n$, L, V or Y (and any combinations thereof) may function as the spacer. In one embodiment, a $C_n$ and/or L group comprise a linear hydrocarbon chain; in one embodiment, a $C_n$ and/or L group comprise a plurality of (CH$_2$—CH$_2$—O—) groups, optionally (CH$_2$—CH$_2$—O—)$_n$, group wherein n is an integer selected among the range of 1 to 24; in one embodiment, a $(C)_n$ and/or L group comprise an amino acid residue (e.g. a lysine residue) or a di-, tri-, tetra, or oligopeptide. In one embodiment, a V group comprises a di-, tri-, tetra, or oligopeptide, optionally wherein the peptide is cleavable in a cell. In one embodiment, $C_n$ comprises a lysine residue or derivative and V comprises a di-, tri-, tetra, or oligopeptide, optionally wherein L is present or absent. Optionally, the di-, tri-, tetra, or oligopeptide(s) comprise or consist of amino acid residues with non-negatively charged side chains (amino acids other than aspartic acid or glutamic acid). Optionally, the di-, tri-, tetra, or oligopeptide(s) comprise or consist of amino acid residues selected from: amino acid residues with positively charged side chains, amino acid residues with polar uncharged side chains, and amino acid residues with hydrophobic side chains.

In one aspect, present disclosure provides a site-specific labeling and functionalization approach that is particularly useful for functionalizing immunoglobulins with drugs, particularly peptides and polypeptides, relatively large chemical entities, negatively charged chemical entities, chemical entities comprising macrocycles or one or a plurality of cyclic groups and/or hydrophobic chemical entities, e.g. typical cytotoxic drugs such as duocarmycins, maytansanoids, alkylating agents, pyrrolobenzodiazepines, auristatins (e.g., MMAE, MMAF) and the like (e.g. analogues thereof) that are derived from natural sources, or analogues or derivatives thereof.

The disclosure relates in one embodiment to a method for conjugating a moiety of interest (Z) to an antibody, comprising:

a) producing (e.g. in a recombinant host cell) an antibody comprising an acceptor glutamine residue (e.g. within the primary sequence of the antibody) flanked at the +2 position by a non-glycosylated, non-aspartic acid, amino acid residue; and b) reacting said antibody comprising an acceptor glutamine residue with a linking reagent comprising a primary amine, in the presence of a transglutaminase enzyme capable of causing the formation of a covalent bond between the acceptor glutamine residue and the linking reagent (at the primary amine of the linking reagent), under conditions sufficient to obtain an antibody comprising an acceptor glutamine residue linked (covalently) to the linking reagent.

The present disclosure relates in one embodiment to a method for conjugating a moiety of interest (Z) to an antibody, comprising:

a) producing (e.g. in a recombinant host cell) an antibody comprising an acceptor glutamine residue (e.g. within the primary sequence of the antibody) at position 297 (EU numbering) and comprising a residue other than a glutamine at position 295 (EU numbering); and b) reacting said antibody comprising an acceptor glutamine residue with a linking reagent comprising a primary amine, in the presence of a transglutaminase enzyme capable of causing the formation of a covalent bond between the acceptor glutamine residue and the linking reagent (at the primary amine of the linking reagent), under conditions sufficient to obtain an antibody comprising an acceptor glutamine residue linked (covalently) to the linking reagent.

In one embodiment provided is a method for conjugating a hydrophobic, high molecular weight or charged organic compound to an antibody, comprising:

a) providing an antibody or antibody fragment comprising a glutamine residue at position 297 (EU numbering) of the heavy chain and lacking an acceptor glutamine at position 295 (EU numbering);

b) reacting said antibody with a linking reagent comprising a moiety of interest (Z), wherein (Z) is a hydrophobic compound, a charged organic compound and/or organic compound having a molecular weight of at least 500, 700 or 800 g/mol, in the presence of a TGase, under conditions sufficient to obtain an antibody comprising an acceptor glutamine linked to said moiety of interest (Z), via the linking reagent. Optionally, the antibody wherein said antibody comprising human heavy and light chain constant regions comprising a N297Q substitution and a Q295X substitution, wherein X is any amino acid other than glutamine. Optionally, X is serine, alanine, glycine or threonine. Optionally, X is asparagine. Optionally, an antibody or composition of Formula IVa or IVb is obtained. Optionally, organic solvent (e.g. organic solvent, polar solvent, nonpolar solvent, DMSO) is absent or is present in the reaction mixture at less than 10% (v/v), optionally further less than 5%, 4%, 3% or 2% (v/v)

In one embodiment provided is a method for conjugating a hydrophobic, high molecular weight or charged organic compound to an antibody, comprising:

a) providing an antibody or antibody fragment comprising a glutamine residue domain (e.g. in a heavy chain constant region, e.g., at position 295 and/or 297);

b) reacting said antibody with a linking reagent comprising a moiety of interest (Z), wherein (Z) is a hydrophobic compound, a charged organic compound and/or organic compound having a molecular weight of at least 500, 700 or 800 g/mol, in the presence of a TGase, under conditions sufficient to obtain an antibody comprising an acceptor glutamine linked to said moiety of interest (Z), via the linking reagent, wherein the reaction mixture is free of organic solvent or contains less than 10% (v/v), optionally further less than 5%, 4%, 3% or 2% (v/v) organic solvent. Optionally, the antibody wherein said antibody comprising human heavy and light chain constant regions comprising a N297Q substitution and a Q295X substitution, wherein X is any amino acid other than glutamine. Optionally, X is serine, alanine, glycine or threonine. Optionally, X is asparagine. Optionally, an antibody or composition of Formula IVa or IVb is obtained.

The disclosure relates in one embodiment to a method for conjugating a moiety of interest (Z) to an antibody, comprising:

a) providing an antibody or antibody fragment comprising a functionalized acceptor glutamine residue at position 297 (EU numbering) of the heavy chain and lacking an acceptor glutamine at position 295 (EU numbering);

b) reacting said antibody with 40 molar equivalents or less, optionally 20 molar equivalents or less, of a linking reagent comprising a moiety of interest (Z) or a reactive group (R), in the presence of a TGase, under conditions sufficient to obtain an antibody comprising an acceptor glutamine linked to said moiety of interest (Z) or a reactive group (R), via the linking reagent. Optionally, the antibody wherein said antibody comprises a N297Q substitution and a Q295X substitution, wherein X is any amino acid other than glutamine, optionally wherein X is a conservative substitution. Optionally, X is serine, alanine, glycine or threonine. Optionally, X is asparagine. Optionally, the linking reagent comprising a moiety of interest (Z) is a compound of Formula Ia. Optionally, the linking reagent comprising reactive group (R) is a compound of Formula Ib or Ic. Optionally, an antibody or composition of Formula IVa or IVb is obtained.

In one embodiment, the linking reagent comprises a moiety-of-interest (Z), wherein Z is a hydrophobic or charged organic compound, and/or is an organic compound having a molecular weight of at least 400, 500, 700 or 800 g/mol. In one embodiment, the linking reagent comprises a protected or unprotected reactive group (R). Optionally, in step (b), the linking reagent, optionally the linking reagent comprising a moiety of interest (Z), is provided in an amount which is less than 80, 40, 20, 10, 5, 4, or 3 molar equivalents to the antibody. In one embodiment, the antibody has two acceptor glutamines and the linking reagent comprising a moiety of interest (Z) is provided in an amount which is less than 40 equivalents to the antibody, optionally between 20 and 40 or between 20 and 75 equivalents to the antibody. In one embodiment, the linking reagent comprises a reactive group (R). Optionally, (e.g. in a multi-step method of the disclosure), the linking reagent comprising a moiety of interest (R) is provided in an amount which is between 2 and 40 or between 2 and 20 molar equivalents to the antibody, optionally wherein the antibody comprises two acceptor glutamines. Optionally, the linking reagent comprising a moiety of interest (R) is provided in an amount which is between 4 and 40 or between 4 and 20 molar equivalents to the antibody, optionally wherein the antibody comprises four acceptor glutamines.

Accordingly, provided is an antibody or antibody fragment comprising an acceptor glutamine residue flanked at the +2 position by a non-aspartic acid residue, or an antibody or antibody fragment comprising a Q295X substitution (wherein X is an amino acid other than Q) and a N297Q substitution, wherein the acceptor glutamine residue of either antibody is functionalized, optionally via a linking reagent, with a compound comprising a moiety-of-interest. Optionally, the moiety of interest is a peptide, a polypeptide, an organic compound, a moiety-of-interest that improves the pharmacokinetic properties, a therapeutic moiety or a diagnostic moiety. Optionally, the moiety-of-interest is a hydrophobic or charged organic compound, and/or is an organic compound having a molecular weight of at least 400, 500, 700 or 800 g/mol. Optionally, the residue at the +2 position is a non-aspartic acid residue. In one embodiment, the residue at the +2 position is a non-aspartic acid, non-glutamine residue. In one embodiment, the residue at the +2 position is a non-aspartic acid, non-asparagine residue. In one embodiment, the residue at the +2 position is a non-negatively charged amino acid (an amino acid other than an aspartic acid or a glutamic acid). Optionally, the acceptor glutamine is in an Fc domain of an antibody heavy chain, optionally further—within the CH2 domain. Optionally, the antibody is free of heavy chain N297-linked glycosylation. Optionally, the acceptor glutamine is at position 295 and the residue at the +2 position is the residue at position 297 (EU index numbering) of an antibody heavy chain. Optionally, the acceptor glutamine is at position 297 and the residue at the +2 position is the residue at position 299 (EU index numbering) of an antibody heavy chain. Optionally, said moiety-of-interest is covalently bound to the acceptor glutamine residue via a linker comprising a NH—(C)$_n$— group, wherein (C)$_n$ is a substituted or unsubstituted carbon chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide; and n is an integer from among the range of 2 to 200, optionally 2 to 100, optionally 2 to 50, optionally 2 to 20.

The present disclosure relates to a method for conjugating a moiety of interest (Z) to an antibody, comprising:

a) providing an antibody having (e.g. within the primary sequence of a constant region) at least one acceptor amino acid residue (e.g. a naturally occurring amino acid) that is reactive with a linking reagent (linker) in the presence of a coupling enzyme, e.g., a transamidase; and b) reacting said antibody with a linking reagent (e.g. a linker comprising a primary amine) comprising a reactive group (R), optionally a protected reactive group or optionally an unprotected reactive group, in the presence of an enzyme capable of causing the formation of a covalent bond between the acceptor amino acid residue and the linking reagent (other than at the R moiety), under conditions sufficient to obtain an antibody comprising an acceptor amino acid residue linked (covalently) to a reactive group (R) via the linking reagent. Optionally, said acceptor residue of the antibody or antibody fragment is flanked at the +2 position by a non-aspartic acid residue. Optionally, the residue at the +2 position is a non-aspartic acid residue. In one embodiment, the residue at the +2 position is a non-aspartic acid, non-glutamine residue. In one embodiment, the residue at the +2 position is a non-aspartic acid, non-asparagine residue. In one embodiment, the residue at the +2 position is a non-negatively charged amino acid (an amino acid other than an aspartic acid or a glutamic acid). Optionally, the acceptor glutamine is in an Fc domain of an antibody heavy chain, optionally further—within the CH2 domain. Optionally, the antibody is free of heavy chain N297-linked glycosylation. Optionally, the acceptor glutamine is at position 295 and the residue at the +2 position is the residue at position 297 (EU index numbering) of an antibody heavy chain.

In one aspect, present disclosure relates to a method for conjugating a moiety of interest (Z) to an antibody, comprising:

a) providing an antibody having at least one acceptor glutamine residue flanked at the +2 position by a non-aspartic acid residue; and b) reacting said antibody with a linker comprising a primary amine (a lysine-based linker) comprising a reactive group (R), in the presence of a TGase, under conditions sufficient to obtain an antibody comprising an acceptor glutamine linked (covalently) to a reactive group (R) via said linker. Optionally the antibody has human heavy and light chain constant regions, wherein the heavy chain comprises a glutamine at residue 295 and/or 297. Optionally, the residue at the +2 position is a non-aspartic acid residue. In one embodiment, the residue at the +2 position is a non-aspartic acid, non-glutamine residue. In one embodiment, the residue at the +2 position is a non-aspartic acid, non-asparagine residue. In one embodiment, the residue at the +2 position is a non-negatively charged amino acid (an amino acid other than an aspartic acid or a glutamic acid). Optionally, the acceptor glutamine is in an Fc domain of an antibody heavy chain, optionally further—within the CH2 domain. Optionally, the antibody is free of heavy chain N297-linked glycosylation. Optionally, the acceptor glutamine is at position 295 and the residue at the +2 position is the residue at position 297 (EU index numbering) of an antibody heavy chain.

In one aspect, present disclosure relates to a method for conjugating a moiety of interest (Z) to an antibody, comprising:

a) providing an antibody having human heavy and light chain constant regions, wherein the heavy chain comprises a glutamine at residue 295 and a N297X mutation, wherein X is selected from the group consisting of alanine, serine or arginine; and b) reacting said antibody with a linker comprising a primary amine (a lysine-based linker) comprising a reactive group (R), in the presence of a TGase, under conditions sufficient to obtain an antibody comprising an acceptor glutamine linked (covalently) to a reactive group (R) via said linker.

The antibody comprising an acceptor residue or acceptor glutamine residue linked to a reactive group (R) via a linker comprising a primary amine (a lysine-based linker) can thereafter be reacted with a reaction partner comprising a moiety of interest (Z) to generate an antibody comprising an acceptor residue or acceptor glutamine residue linked to a moiety of interest (Z) via the linker. Thus, in one embodiment, the method further comprises a step (c): reacting (i) an antibody of step b) comprising an acceptor glutamine linked to a reactive group (R) via a linker comprising a primary amine (a lysine-based linker), optionally immobilized on a solid support, with (ii) a compound comprising a moiety of interest (Z) and a reactive group (R') capable of reacting with reactive group R, under conditions sufficient to obtain an antibody comprising an acceptor glutamine linked to a moiety of interest (Z) via a linker comprising a primary amine (a lysine-based linker). Preferably, said compound comprising a moiety of interest (Z) and a reactive group (R') capable of reacting with reactive group R is provided at a less than 80 times, 40 times, 20 times, 10 times, 5 times or 4 molar equivalents to the antibody. In one embodiment, the antibody comprises two acceptor glutamines and the compound comprising a moiety of interest (Z) and a reactive group (R') is provided at 10 or less molar equivalents to the antibody. In one embodiment, the antibody comprises two acceptor glutamines and the compound comprising a moiety of interest (Z) and a reactive group (R') is provided at 5 or less molar equivalents to the antibody. In one embodiment, the antibody comprises four acceptor glutamines and the compound comprising a moiety of interest (Z) and a reactive group (R') is provided at 20 or less molar equivalents to the antibody. In one embodiment, the antibody comprises four acceptor glutamines and the compound comprising a moiety of interest (Z) and a reactive group (R') is provided at 10 or less molar equivalents to the antibody. In one embodiment, (b) and/or (c) are carried out in aqueous conditions. Optionally, step (c) comprises: immobilizing a sample of an antibody comprising a functionalized acceptor glutamine residue of Formula II on a solid support to provide a sample comprising immobilized antibodies, reacting the sample comprising immobilized antibodies with a compound of Formula III, optionally recovering any unreacted compound and re-introducing such recovered compound to the solid support for reaction with immobilized antibodies, and eluting the antibody conjugates to provide an antibody composition of Formula IVb comprising a Z moiety.

The disclosure provides, inter alia, the compositions having narrow distributions of numbers of conjugates per antibody that result from the methods of the disclosure for conjugating a moiety of interest (Z) to an antibody. Such compositions are advantageous for human therapy. In particular, in one aspect the disclosure provides antibody compositions (e.g. compositions of a plurality of tetrameric, full-length antibodies) having a well-defined distribution of number of conjugates per antibody, and in particular, a narrow Drug-Antibody Ratio (DAR) distribution. In particular, the method permits substantially complete conjugation of antibodies. In one aspect the disclosure provides a composition wherein a high portion of antibodies in the composition (e.g. at least 80%, 85%, 90%, 95% of the antibodies) comprise at least one moiety of interest conjugated, via a linker (e.g. a linker of Formula Ia, Ib or Ic), to one or two acceptor glutamines on each heavy chain, wherein the composition is substantially free of antibodies comprising a number of moieties of interest that is greater than 2 times, optionally 1.5 times, the mean number of conjugates per antibody (e.g., the mean DAR). The disclosure provides a composition wherein a high portion of antibodies in the composition (e.g. at least 80%, 85%, 90%, 95% of the antibodies) comprise at least one moiety of interest conjugated, via a linker, to an acceptor glutamine within a heavy chain, wherein compositions of the disclosure are preferably also free of antibodies having conjugated light chains. For example, the disclosure provides a composition of tetrameric antibodies covalently linked to a moiety of interest (Z), wherein the composition is characterized by a mean DAR of close to 2 (e.g., between 1.5 and 2.0, or between 1.7 and 2.0, between 1.8 and 2.0, or between 1.9 and 2.0) wherein the composition is substantially free of antibodies having more than 2 moieties of interest per antibody. In another example, the disclosure provides a composition of tetrameric antibodies covalently linked to a moiety of interest (Z), wherein the composition is characterized by a mean DAR of close to 4 (e.g., between 3.0 and 4.0, or between 3.4 and 4.0, or between 3.6 and 4.0) wherein the composition is substantially free of antibodies having more than 4 moieties of interest per antibody. Optionally, said acceptor glutamine residue(s) of the antibodies or antibody fragments in the composition is flanked at the +2 position by a non-aspartic acid residue. Optionally, the residue at the +2 position is a non-aspartic acid residue. In one embodiment, the residue at the +2 position is a non-aspartic acid, non-glutamine residue. In one embodiment, the residue at the +2 position is a non-aspartic acid, non-asparagine residue. In one embodiment, the residue at the +2 position is a non-negatively charged amino acid (an amino acid other than an aspartic acid or a glutamic acid). Optionally, the acceptor glutamine is in an Fc domain of an antibody heavy chain, optionally further—within the CH2 domain. Optionally, the antibody is free of heavy chain N297-linked glycosylation. Optionally, the acceptor glutamine is at position 295 and the residue at the +2 position is the residue at position 297 (EU index numbering) of an antibody heavy chain.

The methods of the disclosure also provide a way to rapidly screen a range of drugs, spacers and/or linkers given a particular starting antibody. Such comparisons are made possible because the present approach provides for homogenous antibody: drug stoichiometry, having not only advantages in production processes but also allowing the direct comparison of biological (e.g. cytotoxic) activity between an antibody functionalized with different linker and/or drug combinations.

The technique further provides improved production processes, including economic benefit in that lower quantities of substrate (e.g., drugs or other moieties to be conjugated) can be used, compared to currently available methods. Notably it will be possible to use as little as 20, 10, 5, 4, 3 or 2 equivalents of a moiety of interest: antibody, thereby providing savings for expensive reagents such as drugs.

Decreasing the quantity of substrate is also valuable in that it permits lower concentrations of drugs to be used, which for hydrophobic or otherwise poorly water-soluble drugs in turn permits lower concentrations of solvents to be used. The technique thus further provides processes for functionalization of antibodies with moieties in aqueous conditions on in conditions of low organic solvent concentration (or substantially free of organic solvent). Because certain drugs (e.g. hydrophobic drugs) that require organic solvents for solubility at higher concentration can be coupled using the present disclosure substantially in the absence of organic solvent, in any of the embodiments herein the disclosure provides antibody compositions (for example manufacturing or biological intermediates) functionalized with drugs (e.g. hydrophobic drugs) that are substantially free of organic solvent and/or are in aqueous buffer (e.g. containing 20%, 10%, 5% or less organic solvent, e.g. DMSO).

As demonstrated in FIGS. 26 and 27, presence of organic solvents in the TGase coupling reaction mixture at above 10% strongly inhibits the activity of TGase for coupling onto amino acids in the CH2 domain. In one embodiment, any of the method of the disclosure are performed in aqueous buffer (e.g. substantially free of organic solvent, for example containing 20%, 10%, 5% or less solvent, for example containing between 0.01 and 10% organic solvent, for example between 0.01 and 10% DMSO). In one embodiment, any of the method of the disclosure, a TGase is provided at a concentration of at least 2 U/ml, 4 U/ml, or at least 6 U/ml, or optionally between 2, 4, 5 or 6 U/ml and 100 U/ml, or optionally between 2, 4, 5 or 6 U/ml and 20 U/ml, or optionally between 2, 4, 5 or 6 U/ml and 12 U/ml, or optionally between 2, 4, 5 or 6 U/ml and 10 U/ml, or optionally between 2 or 4 U/ml and 6 U/ml. In one embodiment, any of the method of the disclosure, a TGase-mediated reaction is carried out at neutral pH (about pH 7.4). In one embodiment, any of the method of the disclosure, a TGase-mediated reaction is carried out at about 37° C.

The technique further provides improved production processes for achieving complete functionalization with large, charged or hydrophobic moieties of interest. In one embodiment, any of the method of the disclosure, a TGase-mediated reaction (e.g., a TGase reaction step of a method described herein) is carried out for less than 48 hours, optionally less than 24 hours, optionally between 2 and 18 hours, between 2 and 24 hours, between 2 and 18 hours or between 4 and 18 hours, optionally at about 37° C.

Certain aspects of the disclosure are directed to a linking reagent that can be attached, by the action of a TGase, to a polypeptide at a glutamine residue (Q) within the sequence of the antibody (Ab). The linking reagent comprises a lysine derivative (Lys) or a functional equivalent thereof, that is connected to at least one reactive group (R) or a moiety-of-interest (Z). The lysine derivative (Lys) or a functional equivalent can comprise generally any primary amine chain which is a substrate for TGase, e.g. comprising an alkylamine, oxoamine. In one embodiment, a plurality of reactive groups, preferably non-complementary reactive groups, can be attached to the linking reagent. The reactive group is preferably a functionality that is insensitive to water but selectively undergoes a very high conversion addition reaction with a complementary reagent. The functional equivalent of a lysine derivative may comprise a 2 to 20 carbon chain, or a functional equivalent thereof, with an $H_2N$ or H₂NCH₂ (aminomethylene)) group, or a protected H₂N or H₂NCH₂ group that can be derived from the H₂N or aminomethylene positioned at one or more ends of the carbon chain. The functional equivalent of the carbon chain may comprise a chain of 3 to 20 atoms where one or more of the atoms other than the primary amine can be other than carbon, for example oxygen, sulfur, nitrogen, or other atoms, e.g. with an H₂NOCH₂ group, or a protected H₂NOCH₂ group positioned at one or more ends of the carbon chain. The oxygen, sulfur, or nitrogen atom can be of an ether, ester, thioether, thioester, amino, alkylamino, amido or alkylamido functionality within the carbon chain.

One exemplary functional equivalent of the carbon chain is an oligo (ethylene oxide) chain. The functionality within the carbon chain can be included to couple the reactive group to the H₂NH₂NOCH₂ or H₂NCH₂ group or protected H₂N, H₂NOCH₂ or H₂NCH₂ group. The carbon chain, or its functional equivalent, can be substituted or unsubstituted. The substituents can be alkyl groups, aryl groups, alkyl aryl groups, carboxylic acid groups, amide groups, hydroxy groups, or any other groups that do not compete with the amino group for, or inhibit, conjugation with a glutamine residue of the protein. Typically, when a substituent is present, its presence is in a convenient starting material, such as the carboxylic acid group of lysine, from which the lysine derivative results. The amine at the end of a carbon chain or functional equivalent is necessarily included in the linking reagent.

Examples of starting materials for the functional equivalent of lysine can be an am diaminoalkane, for example, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, or 1,12-diaminododecane. Other starting materials for the functional equivalent of a lysine derivative can be α,ω-diamino oligo (ethylene oxide), for example, H₂N(CH₂CH₂O)ₓCH₂CH₂NH₂ where x is an integer selected among the range of 1 to 6. The α,ω-diamino oligo (ethylene oxide) can be a single oligomer or it can be a mixture of oligomers where x defines an average size. An exemplary protected H₂NCH₂ is the tert-butylcarbamate protected amine of tert-butyl N-(5-aminopentyl)carbamate (N-Boc-cadaverin).

Linking reagents used for direct (one-step) linking of a moiety of interest (Z) to an antibody will advantageously comprise an element that functions as a spacer to distance a large, charged or hydrophobic organic moiety-of-interest (Z) from the acceptor glutamine. The spacer may be embodied in the lysine derivative or functional equivalent thereof, or in a further element of the linker (e.g. an L, V and/or Y group). In one embodiment, the element that functions as a spacer is a lysine derivative (Lys) or a functional equivalent thereof having a structure NH—(C)ₙ—, wherein (C)ₙ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide, and where n is an integer greater than 10, optionally an integer from among the range of 10 to 20. In one embodiment, the linking reagent comprises an L, V and/or Y group that functions as a spacer and is positioned between the NH—(C)ₙ— group and the moiety-of-interest (Z), wherein L is a carbon-comprising framework of 1 to 200 atoms substituted at one or more atoms, optionally wherein the carbon comprising framework is a linear hydrocarbon, a symmetrically or asymmetrically branched hydrocarbon, monosaccharide, a glycan, disaccharide, linear or branched oligosaccharide (asymmetrically branched or symmetrically branched), other natural linear or branched oligomers (asymmetrically branched or symmetrically branched), amino acid residue, di-, tri- or oligopeptide, or any dimer, trimer, or higher oligomer (linear, asymmetrically branched or symmetrically branched) for example resulting from any chain-growth or step-growth polymerization process; V is a non-cleavable moiety or a conditionally-cleavable moiety, optionally following prior conditional transformation, which can be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety"; and Y is a spacer system (e.g., a self-eliminating spacer system or a non-self-elimination spacer system) which is comprised of 1 or more spacers.

In one embodiment provided is an antibody or antibody fragment comprising a functionalized acceptor glutamine residue, wherein said acceptor glutamine residue is flanked at the +2 position by a non-aspartic acid residue, the functionalized acceptor glutamine residue having Formula IVa,

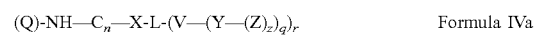

(Q)-NH—Cₙ—X-L-(V—(Y—(Z)_z)_q)_r    Formula IVa or a pharmaceutically acceptable salt or solvate thereof, wherein:

Q is a glutamine residue present in an antibody or antibody fragment;

Cₙ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent, or a bond;

L is independently absent, a bond or a continuation of a bond, or a carbon comprising framework of 5 to 200 atoms substituted at one or more atoms, optionally, wherein the carbon comprising framework comprises a linear framework of 5 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process; r is an integer selected from among 1, 2, 3 or 4;

q is an integer selected from among 1, 2, 3 or 4;

z is an integer selected from among 1, 2, 3 or 4; and

V is independently absent, a non-cleavable moiety or a conditionally-cleavable moiety;

Y is independently absent, a bond or a continuation of a bond, or a spacer system which is comprised of 1 or more spacers; and Z is a moiety that improves the pharmacokinetic properties, a therapeutic moiety or a diagnostic moiety.

In one embodiment said acceptor glutamine residue is flanked at the +2 position by a non-aspartic acid residue other than glutamine, optionally wherein said acceptor glutamine residue is flanked at the +2 position by an alanine, a histidine or a serine. In one embodiment said acceptor glutamine residue is flanked at position +2 by an amino acid residue with a positively charged side chain. In one embodiment said acceptor glutamine residue is flanked at position +2 by an arginine residue. In one embodiment said acceptor glutamine residue is flanked by an amino acid residue with a negatively charged side chain at any one or more of the −1 to −4 positions. In one embodiment said acceptor glutamine residue is flanked by a glutamic acid residue at the −1 position. In one embodiment Z is an organic compound that is charged, hydrophobic and/or has a molecular weight of at least 400 g/mol.

In one embodiment provided is an antibody or antibody fragment comprising a functionalized acceptor glutamine residue at position 297 (EU numbering) of the heavy chain and lacking an acceptor glutamine at position 295 (EU numbering), the functionalized acceptor glutamine residue having Formula IVa,

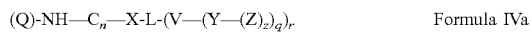

(Q)-NH—C$_n$—X-L-(V—(Y—(Z)$_z$)$_q$)$_r$       Formula IVa or a pharmaceutically acceptable salt or solvate thereof, wherein:

Q is a glutamine residue present in an antibody or antibody fragment;

(C)$_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent, or a bond;

L is independently absent, a bond or a continuation of a bond, or a carbon comprising framework of 5 to 200 atoms substituted at one or more atoms, optionally, wherein the carbon comprising framework comprises a linear framework of 5 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4;

z is an integer selected from among 1, 2, 3 or 4; and

V is independently absent, a non-cleavable moiety or a conditionally-cleavable moiety;

Y is independently absent, a bond or a continuation of a bond, or a spacer system which is comprised of 1 or more spacers; and Z is a moiety that improves the pharmacokinetic properties, a therapeutic moiety or a diagnostic moiety, wherein Z is an organic compound that is electrically negatively charged, hydrophobic and/or that has a molecular weight of at least 400 g/mol.

In one embodiment, the antibody has an amino acid other than asparagine at said position 295. In one embodiment, the antibody has a serine, alanine, glycine or threonine residue at said position 295.

In one embodiment provided is an antibody or antibody fragment comprising a functionalized acceptor glutamine residue, the functionalized acceptor glutamine residue having Formula IVa,

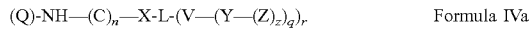

(Q)-NH—(C)$_n$—X-L-(V—(Y—(Z)$_z$)$_q$)$_r$       Formula IVa or a pharmaceutically acceptable salt or solvate thereof, wherein:

Q is a glutamine residue present in the antibody or antibody fragment;

(C)$_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent, or a bond;

L comprises a linear framework of 5 to 30 carbon atoms optionally substituted at one or more atoms;

wherein n, X and L are selected such that —(C)$_n$—X-L collectively comprise a linear framework of 10 to 30 atoms, optionally 10 to 30 carbon atoms optionally substituted at one or more atoms;

r is an integer selected from among 1, 2, 3 or 4;

q is an integer selected from among 1, 2, 3 or 4;

z is an integer selected from among 1, 2, 3 or 4; and

V is a conditionally-cleavable moiety;

Y is independently absent, a bond or a continuation of a bond, or a spacer system which is comprised of 1 or more spacers; and Z is a moiety that improves pharmacokinetic properties, a therapeutic moiety or a diagnostic moiety, wherein Z is an organic compound that is electrically negatively charged, hydrophobic and/or that has a molecular weight of at least 400 g/mol.

In one embodiment provided is an antibody or antibody fragment comprising a functionalized acceptor glutamine residue, the functionalized acceptor glutamine residue having Formula IVa,

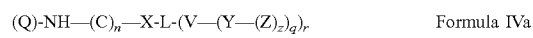

(Q)-NH—(C)$_n$—X-L-(V—(Y—(Z)$_z$)$_q$)$_r$       Formula IVa or a pharmaceutically acceptable salt or solvate thereof, wherein:

Q is a glutamine residue present in a heavy chain constant region of the antibody or antibody fragment;

(C)$_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent, or a bond;

L comprises a linear framework of 5 to 30 carbon atoms optionally substituted at one or more atoms;

r is an integer selected from among 1, 2, 3 or 4;

q is an integer selected from among 1, 2, 3 or 4;

z is an integer selected from among 1, 2, 3 or 4; and

V is independently absent, a bond or a continuation of a bond, a non-cleavable moiety or a conditionally-cleavable moiety;

Y is independently absent, a bond or a continuation of a bond, or a spacer system which is comprised of 1 or more spacers; and Z is a moiety that improves pharmacokinetic properties, a therapeutic moiety or a diagnostic moiety, wherein Z is an organic compound that is electrically negatively charged, hydrophobic and/or that has a molecular weight of at least 400 g/mol.

In one aspect of any of the embodiments herein, n, X and L can be selected such that —(C)$_n$—X-L collectively comprise a linear framework of 10 to 30 atoms, optionally 10 to 30 carbon atoms optionally substituted at one or more atoms.

In one aspect of any of the embodiments herein, $(C)_n$ comprises a $C_{2-5}$ alkyl, optionally a linear $C_{2-5}$ alkyl. In one aspect of any of the embodiments herein, $(C)_n$ comprises a $C_{5-10}$ alkyl, optionally a linear $C_{5-10}$ alkyl. In one aspect of any of the embodiments herein, $(C)_n$ comprises a $C_{11-20}$ alkyl, optionally a linear $C_{11-20}$ alkyl. In one aspect of any of the embodiments herein, $(C)_n$ comprises a $(CH_2-CH_2-O-)_n$ group, wherein n is an integer selected among the range of 2 to 10. In one aspect of any of the embodiments herein, L comprises a $(CH_2-CH_2-O-)_x$ group, wherein x is an integer selected among the range of 2 to 10. In one aspect of any of the embodiments herein, L comprises a $C_{2-5}$ alkyl. In one aspect of any of the embodiments herein, L comprises a $C_{5-10}$ alkyl.

In one aspect of any of the embodiments herein, the groups —(C)—X-L- collectively comprise a structure $(CH_2-CH_2-O-)_x$, wherein x is an integer from among the range of 4 to 10.

In one aspect of any of the embodiments herein, the functionalized acceptor glutamine residue has a structure:

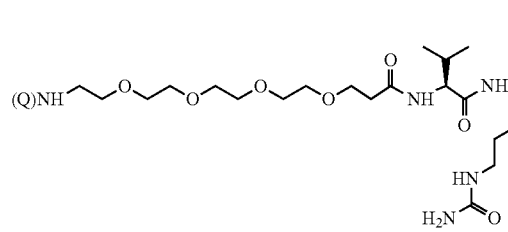

In one embodiment provided is an antibody or antibody fragment comprising a functionalized acceptor glutamine residue, wherein said acceptor glutamine residue is flanked at the +2 position by a non-aspartic acid residue, the functionalized acceptor glutamine residue having Formula II:

$$(Q)\text{-NH}-(C)_n-\text{X-L-}(V-(Y-(R)_z)_q)_r \qquad \text{Formula II}$$

or a pharmaceutically acceptable salt or solvate thereof, wherein:

Q is a glutamine residue present in an antibody or antibody fragment;

$(C)_n$ is a substituted or unsubstituted alkyl or heteroalkyl chain, optionally wherein any carbon of the chain is optionally substituted with alkoxy, hydroxyl, alkylcarbonyloxy, alkyl-S—, thiol, alkyl-C(O)S—, amine, alkylamine, amide, or alkylamide;

n is an integer from among the range of 2 to 20;

X is NH, O, S, absent or a bond;

L is independently absent, a bond or a continuation of a bond, or a carbon comprising framework of 1 to 200 atoms substituted at one or more atoms, optionally wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;
q is an integer selected from among 1, 2, 3 or 4;
z is an integer selected from among 1, 2, 3 or 4; and
V is independently absent, a bond or a continuation of a bond, a non-cleavable moiety or a conditionally-cleavable moiety;

Y is independently absent, a bond or a continuation of a bond, or a spacer system which is comprised of 1 or more spacers; and R is a reactive moiety.

In one embodiment provided is an antibody or antibody fragment comprising a functionalized acceptor glutamine residue, wherein said acceptor glutamine residue is flanked at the +2 position by a non-aspartic acid residue, the functionalized acceptor glutamine residue having Formula IVb,

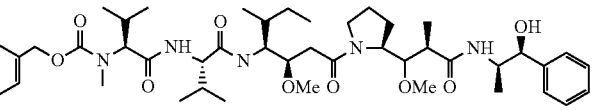

or a pharmaceutically acceptable salt or solvate thereof, wherein:

Q is a glutamine residue present in an antibody or antibody fragment;

$(C)_n$ is a substituted or unsubstituted alkyl or heteroalkyl chain, optionally wherein any carbon of the chain is substituted with a alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent, or a bond;

L is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;
q is an integer selected from among 1, 2, 3 or 4;
z is an integer selected from among 1, 2, 3 or 4;
V is independently absent, a bond or a continuation of a bond, a non-cleavable moiety or a conditionally-cleavable moiety;

Y is independently absent, a bond or a continuation of a bond, or a spacer system which is comprised of 1 or more spacers;

M is independently: R or (RR')-L'-(V'—(Y'—(Z)$_{z'}$)$_{q'}$)$_{r'}$, wherein

R is a reactive moiety;

(RR') is an addition product between R and a complementary reactive moiety R';

L' is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

V' is independently absent, a bond or a continuation of a bond, a non-cleavable moiety or a conditionally-cleavable moiety;

Y' is independently absent, a bond or a continuation of a bond, or a spacer system which is comprised of 1 or more spacers;

Z is independently a reactive group, a moiety that improves the pharmacokinetic properties, a therapeutic or diagnostic moiety, and each Z is directly coupled to either Y or V when Y is absent, or L when both Y and V are absent; and z', q' and r' are each independently an integer selected from among 1, 2, 3 or 4.

In one aspect of any of the embodiments herein, said acceptor glutamine residue is flanked at position +2 by an amino acid residue with a positively charged side chain. Optionally, said acceptor glutamine residue is flanked at position +2 by an arginine residue.

In one embodiment provided is an antibody or antibody fragment comprising an acceptor glutamine residue flanked at the +2 position by an amino acid residue with a positively charged side chain, wherein the acceptor glutamine residue is functionalized with a linker comprising a primary amine and a comprising a moiety-of-interest, optionally wherein the moiety of interest is a reactive group (R).

In one aspect of any of the embodiments herein, said acceptor glutamine residue is flanked by an amino acid residue with a negatively charged side chain at any one or more of the −1 to −4 positions, optionally wherein the amino acid residue is a glutamic acid or aspartic acid.

In one embodiment, an acceptor glutamine residue is flanked at position +2 by an arginine residue.

In one embodiment, the amino acid residue at the +2 position is an acceptor glutamine.

In one embodiment, the amino acid residue at the +2 position is not a glutamine.

In one embodiment, said functionalized acceptor glutamine residue is in an antibody heavy chain, optionally within the CH2 domain.

In one embodiment, the functionalized acceptor glutamine residue is in an antibody heavy chain at position 295 (EU numbering). In one embodiment, the antibody comprises an asparagine at residue 297 that substantially lacks N-linked glycosylation. In one embodiment, the antibody is produced in a host cell that produces antibodies lacking N-linked glycosylation at amino acid residue N297.

In one embodiment, the functionalized acceptor glutamine residue is in an antibody heavy chain at position 297 (EU numbering).

In one embodiment, the antibody comprises a T299X substitution, wherein X is any amino acid other than threonine and results in lack of N-linked glycosylation at amino acid residue N297.

In one embodiment provided is an antibody or antibody fragment comprising a functionalized acceptor glutamine residue at position 297 (EU numbering) of the heavy chain and lacking an acceptor glutamine at position 295 (EU numbering), the functionalized acceptor glutamine residue having Formula II:

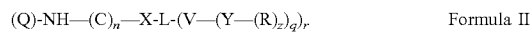

(Q)-NH—(C)$_n$—X-L-(V—(Y—(R)$_z$)$_q$)$_r$      Formula II or a pharmaceutically acceptable salt or solvate thereof, wherein:

Q is a glutamine residue present in an antibody or antibody fragment;

(C)$_n$ is a substituted or unsubstituted alkyl or heteroalkyl chain, optionally wherein any carbon of the chain is optionally substituted with alkoxy, hydroxyl, alkylcarbonyloxy, alkyl-S—, thiol, alkyl-C(O)S—, amine, alkylamine, amide, or alkylamide;

n is an integer from among the range of 2 to 20;

X is NH, O, S, absent or a bond;

L is independently absent, a bond or a continuation of a bond, or a carbon comprising framework of 1 to 200 atoms substituted at one or more atoms, optionally wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4;

z is an integer selected from among 1, 2, 3 or 4; and

V is independently absent, a bond or a continuation of a bond, a non-cleavable moiety or a conditionally-cleavable moiety;

Y is independently absent, a bond or a continuation of a bond, or a spacer system which is comprised of 1 or more spacers; and R is a reactive moiety.

In one embodiment provided is an antibody or antibody fragment comprising a functionalized acceptor glutamine residue at position 297 (EU numbering) of the heavy chain and lacking an acceptor glutamine at position 295 (EU numbering), the functionalized acceptor glutamine residue having Formula IVb,

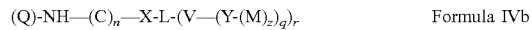

(Q)-NH—(C)$_n$—X-L-(V—(Y-(M)$_z$)$_q$)$_r$      Formula IVb or a pharmaceutically acceptable salt or solvate thereof, wherein:

Q is a glutamine residue present in an antibody or antibody fragment;

(C)$_n$ is a substituted or unsubstituted alkyl or heteroalkyl chain, optionally wherein any carbon of the chain is substituted with a alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent, or a bond;

L is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4;

z is an integer selected from among 1, 2, 3 or 4;

V is independently absent, a bond or a continuation of a bond, a non-cleavable moiety or a conditionally-cleavable moiety;

Y is independently absent, a bond or a continuation of a bond, or a spacer system which is comprised of 1 or more spacers;

M is independently: R or (RR')-L'-(V'—(Y'—(Z)$_{z'}$)$_{q'}$)$_{r'}$, wherein

R is a reactive moiety;

(RR') is an addition product between R and a complementary reactive moiety R';

L' is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

V' is independently absent, a bond or a continuation of a bond, a non-cleavable moiety or a conditionally-cleavable moiety;

Y' is independently absent, a bond or a continuation of a bond, or a spacer system which is comprised of 1 or more spacers;

Z is independently a reactive group, a moiety that improves the pharmacokinetic properties, a therapeutic or diagnostic moiety, and each Z is directly coupled to either Y or V when Y is absent, or L when both Y and V are absent; and z', q' and r' are each independently an integer selected from among 1, 2, 3 or 4.

In one aspect of the embodiments described herein, an antibody comprises a N297Q substitution and a Q295X substitution, wherein X is any amino acid other than glutamine, optionally wherein X is a conservative substitution. Optionally, X is serine, alanine, glycine or threonine. Optionally, X is asparagine.

In one aspect of the embodiments described herein, an R or R' group is a moiety comprising a bioorthogonal-reaction compatible reactive group, for example an unprotected or protected thiol, epoxide, maleimide, haloacetamide, o-phoshenearomatic ester, azide, fulminate, sulfonate ester, alkyne, cyanide, amino-thiol, carbonyl, aldehyde, generally any group capable of oxime and hydrazine formation, 1,2,4,5-tetrazine, norbornene, other stained or otherwise electronically activated alkene, a substituted or unsubstituted cycloalkyne, generally any reactive groups which form via bioorthogonal cycloaddition reaction a 1,3- or 1,5-disubstituted triazole, any diene or strained alkene dienophile that can react via inverse electron demand Diels-Alder reaction, a protected or unprotected amine, a carboxylic acid, an aldehyde, an oxyamine.

In one aspect of the embodiments described herein, $(C)_n$, L and/or R do not comprise a cyclic group.

In one aspect of the embodiments described herein, n is an integer from among the range of 2 to 10, L is absent, and wherein R does not comprise a cyclic group.

In one aspect of the embodiments described herein, R is an azide. Optionally, R' comprises a cyclic group.

In one aspect of the embodiments described herein, n is an integer from among the range of 10 to 20, and R comprises a cyclic group. In one aspect of the embodiments described herein, L is present and R comprises a cyclic group. Optionally, R' is an azide.

In one embodiment, said cyclic group is a polycyclic group. In one embodiment, said cyclic group is a cyclooctyne, optionally a substituted or unsubstituted dibenzylcycolooctyne.

In one aspect of the embodiments described herein, n is an integer from among the range of 10 to 20. In one aspect of the embodiments described herein, $(C)_n$ is a heteroalkyl chain that comprises a $(CH_2—CH_2—O—)_x$ group, wherein x is an integer selected from among the range of 1 to 6. In one aspect of the embodiments described herein, n is an integer from among the range of 2 to 6 and at least one of L, V or Y are present. In one aspect of the embodiments described herein, $NH—(C)_n$ comprises $NH—O—(CH_2)_m—$. In one aspect of the embodiments described herein, $(C)_n$ is a substituted or unsubstituted alkyl or heteroalkyl chain, wherein the carbon adjacent to the nitrogen is unsubstituted. In one aspect of the embodiments described herein, $(C)_n$ is a substituted or unsubstituted alkyl or heteroalkyl chain, wherein the carbon adjacent to the nitrogen is unsubstituted and wherein any carbon of the chain other than the carbon adjacent to the nitrogen is optionally substituted with a O, N or S atom of an ether, ester, thioether, thioester, amine, alkylamine, amide, or alkylamide; wherein n, the length of the alkyl or heteroalkyl chain, is 2 to 20 atoms.

In one aspect of the embodiments described herein, L comprises a linear carbon comprising framework of 5 to 30 carbon atoms optionally substituted at one or more atoms. Optionally, L comprises a $(CH_2—CH_2—O—)_x$ group, wherein x is an integer selected from among the range of 2 to 10.

In one aspect of the embodiments described herein, the groups $—(C)_n—X-L-$ collectively comprises a structure $(CH_2—CH_2—O—)_x$, wherein x is an integer from among the range of 4 to 12.

In one aspect of the embodiments described herein, L is a carbon framework of:

a) 2-15 linear carbon atoms optionally substituted at one or more atoms;

b) 3-15 linear carbon atoms optionally substituted at one or more atoms;

c) 5-15 linear carbon atoms optionally substituted at one or more atoms;

d) 5-20 linear carbon atoms optionally substituted at one or more atoms;

e) 3-30 linear carbon atoms optionally substituted at one or more atoms;

f) 5-30 linear carbon atoms optionally substituted at one or more atoms; or g) 3, 4, 5 or 6 linear carbon atoms optionally substituted at one or more atoms. Optionally, said carbon-comprising framework of linear carbon atoms is unsubstituted.

In one aspect of the embodiments described herein, V comprises a di-, tri-, tetra-, or oligopeptide. Optionally, V is a conditionally-cleavable moiety following prior conditional transformation, which can be cleaved or transformed by a chemical, photochemical, physical, biological, or enzymatic process.

In one aspect of the embodiments described herein, said acceptor glutamine residue is within a heavy chain constant region or within a TGase recognition tag comprising an amino acid sequence -$J^1$-$J^2$-$J^3$-$J^4$-Q-$X^1$—$X^2$—, wherein Q is an acceptor glutamine, $J^1$, $J^2$, $J^3$, and $J^4$ are any amino acid so long as one or more (or all of) of $J^1$, $J^2$, $J^3$, and $J^4$ is an amino acid residue having a negative electrical charge, $X^1$ is any amino acid, and $X^2$ is an amino acid other than D (aspartic acid), optionally wherein $X^2$ is not a glutamine. Optionally, $X^2$ is a non-negatively charged amino acid. Optionally, $X^2$ is a positively charged side chain. Optionally, $X^2$ is a serine, alanine, glycine or threonine.

In one aspect of the embodiments described herein, the antibody or antibody fragment of any of the above claims, wherein the antibody binds to a solid tumor cancer antigen. In one aspect of the embodiments described herein, the antibody binds to a hematological tumor cancer antigen. In one aspect of the embodiments described herein, the antibody or antibody fragment of any of the above claims, wherein the antibody is an internalizing antibody and the functionalized acceptor glutamine residue having Formula IVa or IVb comprises a conditionally-cleavable moiety (V). In one aspect of the embodiments described herein, the antibody or antibody fragment of any of the above claims, wherein the antibody is a non-internalizing antibody and wherein element V of Formula IVa or IVb is independently absent, a bond or a continuation of a bond or a non-cleavable moiety.

In one aspect provided is a composition comprising a plurality of antibodies of any of the above claims, wherein the plurality of antibodies share the same heavy and/or light chain amino acid sequence, and wherein at least 90% of the antibodies in said composition have (m) functionalized acceptor glutamine residues (Q) per antibody, wherein m is an integer selected from 1, 2, 3, or 4.

In one aspect provided is a composition comprising a plurality of antibodies comprising one acceptor glutamine on each heavy chain, wherein at least 80% of the antibodies in the composition comprise on each heavy chain one functionalized acceptor glutamine residue (Q) having the structure of Formula II or IV. In one aspect provided is a composition comprising a plurality of antibodies comprising two acceptor glutamines on each heavy chain, wherein at least 80% of the antibodies in the composition comprise on each heavy chain two functionalized acceptor glutamine residues (Q) having the structure of Formula II or IV.

Optionally, less than 2%, optionally less than 1% of the antibodies are present as soluble aggregates, as assessed using an aggregation assay. Optionally, less than 0.5% of the antibodies are present as soluble aggregates, as assessed using a dye-based aggregation assay. Optionally, less than 1% of the antibodies are present as soluble aggregates, as assessed using a SE-HPLC based aggregation assay. Optionally, the composition is free of antibody fragments, optionally wherein the composition comprises less than 1% antibody fragments. Optionally, the composition is in aqueous solution.

In one aspect provided is a linking reagent, a pharmaceutically acceptable salt or solvate thereof, or a protein-conjugated linking reagent having the general Formula Ib:

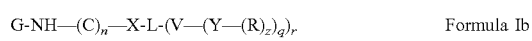
$$G-NH—(C)_n—X-L-(V—(Y—(R)_z)_q)_r \quad \text{Formula Ib}$$

or a pharmaceutically acceptable salt or solvate thereof, wherein:

G is a H, amine protecting group, or upon conjugation, an antibody or antibody fragment attached via an amide bond;

$(C)_n$ is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, absent or a bond;

L is independently absent, a bond or a continuation of a bond, or a carbon comprising framework of 1 to 200 atoms substituted at one or more atoms, optionally, wherein the carbon comprising framework comprises a linear framework of 5 to 30 atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4;

z is an integer selected from among 1, 2, 3 or 4;

V is independently absent, a non-cleavable moiety or a conditionally-cleavable moiety, optionally following prior conditional transformation, which can be cleaved or transformed by a chemical, photochemical, physical, biological, or enzymatic process;

Y is independently absent, a bond or a continuation of a bond, or a spacer system which is comprised of 1 or more spacers; and R is a reactive moiety.

In one embodiment provided is a compound having the structure of Formula III, below,

$$R'\text{-}L\text{-}(V—(Y\text{-}(M)_z)_q)_r \quad \text{Formula III}$$

or a pharmaceutically acceptable salt or solvate thereof, wherein:

R' is a reactive group;

L is independently absent, or a carbon comprising framework of 1 to 200 atoms substituted at one or more atoms, optionally, wherein the carbon comprising framework comprises a linear framework of 5 to 30 atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

V is independently absent, a bond or a continuation of a bond, a non-cleavable moiety or a conditionally-cleavable moiety;

Y is independently absent, a bond or a continuation of a bond, or a spacer system which is comprised of 1 or more spacers;

M is independently: R or (RR')-L'-(V'—(Y'—(Z)$_{z'}$)$_{q'}$)$_{q''}$, wherein

R is a reactive moiety;

(RR') is an addition product between an R and a complementary reactive group R';

L' is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process; V' is independently absent, a bond or a continuation of a bond, a non-cleavable moiety or a conditionally-cleavable moiety;

Y' is independently absent, a bond or a continuation of a bond, or a spacer system which is comprised of 1 or more spacers;

Z is independently a reactive group, a moiety that improves the pharmacokinetic properties, a therapeutic or diagnostic moiety, and each Z is directly coupled to either Y or V when Y is absent, or L when both Y and V are absent; and z', q' and r' are each independently an integer selected from among 1, 2, 3 or 4.

In one embodiment provided is a method for evaluating an antibody conjugate, the method comprising:

a) providing a first antibody composition of Formula II comprising a first X, L, V, Y, L', V', Y', (RR') and/or Z moiety, wherein at least 70%, 80% or 90% of the antibodies in said first antibody composition have (m) functionalized acceptor glutamine residues (Q) per antibody, wherein m is an integer selected from 1, 2, 3, or 4;

b) providing a second antibody composition of Formula II comprising a second X, L, V, Y, L', V', Y', (RR') and/or Z moiety, wherein said second antibody comprises at least one X, L, V, Y, L', V', Y', (RR') and/or Z moiety that differs from a respective X, L, V, Y, L', V', Y', (RR') and/or Z moiety of said first antibody, wherein at least 70%, 80% or 90% of the antibodies in said second antibody composition have (n) functionalized acceptor glutamine residues (Q) per antibody, wherein n is an integer selected from 1, 2, 3, or 4; and c) evaluating the first and second antibody compositions. Optionally, n and m are equal. Optionally, m and n are 2, or wherein m and n are 4.

In one embodiment provided is a kit comprising at least two antibody compositions of Formula II, wherein the kit comprises a first antibody composition and a second antibody composition in separate containers, wherein the second antibody composition comprises antibodies having at least one X, L, V, Y, L', V', Y', (RR') and/or Z moiety that differs from a respective X, L, V, Y, L', V', Y', (RR') and/or Z moiety of said first antibody. Optionally, the antibodies of the first and second antibody compositions share heavy and/or light chain amino acid sequences.

In one aspect of the embodiments described herein, the antibody is a full length antibody.

In one aspect of the embodiments described herein, the antibody is an antibody fragment.

In one embodiment, provided is a pharmaceutical composition comprising an antibody or composition of any of the above claims, and a pharmaceutically acceptable carrier. Optionally, the composition comprises trehalose and Polysorbate 80

In one embodiment, provided is a method of treating a disease comprising administering to a mammal a composition described herein (e.g. pharmaceutical composition).

In one embodiment, provided is a method of detecting an analyte or diagnosing a disease, comprising obtaining a biological sample (e.g. from an individual) and bringing the sample into contact with an antibody or composition as disclosed herein comprising a diagnostic moiety (Z), and optionally further detecting the presence of said diagnostic moiety in the biological sample.

In one embodiment of the therapeutic or diagnostic methods, the disease is a solid tumor. In one embodiment of the therapeutic or diagnostic methods, the disease is a hematological malignancy.

In one aspect of any of the embodiments herein, Z is a hydrophobic compound. In one aspect of any of the embodiments herein, Z is an organic compound comprising a molecular weight of at least 500 g/mol. In one aspect of any of the embodiments herein, Z is an organic compound comprising a molecular weight of at least 700 g/mol. In one aspect of any of the embodiments herein, Z is an organic compound comprising one or more cyclic groups, optionally a macrocycle, polycyclic or tricyclic group. In one aspect of any of the embodiments herein, Z is a negatively charged compound. In one aspect of any of the embodiments herein, Z is a cytotoxic anti-cancer agent. In one aspect of any of the embodiments herein, Z is selected from the group consisting of taxanes, anthracyclines, camptothecins, epothilones, mytomycins, combretastatins, vinca alkaloids, nitrogen mustards, maytansinoids, calicheamycins, duocarmycins, tubulysins, amatoxins, dolastatins and auristatins, enediynes, pyrrolobenzodiazepines, and ethylenimines.

In one embodiment provided is a method for preparing an antibody or antibody fragment comprising a moiety of interest (Z) bound thereto, comprising:

(a) immobilizing an antibody or antibody fragment comprising a functionalized acceptor glutamine comprising a reactive moiety R of Formula II on a solid support to provide an immobilized antibody, optionally comprising a step of applying an antibody-containing sample to a solid support;

(b) reacting the immobilized antibody or antibody fragment of step (a) with a compound comprising a moiety-of-interest Z and a reaction partner R' (e.g. a compound of Formula III) and, optionally comprising a step of applying a compound comprising a moiety Z and a reactive group R' to a solid support, to generate an antibody-moiety-of-interest conjugate. Optionally the method further comprises a washing step to remove any unreacted materials. Optionally the method further comprises a step of recovering unreacted compound comprising a moiety Z and a reactive group R' and re-applying said compound to the solid support to provide for higher completion of the reaction between antibody comprising reactive group (R) and compound comprising reactive group (R'). Optionally the method further comprises a step of eluting immobilized antibody conjugates from the solid support to provide antibody conjugate compositions. Optionally the antibody-moiety-of-interest conjugate obtained is an antibody or antibody fragment of Formula IVb.

Reference to "Formulas I", "Formula II", "Formula III" or "Formula IV", unless the context clearly indicates otherwise, designates all compounds derived from such Formulas I to IV, including e.g., Formula I includes reference to Ia, Ib and/or Ic, Formula IV includes IVa and IVb The disclosure of U.S. application Ser. No. 13/725,385 filed on Dec. 21, 2012, and entitled "Enzymatic Conjugation of Polypeptides" is hereby incorporated by reference in its entirety.

Any of the methods disclosed herein can further be characterized as comprising any step described in the application, including notably in the "Detailed Description of the Invention"). The disclosure further relates to an antibody obtainable by any of present methods. The disclosure further relates to pharmaceutical or diagnostic formulations of the antibodies of the present disclosure. The disclosure further relates to methods of using an antibody of Formula IV in a method of treatment or diagnosis.

These and additional advantageous aspects and features of the invention may be further described elsewhere herein.

DETAILED DESCRIPTION OF THE INVENTION

Introduction

Figure 1:
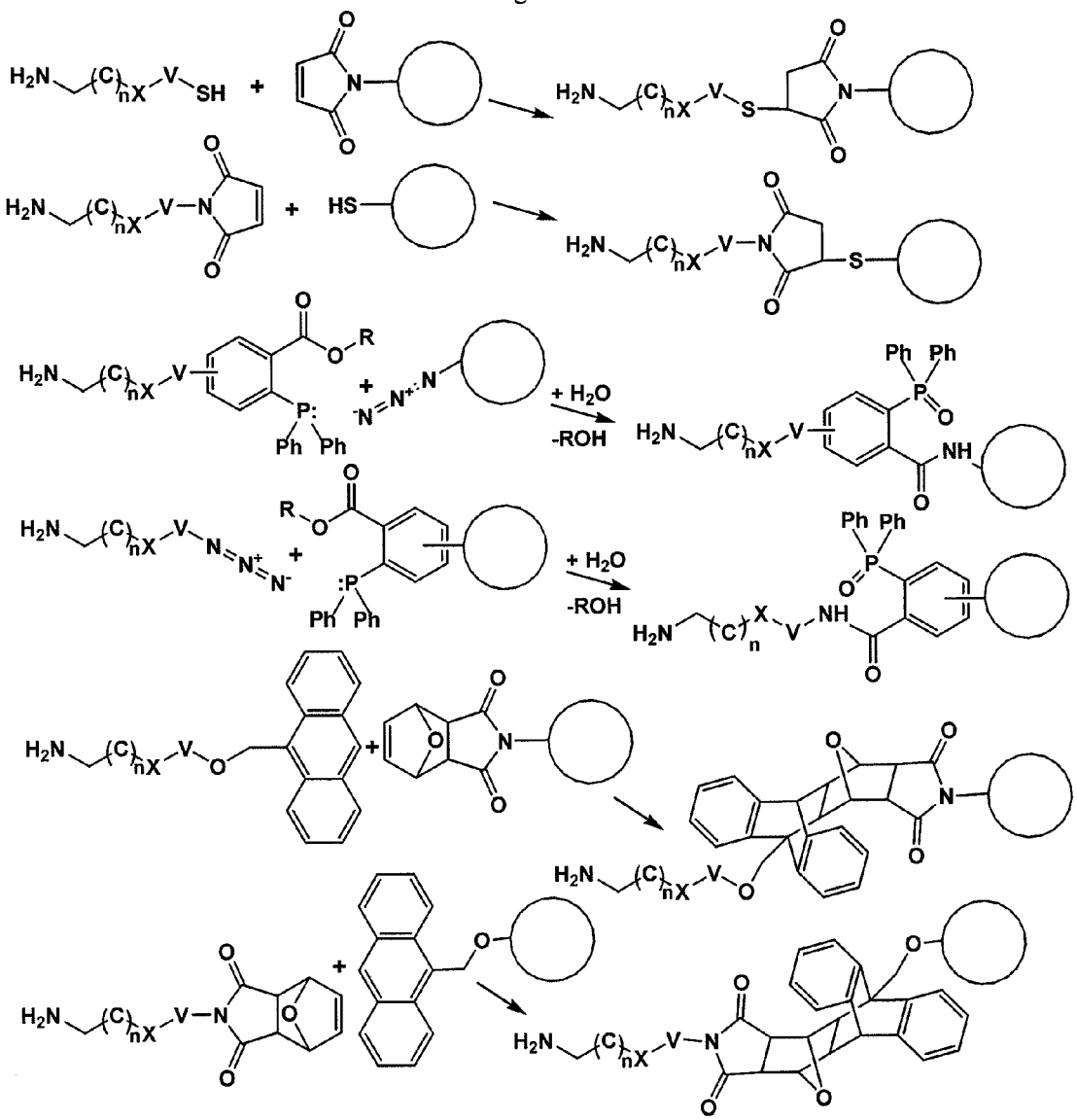
FIG. 1 shows reaction schemes for thio-maleimide additions, Staudinger ligations, and Diels-Alder cycloadditions, where reactive groups of linking reagents having a single reactive functionality combine with complementary reactive group attached to a therapeutic or diagnostic moiety.

According to the present disclosure, the functionalization of antibodies is site-specific and occurs via, respectively between a primary amine (e.g. of a lysine or lysine-like moiety) and an acceptor glutamine residue of an antibody by transglutaminase.

The inventors now present a convenient method for the site-specific functionalization by large chemical molecules (e.g., cytotoxic drugs such as duocarmycins, auristatins, calcheamycins that are natural product derivatives or polymers) of immunoglobulins under near physiological conditions. The enzymatic activity of the transglutaminase family catalyzes an acyl transfer reaction between the γ-carboxamide groups of peptide-bound glutamine residues and various primary amines or ε-amino groups of lysine residues, thus forming isopeptidic bonds which are stable and resistant to chemical, enzymatic, and physical degradation. The function of TGases can be described as incorporation of alkylamine derivatives into specific glutamine residues or vice versa. This specificity has been recognized before and has already been applied successfully for different purposes.

Definitions

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can be replaced by "consisting essentially of", or by "consisting of".

The term "transglutaminase", used interchangeably with "TGase" or "TG", refers to an enzyme capable of cross-linking proteins through an acyl-transfer reaction between the γ-carboxamide group of peptide-bound glutamine and the ε-amino group of a lysine or a structurally related primary amine such as amino pentyl group, e.g. a peptide-bound lysine, resulting in a ε-(γ-glutamyl)lysine isopeptide bond. TGases include, inter alia, bacterial transglutaminase (BTG) such as the enzyme having EC reference EC 2.3.2.13 (protein-glutamine-γ-glutamyltransferase).

The term "acceptor glutamine residue", when referring to a glutamine residue of an antibody, means a glutamine residue that is recognized by a TGase and can be cross-linked by a TGase through a reaction between the glutamine and a lysine or a structurally related primary amine such as amino pentyl group. Preferably the acceptor glutamine residue is a surface-exposed glutamine residue.

The term "TGase recognition tag" refers to a sequence of amino acids comprising an acceptor glutamine residue and that when incorporated into (e.g. appended to) a polypeptide sequence, under suitable conditions, is recognized by a TGase and leads to cross-linking by the TGase through a reaction between an amino acid side chain within the sequence of amino acids and a reaction partner. The recognition tag may be a peptide sequence that is not naturally present in the polypeptide comprising the enzyme recognition tag.

The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

An "antibody fragment" comprises a portion of a full-length antibody, preferably antigen-binding or variable regions thereof. Examples of antibody fragments include Fab, Fab', F(ab)$_2$, F(ab')$_2$, F(ab)$_3$, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO2005040219, and published U.S. Patent Applications 20050238646 and 20020161201.

By "variable region" as used herein is meant the region of an antibody that comprises one or more Ig domains substantially encoded by any of the VL (including Vkappa and Vlambda) and/or VH genes that make up the light chain (including kappa and lambda) and heavy chain immunoglobulin genetic loci respectively. A light or heavy chain variable region (VL and VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

By "constant region" of an antibody as defined herein is meant the region of the antibody that is encoded by one of the light or heavy chain immunoglobulin constant region genes. By "constant light chain" or "light chain constant region" as used herein is meant the region of an antibody encoded by the kappa (Ckappa) or lambda (Clambda) light chains. The constant light chain typically comprises a single domain, and as defined herein refers to positions 108-214 of Ckappa, or Clambda, wherein numbering is according to the EU index of Kabat (Kabat et al., 1991, Sequences of Proteins of Immunological Interest, 5th Ed., United States Public Health Service, National Institutes of Health, Bethesda) and/or Edelman, G. M. et al., Proc. Natl. Acad. USA, 63, 78-85 (1969). By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447. Unless indicated otherwise, numbering within the constant region is according to the EU index of Kabat (1991) and/or Edelman, G. M. et al., Proc. Natl. Acad. USA, 63, 78-85 (1969).

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein, or any other antibody embodiments as outlined herein.

By "Fv" or "Fv fragment" or "Fv region" as used herein is meant a polypeptide that comprises the VL and VH domains of a single antibody.

By "Fc", "Fc domain" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, as illustrated in FIG. 1, Fc comprises immunoglobulin domains Cγ2 and Cγ3 and the hinge between Cγ1 and Cγ2 (Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, as described below.

By "full length antibody" as used herein is meant the structure that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region.

By "amino acid modification" herein is meant an amino acid substitution, insertion, and/or deletion in a polypeptide sequence. The preferred amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%, 98%, or 99% homogeneity for antibody molecules in the context of all present peptide species in the composition or at least with respect to substantially active peptide species in the context of proposed use.

"Treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

The term "reactive moiety" herein refers to a moiety that can be coupled with another moiety without prior activation or transformation.

The term "protecting group" refers to a group that temporarily protects or blocks, i.e., intended to prevent from reacting, a functional group, e.g., an amino group, a hydroxyl group, or a carboxyl group, during the transformation of a first molecule to a second molecule.

The phrase "moiety that improves the pharmacokinetic properties", when referring to a compound (e.g. an antibody) refers to a moiety that changes the pharmacokinetic properties of the one or more moieties Z in such a way that a better therapeutic or diagnostic effect can be obtained. The moiety can for example increase the water solubility, increase the circulation time, or reduce immunogenicity.

The phrase "linking group" refers to a structural element of a compound that links one structural element of said compound to one or more other structural elements of said same compound.

The phrase "a number representing degree of branching" is used to denote that the subscript number next to a closing bracket represents how many units of the moiety within the brackets are attached to the moiety directly to the left of the corresponding opening bracket For example, A-(B)$_b$ with b being a number representing a degree of branching means that b units B are all directly attached to A This means that when b is 2, the formula reduces to B-A-B.

The phrase "a number representing degree of polymerization" is used to denote that the subscript number next to a closing bracket represents how many units of the moiety within the brackets are connected to each other. For example, A-(B)$_1$, with b being a number representing a degree of polymerization means that when b is 2, the formula reduces to A-B-B.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

As used herein, "alkyl" refers to a straight or branched hydrocarbon chain that comprises a fully saturated (no double or triple bonds) hydrocarbon group. The alkyl group may have, for example, 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, the term "heteroalkyl" refers to a straight or branched alkyl group that contains one or more heteroatoms, that is, an element other than carbon (including but not limited to oxygen, sulfur, nitrogen, phosphorus) in place of one or more carbon atoms.

Whenever a group is described as being "substituted" that group substituted with one or more of the indicated substituents. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, heteroalkyl, aryl, heteroaryl, heteroalicyclyl, aralkyl, heteroaralkyl, (heteroalicyclyl)alkyl, hydroxy, alkoxy, aryloxy, acyl, mercapto, alkylthio, arylthio, cyano, halogen, thiocarbonyl, carbamyl, thiocarbamyl, amido, sulfonamido, sulfonamido, carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

Where the number of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexyl amine, triethanolamine, ethylenediamine, and salts with amino acids such as arginine and lysine.

Producing Antibodies

Antibodies may be produced by a variety of techniques known in the art. Typically, they are produced by immunization of a non-human animal, preferably a mouse, with an immunogen comprising a polypeptide, or a fragment or derivative thereof, typically an immunogenic fragment, for which it is desired to obtain antibodies (e.g. a human polypeptide). The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). Other protocols may also be used as long as they result in the production of B cells expressing an antibody directed to the antigen used in immunization. Lymphocytes from a non-immunized non-human mammal may also be isolated, grown in vitro, and then exposed to the immunogen in cell culture. The lymphocytes are then harvested and the fusion step described below is carried out. For preferred monoclonal antibodies, the next step is the isolation of splenocytes from the immunized non-human mammal and the subsequent fusion of those splenocytes with an immortalized cell in order to form an antibody-producing hybridoma. The hybridoma colonies are then assayed for the production of antibodies that specifically bind to the polypeptide against which antibodies are desired. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference).

Human antibodies may also be produced by using, for immunization, transgenic animals that have been engineered to express a human antibody repertoire (Jakobovitz et Nature 362 (1993) 255), or by selection of antibody repertoires using phage display methods. For example, a XenoMouse (Abgenix, Fremont, Calif.) can be used for immunization. A XenoMouse is a murine that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Antibodies may also be produced by selection of combinatorial libraries of immunoglobulins, as disclosed for instance in (Ward et al. Nature, 341 (1989) p. 544, the entire disclosure of which is herein incorporated by reference). Phage display technology (McCafferty et al (1990) Nature 348:552-553) can be used to produce antibodies from immunoglobulin variable (V) domain gene repertoires from unimmunized donors. See, e.g., Griffith et al (1993) EMBO J. 12:725-734; U.S. Pat. No. 5,565,332; U.S. Pat. No. 5,573,905; U.S. Pat. No. 5,567,610; U.S. Pat. No. 5,229,275). When combinatorial libraries comprise variable (V) domain gene repertoires of human origin, selection from combinatorial libraries will yield human antibodies.

Additionally, a wide range of antibodies are available in the scientific and patent literature, including DNA and/or amino acid sequences, or from commercial suppliers. Examples of antibodies include antibodies that recognize an antigen expressed by a target cell that is to be eliminated, for example a proliferating cell or a cell contributing to a pathology. Examples include antibodies that recognize tumor antigens, microbial (e.g. bacterial) antigens or viral antigens. Other examples include antigens present on immune cells that are contributing to inflammatory or autoimmune disease, including rejection of transplanted tissue (e.g. antigens present on T cells (CD4 or CD8 T cells).

Antibodies will typically be directed to a pre-determined antigen. As used herein, the term "bacterial antigen" includes, but is not limited to, intact, attenuated or killed bacteria, any structural or functional bacterial protein or carbohydrate, or any peptide portion of a bacterial protein of sufficient length (typically about 8 amino acids or longer) to be antigenic. Examples include gram-positive bacterial antigens and gram-negative bacterial antigens. The bacterial antigen is derived from a bacterium selected from the group consisting of *Helicobacter* species, in particular *Helicobacter pyloris*; *Borelia* species, in particular *Borelia burgdorferi*; *Legionella* species, in particular *Legionella pneumophilia*; *Mycobacteria* s species, in particular *M. tuberculosis, M. avium, M. intracellulare, M. kansasii, M. gordonae*; *Staphylococcus* species, in particular *Staphylococcus aureus*; *Neisseria* species, in particular *N. gonorrhoeae, N. meningitidis*; *Listeria* species, in particular *Listeria monocytogenes*; *Streptococcus* species, in particular *S. pyogenes, S. agalactiae; S. faecalis; S. bovis, S. pneumonias*; anaerobic *Streptococcus* species; pathogenic *Campylobacter* species; *Enterococcus* species; *Haemophilus* species, in particular *Haemophilus influenzue*; *Bacillus* species, in particular *Bacillus anthracis*; *Corynebacterium* species, in particular *Corynebacterium diphtheriae*; *Erysipelothrix* species, in particular *Erysipelothrix rhusiopathiae*; *Clostridium* species, in particular *C. perfringens, C. tetani*; *Enterobacter* species, in particular *Enterobacter aerogenes*, *Klebsiella* species, in particular *Klebsiella 1S pneumoniae*, *Pasturella* species, in particular *Pasturella multocida*, *Bacteroides* species; *Fusobacterium* species, in particular *Fusobacterium nucleatum*; *Streptobacillus* species, in particular *Streptobacillus moniliformis*; *Treponema* species, in particular *Treponema pertenue*; *Leptospira*; pathogenic *Escherichia* species; and *Actinomyces* species, in particular *Actinomyces israelli*.

As used herein, the term "viral antigen" includes, but is not limited to, intact, attenuated or killed whole virus, any structural or functional viral protein, or any peptide portion of a viral protein of sufficient length (typically about 8 amino acids or longer) to be antigenic. Sources of a viral antigen include, but are not limited to viruses from the families: Retroviridae (e.g., human immunodeficiency viruses, such as HIV-I (also referred to as HTLV-III, LAV or HTLV-III/ LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, *rubella* viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviruses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses). Alternatively, a viral antigen may be produced recombinantly.

As used herein, the terms "cancer antigen" and "tumor antigen" are used interchangeably and refer to antigens (e.g., carbohydrates, polypeptides, or any peptide of sufficient length (typically about 8 amino acids or longer) to be antigenic) that are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

The cancer antigens are usually normal cell surface antigens which are either over-expressed or expressed at abnormal times. Ideally the target antigen is expressed only on proliferative cells (preferably tumour cells), however this is rarely observed in practice. As a result, target antigens are usually selected on the basis of differential expression between proliferative and healthy tissue. Antibodies have been raised to target specific tumour related antigens including: Cripto, CD4, CD20, CD30, CD19, CD33, Glycoprotein NMB, CanAg, Her2 (ErbB2/Neu), CD56 (NCAM), CD22 (Siglec2), CD33 (Siglec3), CD79, CD138, CD171, PSCA, PSMA (prostate specific membrane antigen), BCMA, CD52, CD56, CD80, CD70, E-selectin, EphB2, Melanotransferrin, Mud 6 and TMEFF2. Examples of cancer antigens also include B7-H3, B7-H4, B7-H6, PD-L1, MAGE, MART-1/ Melan-A, gp100, adenosine deaminase-binding protein (ADAbp), cyclophilin b, colorectal associated antigen (CRC)-C017-1A/GA733, carcinoembryonic antigen (CEA) and its immunogenic epitopes CAP-1 and CAP-2, etv6, aml1, prostate specific antigen (PSA), T-cell receptor/CD3-zeta chain, MAGE-family of tumor antigens, GAGE-family of tumor antigens, BAGE, RAGE, LAGE-1, NAG, GnT-V, MUM-1, CDK4, MUC family, VEGF, VEGF receptors, PDGF, TGF-alpha, EGF, EGF receptor, a member of the human EGF-like receptor family such as HER-2/neu, HER-3, HER-4 or a heterodimeric receptor comprised of at least one HER subunit, gastrin releasing peptide receptor antigen, Muc-1, CA 125, $\alpha v \beta 3$ integrins, $\alpha 5 \beta 1$ integrins, $\alpha IIb \beta 3$-integrins, PDGF beta receptor, SVE-cadherin, IL-8, hCG, IL-6, IL-6 receptor, IL-15, $\alpha$-fetoprotein, E-cadherin, $\alpha$-catenin, $\beta$-catenin and $\gamma$-catenin, p120ctn, PRAME, NY-ESO-1, cdc27, adenomatous polyposis *coli* protein (APC), fodrin, Connexin 37, Ig-idiotype, p15, gp75, GM2 and GD2 gangliosides, viral products such as human papillomavirus proteins, imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2, although this is not intended to be exhaustive.

In one embodiment, particularly when the antibody drug conjugates are used for the purpose of killing cells that express cancer antigen, the cancer antigen is an antigen that is expressed on the surface of a tumor cell and is internalized by the cell when bound by an antibody having a functionalized glutamine described herein. Such antibodies will be particularly well suited to use in conjugation with a linking comprising a conditionally cleavable linker (e.g. as a V group in Formulae I to IV) that is cleaved once the antibody drug conjugate is internalized into a cancer cell. As used herein, an antibody that is "internalized" or that "internalizes" is one that is taken up by (i.e., enters) the cell upon binding to an antigen (e.g. cancer antigen) on a mammalian cell. For therapeutic applications, internalization in vivo is contemplated.

In another embodiment, for example when the antibody drug conjugates are used for diagnostic use, the cancer antigen is an antigen that is expressed on the surface of a tumor cell but is not substantially internalized by the cell when bound by an antibody having a functionalized glutamine described herein. Such antibodies will be particularly well suited to use in conjugation with a linker comprising a detectable moiety (e.g. as a Z group in Formulae I to IV) that is not internalized into a cell (e.g. a cancer cell, an infected cell, etc.) and can therefore be detected.

Whether an antibody internalizes upon binding an antigen on a mammalian cell, or whether a antigen undergoes intracellular internalization (e.g. upon being bound by an antibody) can be determined by various assays. For example, to test internalization in vivo, the test antibody is labeled and introduced into an animal known to have target antigen expressed on the surface of certain cells. The antibody can be radiolabeled or labeled with fluorescent or gold particles, for instance. Animals suitable for this assay include a mammal such as a nude mouse that contains target antigen-expressing tumor transplant or xenograft, or a mouse into which cells transfected with human target antigen have been introduced, or a transgenic mouse expressing the human target antigen transgene. Appropriate controls include animals that did not receive the test antibody or that received an unrelated antibody, and animals that received an antibody to another antigen on the cells of interest, which antibody is known to be internalized upon binding to the antigen. The antibody can be administered to the animal, e.g., by intravenous injection. At suitable time intervals, tissue sections of the animal can be prepared and analyzed by light microscopy or electron microscopy, for internalization as well as the location of the internalized antibody in the cell. For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Optionally, in microscopy, co-localization with a known polypeptide or other cellular component can be assessed; for example co-localization with endosomal/lysosomal marker LAMP-1 (CD107a) can provide information about the subcellular localization of the internalized antibody. Alternatively, in a quantitative biochemical assay, a population of cells comprising target antigen-expressing cells are contacted in vitro or in vivo with a radiolabeled test antibody and the cells (if contacted in vivo, cells are then isolated after a suitable amount of time) are treated with a protease or subjected to an acid wash to remove uninternalized antibody on the cell surface. The cells are ground up and the amount of protease resistant, radioactive counts per minute (cpm) associated with each batch of cells is measured by passing the homogenate through a scintillation counter. Based on the known specific activity of the radiolabeled antibody, the number of antibody molecules internalized per cell can be deduced from the scintillation counts of the ground-up cells. Cells are "contacted" with antibody in vitro preferably in solution form such as by adding the cells to the cell culture media in the culture dish or flask and mixing the antibody well with the media to ensure uniform exposure of the cells to the antibody. Instead of adding to the culture media, the cells can be contacted with the test antibody in an isotonic solution such as PBS in a test tube for the desired time period. In vivo, the cells are contacted with antibody by any suitable method of administering the test antibody such as the methods of administration described below when administered to a patient.

For antibody conjugates designed to kill cells, the faster the rate of internalization of the antibody upon binding to the target antigen-expressing cell in vivo, the faster the desired killing or growth inhibitory effect on the target antigen-expressing cell can be achieved, e.g., by a cytotoxic immunoconjugate. Preferably, the kinetics of internalization of the antibodies are such that they favor rapid killing of the target antigen expressing target cell. Therefore, it is desirable that the antibody exhibit a rapid rate of internalization preferably, within 24 hours from administration of the antibody in vivo, more preferably within about 12 hours, even more preferably within about 1 hour.

DNA encoding an antibody of interest can be placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

In certain embodiments, the DNA of a hybridoma or other cell producing an antibody can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody.

Humanized antibodies can also be prepared. Humanized antibodies are typically specific chimeric immunoglobulins, immunoglobulin chains or fragments thereof (such as Fv, Fab, Fab', F (ab') 2, "dab", or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (the parent or donor antibody) while maintaining the desired specificity, affinity, and capacity of the original antibody. The CDRs of the parent antibody, some or all of which are encoded by nucleic acids originating in a non-human organism, are grafted in whole or in part into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239:1534-1536.

The antibody may or may not further comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.

Wild-type full-length IgG antibodies of human isotype will possess a conserved acceptor glutamine at residue 295 of the heavy chain which when in non-glycosylated form will be accessible to a TGase and therefore reactive with a compound of Formula I in the presence of a TGase, under suitable conditions, to form a conjugate from the antibody and the compound of Formula II. The antibody will lack glycosylation at the asparagine at residue 297 of the heavy chain.

Additional or alternative sites reactive with a compound of Formula I in the presence of a TGase can be created by engineering the antibodies. The compounds include glutamine engineered antibodies where one or more amino acids of a wild-type or parent antibody are replaced with (substituted by) a glutamine amino acid, or where a glutamine residue, optionally together with other amino acid residues, is introduced or added to a wild-type or parent antibody (e.g. wherein the glutamine residue is added to an antibody fragment).

It should be noted that a single site mutation that provides a glutamine that is accessible to a TGase may yield more than one engineered glutamine residue that can be conjugated if the antibody comprises more than one engineered chain. For example, a single site mutation will yield two engineered glutamine residues in a tetrameric IgG due to the dimeric nature of the IgG antibody. The engineered glutamine residues will be in addition to any acceptor glutamine already present in an antibody, if any. The glutamine amino acid residues that are reactive, in the presence of a TGase under suitable conditions, with a compound of Formula I may be located in the heavy chain, typically in the constant domain.

In one embodiment, an asparagine at amino acid position 297 (EU Index) is substituted with a glutamine residue. The antibody will have a constant region with a N297Q substitution (a N297Q variant antibody). An antibody having a N297Q substitution and a glutamine at residue 295 (EU Index) will therefore have two acceptor glutamines and thus two conjugation sites per heavy chain. In tetravalent form will therefore have four conjugates per antibody. Such an antibody will be particularly well adapted for use in conjunction with the multi-step method; the antibody can be reacted with a compound of Formula Ib or Ic to form an antibody of Formula II.

In one embodiment, an asparagine at amino acid position 297 is substituted with a non-glutamine residue. The antibody will have a constant region with a or Q295X (e.g., Q295X/N297Q), N297X, S298X and/or T299X substitution (a Q295X, N297X, S298X and/or T299X variant antibody), wherein X is any amino acid (other than a glutamine or the residue Q, N, S or T naturally present at the respective 297, 298 or 299 residue), optionally wherein the substitution is a conservative substitution. An antibody having a Q295X will be understood to have an introduced glutamine at a different position, e.g., the antibody will also have a N297Q substitution. Such an antibody, when comprising a glutamine at position 295 (a glutamine is naturally present in human constant regions at position 295) but no other acceptor glutamine residues, will have two conjugates per antibody when the antibody comprises two heavy chains. Such an antibody will additionally have the advantage of being devoid of closely spaced acceptor glutamine residues such as could be present in an antibody having an acceptor glutamine at positions 295 and 297, where the closely spaced acceptor residues when functionalized with a linker comprising a reactive moiety (R) could lead to unwanted reactions between unprotected reactive group R. Such unwanted reactions between (R) groups would make them unavailable for reactions with a compound of Formula III and a resulting composition of antibodies of Formula IVb would have increased heterogeneity.

As shown herein, TGase provides limited ability to directly (in a single coupling reaction) couple linkers comprising large and/or hydrophobic moieties (e.g., V, Y or Z) to PNGaseF-deglycosylated antibodies. PNGaseF treatment of N297-glycosylated antibodies leads to the deamidation of the asparagine such that an aspartic acid residue is formed at position 297 (EU numbering) following removal of the N-linked glycan (residue 297 is at the +2 position relative to the glutamine at position 295 of the heavy chain in human IgG antibodies). This negatively charged aspartic acid residue is believed to affect the ability of TGase to couple linkers comprising large and/or hydrophobic moieties, and resulting antibody-linker conjugate compositions are heterogeneous, characterized by antibodies having non-functionalized acceptor glutamines. However, by modifying the antibody such that the residue at the +2 position (C-terminal to the acceptor glutamine), TGase becomes able to functionalize all acceptor glutamines on substantially all antibodies in a composition with linkers comprising large and/or hydrophobic moieties. Consequently, antibodies comprising a functionalized acceptor glutamine residue flanked at position +2 by a non-aspartic acid residue can be used as an advantageous substrate for TGase-mediated conjugation of linkers comprising large and/or hydrophobic moieties, particularly when a one-step conjugation reaction scheme is used.

An advantageous approach for preparing conjugated antibodies will thus involve providing as starting materials antibodies lacking N297-linked glycosylation (such N-linked glycosylation interferes with TGase coupling onto residue 295), wherein the +2 position relative to an acceptor glutamine is a non-aspartic acid residue. The residue at the +2 position can be any suitable amino acid that permits efficient TGase-mediated conjugation. Optionally, the residue at the +2 position is a non-negatively charged amino acid, e.g. any electrically neutral amino acid, a serine, etc. Optionally, the residue at the +2 position is selected from the group consisting of: amino acids with positively charged side chains, amino acids with polar uncharged side chains, and amino acids with hydrophobic side chains.

One approach for preparing antibodies comprising a functionalized acceptor glutamine residue flanked at position +2 by a non-aspartic acid residue is to prepare antibodies having an asparagine at position 297 but lacking N-linked glycosylation by a suitable method that does not transform the asparagine at residue 297 to an aspartic acid. For example, antibodies can be produced in a host cell (e.g. a prokaryotic cell, E. coli) that does not yield N-glycosylated antibodies. Such antibodies will typically have a glutamine in their heavy chain at position 295 and a non-glycosylated asparagine at position 297, i.e. the residue at the +2 position relative to an acceptor glutamine is an asparagine.

Preparing antibodies comprising a functionalized acceptor glutamine residue flanked at the +2 position by a non-aspartic acid residue can also be achieved by protein engineering. For example, an antibody having a glutamine naturally present at heavy chain residue 295 (EII numbering) can comprise a modification at residue 297 such that the asparagine is deleted or replaced by a different amino acid. Advantageously, the asparagine at amino acid position 297 is substituted with a non-glutamine, non-aspartic acid residue (e.g., a non-negatively charged amino acid, any conservative substitution, an amino acid with a positively charged side chain, an amino acid with a polar uncharged side chain, an amino acid with a hydrophobic side chain, e.g. a serine). The antibody will thus have a constant region with a N297X substitution (a N297X variant antibody), wherein X is any amino acid other than asparagine, glutamine or aspartic acid.

In another example, an antibody having a glutamine naturally present at heavy chain residue 295 and an asparagine at residue 297 (EU numbering) can comprise a modification at residues 295 and 297 such that the glutamine at residue 295 is deleted or replaced by a different amino acid (e.g., a non-negatively charged amino acid and the asparagine at residue 297 is replaced by a glutamine which then serves as the acceptor glutamine. The antibody will thus have a constant region with Q295X and N297Q substitutions (a Q295X N297Q variant antibody), wherein X is any amino acid other than glutamine, optionally wherein the substitution is a non-negatively charged amino acid.

In another example, an antibody having an acceptor glutamine (e.g. a glutamine naturally present at heavy chain residue 295) and an asparagine at residue 297 (EU numbering) comprises a modification at a non-297 residue (a residue that is not at position 297, EU numbering) in an Fc domain (e.g. CH1, CH2 and/or CH3 domain), wherein the modification abrogates N297-linked glycosylation. Such an antibody will have an acceptor glutamine (e.g. at residue 295) together with an aglycosylated asparagine at residue 297. For example, modifications leading to elimination of asparagine-linked glycosylation at N297 include a substitution at residue T299 (or optionally additional substitutions at other residues, e.g. substitutions at both T299 and S298), see, e.g., any of the mutations and combinations of mutations disclosed in Sazinsky et al. 2008 Proc. Nat. Acad. Sci. U.S.A. 105(51):20167-20172. An exemplary antibody can thus have a constant region with a T299X substitution (a T299X variant antibody), wherein X is an amino acid other than threonine, wherein the modification abrogates N297-linked glycosylation.

In one embodiment, an antibody comprises a heavy chain constant region comprising an amino acid sequence HNAK-TKPREEQ-$X^1$—$X^2$-STYRVVSVLT (SEQ ID NO: 3), wherein $X^1$ is Y (tyrosine) or F (phenylalanine) and $X^2$ is an amino acid other than D (aspartic acid). Optionally, $X^2$ is a non-negatively charged amino acid, any conservative substitution, an amino acid with a positively charged side chain, an amino acid with a polar uncharged side chain, an amino acid with a hydrophobic side chain, e.g. a serine.

In one embodiment, an antibody comprises a heavy chain constant region comprising an amino acid sequence HNAK-TKPREEQ-$X^1$—NS—$X^2$—YRVVSVLT (SEQ ID NO: 4), wherein $X^1$ is Y or F and $X^2$ is an amino acid other than T (threonine).

In one embodiment, an antibody comprises a heavy chain constant region (e.g. a constant domain, a CH2 domain) comprising an amino acid sequence -$J^1$-$J^2$-$J^3$-$J^4$-Q-$X^1$—$X^2$—, wherein Q is an acceptor glutamine, $J^1$, $J^2$, $J^3$, and $J^4$ are any amino acid so long as one or more (or all of) of J', $J^2$, $J^3$, and $J^4$ is an amino acid residue having a negative electrical charge, optionally a glutamic acid (E) or an aspartic acid residue (D), $X^1$ is any amino acid (e.g. Y (tyrosine) or F (phenylalanine), and $X^2$ is an amino acid other than D (aspartic acid). Optionally, $X^2$ is a non-negatively charged amino acid, any conservative substitution, an amino acid with a positively charged side chain (e.g. an arginine), an amino acid with a polar uncharged side chain, an amino acid with a hydrophobic side chain, e.g. a serine. In on embodiment, $J^1$ and $J^2$ are each an amino acid residue having a negative electrical charge, optionally a glutamic acid (E) or an aspartic acid residue (D); optionally at least one or $J^1$ and $J^2$ is an aspartic acid residue. In on embodiment, $J^2$ and $J^3$ are each an amino acid residue having a negative electrical charge, optionally a glutamic acid (E) or an aspartic acid residue (D); optionally at least one or $J^2$ and $J^3$ is an aspartic acid residue. In on embodiment, $J^3$ and $J^4$ are each an amino acid residue having a negative electrical charge, optionally a glutamic acid (E) or an aspartic acid residue (D); optionally at least one or $J^3$ and $J^4$ is an aspartic acid residue.

In one embodiment, an antibody comprises a heavy chain constant region (e.g. a CH2 domain) comprising an amino acid sequence -$J^1$-Q-$X^1$—$X^2$—, wherein Q is an acceptor glutamine, $J^1$ is an amino acid residue having a negative electrical charge, optionally a glutamic acid (E) or an aspartic acid residue (D), $X^1$ is any amino acid (e.g. Y (tyrosine) or F (phenylalanine), and $X^2$ is an amino acid other than D (aspartic acid). Optionally, $X^2$ is a non-negatively charged amino acid, any conservative substitution, an amino acid with a positively charged side chain (e.g. an arginine), an amino acid with a polar uncharged side chain, an amino acid with a hydrophobic side chain, e.g. a serine.

In one embodiment, an antibody comprises a heavy chain constant region (e.g. a CH2 domain) comprising an amino acid sequence -$J^1$-Q-$X^1$—$X^2$—, wherein Q is an acceptor glutamine, $J^1$ is an amino acid residue having a negative electrical charge, optionally a glutamic acid (E) or an aspartic acid residue (D) $X^1$ is any amino acid (e.g. Y (tyrosine) or F (phenylalanine), and $X^2$ is an amino acid with a positively charged side chain (e.g. an arginine). In one embodiment, an antibody comprises a TGase recognition tag (e.g. inserted into a heavy or light chain constant region, fused to the C-terminus of a heavy chain CH3 domain or to the C-terminus of a light chain Cκ or Cλ domain) compris-ing an amino acid sequence -$J^1$-$J^2$-$J^3$-$J^4$-Q-$X^1$—$X^2$—, wherein Q is an acceptor glutamine, $J^1$, $J^2$, $J^3$, and $J^4$ are any amino acid so long as one or more (or all of) of $J^1$, $J^2$, $J^3$, and $J^4$ is an amino acid residue having a negative electrical charge, optionally a glutamic acid (E) or an aspartic acid residue (D), $X^1$ is any amino acid (e.g. Y (tyrosine) or F (phenylalanine), and $X^2$ is an amino acid other than D (aspartic acid). Optionally, $X^2$ is a non-negatively charged amino acid, any conservative substitution, an amino acid with a positively charged side chain (e.g. an arginine), an amino acid with a polar uncharged side chain, an amino acid with a hydrophobic side chain, e.g. a serine. In on embodiment, $J^1$ and $J^2$ are each an amino acid residue having a negative electrical charge, optionally a glutamic acid (E) or an aspartic acid residue (D); optionally at least one or $J^1$ and $J^2$ is an aspartic acid residue. In on embodiment, $J^2$ and $J^3$ are each an amino acid residue having a negative electrical charge, optionally a glutamic acid (E) or an aspartic acid residue (D); optionally at least one or $J^2$ and $J^3$ is an aspartic acid residue. In on embodiment, $J^3$ and $J^4$ are each an amino acid residue having a negative electrical charge, optionally a glutamic acid (E) or an aspartic acid residue (D); optionally at least one or $J^3$ and $J^4$ is an aspartic acid residue.

In one embodiment, an antibody comprises a TGase recognition tag (e.g. inserted into a heavy or light chain constant region, fused to the C-terminus of a heavy chain CH3 domain or to the C-terminus of a light chain Cκ or Cλ domain) comprising an amino acid sequence -$J^1$-Q-$X^1$—$X^2$—, wherein Q is an acceptor glutamine, $J^1$ is an amino acid residue having a negative electrical charge, optionally a glutamic acid (E) or an aspartic acid residue (D), $X^1$ is any amino acid (e.g. Y (tyrosine) or F (phenylalanine), and $X^2$ is an amino acid other than D (aspartic acid). Optionally, $X^2$ is a non-negatively charged amino acid, any conservative substitution, an amino acid with a positively charged side chain (e.g. an arginine), an amino acid with a polar uncharged side chain, an amino acid with a hydrophobic side chain, e.g. a serine.

In one embodiment, an antibody comprises a TGase recognition tag (e.g. inserted into a heavy or light chain constant region, fused to the C-terminus of a heavy chain CH3 domain or to the C-terminus of a light chain Cκ or Cλ domain) comprising an amino acid sequence -$J^1$-Q-$X^1$—$X^2$—, wherein Q is an acceptor glutamine, $J^1$ is an amino acid residue having a negative electrical charge, optionally a glutamic acid (E) or an aspartic acid residue (D) $X^1$ is any amino acid (e.g. Y (tyrosine) or F (phenylalanine), and $X^2$ is an amino acid with a positively charged side chain (e.g. an arginine), In one embodiment, an antibody comprises a heavy chain constant region amino acid sequence of SEQ ID NOS: 6 or 8, a fragment of at least 10, 25, 50, 100 amino acid residues thereof, or an amino acid sequence at least 80%, 90%, 95% or 99% identical to the foregoing, wherein the heavy chain constant region comprises a glutamine residue flanked at the +2 position by a non-aspartic acid residue. Optionally the residue at the at the +2 position is an amino acid other than an asparagine, glutamine or aspartic acid. Optionally the residue at at the +2 position is a non-negatively charged amino acid.

Such antibodies lacking aspartic acid at the +2 position will form a substrate for efficient TGase mediated conjugation of linkers comprising large and/or hydrophobic moieties.

Engineered antibodies can be prepared by a variety of methods which include, but are not limited to, isolation from a natural source (in the case of naturally occurring amino acid sequence variants), preparation by site-directed (or oligonucleotide-mediated) mutagenesis (Carter (1985) et al Nucleic Acids Res. 13:4431-4443; Ho et al (1989) Gene (Amst.) 77:51-59; Kunkel et al (1987) Proc. Natl. Acad. Sci. USA 82:488; Liu et al (1998) J. Biol. Chem. 273:20252-20260), PCR mutagenesis (Ito et al (1991) Gene 102:67-70; and Vallette et al (1989) Nuc. Acids Res. 17:723-733) and cassette mutagenesis (Wells et al (1985) Gene 34:315-323) of an earlier prepared DNA encoding the polypeptide. Mutagenesis protocols, kits, and reagents are commercially available, e.g. QuikChange® Multi Site-Direct Mutagenesis Kit (Stratagene, La Jolla, Calif.). Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition). Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies (Sambrook et al Molecular Cloning, A Laboratory Manual. Cold Spring Harbor Laboratory Press, Cold Spring Harbor, N.Y., 1989; and Ausubel et al Current Protocols in Molecular Biology, Greene Publishing and Wiley-Interscience, New York. N.Y., 1993).

Antibodies may be chemically synthesized using known oligopeptide synthesis methodology or may be prepared and purified using recombinant technology. In vitro protein synthesis may be performed using manual techniques or by automation.

In one embodiment provided is a method of preparing (making) an antibody for use in a one-step TGase-mediated coupling reaction (e.g. with a linker of Formula Ia, Ib or Ic), comprising:
 (a) providing a parent antibody having in a heavy chain:
  (i) an acceptor glutamine residue at residue 295 and (ii) an asparagine at position 297; and
 (b) substituting the asparagine present at position 297 of said parent antibody by a non-glutamine residue, in order to generate an antibody having an acceptor glutamine residue at residue 295 and lacking N-linked glycosylation at position 297. Optionally, the amino acid that replaces the asparagine at position 297 is a residue other than an aspartic acid. Optionally, the amino acid that replaces the asparagine at position 297 is a positively charged residues, e.g. an arginine.

In one embodiment provided is a method of preparing (making) an antibody for use in a one-step TGase-mediated coupling reaction (e.g. with a linker of Formula Ia, Ib or Ic), comprising:
 (a) providing a parent antibody having in a heavy chain:
  (i) an acceptor glutamine residue at residue 295 and (ii) an threonine at position 299; and
 (b) modifying (e.g. substituting with another amino acid) the threonine at position 299 of said parent antibody in order to generate an antibody having an acceptor glutamine residue at residue 295 and lacking N-linked glycosylation at position 297.

In one embodiment provided is a method of preparing (making) an antibody for use in a one-step TGase-mediated coupling reaction (e.g. with a linker of Formula Ia, Ib or Ic), comprising:
 (a) providing a parent antibody having in a heavy chain:
  (i) a glutamine residue at residue 295 and (ii) an asparagine at position 297; and
 (b) substituting the glutamine present at position 295 of said parent antibody by any amino acid (e.g. other than non-glutamine, a conservative substitution, a serine, glycine, asparagine, threonine), and substituting the asparagine at position 297 by a glutamine, in order to generate an antibody having an acceptor glutamine residue and lacking N-linked glycosylation at residue 297, and lacking an acceptor glutamine at position 295. The method may optionally further comprises a step (c) reacting the antibody of step (b)
with a compound of Formula I (e.g. a compound of Formula Ia, Ib or Ic) in the presence of a TGase under suitable conditions, such that an antibody of Formula II, IVa or IVb is formed.

In one embodiment provided is a method of preparing (making) a glutamine engineered antibody, comprising:
 (a) introducing one or more acceptor glutamine residues into a parent antibody in order to generate a glutamine engineered antibody; and
 (b) reacting the glutamine engineered antibody with a compound of Formula I (e.g. a compound of Formula Ia, Ib or Ic) in the presence of a TGase under suitable conditions, such that an antibody of Formula II, IVa or IVb is formed.

Step (a) of the method of preparing a glutamine engineered antibody may comprise:
 (i) mutagenizing a nucleic acid sequence encoding the glutamine engineered antibody;
 (ii) expressing the glutamine engineered antibody; and
 (iii) isolating and purifying the glutamine engineered antibody.

In one example, the cancer antigen is human L1-CAM (CD171; L1 cell adhesion molecule) which has been found to be expressed in a variety of cancers (see, e.g., Kajiwara et al, (2011) Am. J. Clin. Pathol. 136 (1), 138-144). The L1-CAM nucleotide and amino acid sequences are disclosed in Genbank accession numbers NM_024003.2 and NP_076493.1, respectively, the disclosures of which are incorporated by reference. An example of an anti-L1-CAM antibody suitable for use in is a chCE7-derived antibody, e.g, having a heavy chain comprising CDRs (e.g., CDR-H1, -H2 and -H3) from chCE7 heavy chain shown in SEQ ID NO: 1 and a light chain comprising CDRs (e.g., CDR-L1, -L2 and -L3) from chCE7 heavy chain shown in SEQ ID NO 2, optionally wherein any of said CDRs further comprises one, two, three, four or five amino acid modifications so long as the antibody retains specific binding to L1-CAM. ChCE7 is composed of murine VL and murine VH fused to the Fc part of human IgG1 (see, e.g., Jeger et al., (2010) Angew. Chem. Int., 49, 9995-9997). chCE7 optionally comprises specific mutations were introduced in the CH2 domain of the chCE7 heavy chain using overlapping polymerase chain reaction (PCR) and standard molecular biology techniques (Q295N and N297Q variants), including chCE7 N297Q variants with an acceptor glutamine at position 295 and 297, and chCE7agIQ295N, N297Q variants with an acceptor glutamine at position 297.

An exemplary humanized CE7 antibody comprises a VH domain comprising a CDR-H1 sequence corresponding to residues 31-35 of SEQ ID NO: 1, a CDR-H2 sequence corresponding to residues 50-66 of SEQ ID NO: 1, and a CDR-H3 sequence corresponding to residues 99-109 of SEQ ID NO:1, wherein any CDR may optionally comprise one, two, three, four or more amino acid substitutions. An exemplary humanized CE7 antibody may also or alternatively comprise a VL domain comprising a CDR-L1 sequence corresponding to residues 24-34 of SEQ ID NO: 2, a CDR-L2 sequence corresponding to residues 50-56 of SEQ ID NO: 2, and an CDR-L3 sequence corresponding to residues 89-95 (or 89-97) of SEQ ID NO: 2, wherein any CDR may optionally comprise one, two, three, four or more amino acid substitutions.

Fragments and derivatives of antibodies (which are encompassed by the term "antibody" or "antibodies" as used in this application, unless otherwise stated or clearly contradicted by context), can be produced by techniques that are known in the art. "Fragments" comprise a portion of the intact antibody, generally the antigen binding site or variable region. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or a "dAb".

The DNA of a hybridoma producing an antibody may be modified so as to encode a fragment. The modified DNA is then inserted into an expression vector and used to transform or transfect an appropriate cell, which then expresses the desired fragment.

The fragment will comprise a variable region domain that will generally be covalently attached to at least one, two or more glutamine residue covalently linked through a —NH—$(C)_n$—X-L moiety (and optionally further a V and/or Y moiety, optionally further an R or RR' moiety, to a moiety-of-interest Z, e.g. a polymer molecule, a drug, a radioactive moiety. The variable region will comprise hypervariable region or CDR sequences, and FR sequences.

The location of the glutamine residue may be varied according to the size and nature of the antibody fragment required. Thus, in one extreme example an acceptor glutamine residue to be conjugated to a lysine-based linker of Formula I may be attached directly to a C-terminal amino acid of the variable region domain. This may be for example the C-terminus of a VH or VL chain as described above. If desired, in this example, further amino acids, including further acceptor glutamine residues, may be covalently linked to the C-terminus of the first glutamine residue. In one example, a peptide "tag" comprising one or more non-glutamine residues followed by an acceptor glutamine residue (the acceptor glutamine residue is C-terminal to the non-glutamine residue in the tag) is attached directly to a C-terminal amino acid of the variable region domain. In one example, a peptide "tag" comprising one or more glutamine residues followed by one or more non-glutamine residues (the non-glutamine residues are C-terminal to the glutamine residue in the tag) is attached directly to a C-terminal amino acid of the variable region domain. A peptide tag can be of any suitable length, e.g a tag may comprise between 2 and 50, preferably 2 and 20 or 2 and 10 amino acid residues.

In practice however, it is generally preferable that the variable region domain is covalently attached at a C-terminal amino acid to at least one other antibody domain or a fragment thereof which contains, or is attached to one or more acceptor glutamine residues. Thus, for example where a VH domain is present in the variable region domain this may be linked to an immunoglobulin CH1 domain or a fragment thereof. Similarly a VL domain may be linked to a CK domain or a fragment thereof. In this way for example the fragment may be a Fab fragment wherein the antigen binding domain contains associated VH and VL domains covalently linked at their C-termini to a CH1 and CK domain respectively. The CH1 domain may be extended with further amino acids, for example to provide a hinge region domain as found in a Fab' fragment, or to provide further domains, such as antibody CH2 and CH3 domains. In one example, a polypeptide "tag" comprising one or a plurality (e.g. 2, 3, 4, 5, 6) non-glutamine residues followed by a glutamine residue (the glutamine residue is C-terminal to the non-glutamine residue in the tag) is attached directly to a C-terminal amino acid of a full or truncated CH1, CH2 or CH3 domain, or to a C-terminal amino acid of a full or truncated CK domain. In one example, a polypeptide "tag" comprising one or more glutamine residues followed by one or more non-glutamine residues (the non-glutamine residues are C-terminal to the glutamine residue in the tag) is attached directly to a C-terminal amino acid of a full or truncated CH1, CH2 or CH3 domain, or to a C-terminal amino acid of a full or truncated CK domain.

The present disclosure provides an antibody fragment in which the variable region domain is monomeric and comprises an immunoglobulin heavy (VH) or light (VL) chain variable domain, or is dimeric and contains VH-VH, VH-VL or VL-VL dimers in which the VH and VL chains are non-covalently associated or covalently coupled, wherein the fragment (i.e. the VL and/or VH) is covalently linked through a —NH—$(C)_n$—X-L moiety (and optionally further a V and/or Y moiety, optionally further L', V', Y', and (RR') moieties, to a moiety-of-interest Z, e.g. a polymer molecule, a drug, a radioactive moiety. Preferably each VH and/or VL domain is covalently attached at a C-terminal amino acid to at least one other antibody domain or a fragment thereof.

In one embodiment, the disclosure provides a monovalent antibody fragment comprising a heavy chain and a light chain, wherein: said heavy chain consists of a VH domain covalently linked at its C-terminus to a CH1 domain; said light chain consists of a VL domain, which is complementary to the VH domain, covalently linked at its C-terminus to a CL domain; said CH1 domain comprises (e.g., the CH1 is extended) to provide a hinge domain which comprises a glutamine residue; and the glutamine residue in the hinge domain is covalently linked through a —NH—$(C)_n$—X-L moiety. In another embodiment, the disclosure provides a monovalent antibody fragment comprising a heavy chain and a light chain, wherein: said heavy chain consists of a VH domain covalently linked at its C-terminus to a CH1 domain; said light chain consists of a VL domain, which is complementary to the VH domain, covalently linked at its C-terminus to a CL domain; said CL domain comprises (e.g., the CL is extended) to provide a hinge domain which comprises a glutamine residue; and the glutamine residue in the hinge domain is covalently linked through a —NH—$(C)_n$—X-L moiety.

In one embodiment, the antibody fragment is linked through a —NH—$(C)_n$—X-L moiety to a polymer (e.g. a PEG-comprising molecule).

Lysine-based linkers

Certain aspects of the disclosure are directed to a linking reagent that can be attached, by the action of a TGase, to a polypeptide at a glutamine residue (Q) within the sequence of the polypeptide, for example an antibody (Ab). The linking reagent contains a primary amine that functions as a TGase substrate for conjugation onto an acceptor glutamine on an antibody, for example a lysine derivative (Lys), including but not limited to a lysine amino acid residue, or a functional equivalent thereof, that is connected to at least one reactive group (R). In one embodiment, a moiety-of-interest (Z), and optionally one or more other groups, are attached to the linking reagent. In one embodiment, for use in a multi-step conjugation process, a plurality of reactive groups, preferably non-complementary reactive groups, can be attached to the linking reagent. The reactive group is preferably a functionality that is insensitive to water but selectively undergoes a very high conversion addition reaction with a complementary reagent.

The lysine derivative can be a 2 to 20 alkyl or heteroalkyl chain, or a functional equivalent thereof, with an $H_2N$, $H_2NOCH_2$, $H_2NCH_2$ (aminomethylene) group or a protected $H_2N$, $H_2NOCH_2$, $H_2NCH_2$ group positioned at one or more ends of the alkyl or heteroalkyl chain. The heteroalkyl chain can be a chain of 3 to 20 atoms where one or more non-terminal atoms can be other than carbon, for example oxygen, sulfur, nitrogen, or other atoms. The oxygen, sulfur, or nitrogen atom can be of an ether, ester, thioether, thioester, amino, alkylamino, amido or alkylamido functionality within the carbon chain.

The heteroalkyl chain can be an oligo (ethylene oxide) chain. The functionality within the alkyl or heteroalkyl chain can be included to couple the reactive group to the $H_2N$, $H_2NOCH_2$, $H_2NCH_2$ group or protected $H_2N$, $H_2NOCH_2$, $H_2NCH_2$ group. The alkyl or heteroalkyl chain can be substituted or unsubstituted. The substituents can be alkyl groups, aryl groups, alkyl aryl groups, carboxylic acid groups, amide groups, hydroxy groups, or any other groups that do not compete with the amino group for, or inhibit, conjugation with a glutamine residue of the protein. Typically, when a substituent is present, its presence is in a convenient starting material, such as the carboxylic acid group of lysine, from which the lysine derivative results. The $H_2N$, $H_2NOCH_2$, $H_2NCH_2$ end of a alkyl or heteroalkyl chain is necessarily included in the linking reagent.

Exemplary starting materials for the functional equivalent of lysine can be an α,ω-diaminoalkane, for example, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, or 1,12-diaminododecane. Other starting materials for the functional equivalent of a lysine derivative can be α,ω-diamino oligo (ethylene oxide), for example, $H_2N(CH_2CH_2O)_xCH_2CH_2NH_2$ where x is 1 to about 6. The α,ω-diamino oligo (ethylene oxide) can be a single oligomer or it can be a mixture of oligomers where x defines an average size. An exemplary protected $H_2NCH_2$ is the tert-butylcarbamate protected amine of tert-butyl N-(5-aminopentyl)carbamate (N-Boc-cadaverin).

The linking reagent, a pharmaceutically acceptable salt or solvate thereof, or a protein conjugated linking reagent may comprise the general Formula Ia or Ib. Formulae Ia (having an Z group) and Ib (having a R group) are shown as follows:

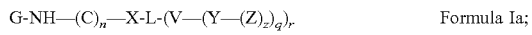  Formula Ia;

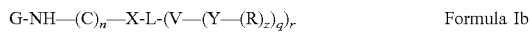  Formula Ib or a pharmaceutically acceptable salt or solvate thereof wherein:

G is an H, amine protecting group, or an immunoglobulin (Ab) or other protein attached via an amide bond;

$(C)_n$ is a substituted or unsubstituted alkyl or heteroalkyl chain, optionally where the carbon adjacent to the nitrogen is unsubstituted, optionally wherein any carbon of the chain is substituted alkoxy, hydroxyl, alkylcarbonyloxy, alkyl-S—, thiol, alkyl-C(O)S—, amine, alkylamine, amide, or alkylamide (e.g. with a O, N or S atom of an ether, ester, thioether, thioester, amine, alkylamine, amide, or alkylamide);

n is an integer selected from among the range of 2 to 20, preferably 3 to 6;

X is NH, O, S, or absent;

L is a bond or a carbon comprising framework of 1 to 200 atoms substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra-, or oligopeptide, other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4; and z is an integer selected from among 1, 2, 3 or 4;

V is independently absent, a bond or a continuation of a bond if L is a bond, a non-cleavable moiety or a conditionally-cleavable moiety, optionally following prior conditional transformation, which can be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent, a bond or a continuation of a bond if V is a bond or continuation of a bond, or a spacer system (e.g., a self-eliminating spacer system or a non-self-elimination spacer system) which is comprised of 1 or more spacers;

Z is a moiety that improves the pharmacokinetic properties, a therapeutic moiety or a diagnostic moiety; and R is a reactive moiety, preferably a moiety comprising an unprotected or protected thiol, maleimide, haloacetamide, o-phoshenearomatic ester, azide, fulminate, alkyne, cyanide, anthracene, 1,2,4,5-tetrazine, norbornene, other stained or otherwise electronically activated alkene or, optionally, a protected or unprotected amine when X is absent and L, V, or Y is other than a bond or a continuation of a bond. In an alternative embodiment R is a reactive moiety, preferably a moiety comprising an unprotected or protected thiol, an unprotected or protected amine, maleimide, haloacetamide, o-phoshenearomatic ester, azide, fulminate, alkyne, cyanide, anthracene, 1,2,4,5-tetrazine, norbornene, other stained or otherwise electronically activated alkene, provided that R is not an amine when n=5 and X, L, V and Y are absent. Optionally, R is not an amine when n=4 and X, L, V and Y are absent. When more than one R group is present in a compound of the formula Ib, the R groups will preferably be compatible such that no R group is a complementary reagent to any other R group.

The $(C)_n$ group may for example be a straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O—$C_{1-5}$ alkyl, —O—$C_{5-10}$ alkyl, —O—C$_{11-20}$ alkyl, CH$_2$—(CH$_2$—O—CH$_2$)$_{1-12}$—CH$_2$ or (CH$_2$—CH$_2$—O—)$_{1-12}$, an amino acid, an oligopeptide, glycan, sulfate, phosphate or carboxylate.

In one example the (C)$_n$ group is a carbon comprising framework substituted with one or more O atoms. In one embodiment, the carbon adjacent to the nitrogen is substituted with an O atom. In one embodiment, the carbon adjacent to the nitrogen is unsubstituted. In one embodiment, the (C)$_n$ group is or comprises an ethylene oxide group, e.g. a CH$_2$—(CH$_2$—O—CH$_2$) CH$_2$ group or an (CH$_2$—CH$_2$—O—)$_n$, where n is an integer from 1 to 10.

The L group can be a carbon comprising framework, where L is a linear hydrocarbon, a symmetrically or asymmetrically branched hydrocarbon, monosaccharide, disaccharide, linear or branched oligosaccharide (asymmetrically branched or symmetrically branched), an amino acid, a di-, tri-, tetra-, or oligopeptide, other natural oligomer, dimer, trimer, or higher oligomer (linear asymmetrically branched or symmetrically branched) resulting from any chain-growth or step-growth polymerization process. For example, L may comprise or be a straight, branched and/or cyclic C$_{2-30}$ alkyl, C$_{2-30}$ alkenyl, C$_{2-30}$ alkynyl, C$_{2-30}$ heteroalkyl, C$_{2-30}$ heteroalkenyl, C$_{2-30}$ heteroalkynyl, optionally wherein one or more homocyclic aromatic compound radical or heterocyclic compound radical may be inserted; notably, any straight or branched C$_{2-5}$ alkyl, C$_{5-10}$ alkyl, C$_{11-20}$ alkyl, —O—C$_{1-5}$ alkyl, —O—C$_{5-10}$ alkyl, —O—C$_{11-20}$ alkyl, CH$_2$—(CH$_2$—O—CH$_2$)$_{1-30}$—CH$_2$ or (CH$_2$—CH$_2$—O—)$_{1-30}$, e.g., (CH$_2$—CH$_2$—O—)$_{12}$, (CH$_2$—CH$_2$—O—)$_{1-24}$, an amino acid, an oligopeptide, glycan, sulfate, phosphate, carboxylate. Optionally, L is absent.

L, V and/or Y have r, q, and/or z sites of attachment for the respective V, Y, and Z or R groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

In one example the carbon comprising framework of the L group is optionally substituted with one or more O atoms. In one embodiment, the L group comprises one or more ethylene oxide groups (CH$_2$—O—CH$_2$). Optionally, the L group comprises a carbon framework comprising a (CH$_2$—CH$_2$—O—)$_n$ group, wherein n is an integer selected among the range of 1 to 10 (e.g., 1, 2, 3, 4, 5, 6, 7, 8, 9 or 10).

In Formulae Ia, Ib, II, IVa and IVb, the linking group L links the aminopeptidyl moiety —NH—(C)$_n$—X to the reactive group R or Z, optionally through one or more V and/or Y moieties where present. L may be a bond connecting V, Y, R or Z directly to the aminopeptidyl moiety. In another aspect, however, L is a linking group that functionally links or spaces the one or more moieties V and/or Y reactive moiety R or moiety of interest (Z). In Formulae Ib, Ic, II and IVb, spacing improves efficiency and completion of BTGase coupling, make additionally the reactive moiety R more accessible to the reaction partner, for example when the reactive moiety is present on a lysine-based linker and coupled to the antibody and then brought into contact with a reaction partner. In Formulae Ia and IVa, the linking group L links the aminopeptidyl moiety —NH—(C)—X to the moiety-of-interest (Z), optionally through one or more V and/or Y moieties where present. L may be a bond connecting V, Y or Z directly to the aminopeptidyl moiety. In another aspect, however, L is a linking group that functionally links or spaces the one or more moieties V and/or Y reactive moiety Z. In Formulae Ia and IVa, spacing improves efficiency and completion of BTGase coupling, providing for highly homogenous compounds. In antibodies comprising a functionalized acceptor glutamine of Formula IVa or IVb spacing may also provide for a better accessibility of V, which in the case of enzymatic cleavage or transformation of V, may improve the rate at which V is transformed and/or cleaved.

L and (C)$_n$ groups can be configured based on the overall structure of the linker that is to be used. Particularly when a multi-step method of the disclosure is used and the linker (e.g. the linker of Formula Ia, Ib or Ic is free of or does not comprise a large, charged or hydrophobic moiety (e.g. a cyclic, polycyclic or macrocyclic moiety), the L group may be a bond or a shorter carbon framework. For example, L may represent or comprise a carbon framework of 1, 2, 3, 4, 5, or 6 linear carbon atoms, unsubstituted or optionally substituted at one or more atoms. Preferably, where L additionally comprises other groups, the 5-20 linear carbon atoms will be adjacent to the (C)$_n$ group, or where present, the X group.

When a linker (e.g. the linker of Formula Ia, Ib or Ic or an antibody of Formula II, IVa or IVb) comprises a large, charged or hydrophobic moiety (e.g. a cyclic, polycyclic or macrocyclic moiety), for example, wherein V, Y and/or Z comprises a large, charged or hydrophobic moiety (e.g. a cyclic, polycyclic or macrocyclic moiety), the L group may be longer carbon framework. For example, L may represent or comprise a carbon framework of:

a) 2-30 linear carbon atoms optionally substituted at one or more atoms;

b) 2-15 linear carbon atoms optionally substituted at one or more atoms;

c) 5-20 linear carbon atoms optionally substituted at one or more atoms;

d) 5-30 linear carbon atoms optionally substituted at one or more atoms;

e) 5-15 linear carbon atoms optionally substituted at one or more atoms; or f) 4, 5 or 6 linear carbon atoms optionally substituted at one or more atoms.

Preferably, the 5-20 linear carbon atoms will be adjacent to (the continuation of) the (C)$_n$ group, or where present, the X group.

In some embodiments, L is a —(C═O)—C$_{1-6}$ alkyl group. In some embodiments, L is a C$_{1-6}$ alkoxy-C$_{1-6}$ alkyl group. In some embodiments, L is a —(C═O)—C$_{1-6}$ alkoxy-C$_{1-6}$ alkyl group. In some embodiments, L is a —(C═O)—C$_{10-20}$ alkyl group. In some embodiments, L is a C$_{1-6}$ alkyl group. In some embodiments, L is a C$_{10-20}$ alkyl group. In some embodiments, L is a —(C═O)—O—C$_{1-6}$ alkyl group. In some embodiments, L is a —(C═O)—O—C$_{2-20}$ alkyl group. In some embodiments, L is a —(C═O)— group. In some embodiments, L is selected among

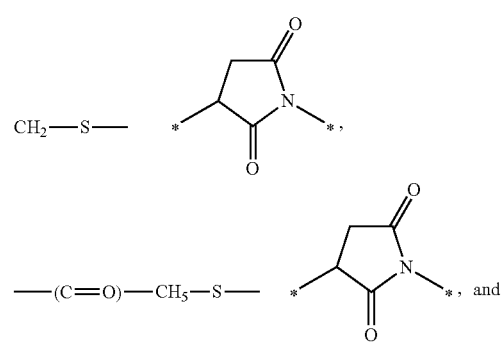

-continued

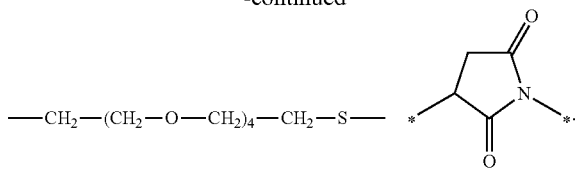

In some embodiments, L is or comprises an amino acid or a di-, tri-tetra- or oligopeptide. In some embodiments, L is selected from among alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and citrulline.

In any of the compounds of the disclosure (e.g. in any of Formula I, II and/or IV), linking element (L) can optionally be characterized as having a chain length of at least 2.8 Angstroms, 3, Angstroms, 4 Angstroms, 5 Angstroms, 10 Angstroms, 15 Angstroms, 18 Angstroms, 30 Angstroms, 40 Angstroms or 60 Angstroms. Optionally L has a length of no more than 100 Angstroms, optionally no more than 60 Angstroms. Optionally, L is characterized as having a length of between 2.8, 3, 4, 5, 10, 20 or 30 Angstroms and 60 Angstroms. Optionally, L is characterized as having a length of between 2.8 and 19 Angstroms, or between 4 and 19 Angstroms.

Examples of compounds of Formula Ia include but are not limited to compound having the $(C)_n$, X, L, V, Y and Z groups shows in Table 2 herein. Examples of compounds of Formula Ib include but are not limited to compound having the $(C)_n$, X, L, V, Y and R groups shows in Table 3 herein. R groups in Table 3 indicated as (S) can also be $S(C=O)CH_3$ when present as a protected reactive group. The symbol (–) in the tables indicates that the particular X, L, V or Y moiety is absent. V and Y groups, for example, can comprise any structural features in the sections titled "The V Moiety" and "The Y Moiety" herein. The L, V and/or Y groups of Formulae Ia and Ib represented in each of Tables 2 and 3 can have r, q, and/or z sites of attachment for the respective V, Y, and R or Z groups, where r and q represent the degree of branching or polymerization; r, q, and/or z can be selected from 1, 2, 3 or 4.

A compound may contain more than one L moiety. Any L' moiety can be defined in the same way as a L moiety. The L moieties may or may not be the same. The linking group L may be a water-soluble moiety or contain one or more water-soluble moieties, such that L contributes to the water solubility of a compound of Formula (I)-(VI). An L may also be a moiety or contain one or more moieties that reduce(s) aggregation, which may or may not be a moiety/moieties that also increase(s) the water solubility.

L may be for example a linear linker or a branched linker. In one aspect, the L moiety is branched, optionally further a dendritic structure, so that it can be connected to at least two, three, four or more V, Y or R moieties (or Z where applicable). Each V—Y moiety is however only attached once to an L moiety. Branching can occur at one or more branching atoms that may for example be carbon, nitrogen, silicon, or phosphorus.

When the lysine-based linker comprises branching in L, the number of branches in L that are connected to V and/or Y will generally be prepared so as to equal the total number of branches available for reaction. That is, in preparing the lysine-based linker, chemical conversion will preferably be carried to completion, thereby maintain the controlled stoichiometry offered by the site-specific TGase-mediated conjugation approach. Thus, preferably, when L is branched, compounds of will be functionalized such that each L, V or Y is connected to a R or Z moiety, such that the components of the mixture of antibodies (or the lysine-based linker during preparation) substantially all have the same r value. For example, it can be specified that 90%, 95%, 98% of the antibodies or the lysine-based linker have the same r value. In one embodiment, L is a linear linker. In another embodiment, L is a branched linker.

Any one of the L moieties disclosed herein can be utilized in Formula Ia, Ib, Ic, II, IVa, and IVb. Any one of the L moieties described herein can be used in combination with any of the $(C)_n$, X, V, Y, Z, R, M, z, q, and r groups described herein. Any one of the L' moieties disclosed herein can be utilized in Formula III. Any one of the L' moieties described herein can be used in combination with any of the R', V', Y', Z, z', q', and r' groups described herein.

Exemplary linkers of Formula Ia include but are not limited to:

Compound Ia-1

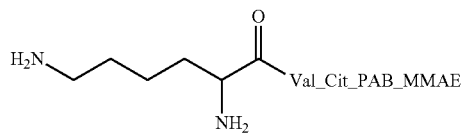

Compound Ia-2

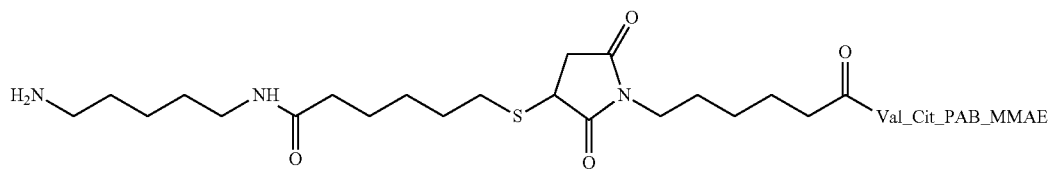

Compound Ia-3

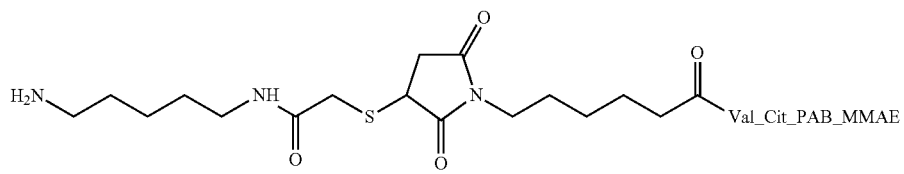

-continued
Compound Ia-4
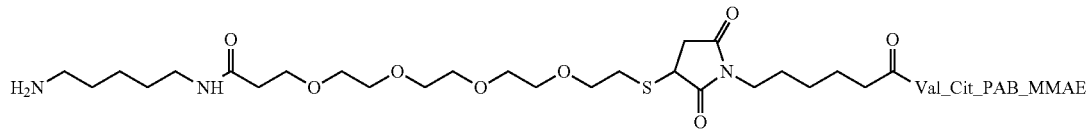
Compound Ia-5
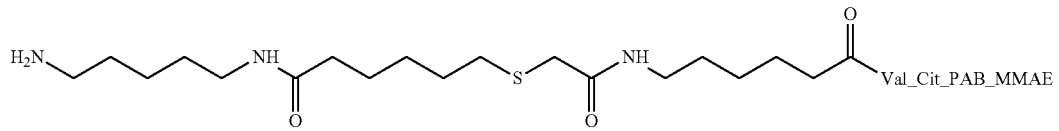
Compound Ia-6
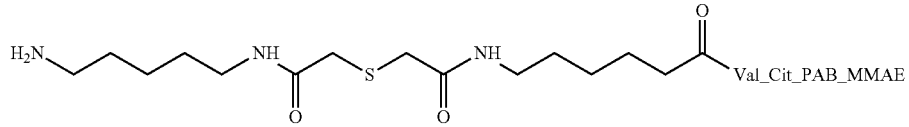
Compound Ia-7
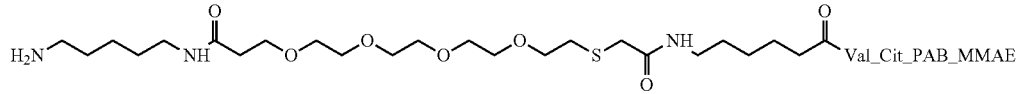
Compound Ia-8
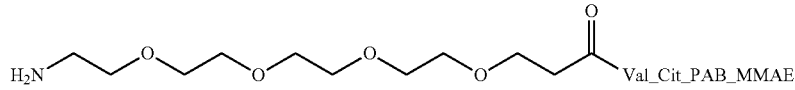
Compound Ia-9
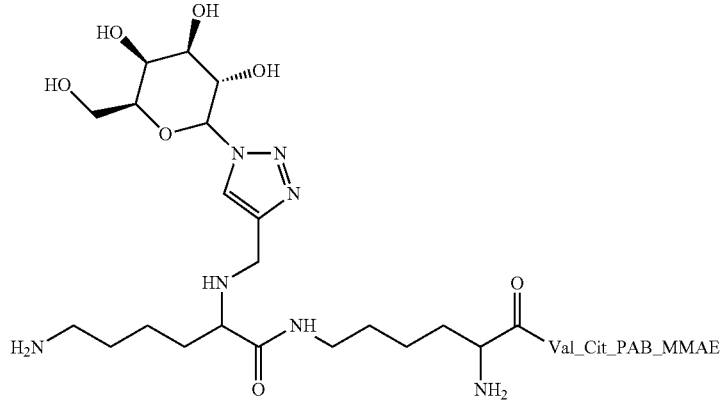
Compound Ia-10
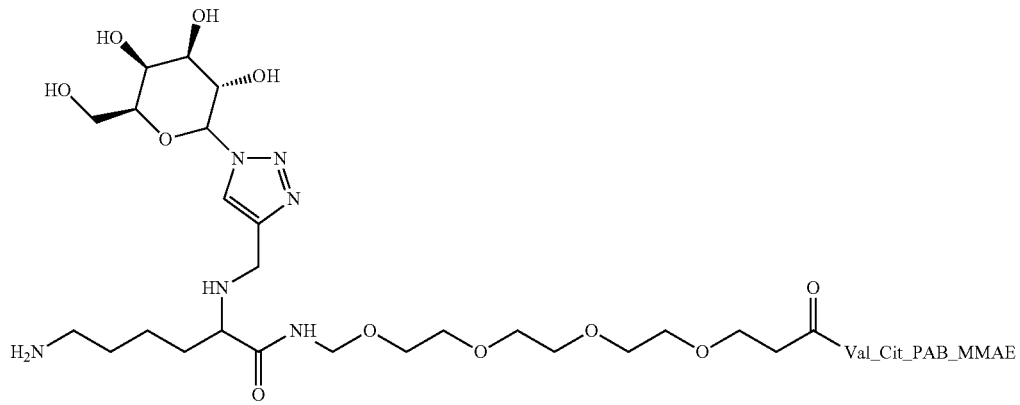
Compound Ia-11
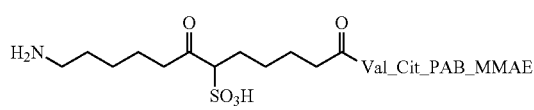
Compound Ia-12
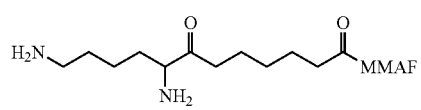

-continued
Compound Ia-13
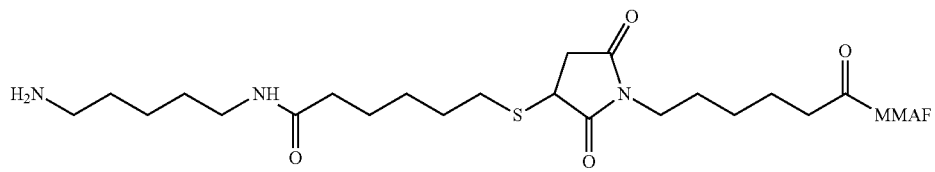
Compound Ia-14
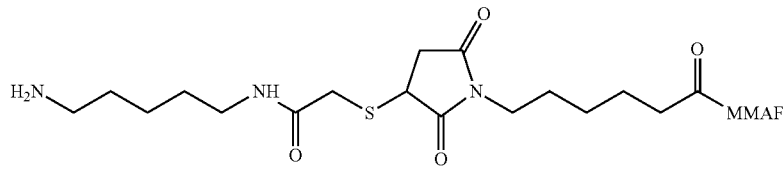
Compound Ia-15
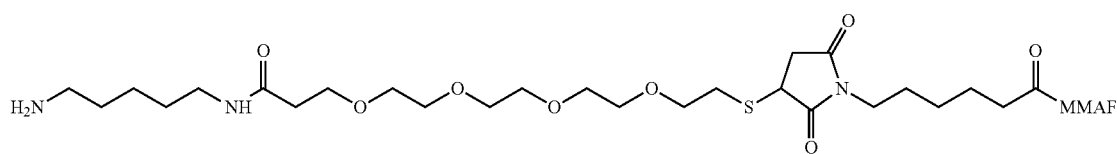
Compound Ia-16
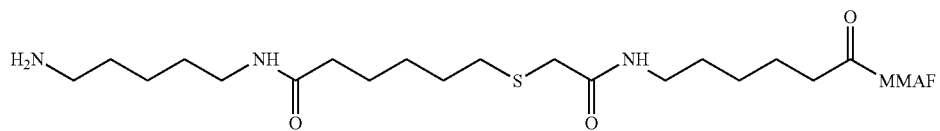
Compound Ia-17
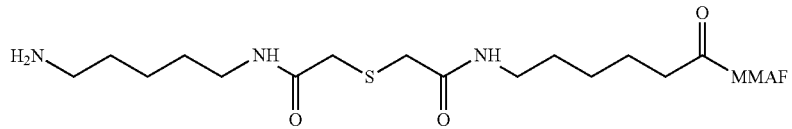
Compound Ia-18
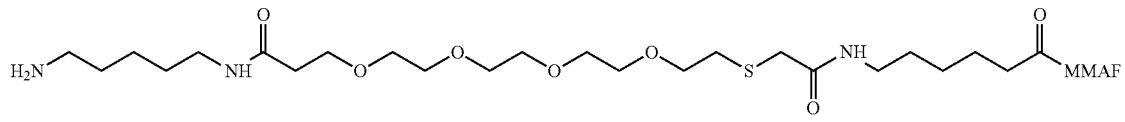
Compound Ia-19
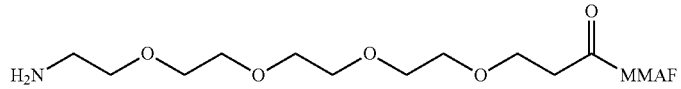
Compound Ia-20
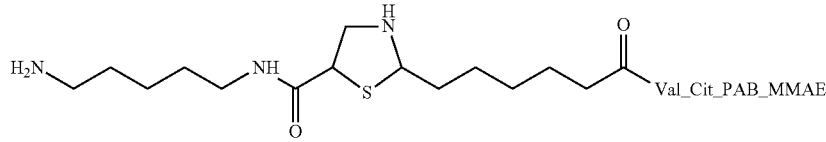
Compound Ia-21
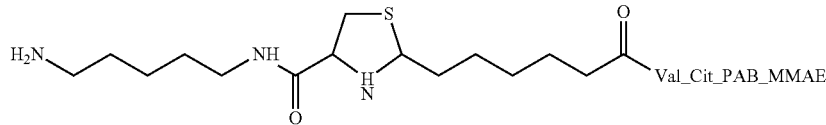
Compound Ia-22
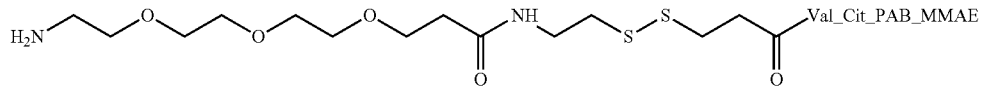
Compound Ia-23
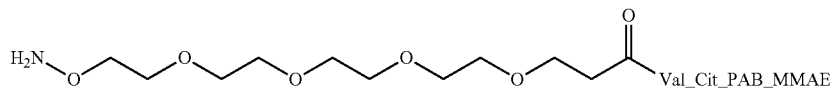

Exemplary linkers of Formula Ib include but are not limited to:
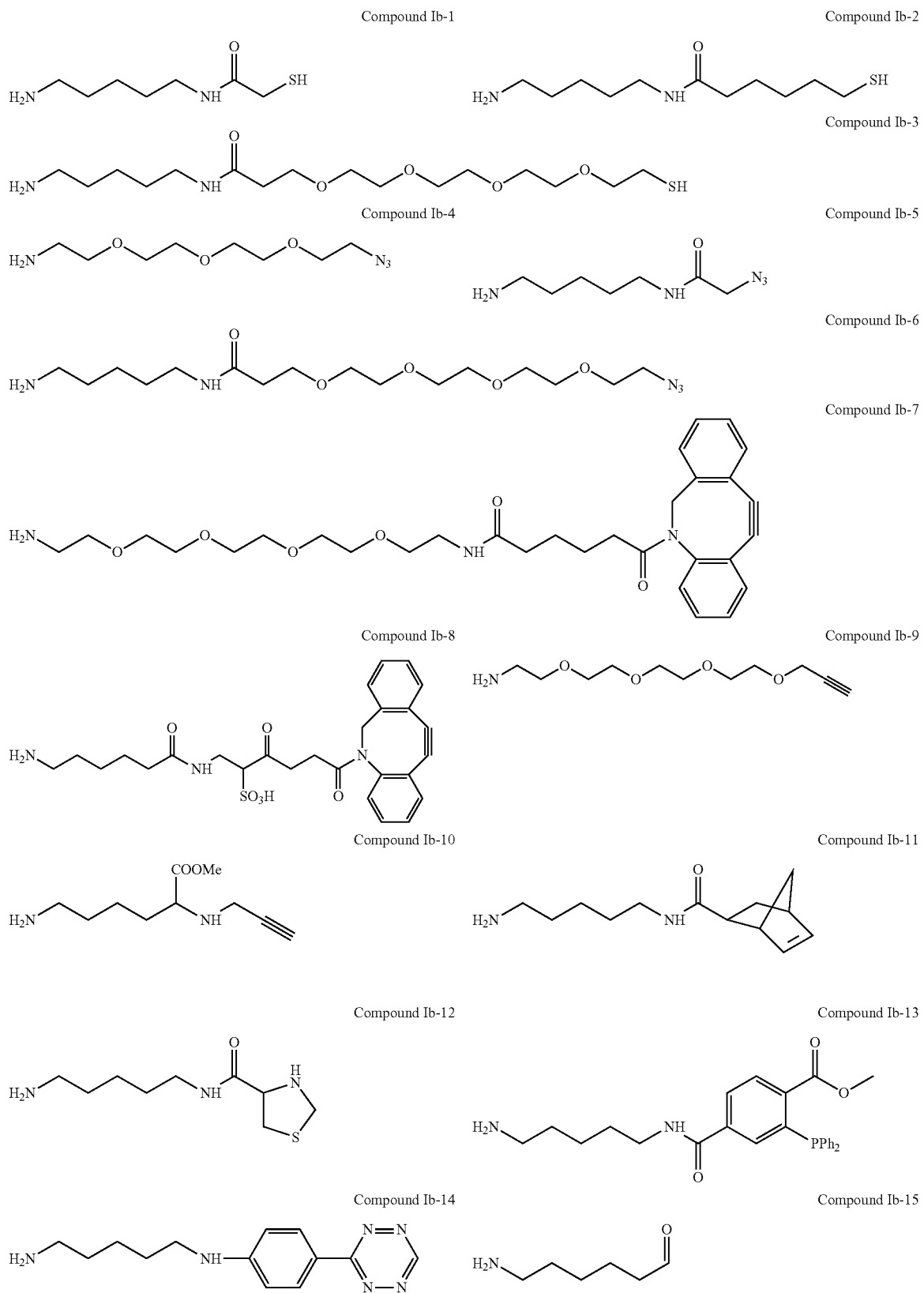

The Reactive Moiety R

R is a reactive moiety, for example a moiety comprising an unprotected or protected bioorthogonal-reaction compatible reactive group, for example an unprotected or protected thiol, epoxide, maleimide, haloacetamide, o-phoshenearomatic ester, azide, fulminate, sulfonate ester, alkyne, cyanide, amino-thiol, carbonyl, aldehyde, generally any group capable of oxime and hydrazine formation, 1,2,4,5-tetrazine, norbornene, other stained or otherwise electronically activated alkene, a substituted or unsubstituted cycloalkyne, generally any reactive groups which form via bioorthogonal cycloaddition reaction a 1,3- or 1,5-disubstituted triazole, any diene or strained alkene dienophile that can react via inverse electron demand Diels-Alder reaction, a protected or unprotected amine, a carboxylic acid, an aldehyde, or an oxyamine.

When more than one R group is present in a compound of the formula, the R groups will preferably be compatible such that no R group is a complementary reagent to any other R group. The L, V and/or Y groups of formulae I-IV can have r, q, and/or z sites of attachment for the respective V, Y, and R groups, where r and q represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

The reactive group of the linking reagent can for example chosen to undergo thio-maleimide (or haloacetamide) addition, Staudinger ligation, Huisgen 1,3-cycloaddition (click reaction), or Diels-Alder cycloaddition with a complementary reactive group attached to an agent comprising a therapeutic moiety, a diagnostic moiety, or any other moiety for a desired function.

Optionally, two or more compatible reactive groups can be attached to the linking reagent.

In one embodiment, the reactive group is a haloacetamide, (e.g. bromo-acetamide, iodo-acetamide, cloro-acetamide). Such reactive groups will be more stable in vivo (and in serum) compared with maleimide groups.

In one embodiment, the reactive group is a reagent capable of undergoing a "click" reaction. For example a 1,3-dipole-functional compound can react with an alkyne in a cyclization reaction to form a heterocyclic compound, preferably in the substantial absence of added catalyst (e.g., Cu(I)). A variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

Examples include o-phosphenearomatic ester, an azide, a fulminate, an alkyne (including any strained cycloalkyne), a cyanide, an anthracene, a 1,2,4,5-tetrazine, or a norbornene (or other strained cycloalkene).

In one embodiment, R is a moiety having a terminal alkyne or azide; such moieties are described for example in U.S. Pat. No. 7,763,736, the disclosure of which is incorporated herein by reference. Suitable reaction conditions for use of copper (and other metal salt) as catalysts of click-reactions between terminal alkynes and azides are provided in U.S. Pat. No. 7,763,736.

In one embodiment, R is a substituted or unsubstituted cycloalkyne. Cycloalkynes, including heterocyclic compounds, will preferably be used in linking reagents in which an L group is present, preferably wherein L is an alkyl or heteroalkyl chain of 3-30, optionally 5-30 or 5-15 linear carbon atoms, optionally substituted at one or more atoms. Optionally, L is a $(CH_2-CH_2-O)_{1-24}$ group or a $(CH_2)_{x1}-(CH_2-O-CH_2)_{1-24}(CH_2)_{x2}-$, wherein $x_1$ and $x_2$ are independently an integer selected among the range of 0 to 20. As shown herein, presence of an L group enables high TGase-mediated coupling when cycloalkynes are used.

Cycloalkynes, including specific compounds, are described for example in U.S. Pat. No. 7,807,619, the disclosure of which is incorporated herein by reference.

In some embodiments, a cycloalkyne may be a compound of Formula A:

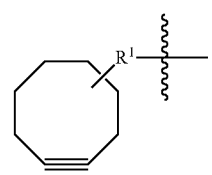

Formula A where:

$R^1$ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, and a halosulfonyl;

$R^1$ can be at any position on the cyclooctyne group other than at the two carbons joined by the triple bond.

In some embodiments, the modified cycloalkyne is of Formula A, wherein one or more of the carbon atoms in the cyclooctyne ring, other than the two carbon atoms joined by a triple bond, is substituted with one or more electron-withdrawing groups, e.g., a halo (bromo, chloro, fluoro, iodo), a nitro group, a cyano group, a sulfone group, or a sulfonic acid group. Thus, e.g., in some embodiments, a subject modified cycloalkyne is of Formula B:

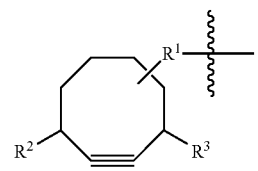

Formula B where:

each of $R^2$ and $R^3$ is independently: (a) H; (b) a halogen atom (e.g., bromo, chloro, fluoro, iodo); (c) $-W-(CH_2)_n-Z$ (where: n is an integer from 1-4 (e.g., n=1, 2, 3, or 4); W, if present, is O, N, or S; and Z is nitro, cyano, sulfonic acid, or a halogen); (d) $-(CH_2)_n-W-(CH_2)_n-R^4$ (where: n and m are each independently 1 or 2; W is O, N, S, or sulfonyl; if W is O, N, or S, then $R^4$ is nitro, cyano, or halogen; and if W is sulfonyl, then $R^4$ is H); or (e) $R^4$ (where: n is an integer from 1-4 (e.g., n=1, 2, 3, or 4); and $R^4$ is nitro, cyano, sulfonic acid, or a halogen); and $R^1$ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone and a halosulfonyl. $R^1$ can be at any position on the cyclooctyne group other than at the two carbons linked by the triple bond.

In one embodiment, R is a substituted or unsubstituted heterocyclic strained alkyne. Cycloalkynes, including specific compounds, are described for example in U.S. Pat. No. 8,133,515, the disclosure of which is incorporated herein by reference. In one embodiment, the alkyne is of the Formula C:

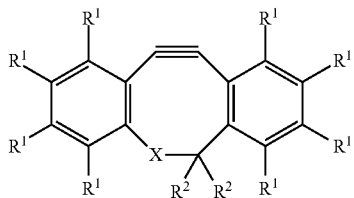

Formula C wherein:

each $R^1$ is independently selected from the group consisting of hydrogen, halogen, hydroxy, alkoxy, nitrate, nitrite, sulfate, and a $C_1$-$C_{10}$ alkyl or heteroalkyl;

each $R^2$ is independently selected from the group consisting of hydrogen, halogen, hydroxy, alkoxy, nitrate, nitrite, sulfate, and a $C_1$-$C_{10}$ organic group; X represents N—$R^3R^4$, NH—$R^4$, CH—N—$OR^4$, C—N—$NR^3R^4$, $CHOR_4$, or $CHNHR_4$; and each $R^3$ represents hydrogen or an organic group and $R^4$ represents linking moiety C (or $(C)_n$) of a linker. In one embodiment, R or R' is a DBCO (dibenzycyclooctyl) group below:

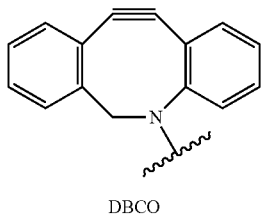 [SMILES: *N1Cc2ccccc2C#Cc2ccccc21 ; "DBCO"]

DBCO

Alkynes such as those described herein above can be reacted with at least one 1,3-dipole-functional compound (e.g., embodied as an R' moiety in a compound of Formula III) in a cyclization reaction to form a heterocyclic compound, preferably in the substantial absence of added catalyst (e.g., Cu(I)). A wide variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

The reactive moiety R is connected to L, or when present, V or Y, and is able to react with a suitable functional group (R') on a reaction partner, e.g. a complementary reagent of Formula III which undergoes a high conversion addition reaction when brought into contact with a reactive moiety R. When reactive moiety R is present in an antibody of Formula II, the reaction results in formation of an antibody of Formula IV. In this reaction, the moieties R and R' are transformed into the moiety (RR'). Any R' moiety can be defined in the same way as a R moiety, so long as R and R' are complementary when used in moieties that are to be reacted together.

A compound may contain more than one reactive moiety R. The R moieties may or may not be the same. Any one of the R moieties disclosed herein can be utilized in Formula Ib and II. Any one of the R moieties described herein can be used in combination with any of the $(C)_n$, X, L, V, Y, z, q, and r groups described herein. Any one of the R' moieties disclosed herein can be utilized in Formula III. Any one of the R' moieties described herein can be used in combination with any of the L', V', Y', Z, z', q', and r' groups described herein.

FIG. 1 shows reaction schemes for thio-maleimide additions, Staudinger ligations, and Diels-Alder cycloadditions, where reactive groups of linking reagents having a single reactive functionality combine with complementary reactive group attached to a therapeutic or diagnostic moiety.

Figure 2:
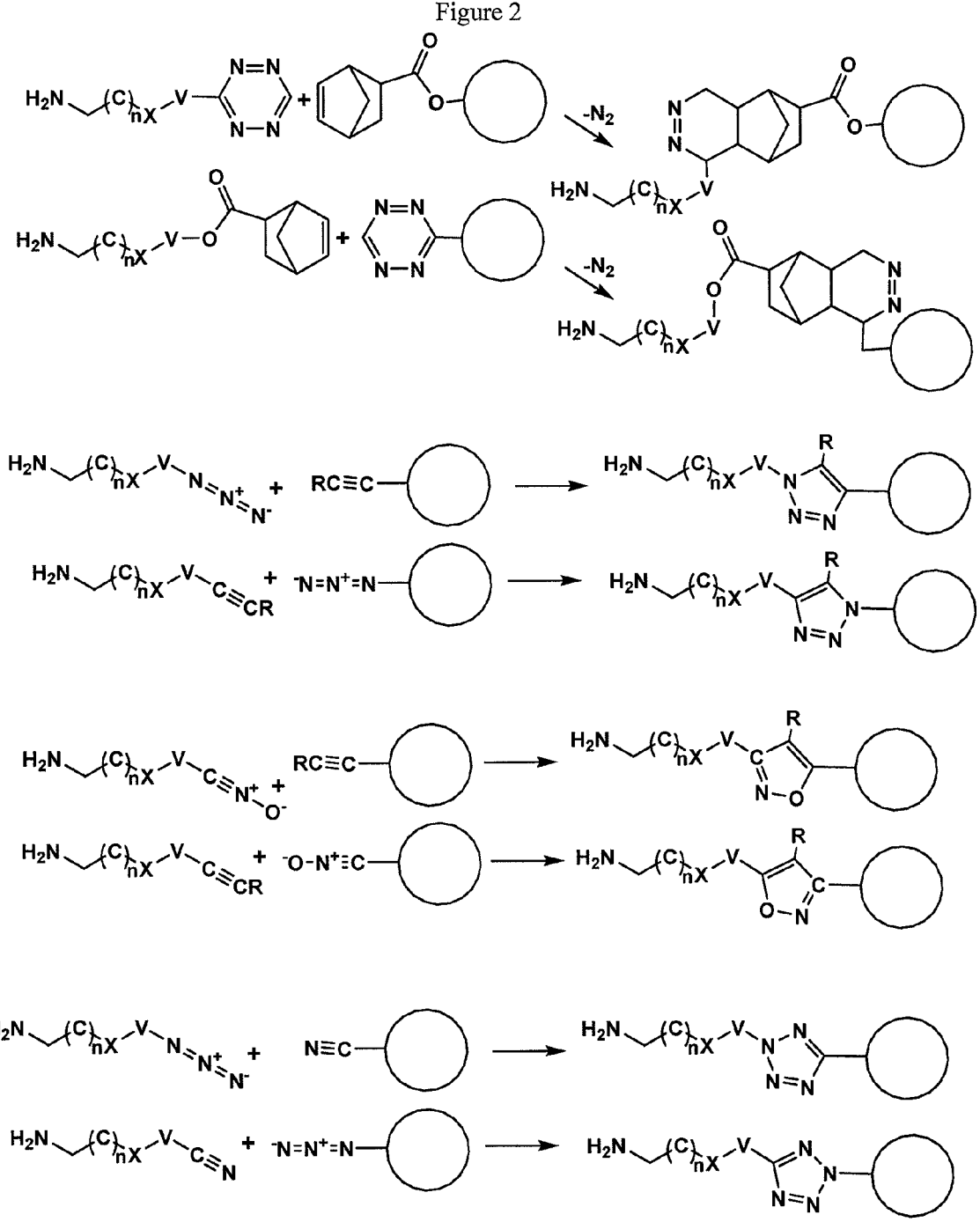
FIG. 2 shows reaction schemes for Diels-Alder cycloadditions and click reactions where the reactive groups of linking reagents combine with complementary reactive group attached to an agent including a therapeutic, diagnostic, or other moiety.

FIG. 2 shows reaction schemes for Diels-Alder cycloadditions and click reactions where the reactive groups of linking reagents combine with complementary reactive group attached to an agent including a therapeutic, diagnostic, or other moiety.

It should be understood that, although not illustrated in FIGS. 1 and 2, the $H_2NCH_2$ group of the linking reagent may have undergone reaction with the glutamine residue of a protein (e.g. antibody) prior to the high conversion addition reaction or that the aminomethylene may be in a protected state. Alternatively, in other embodiments, the $H_2NCH_2$ group of the linking reagent will not have undergone reaction with the glutamine residue of a protein (e.g. antibody) prior to the high conversion addition reaction or that the aminomethylene may be in a protected state; in this case the linking reagent and reaction partner can be used to conveniently form various combinations of linkers having different V, Y, and/or Z moieties that are ready to conjugate to an antibody.

Figure 3:
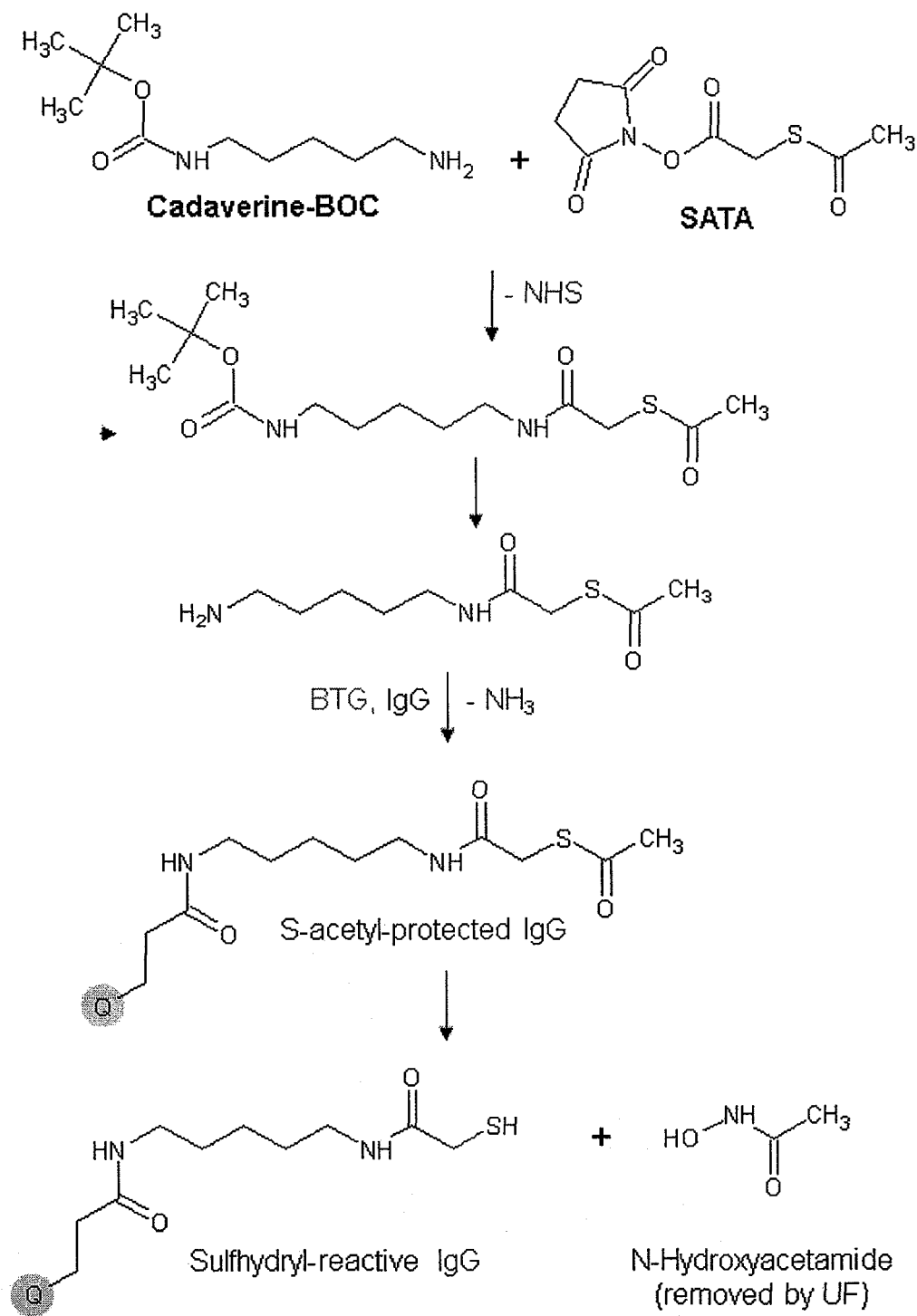
FIG. 3 shows the preparation of an exemplary linking reagent and its conjugation with a protein, where: V and Y are absent, R is a thiol (sulfhydryl) reactive group that is ultimately generated from the S-acetyl protected thiol, $SC(O)CH_3$, r is 0; q is 0; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein.
Figure 4:
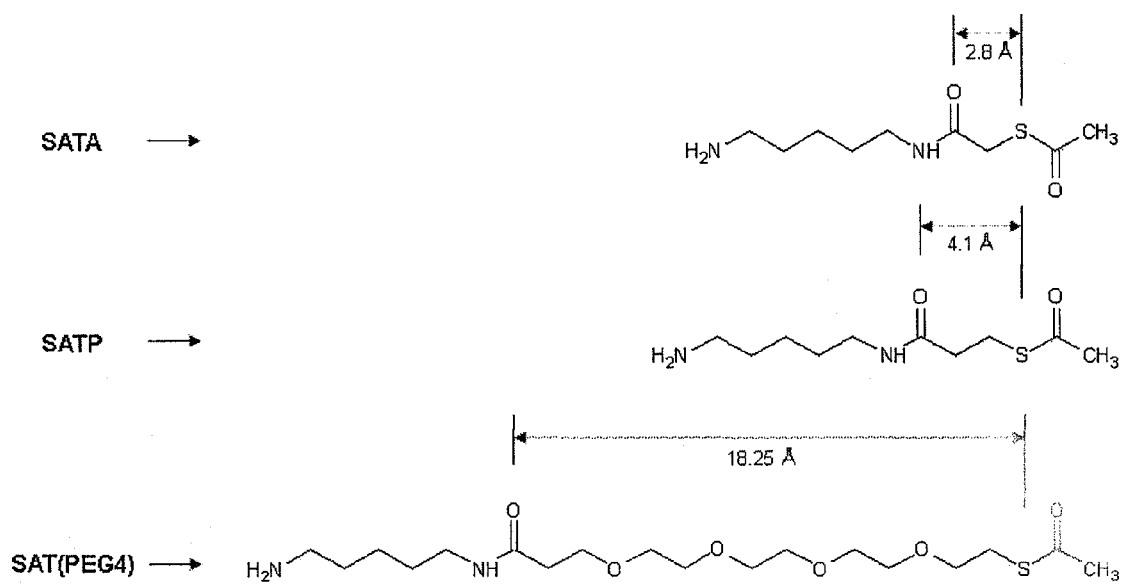
FIG. 4 illustrates the preparation of various exemplary linking reagents, according to various embodiments disclosed herein, with a single S-acetyl protected thiol reactive group that can be prepared from an N-succinimidyl-S-acetylthioester reagent.

The preparation of an exemplary linking reagent, according to one embodiment, and its conjugation with a protein is illustrated in FIG. 3, where: V and Y are absent, R is a thiol (sulfhydryl) reactive group that is ultimately generated from the S-acetyl protected thiol, $SC(O)CH_3$, r is 1; q is 1; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein. FIG. 4 illustrates the preparation of various exemplary linking reagents, according to various embodiments, with a single S-acetyl protected thiol reactive group that can be prepared from an N-succinimidyl-S-acetylthioester reagent. In addition to S-acetyl, other S-protecting groups can be employed, including p-hydroxyphenylacyl, 2-quinoline, or Hqm and Hgm groups that can be deprotected by the addition of hydrazine.

Figure 5:
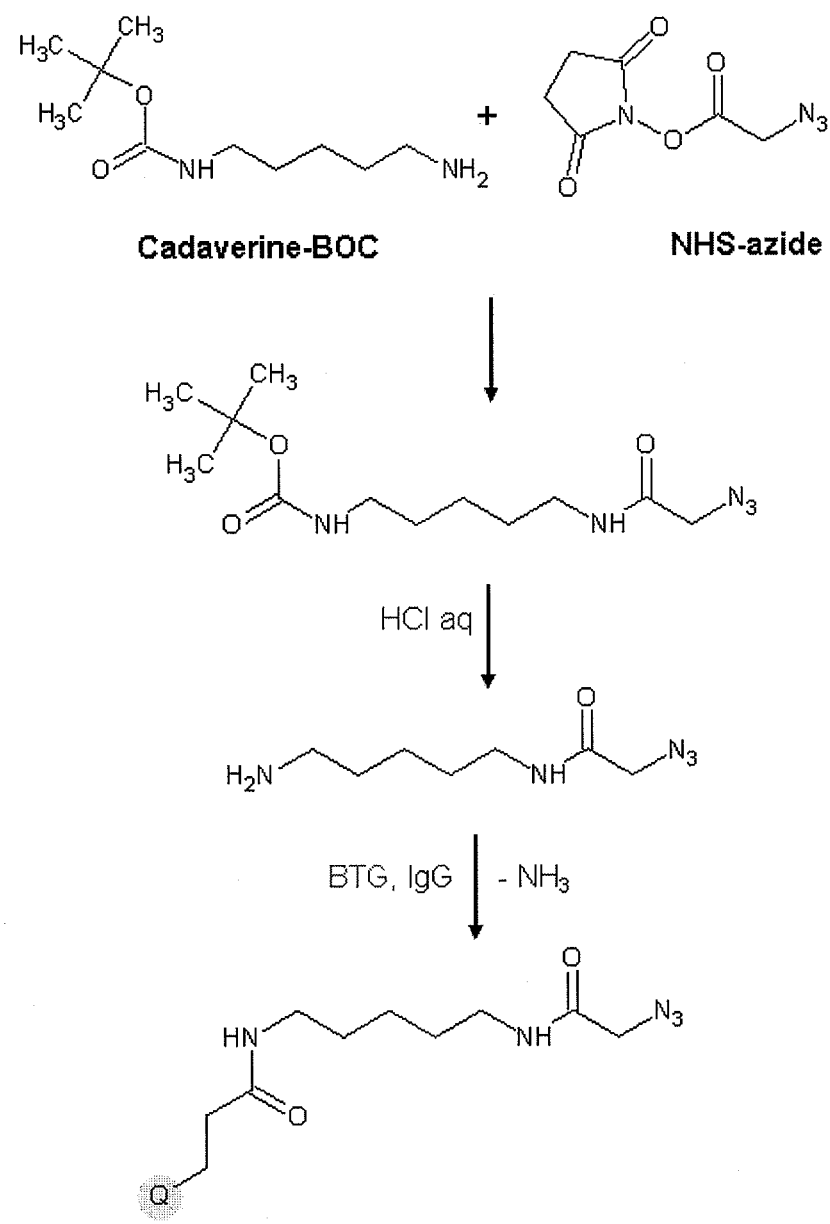
FIG. 5 illustrates the preparation of an exemplary linking reagent, according to an embodiment disclosed herein, and its conjugation with a protein, where: V and Y are absent, R is an azide reactive group, r is 0; q is 0; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein.
Figure 6:
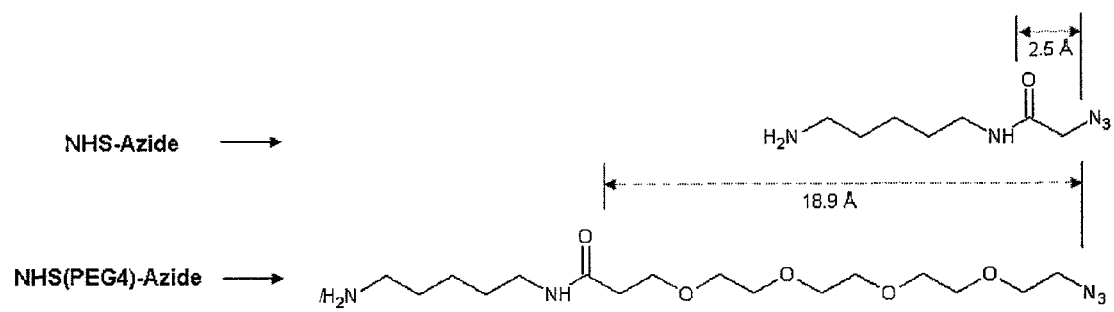
FIG. 6 illustrates the preparation of various exemplary linking reagents, according to embodiments disclosed herein, with a single azide reactive group that can be prepared from an N-succinimidyl-azide reagent.

FIG. 5 illustrates the preparation of an exemplary linking reagent, according to one embodiment, and its conjugation with a protein, where: V and Y are absent, R is an azide reactive group, r is 1; q is 1; z is 1; L is the two carbon comprising framework $C(O)CH_2$; X is NH; $(C)_n$ is $(CH_2)_5$; and G is transformed from the $(H_3C)_3COC(O)$ protecting group to H and ultimately to the amide upon conjugation of a glutamine residue of a protein. FIG. 6 illustrates the preparation of various exemplary linking reagents with a single azide reactive group that can be prepared from an N-succinimidyl-azide reagent.

Figure 7:
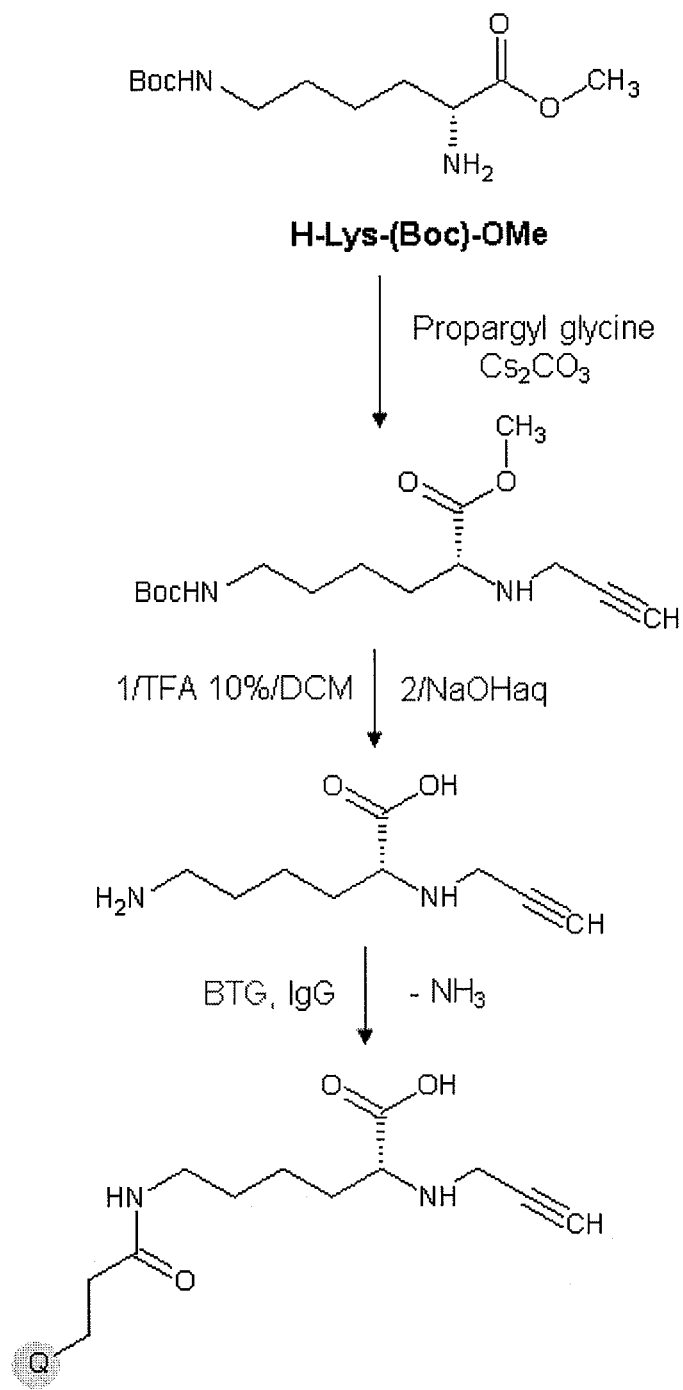
FIG. 7 depicts the preparation of an exemplary linking reagent, according to an embodiment disclosed herein, and its conjugation with a protein, where: V and Y are absent, R is an alkyne reactive group, r is 0; q is 0; z is 1; L is a one carbon comprising framework $CH_2$; X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein.
Figure 8:
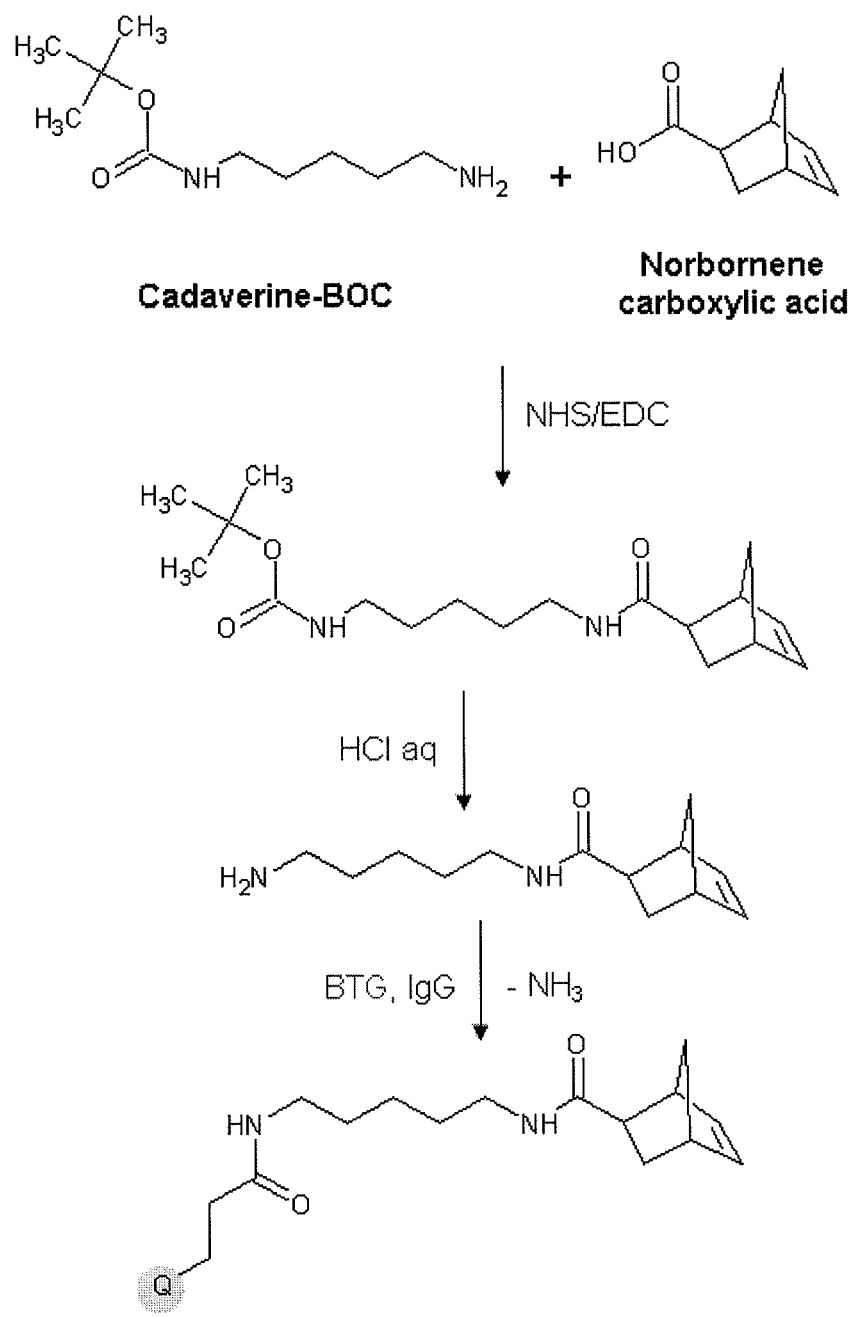
FIG. 8 shows the preparation of an exemplary linking reagent, according to an embodiment disclosed herein, and its conjugation with a protein, where: R is a norbornene reactive group, r is 0; q is 0; z is 1; L is the one carbon comprising framework $C(O)$; X is NH; $(C)_n$ is $(CH_2)_4CH(CO_2H)$; and G is transformed from the $(H_3C)_3COC(O)$ protecting group to H and ultimately to the amide upon conjugation of a glutamine residue of a protein.
Figure 9:
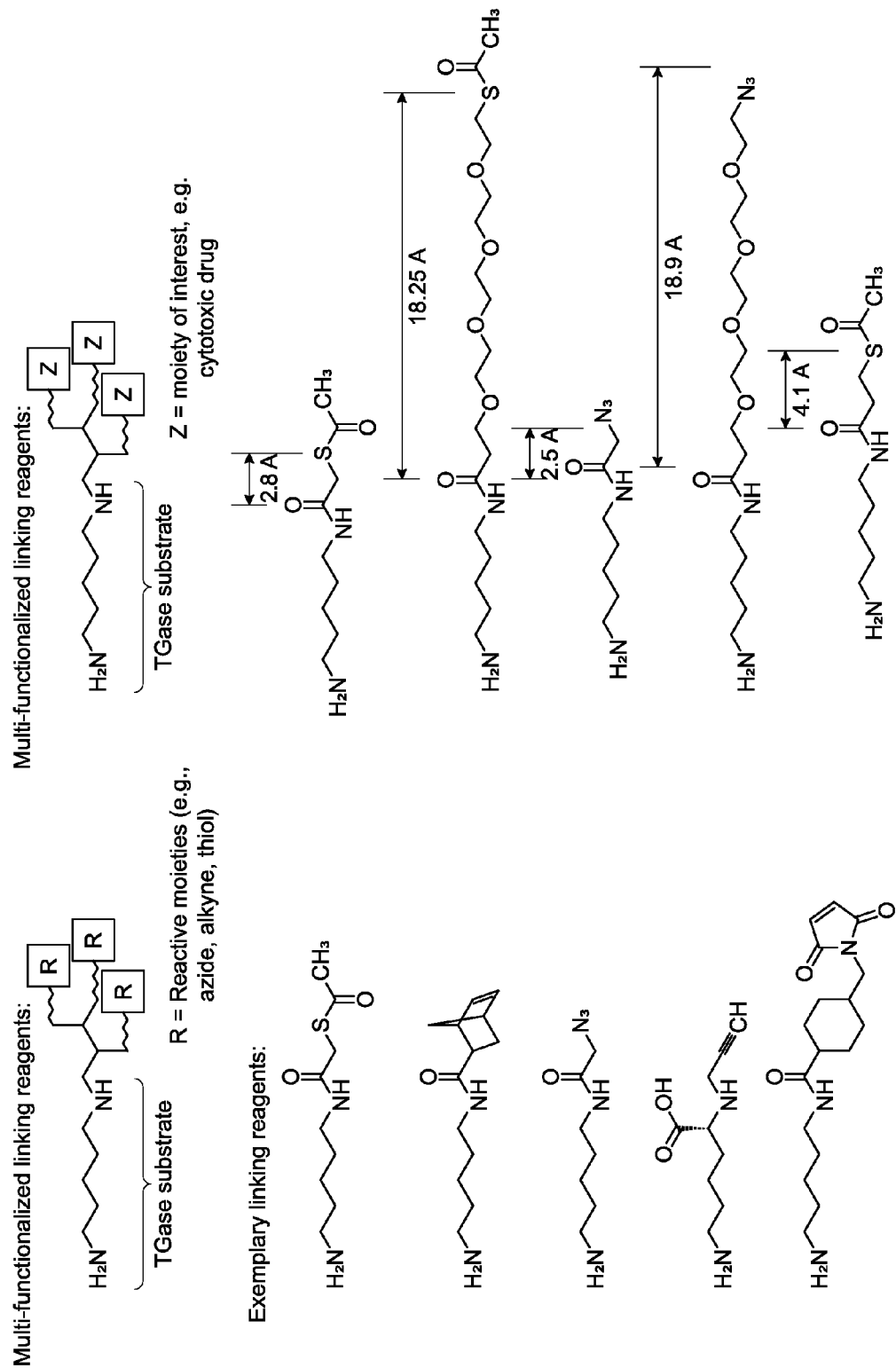
FIG. 9 shows various examples of linking reagents disclosed herein.
Figure 10A:
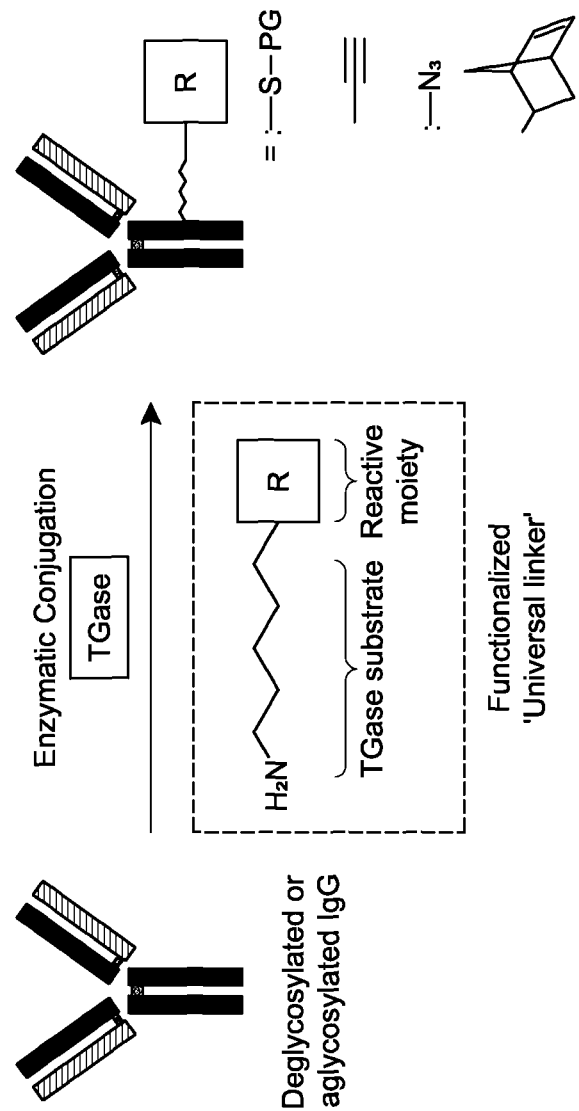
FIGS. 10A and 10B show a general scheme for preparing conjugated antibodies.
Figure 10B:
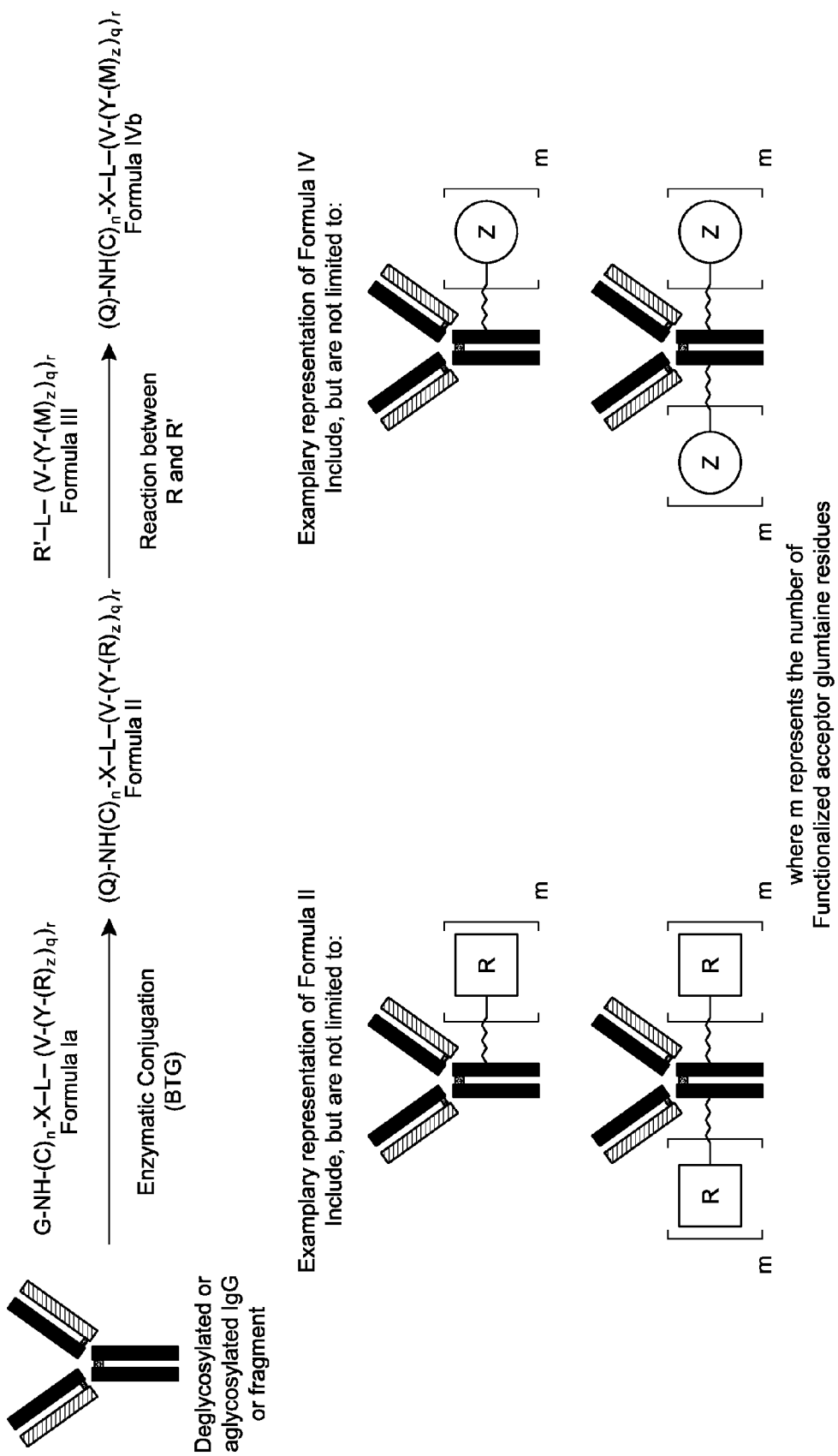
Figure 11:
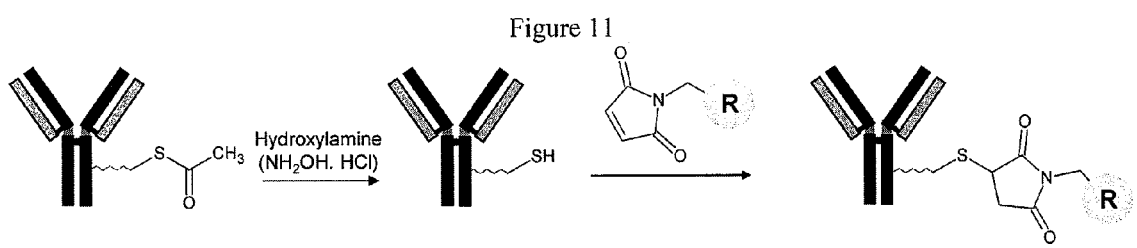
FIG. 11 shows a scheme for preparing an antibody conjugate from a S-acetyl-cadaverin linker of FIG. 3, where "R" in the figure is a moiety-of-interest Z.
Figure 12:
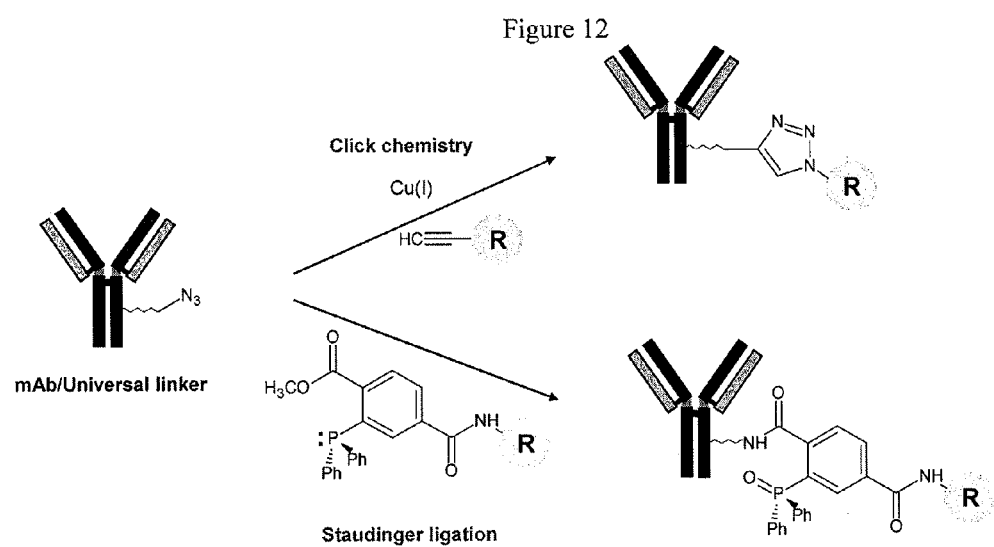
FIG. 12 shows a scheme for preparing an antibody conjugate from an azide-cadaverin linker of FIG. 5, where "R" in the figure is a moiety-of-interest Z.
Figure 13:
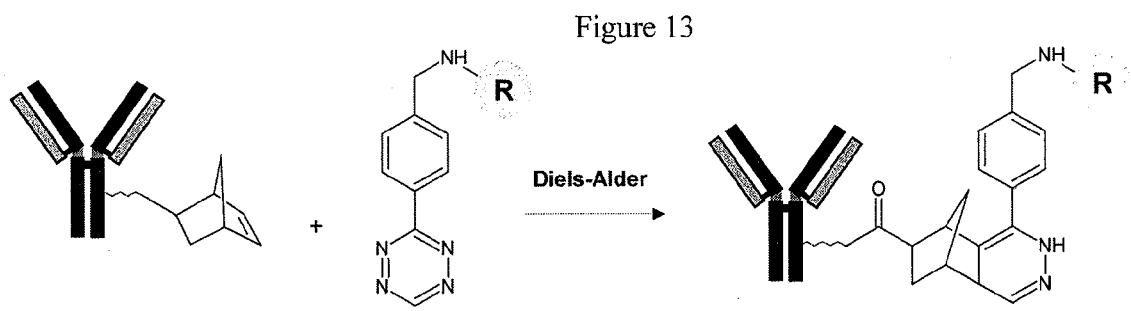
FIG. 13 shows a scheme for preparing an antibody conjugate from a norbornyl-cadaverin linker of FIG. 8, where "R" in the figure is a moiety-of-interest Z.
Figure 14:
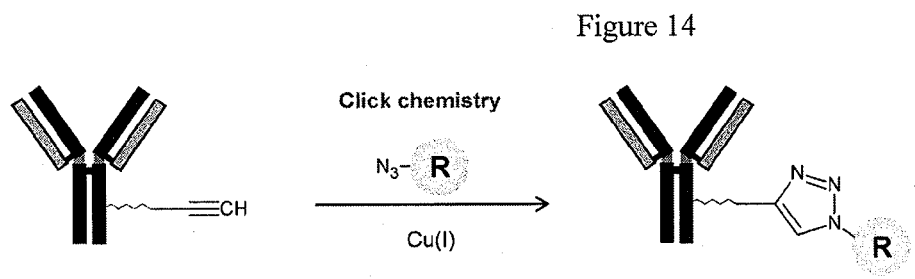
FIG. 14 shows a scheme for preparing an antibody conjugate from alkyne-lysine linker of FIG. 7, where "R" in the figure is a moiety-of-interest Z.

FIG. 7 depicts the preparation of an exemplary linking reagent, according to an embodiment of the invention, and its conjugation with a protein, where: V and Y are absent, R is an alkyne reactive group r is 1; q is 1; z is 1; L is a one carbon comprising framework $CH_2$; X is NH; $(C)_n$ is $(CH_2)$ $_4$CH(CO$_2$H); and G is transformed from the (H$_3$C)$_3$COC(O) protecting group to H and ultimately to the amide upon conjugation of a glutamine residue of a protein. FIG. 8 shows the preparation of an exemplary linking reagent and its conjugation with a protein, where: R is a norbornene reactive group; r is 1; q is 1; z is 1; L is the one carbon comprising framework C(O); X is NH; (C)$_n$ is (CH$_2$)$_4$CH (CO$_2$H); and G is transformed from the (H$_3$C)$_3$COC(O) protecting group to H and ultimately to the amide upon conjugation of a glutamine residue of a protein.

The selective and very high conversion addition reaction that can be carried out with the linking reagents, according to this aspect, can be uncatalyzed or catalyzed reactions. For example, the 2+4 Diels-Alder cycloadditions, thio-maleimide (or haloacetamide) additions, and Staudinger ligations can be carried out without a catalyst. Other very high conversion addition reactions, for example any of the click reactions, can be catalyzed with metal salts, such as Cu, Ru, Ni, Pd, and Pt salts.

The linking group (RR') in M of compounds of Formula IV represents the remainder of R when the reactive moiety R of Formula II has reacted with a reactive moiety R' in a compound of Formula III. This group (RR') then links the moiety Z (e.g. comprised in the compound of formula IV) with L, V or Y. The group that remains may be a bond.

The V Moiety

The V moiety may be incorporated in the lysine-based linker (e.g. connected to L, optionally through Y). However, the V moiety may instead or in addition be incorporated in a compound comprising a moiety-of-interest Z (e.g. a compound R'—V—Y—Z of formula III) that will be reacted with an antibody conjugated with a lysine-based linker to form an antibody conjugated to the moiety-of-interest Z. Any V' moiety can be defined in the same way as a V moiety.

The V moiety is a group that is either non-cleavable or conditionally cleavable, optionally after prior conditional transformation. In the latter case, it is designed to be transformed and/or cleaved from Y, or Z when Y is absent, by a chemical, photochemical, physical, biological, or enzymatic process, e.g. in certain conditions. This condition may for example comprise bringing a compound in an aqueous environment, which leads to hydrolysis of V, or bringing a compound in an environment that contains an enzyme that recognizes and cleaves V, or bringing a compound under reducing conditions, which leads to reduction of V, or bringing a compound in contact with radiation, e g, UV light, which leads to transformation and/or cleavage, or bringing a compound in contact with heat, which leads to transformation and/or cleavage, or bringing a compound under reduced pressure or bringing a compound under elevated or high pressure, which leads to transformation and/or cleavage. This condition may further be met after administrating a compound to an animal, e.g., a mammal: the condition may be met when the compound localizes to for example a specific organ, tissue, cell, subcellular target, or microbial target, for example by the presence of internal factors (e.g., target-specific enzymes or hypoxia) or application of external factors (e g., radiation, magnetic fields) or the condition may already be met directly upon administration (e.g., enzymes). In general, transformation of V will directly or indirectly lead to cleavage of V from Y, or Z when Y is absent. It may occur that two or more separate transformations and/or cleavages, requiring the same or different conditions, are required in order to cleave V completely from Y or Z. In this way, increased selectivity may be obtained. A compound may contain more than one V moiety. These V moieties may or may not be the same and may or may not require the same conditions for transformation and/or cleavage.

V may comprise for example a carbon comprising framework of 1 to 200 atoms, optionally a carbon comprising framework of at least 10 atoms, e.g. 10 to 100 atoms or 20 to 100 atoms, substituted at one or more atoms, optionally wherein the carbon comprising framework is a linear hydrocarbon or comprises a cyclic group, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), an amino acid, a di-, tri-, tetra-, or oligopeptide, or more generally any dimer, trimer, or higher oligomer (linear, asymmetrically branched or symmetrically branched) resulting from any chain-growth or step-growth polymerization process.

Generally, V may be any straight, branched and/or cyclic C$_{2-30}$ alkyl, C$_{2-30}$ alkenyl, C$_{2-30}$ alkynyl, C$_{2-30}$ heteroalkyl, C$_{2-30}$ heteroalkenyl, C$_{2-30}$ heteroalkynyl, optionally wherein one or more homocyclic aromatic compound radical or heterocyclic compound radical may be inserted; notably, any straight or branched C$_{2-5}$ alkyl, C$_{5-10}$ alkyl, C$_{11-20}$ alkyl, —O—C$_{1-5}$ alkyl, —O—C$_{5-10}$ alkyl, —O—C$_{11-20}$ alkyl, or (CH$_2$—CH$_2$—O—)$_{1-24}$ or (CH$_2$)$_{x1}$—(CH$_2$—O—CH$_2$)$_{1-24}$—(CH$_2$)$_{x2}$-group, wherein x1 and x2 are independently an integer selected among the range of 0 to 20, an amino acid, an oligopeptide, glycan, sulfate, phosphate, or carboxylate. Optionally, V may be or absent. In some embodiments, V is a C$_{2-6}$ alkyl group.

In one aspect, a compound is used to target one or more therapeutic and/or diagnostic moieties Z to target cells. In this instance, V may for example contain a substrate molecule that is cleaved by an enzyme present in the vicinity of the target cells or inside the target cells, for example tumor cells. V can for example contain a substrate that is cleaved by an enzyme present at elevated levels in the vicinity of or inside the target cells as compared to other parts of the body, or by an enzyme that is present only in the vicinity of or inside the target cells.

If target cell specificity is achieved solely based upon the selective transformation and/or cleavage of V at the target site, the condition (eventually) causing the cleavage should preferably, at least to a certain degree, be target cell-specific, whereas the presence of another target-specific moiety in the compound, for instance when the antibody recognizes an antigen present on a target cell with a degree of specificity, reduces or takes away this requirement. For example, when an antibody causes specific internalization into a target cell, an enzyme also present in other cells may transform and/or cleave V. In one embodiment, transformation and/or cleavage of V occurs intracellularly. In another embodiment, transformation and/or cleavage of V occurs extracellularly.

In one embodiment, the V moiety is a conditionally cleavable moiety.

In one embodiment, V contains a di-, tri-, tetra-, or oligopeptide which consists of an amino acid sequence recognized by a protease, for example plasmin, a cathepsin, cathepsin B, prostate-specific antigen (PSA), urokinase-type plasminogen activator (u-PA), or a member of the family of matrix metalloproteinases, present in the vicinity of or inside the target cells, for example tumor cells. In one embodiment the disclosure provides a conjugate wherein V is a dipeptide, tripeptide, tetrapeptide, or oligopeptide moiety comprised of natural L amino acids, unnatural D amino acids, or synthetic amino acids, or a peptidomimetic, or any combination thereof. In one embodiment, V is a peptide. In another embodiment, V is a dipeptide. In another embodiment, V is a tripeptide. In another embodiment, V is a tetrapeptide. In yet another embodiment, V is a peptidomimetic.

In one embodiment, V contains a substrate for an enzyme.

In another embodiment, V contains a beta-glucuronide that is recognized by beta-glucuronidase present in the vicinity of or inside tumor cells.

In one embodiment, V contains a substrate for an extracellular enzyme. In another embodiment, V contains a substrate for an intracellular enzyme.

In yet another embodiment, V contains a substrate for a lysosomal enzyme.

In yet another embodiment, V contains a substrate for the serine protease plasmin.

In yet another embodiment, V contains a substrate for one or more of the cathepsins, for example cathepsin B. When V is cleaved extracellularly, the one or more Z moieties may be released extracellularly. This may provide the advantage that these Z moieties are not only able to affect or detect the cell(s) directly surrounding the site of activation, but also cells somewhat further away from the site of activation due to diffusion (bystander effect).

In one embodiment the disclosure provides a compound wherein V comprises a tripeptide. The tripeptide may be linked via its C-terminus to Y. In one embodiment, the C-terminal amino acid residue of the tripeptide is selected from arginine, citrulline, and lysine, the middle amino acid residue of the tripeptide is selected from alanine, valine, leucine, isoleucine, methionine, phenylalanine, cyclohexylglycine, tryptophan and proline, and the N-terminal amino acid residue of the tripeptide is selected from any natural or unnatural amino acid.

In another embodiment the disclosure provides to a compound wherein V comprises a dipeptide. The dipeptide may be linked via its C-terminus to Y. In one embodiment, the C-terminal amino acid residue of the dipeptide is selected from alanine, arginine, citrulline, and lysine, and the N-terminal amino acid residue of the dipeptide is selected from any natural or unnatural amino acid. In one embodiment, V is selected from phenylalanine-lysine and valine-citrulline.

An example of a linker comprising a lysine residue as $(C)_n$ moiety and a valine-citrulline as the (V) moiety is shown below:

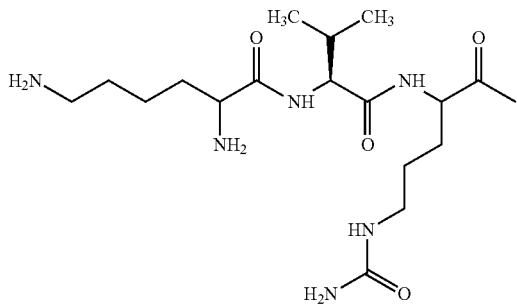 [SMILES: CC(=O)C(CCCNC(N)=O)NC(=O)[C@@H](NC(=O)C(N)CCCCN)C(C)C]

Optionally, the di-, tri-, tetra, or oligopeptide(s) comprise or consist or amino acids with non-negatively charged side chains (amino acids other than aspartic acid or glutamic acid). Optionally, the di-, tri-, tetra, or oligopeptide(s) comprise or consist or amino acids selected from: amino acids with positively charged side chains, amino acids with polar uncharged side chains, and amino acids with hydrophobic side chains.

In another aspect, a compound is used to improve the pharmacokinetic properties of Z. V may in this case for example be or contain a group that is cleaved by ubiquitous enzymes, e.g., esterases that are present in the circulation, by pH-controlled intramolecular cyclization, or by acid-catalyzed, base-catalyzed, or non-catalyzed hydrolysis, or V may for example be or contain a disulfide. V may therefore, optionally together with the connecting atom of L and/or Y (or Z if Y is absent), for example form a carbonate, carbamate, urea, ester, amide, imine, hydrazone, oxime, disulfide, acetal, or ketal group. It is understood that V can also be or contain such a moiety and/or be transformed and/or cleaved in the same or a similar way when a compound of this invention is used for other purposes than solely improving the pharmacokinetic properties of Z.

When the compounds are used for other purposes, e.g., an ex vivo diagnostic assay, V may be or contain any of the moieties mentioned above and transformation and/or cleavage of V may occur by any one of the processes mentioned above or by any other functional transformation or cleavage process known to a person skilled in the art. For example, in a diagnostic assay, V may be cleaved or transformed by an enzyme, by reduction, or below, above, or at a certain pH.

When V is conditionally cleavable, the compounds are designed to eventually release at least one Z after cleavage and optional prior transformation of V. Release of Z from a compound via another mechanism is however not excluded.

In any embodiment, V may contain a blocking group to prevent premature transformation and/or cleavage of V before the condition is met under which V is designed to be transformed and/or cleaved.

In another aspect, V is a moiety that is non-cleavable. This means that V cannot be cleaved from Y, or Z when Y is absent, under the conditions the compound containing such a V moiety is designed to be applied, meaning that Z cannot be released in this way. Release of Z from a compound via another mechanism is however not excluded. When V is a non-cleavable moiety, Y may optionally be absent. A non-cleavable V moiety may be any moiety that cannot be cleaved, or that can be cleaved only very slowly, under the conditions the compound containing such a V moiety is designed to be applied, e.g. in vivo or in vitro. For example, when applied in vivo, V will not or only very slowly be cleaved by enzymes present in the in vivo model used or by hydrolysis or as a consequence of other biological processes that may occur in said model. Such V may therefore, optionally together with the connecting atom of L and/or Z, for example, be a carbonyl group, an amide group, an urea group, an ester group, a carbonate group, a carbamate group, or an optionally substituted methyleneoxy or methyleneamino group V may be preferred to be non-cleavable when it is not required that the one or more moieties Z are released. This may for example be the case when Z does not require to become released before it can exert its therapeutic or diagnostic properties.

In one embodiment V is connected to L via a functional group in the side chain of one of the natural or unnatural amino acids. In another embodiment, the N-terminal amino acid of V is connected via its alpha amino group to L.

Any one of the V moieties disclosed herein can be utilized in Formula Ia, Ib, Ic, II, IVa and IVb. Any one of the V moieties described herein can be used in combination with any of the $(C)_n$, X, L, R, Y, Z, M, z, q, and r groups described herein. Any one of the V' moieties disclosed herein can be utilized in Formula III. Any one of the V' moieties described herein can be used in combination with any of the R', V', Y', Z, z', q', and r' groups described herein.

The Spacer System Y

The spacer system Y, when present, links V and optionally L to one or more moieties R, and following reaction with a compound of Formula III, a moiety-of-interest Z. In one embodiment, Y is absent. In another embodiment, Y is a self-elimination spacer system. A spacer system Y may be incorporated in a compound to for example improve the properties of Z or the compound in general, to provide suitable coupling chemistries, or to create space between V and Z. Any Y' moiety can be defined in the same way as a Y moiety.

Spacer system Y may comprise for example a carbon comprising framework of 1 to 200 atoms, optionally a carbon comprising framework of at least 10 atoms, e.g. 10 to 100 atoms or 20 to 100 atoms, substituted at one or more atoms, optionally wherein the carbon comprising framework is a linear hydrocarbon or comprises a cyclic group, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), an amino acid, a di-, tri-, tetra-, or oligopeptide, or more generally any dimer, trimer, or higher oligomer (linear, asymmetrically branched or symmetrically branched) resulting from any chain-growth or step-growth polymerization process.

Y may be any straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O—$C_{1-5}$ alkyl, —O—$C_{5-10}$ alkyl, —O—$C_{11-20}$ alkyl, or $(CH_2$—$CH_2$—O—$)_{1-24}$ or $(CH_2)_{x1}$—$(CH_2$—O—$CH_2)_{1-24}$—$(CH_2)_{x2}$— group, wherein x1 and x2 are independently an integer selected among the range of 0 to 20, an amino acid, an oligopeptide, glycan, sulfate, phosphate, or carboxylate. Optionally, Y is absent. In some embodiments, Y is a $C_{2-6}$ alkyl group.

A compound may contain more than one spacer system Y. These moieties Y may or may not be the same. In some embodiments the spacer system Y is a self-elimination spacer that is connected to one or more other self-elimination spacers via a direct bond. Herein, a single self-elimination spacer may also be referred to as a spacer system. A spacer system may be branched or unbranched and contain one or more attachment sites for Z as well as V. Self-elimination spacers that are able to release only a single moiety are called 'single release spacers'. Self-elimination spacers that are able to release two or more moieties are called 'multiple release spacers'. Spacers, may be either branched or unbranched and self-eliminating through a 1,2+2n-elimination (n>/=1), referred to as "electronic cascade spacers". Spacers may eliminate through a cyclization process under formation of a cyclic urea derivative, referred to as "w-amino aminocarbonyl cyclization spacers".

The spacer system Y may self-eliminating or non-self-eliminating. A "self-eliminating" spacer unit allows for release of the drug moiety without a separate hydrolysis step. When a self-eliminating spacer is used, after cleavage or transformation of V, the side of Y linked to V becomes unblocked, which results in eventual release of one or more moieties Z. The self-elimination spacer systems may for example be those described in WO 02/083180 and WO 2004/043493, which are incorporated herein by reference in their entirety, as well as other self-elimination spacers known to a person skilled in the art. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. In one embodiment, the spacer unit is p-aminobenzyloxycarbonyl (PAB). Examples of self-eliminating spacer units further include, but are not limited to, aromatic compounds that are electronically similar to p-aminobenzyl alcohol (see, e.g. US 2005/0256030 A1), such as 2-aminoimidazol-5-methanoi derivatives (Hay et al. (1999) Bioorg. Med. Chem. Lett. 9:2237) and ortho- or para-aminobenzylacetals. Spacers can be used mat undergo cyclization upon amide bond hydrolysis, such as substituted and unsubstituted 4-aminobutyric acid amides (Rodrigues et al. Chemistry Biology, 1995, 2, 223) and 2-aminophenyl-propionic acid amides (Amsberry, et al., J. Org. Chem., 1990, 55. 5867). Elimination of amine-containing drugs that are substituted at the α-position of glycine (Kingsbury, et al., J. Med. Chem., 1984, 27, 1447) are also examples of self-immolative spacers.

A "non-self-eliminating" spacer unit is one in which part or all of the spacer unit remains bound to the moiety Z upon enzymatic (e.g., proteolytic) cleavage of the antibody-moiety-of-interest conjugate. Examples of non-self-eliminating spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an antibody-moiety-of-interest conjugate containing a glycine-glycine spacer unit by a tumor-cell associated protease would result in release of a glycine-glycine-drug moiety from the remainder of the antibody-moiety-of-interest conjugate. In one such embodiment, the glycine-glycine-drug moiety is then subjected to a separate hydrolysis step in the tumor cell, thus cleaving the glycine-glycine spacer unit from the drug moiety.

A spacer system Y may be connected to more than one V moiety. In this case, transformation and/or cleavage of one of these V moieties may trigger the release of one or more Z moieties. When V moieties that are transformed or cleaved under different conditions are connected to the same Y, release of one or more Z moieties may occur when a compound is brought under one of several different conditions.

Any one of the Y moieties disclosed herein can be utilized in Formula Ia, Ib, Ic, II, IVa and IVb. Any one of the Y moieties described herein can be used in combination with any of the $(C)_n$, X, L, V, Y, R, Z, M, z, q, and r groups described herein. Any one of the Y' moieties disclosed herein can be utilized in Formula III. Any one of the Y' moieties described herein can be used in combination with any of the R', L', V', Z, z', q', and r' groups described herein.

Conjugation of Lysine-Based Linkers to an Antibody

Enzymes of the TG-family catalyze covalent protein crosslinking by forming proteinase resistant isopeptide bonds between a lysine donor residue of one protein and an acceptor glutamine residue of another protein, and is accompanied by the release of ammonia. The antibodies that are to be conjugated to the lysine-based linker may or may not be free of N-linked glycosylation (e.g. an antibody which does not comprise glycosylation sites or a modified full-length antibody). For conjugation onto the acceptor glutamines within the CH2 domain, and particularly at residue Q295, antibodies will be free of N-linked glycosylation. Full-length wild-type IgG antibodies naturally comprise N-linked glycosylation at residue 297 of the heavy chain which interferes and prevents with TGase-mediated conjugation onto glutamine residues in the CH2 domain. Deglycosylation can be carried out according to any suitable method. For example, antibody in PBS buffer (PBS (10×): Weight 2.1 g KH$_2$PO$_4$, 90 g NaCl, 4.8 g Na$_2$HPO$_4$×2H$_2$O is transferred to a 1 L glass bottle, to which is added water to a volume of 1 L. To get PBS 1X, use 100 mL PBS (10×) and add water to a volume of 900 mL. pH is adjusted to 7.2 and filled to 1 L with water), and incubated with 6 Units/mg protein of N-glycosidase F (PNGase F) from *Flavobacterium meningosepticum* (Roche, Switzerland) overnight at 37° C. The enzyme is then removed by centrifugation-dialysis (Vivaspin MWCO 50 kDa, Vivascience, Winkel, Switzerland). The product can be analyzed by LC/MS. Alternatively, an antibody will be naturally free of N-linked glycosylation, for example as a result of an amino acid modification, e.g. at residues 297, 298 and/or 299 (EU numbering). For conjugation onto the acceptor glutamines within the CH3 domain (including on a TGase recognition tag fused to a CH3 domain) antibodies need not be free of (may comprise) N-linked glycosylation.

Once antibody and lysine-based linker substrates are prepared they can be reacted by bringing them into contact with one another in a reaction vessel in the presence of a bacterial transglutaminase (BTG) (see, e.g. EC 2.3.2.13, protein-glutamine-γ-glutamyltransferase). The BTG will capable of causing, under suitable conditions, the formation of a covalent bond between the acceptor glutamine residue of the antibody and the linking reagent (at the primary amine of the linking reagent) In one embodiment, the TGase is from *S. mobaraense*. In another embodiment, the TGase is a mutant TGase having 1, 2, 3, 4, 5, 10 or more amino acid modifications (e.g. substitutions, insertions, deletions), optionally the TGase has at least 80% sequence identity with native TGase, e.g. a TGase from *S. mobaraense*. A preferred example is recombinant bacterial transglutaminase derived from *streptomyces mobaraensis* (available from Zedira, Darmstadt, Germany).

The TGase-catalyzed reaction can be carried out under mild conditions, from several hours to a day (e.g. overnight). Recombinant BTG (EC 2.3.2.13) from *streptomyces mobaraensis* (Zedira, Darmstadt, Germany) are typically used at a concentration of between 1 and 20 U/mL. The lysine-based linker substrates are reacted with antibody (1 mg/mL) at ligand concentrations between 400 and 600 mol/L, providing a 60 to 90-fold excess of the substrates over the antibody, or optionally at lower excess of substrates, e.g. 1- to 20-fold, or 10-20 fold excess over acceptor glutamines. The reactions are performed in potassium-free phosphate buffered saline (PBS; pH 8) at 37° C. After 4 h to several days (depending on the antibody and the ligand), steady-state conditions are achieved. Excess ligand and enzyme are then removed using centrifugation-dialysis (Vivaspin MWCO 50 kDa, Vivascience, Winkel, Switzerland).

An acceptor glutamine present on an antibody (e.g. part of the antibody's primary structure, including for example an antibody fragment with a peptide tag) will, under suitable conditions, be recognized by a TGase and covalently bound to a lysine-based linker (e.g., compound of Formula I). The results is an antibody of Formula II (the acceptor glutamine is functionalized with the compound of Formula I). Resulting antibody conjugates can be analyzed using any suitable method. Preferably, the stoichiometry of the conjugated antibodies can be characterized by liquid chromatography mass spectrometry (LC/MS) using a top-down approach in order to assess the number of lysine-based linker and/or where applicable moieties-of-interest conjugated to antibodies, and in particular the homogeneity of the composition. Conjugates can be reduced before LC/MS analysis and light chains and heavy chains are measured separately.

Reaction Partners Comprising a Moiety-of-Interest Z and Reactive Group R'

Once a lysine-based linker (e.g., compound of Formula I) comprising a reactive moiety R is conjugated to an antibody (e.g., resulting in an antibody of Formula II) the antibody can be reacted with a compound comprising a moiety Z and a reactive group R', thereby forming an antibody-moiety-of-interest conjugate. Typically, the conjugated antibody (e.g. the antibody of Formula II) is subjected to a deprotection step to provide an unprotected reactive group (R) and the antibody is then reacted with a compound comprising a reaction partner R'.

R' is a reactive moiety, for example a moiety comprising an unprotected or protected bioorthogonal-reaction compatible reactive group, for example an unprotected or protected thiol, epoxide, maleimide, haloacetamide, o-phoshenearomatic ester, azide, fulminate, sulfonate ester, alkyne, cyanide, amino-thiol, carbonyl, aldehyde, generally any group capable of oxime and hydrazine formation, 1,2,4,5-tetrazine, norbornene, other stained or otherwise electronically activated alkene, a substituted or unsubstituted cycloalkyne, generally any reactive groups which form via bioorthogonal cycloaddition reaction a 1,3- or 1,5-disubstituted triazole, any diene or strained alkene dienophile that can react via inverse electron demand Diels-Alder reaction, a protected or unprotected amine, a carboxylic acid, an aldehyde, an oxyamine, so long as such group when unprotected is reactive with R (when R' is unprotected).

When more than one R' group is present in a compound of the formula, the R' groups will preferably be compatible such that no R' group is a complementary reagent to any other R' group. The L', V' and/or Y' groups of formulae I-IV can have r, q, and/or z sites of attachment for the respective V', Y', and R' groups, where r and q represent the degree of branching or polymerization. The sites of attachment can comprise a bond or comprise a functional group selected from an alkene, alkyne, ether, thioether, ester, thioester, amine, amide, alkylamine, or other functional group readily generated by a condensation or addition reaction.

In one embodiment, R' is a moiety having a terminal alkyne or azide.

In one embodiment, R' is a substituted or unsubstituted cycloalkyne, for example a compound of Formula A:

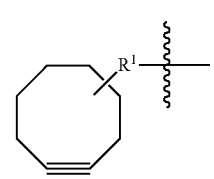

Formula A where:

R$^1$ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone and a halosulfonyl.

R$^1$ can be at any position on the cyclooctyne group other than at the two carbons joined by the triple bond.

In some embodiments, the modified cycloalkyne is of Formula A, wherein one or more of the carbon atoms in the cyclooctyne ring, other than the two carbon atoms joined by a triple bond, is substituted with one or more electron-withdrawing groups, e.g., a halo (bromo, chloro, fluoro, iodo), a nitro group, a cyano group, a sulfone group, or a sulfonic acid group. Thus, e.g., in some embodiments, a subject modified cycloalkyne is of Formula B:

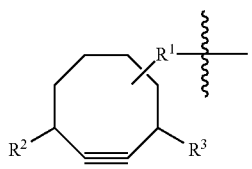

Formula B where:

each of $R^2$ and $R^3$ is independently: (a) H; (b) a halogen atom (e.g., bromo, chloro, fluoro, iodo); (c) —W—(CH$_2$)—Z (where: n is an integer from 1-4 (e.g., n=1, 2, 3, or 4); W, if present, is O, N, or S; and Z is nitro, cyano, sulfonic acid, or a halogen); (d) —(CH$_2$)$_m$—W—(CH$_2$)$_m$—$R^4$ (where: n and m are each independently 1 or 2; W is O, N, S, or sulfonyl; if W is O, N, or S, then $R^4$ is nitro, cyano, or halogen; and if W is sulfonyl, then $R^4$ is H); or (e) —CH$_2$)$_n$—$R^4$ (where: n is an integer from 1-4 (e.g., n=1, 2, 3, or 4); and $R^4$ is nitro, cyano, sulfonic acid, or a halogen); and $R^1$ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone and a halosulfonyl. R' can be at any position on the cyclooctyne group other than at the two carbons linked by the triple bond.

In one embodiment, R is a substituted or unsubstituted heterocyclic strained alkyne. Cycloalkynes, including specific compounds, are described for example in U.S. Pat. No. 8,133,515, the disclosure of which is incorporated herein by reference. In one embodiment, the alkyne is of the Formula C:

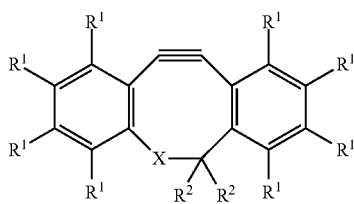

Formula C wherein:

each $R^1$ is independently selected from the group consisting of hydrogen, halogen, hydroxy, alkoxy, nitrate, nitrite, sulfate, and a $C_1$-$C_{10}$ alkyl or heteroalkyl;

each $R^2$ is independently selected from the group consisting of hydrogen, halogen, hydroxy, alkoxy, nitrate, nitrite, sulfate, and a $C_1$-$C_{10}$ organic group; X represents N—$R^3R^4$, NH—$R^4$, CH—N—OR$^4$, C—N—NR$^3$R$^4$, CHOR$_4$, or CHNHR$_4$; and each $R^3$ represents hydrogen or an organic group and $R^4$ represents linking moiety C (or (C)$_n$) of a linker. In one embodiment, R or R' is a DBCO (dibenzycyclooctyl) group below:

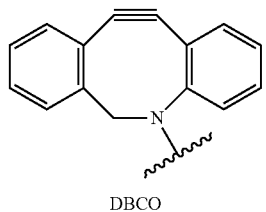 [SMILES: *N1Cc2ccccc2C#Cc2ccccc21 ; "DBCO"]

DBCO

Alkynes such as those described herein above can be reacted with at least one 1,3-dipole-functional compound (e.g., embodied in reactive group R of Formula Ia or Ib in a cyclization reaction to form a heterocyclic compound, preferably in the substantial absence of added catalyst (e.g., Cu(I)).

In one embodiment, when R' is a cycloalkyne, including a heterocyclic compound, the linking reagent of Formula Ia or Ib may comprise a non-cyclic R group, optionally furthermore wherein L is a bond or a shorter carbon framework as L group. For example, R may be a non-cyclic group and L may comprise a carbon framework of 1-5 linear carbon atoms, optionally substituted at one or more atoms.

Any one of the R' moieties disclosed herein can be utilized in Formula III. Any one of the R' moieties described herein can be used in combination with any of the L', V', Y', Z, z', q', and r' groups described herein.

The compounds of (e.g. Formula III) to be used in reaction with an antibody can be reacted with antibody (e.g., 1 mg/mL) at ligand concentrations between 2 and 20 (or between 4 and 20) molar equivalents to the antibody, optionally between 2 and 10 (or between 4 and 10) molar equivalents to the antibody, optionally at a less than, or about, 20, 10, 5, 4 or 2 molar equivalents to the antibody. However it will be appreciated that higher excesses (equivalents of reaction partner (e.g. Formula III) to antibody (40 to 80 fold, 60 to 90-fold) can also be used.

The compounds of Formula III to be used in reaction with an antibody conjugated to a lysine-based linker (but without a moiety-of-interest), e.g., an antibody of Formula II, as well as the resulting antibody conjugates therefore comprise one or more moieties-of-interest Z. The compounds of Formula III may additionally comprise a moiety V and/or Y, typically depending on which elements are included in the lysine-based linker.

The compounds of Formula III to be used in reaction with an antibody conjugated to a lysine-based linker (e.g. an antibody of Formula II) will comprise moieties Z connected to linker L' when Y' and V' are absent, connected to the spacer system Y' or, when Y' is absent, connected to V'. Consequently, a compound of Formula III may comprise a moiety Z connected to or comprising a reactive group R', optionally the moiety Z connected to a reactive group R' via a spacer system Y' or, when Y' is absent, to a reactive group R' via V', or to a reactive group R' via a V'—Y', wherein Z is preferably connected to Y' and V' is connected to R' and Y'.

A compound of Formula III may contain one, two or more Z moieties that are the same or that differ from one another, e.g. different therapeutic moieties, and/or diagnostic moieties.

In one embodiment, the antibody of Formula II is reacted with a compound of Formula III comprising a moiety of interest Z comprising and a reactive group R' capable of forming a bond with reactive group R of Formula Ib, Ic or II, optionally wherein the compound further comprises a V' and/or Y' group. The compound comprising a moiety of interest Z comprising and a reactive group R' preferably comprises a structure of Formula III, below,

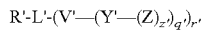  Formula III where:

R' is a reactive group, e.g. a reactive group complementary for forming at least one bond with reactive group R of Formula Ib, Ic or II;

L' is a bond or a carbon comprising framework of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

V' is independently absent, a non-cleavable moiety or a conditionally-cleavable moiety that can optionally be cleaved or transformed by a chemical, photochemical, physical, biological, or enzymatic process, cleavage of V ultimately leading to release of one or more Z moieties. In some embodiments, V is, preferably, a di-, tri-, tetra-, or oligopeptide as described below in the section entitled "The V Moiety", Y' is independently absent or a spacer system (e.g., a self-eliminating spacer system or a non-self-elimination spacer system) which is comprised of 1 or more spacers, Z is independently a reactive group (optionally protected) other than a complementary reactive group for reaction with R', a moiety that improves the pharmacokinetic properties, a therapeutic moiety, or diagnostic moiety;

q' and r' are an integer selected among 1, 2, 3 or 4, representing degree of branching; and z' is an integer selected among 1, 2, 3 or 4. Optionally, V' and Y' can be inverted.

Where Z is a reactive group, it can be a moiety comprising an unprotected or protected thiol, maleimide, haloacetamide, o-phoshenearomatic ester, azide, fulminate, alkyne, cyanide, anthracene, 1,2,4,5-tetrazine, norbornene, other stained or otherwise electronically activated alkene or, optionally, a protected or unprotected amine when X is absent and L, V, or Y is other than a bond or a continuation of a bond. In an alternative embodiment Z can be a reactive moiety, preferably a moiety comprising an unprotected or protected thiol, an unprotected or protected amine, maleimide, haloacetamide, o-phoshenearomatic ester, azide, fulminate, alkyne, cyanide, anthracene, 1,2,4,5-tetrazine, norbornene, other stained or otherwise electronically activated alkene. Preferably R is not an amine when n=5 and X, L, V and Y are absent. Preferably R is not an amine when n=4 and X, L, V and Y are absent.

The moiety R' is connected to Z, or optionally to Z via V' and/or Y' and is able to react with a suitable functional group R on a reaction partner, e.g. group R on the lysine-based linker of formula Ib, Ic or II. As discussed above, when the reactive moiety R' is designed to react with a reactive group R, a compound of Formula Ic or IVb is formed.

The L' group can be a carbon comprising framework, where L is a symmetrically or asymmetrically branched hydrocarbon, monosaccharide, disaccharide, oligosaccharide, other natural oligomer, dimer, trimer, or higher oligomer resulting from any chain-growth or step-growth polymerization process, wherein L' has r', q', and/or z' sites of attachment for the respective V', Y', and R' groups, where r' and q' represent the degree of branching or polymerization. The sites of attachment can comprise a bond or comprise a functional group selected from an alkene, alkyne, ether, thioether, ester, thioester, amine, amide, alkylamide, or other functional group readily generated by a condensation or addition reaction.

The linking group (RR') in M of compounds of Formula (Ic) and (IVb) represents the R' addition product of a reactive moiety R' and a reactive moiety R. This group then links the moiety Z) with L, V or Y, preferably via (RR') of M is L', V', and/or Y'. The group that remains may be a bond. Typically, however, L', V', and/or Y' is a linking group. RR' can be an addition product of a: thio-maleimide (or haloacetamide) addition, for example, a N,S-disubstituted-3-thio-pyrrolidine-2,5-dione; Staudinger ligation, for example, a N,3- or N,4-substituted-5-dipenylphosphinoxide-benzoic amide; Huisgen 1,3-cycloaddition (click reaction), for example, a N,S-disubstituted-3-thio-pyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction. Some reactions and the RR' reaction products are illustrated in FIGS. 1 and 2.

Examples of compounds of Formula III include but are not limited to compound having the R', L', V', Y' and Z groups shows in Table 4 herein. Examples of compounds of Formula III include but are not limited to compound having the R', L', V', Y' and Z groups shows in Table 3 herein. The symbol (–) in the tables indicates that the particular R', L', V', Y' or Z is absent. V and Y groups, for example, can comprise any structural features in the sections titled "The V Moiety" and "The Y Moiety" herein. The L, V and/or Y groups of Formula III represented in Table 4 can have r', q', and/or z' sites of attachment for the respective V, Y, and R or Z groups, where r and q represent the degree of branching or polymerization; r', q', and/or z' can be selected from 1, 2, 3 or 4.

Non-limiting examples of compounds of Formula Ia and reaction partners of Formula III are shown in Table 5.

In one embodiment provided is a method comprising reacting a compound of Formula II with a compound for Formula III to obtain a compound of Formula IVb.

It will be appreciated that different configurations of reactions partners (i.e. antibodies having a functionalized glutamine of Formula II and compound for Formula III) can be envisaged. For example, in some cases it may be advantageous to maintain a particular linker and spacer system and evaluate different moieties Z for their effect on an antibody, in which case the lysine-based linker may comprise L-V—Y—R and the reaction partner will not comprise V—Y (e.g. the reaction partner will comprise R'—Z. An example of configurations is shown in Table 1. Also provided are exemplary methods of evaluating a V, Y and/or Z moiety comprising: (a) reacting an antibody having a functionalized glutamine of Formula II of rows 1-10 with two, three, four or more compounds of Formula III of the respective row 1-10, wherein the compounds of Formula III differ in their V, Y and/or Z moiety, and (b) evaluating the effect of said differing V, Y and/or Z moiety on the antibodies (e.g. yield and stoichiometry of coupling, biological activity, stability or generally any pharmacological properties). For each respective row 1-10, the method may be characterized as a method for evaluation according to column 4 "Exemplary evaluation methods".

The present methods can comprise a step of immobilizing an antibody comprising a lysine-based linker (e.g., compound of Formula Ia or Ib) comprising a reactive moiety R conjugated thereto on a solid support to provide an immo-

TABLE 1

| Functionalized acceptor glutamine of antibody (Formula II) | Reaction partner (Formula III) | Exemplary evaluation method |
|---|---|---|
| 1 (Q)—NH—(C)$_n$—X—L—(V—((Y)—(R)$_z$)$_q$)$_r$ | R'—L'—(Z)$_{z'}$ | Evaluating Z moieties in the context of a particular V—Y |
| 2 (Q)—NH—(C)$_n$—X—L—(V— (R)$_z$)$_r$ | R'—L'—(Y'—(Z)$_{z'}$)$_{q'}$ | Evaluating Y' moieties or Y'—Z couples in the context of a particular V |
| 4 (Q)—NH—(C)$_n$—X—L—(V—(R)$_z$)$_r$ | R'—L'—(Z)$_{z'}$ | Evaluating Z moieties in the context of a particular V |
| 5 (Q)—NH—(C)$_n$—X—L—(Y—(R)$_z$)$_r$ | R'—L'—(Z)$_{z'}$ | Evaluating Z moieties in the context of a particular Y |
| 6 (Q)—NH—(C)$_n$—X—L—(R)$_z$ | R'—L'—(Y'—(Z)$_{z'}$)$_{q'}$ | Evaluating Y' moieties or Y'—Z couples |
| 7 (Q)—NH—(C)$_n$—X—L—(R)$_z$ | R'—L'—(V'—(Z)$_{z'}$)$_{r'}$ | Evaluating V' moieties or V'—Z couples |
| 8 (Q)—NH—(C)$_n$—X—L—(R)$_z$ | R'—L'—(Z)$_{z'}$ | Evaluating Z moieties |
| 9 (Q)—NH—(C)$_n$—X—L—(R)$_z$ | R'—(Z)$_{z'}$ | Evaluating Z moieties |
| 10 (Q)—NH—(C)$_n$—X—L—(R)$_z$ | R'—L'—(V'—(Y'—(Z)$_{z'}$)$_{q'}$)$_{r'}$ | Evaluating Y' moieties, V' moieties, or V'—Y'—Z couples |

The step of reacting an antibody having a lysine-based linker (e.g., compound of Formula Ib or Ic) comprising a reactive moiety R conjugated thereto with a compound comprising a moiety Z and a reactive group R' to form an antibody-moiety-of-interest conjugate can advantageously be carried out by binding the antibody onto a solid support. Use of a solid support for this step can allow for antibody samples of different initial concentrations and amounts to be reacted and then compared for activity. Use of a solid support also permits improved purification of functionalized antibodies. Finally, use of a solid support for this step allows an increase in efficiency in production and/or increase in completion of reactions because the compound comprising a moiety Z and a reactive group R' can be recovered and then reintroduced to the solid support; this may reduce loss of expensive reagents such as cytotoxic drugs.

The amount of antibody used in solid-support based methods may be small amounts (e.g., 1 to 500 µg) of antibody.

Generally, the solid support may be any suitable insoluble, functionalized material to which the antibodies can be reversibly attached, either directly or indirectly, allowing them to be separated from unwanted materials, for example, excess reagents, contaminants, and solvents. Examples of solid supports include, for example, functionalized polymeric materials, e.g., agarose, or its bead form Sepharose®, dextran, polystyrene and polypropylene, or mixtures thereof; compact discs comprising microfluidic channel structures; protein array chips; pipet tips; membranes, e.g., nitrocellulose or PVDF membranes; and microparticles, e.g., paramagnetic or non-paramagnetic beads. In some embodiments, an affinity medium will be bound to the solid support and the antibody will be indirectly attached to solid support via the affinity medium. In one aspect, the solid support comprises a protein A affinity medium or protein G affinity medium. A "protein A affinity medium" and a "protein G affinity medium" each refer to a solid phase onto which is bound a natural or synthetic protein comprising an Fc-binding domain of protein A or protein G, respectively, or a mutated variant or fragment of an Fc-binding domain of protein A or protein G, respectively, which variant or fragment retains the affinity for an Fc-portion of an antibody.

bilized antibody. In some embodiments, the solid support will have the capacity to bind more antibody than the amount present in the antibody-containing sample or, in other words, the amount of antibody bound to the solid support following the immobilization step will be less than the capacity of the solid support. Because the samples generally vary with respect to antibody quantity, there will be corresponding variability in the amount of immobilized antibody from one sample as compared to another.

It will be possible to optionally limit the quantity of bound antibody and the solid support will only have the capacity to bind up to a certain amount of antibody (e.g., up to 5 µg, up to 10 µg, or up to 15 µg of protein). In these embodiments, although there will be a limit as to the maximum amount of antibody that can be bound to the solid support, there may still be variability in the amount of immobilized antibody in one sample as compared to another. This is because one or more of the samples might contain a small quantity of antibody, less than the maximum loading capacity of the solid support. One approach for preparing a solid support that has limited capacity for binding antibody is to make a very low-capacity resin such that a larger volume of resin slurry (20 uL for example) contains only enough capacity to bind 5 ug of antibody. An alternative approach is to reduce the effective capacity of a resin by diluting the resin with an appropriate volume of non-functionalized resin. For example, a protein. G-sepharose resin with a binding capacity of 20 ug/uL could be converted to a mixed resin with an effective binding capacity of 0.5 ug/uL by mixing 1 part of protein G-sepharose with 40 parts unfunctionalized sepharose. In performing such a resin dilution, in some embodiments, the diluent will be a resin which is constructed from the same base material as the affinity resin, has pore sizes small enough to exclude antibodies, and lacks any surface functionality which may interact with antibodies or the chemical reagents used to prepare antibody conjugates.

Antibodies are generally immobilized on a solid support by the step of applying an antibody-containing sample to a solid support. If desired, a washing step can be performed following immobilization to separate the immobilized antibodies from the cell culture supernatant or other components of the antibody-containing samples.

Once the antibodies are immobilized on the solid support, the conjugated antibody (e.g. the antibody of Formula II) is typically subjected to a deprotection step to provide an unprotected reactive group (R) and the antibody is then reacted with a compound comprising a reaction partner R'.

A reaction step is then performed comprising applying a compound comprising a moiety Z and a reactive group R' (e.g. a compound of Formula III) to a solid support to generate an antibody-moiety-of-interest conjugate (e.g., antibody of Formula IVb).

In some embodiments, the compound comprising a moiety Z and a reactive group R' will be provided in molar excess (molar excess as to the reactive groups (R)).

After contacting the reduced antibodies with the appropriate amount compound comprising reactive group (R'), a washing step can be performed to remove any unreacted materials. Optionally, unreacted compound comprising a moiety Z and a reactive group R' is recovered; optionally, unreacted compound is re-applied to the solid support to provide for higher completion of the reaction between antibody comprising reactive group (R) and compound comprising reactive group (R').

Subsequently, the immobilized antibody conjugates can be eluted from the solid support to provide antibody conjugate compositions. Methods of eluting proteins from solid supports are known in the art and the skilled practitioner will be able to select an appropriate buffer for elution. For example, in embodiments, where the solid support comprises protein A or protein G resin, the antibody conjugates can be eluted with standard low pH buffers for elution from protein A or protein G columns.

The Moiety Z

The moieties Z can be connected to Y or Y' or, when absent, to V or V', or, when absent, to L or, when absent to X, or when absent to $(C)_n$. Connections to Y, V or L may optionally be via R or RR'. Connection may be via any suitable atoms. In one embodiment, Z is coupled via oxygen (from for example a hydroxyl group or carboxyl group), carbon (from for example a carbonyl group), nitrogen (from for example a primary or secondary amino group), or sulfur (from for example a sulfhydryl group). In one embodiment, Z is coupled via a group such that its therapeutic abilities or diagnostic characteristics are, at least partly, blocked or masked. In case a compound is to be used for treating or preventing disease in an animal, e.g., a mammal, the Z moieties are generally therapeutic moieties. In case a compound is used to make a diagnosis or used in an ex vivo or in vivo diagnostic assay, the Z moieties are generally diagnostic moieties, for example chromogenic, fluorogenic, phosphorogenic, chemiluminescent, or bio luminescent compounds.

In one embodiment, the Z moiety is compound, preferably an organic compound, having a molecular weight of at least 300 g/mol, 400 g/mol, 500 g/mol, 600 g/mol, 700 g/mol, 800 g/mol, 900 g/mol, 1000 g/mol or 2000 g/mol.

In one embodiment, the Z moiety is a chemical compound displaying hydrophobic properties, optionally additionally having a molecular weight of at least 300 g/mol, 400 g/mol, 500 g/mol, 600 g/mol, 700 g/mol, 800 g/mol, 900 g/mol. 1000 g/mol or 2000 g/mol. Hydrophobic character may be determined, for example, by decreased water solubility, decreased polarity, decreased potential for hydrogen bonding, and/or an increased oil/water partition coefficient. The presently disclosed methods can be used to produce antibody conjugates where moiety of interest (Z) comprises a hydrophobic drug. As used herein, the term "hydrophobic" is a physical property of a molecule that is repelled from a mass of water. Hydrophobic compounds can be solubilized in nonpolar solvents, including but not limited to, organic solvents. Hydrophobicity can be conferred by the inclusion of apolar or nonpolar chemical groups that include, but are not limited to, saturated and unsaturated aliphatic hydrocarbon groups and such groups substituted by one or more aromatic, cycloaliphatic or heterocyclic group(s). Conversely, "hydrophilic" molecules are capable of hydrogen bonding with a water molecule and are therefore soluble in water and other polar solvents. The terms "hydrophilic" and "polar" can be used interchangeably. Hydrophilic characteristics derive from the presence of polar or charged groups, such as carbohydrates, phosphate, carboxylic, sulfato, amino, sulfhydryl, nitro, hydroxy and other like groups.

Hydrophobic molecules are poorly water soluble, for example, having a solubility of less than about 10 mg/ml. In some embodiments, the hydrophobic compound can have a solubility of less than about 1 mg/ml in water. In other embodiments, the hydrophobic compound has solubility in water of less than about 50, μg/ml, 10 μg/ml, and in particular embodiments, about 1 μg/ml or 2.5 μg/ml. In other embodiments, the hydrophobic compound can have a solubility of about 0.001 μg/ml to about 10 mg/ml, including but not limited to 0.001 μg/ml, 0.01 μg/ml, 0.1 μg/ml, 1 μg/ml, 2 μg/ml, 5 μg/ml, 10 μg/ml, 50 μg/ml, 100 μg/ml, 500 μg/ml, 1 mg/ml, 5 mg/ml, and 10 mg/ml, and any other concentration between 0.001 μg/ml and 10 mg/ml.

Representative, non-limiting examples of hydrophobic drugs that can be formulated using the presently disclosed methods include taxanes, e.g. paclitaxel (PTX), and camptothecin (CPT), maytansanoids, duocarmycins, dolastatins and auristatins. Such drugs are poorly soluble in water, e.g. PTX has a solubility in water of less than about 1 μg/ml, CPT has a water solubility of about 2.5 μg/ml. Linkers and modified antibodies can advantageously link hydrophobic drugs to antibodies.

In other embodiments, in view of hydrophobic drugs being poor substrates for TGase (in the absence of improved linkers or modified antibodies), the Z moiety may advantageously be a hydrophilic drug. Examples of hydrophilic drugs include amatoxins. Amatoxins are cyclic peptides composed of 8 amino acids as isolated from the genus *Amanita*. Amatoxins also include a range of chemical derivatives, semisynthetic analogs and synthetic analogs built from building blocks according to the master structure of the −5 natural compounds (cyclic, 8 aminoacids), synthetic or semisynthetic analogs containing non-hydroxylated amino acids instead of the hydroxylated amino acids, synthetic or semisynthetic analogs, in which the thioether sulfoxide moiety is replaced by a sulfide, sulfone, or by atoms different from sulfur, e.g. a carbon atom as in a carbaanalog of amanitin. Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or proteins. Amatoxins are described for example in European Patent publication no. 1859811, PCT publication nos. WO2010/115630 and WO2012/041504).

In one embodiment, the Z moiety is a large compound (e.g., molecular weight of at least 300 g/mol, 400 g/mol, 500 g/mol, 600 g/mol or 700 g/mol) comprising a polycyclic group, tricycle or one or more macrocycles. Such groups are often typical of hydrophobic and/or rigid structures. Examples of cytotoxic drugs that comprise a macrocycle (e.g. a ring of nine or more atoms) include maytansinoids, amatoxins, epothilones and taxanes. In one embodiment, the Z moiety comprises a ring of 9, 10, 11, 12, 13, 14, 15, 16, 17 or 18 atoms, or between 9 and 200 atoms. In one embodiment, the Z moiety is a chemical compound having a negative charge, optionally additionally displaying hydrophobic properties and/or having a molecular weight of at least 300 g/mol, 400 g/mol, 500 g/mol, 600 g/mol, 700 g/mol, 800 g/mol, 900 g/mol, 1000 g/mol or 2000 g/mol.

When more than one Z moiety is connected to a self-elimination spacer system Y or Y', at least one Z should be released upon self-elimination of Y or Y'. The moiety Z initially released may be a moiety that is not a fully active moiety itself. In other words, Z may be a moiety that has limited diagnostic or therapeutic abilities, e.g. a moiety that acts as a prodrug. Such a Z moiety may require further processing or metabolism, e.g., hydrolysis, enzymatic cleavage, or enzymatic modification (for example phosphorylation, reduction, or oxidation) in order to become fully active. In one embodiment, such further processing is intentionally designed for Z to for example allow Z to reach its final target or cross a biological barrier, e.g., a cell membrane or a nuclear membrane, before it is fully activated. Z may for example contain a hydrophobic moiety that enables Z to cross a cell membrane. This hydrophobic moiety may then be hydrolyzed or removed in any other way intracellularly.

In one aspect, a Z moiety may be a backbone (e.g. polymer) to which a plurality of drugs or diagnostic moieties are linked. For example, Z may be a polyacetal- or polyacetal derivative-based polymer comprising a plurality of drug molecules, see, e.g., Yurkovetskiy et al. (2004) Mol. Pharm. 1(5): 375-382 and WO 2011/120053, the disclosures of which are incorporated herein by reference; for example Z may be a polymer compound of Formula I of WO 2011/120053 comprising a plurality of cytotoxic anti-cancer agents.

In one aspect, one or more moieties Z are each selected from a therapeutic or diagnostic agent.

In another embodiment, one or more moieties Z are each a therapeutic agent. In another embodiment, all moieties Z are each a therapeutic agent In yet another embodiment, the moieties Z each are the same therapeutic moiety.

In yet another embodiment, the moieties Z comprise at least two different therapeutic moieties.

The moiety Z includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

In one embodiment, the one or more moieties Z are each independently chosen from an antibiotic, an anti-bacterial agent, an antimicrobial agent, an anti-inflammatory agent, an anti-infectious disease agent, an anti-autoimmune disease agent, an anti-viral agent, or an anticancer agent, preferably a cytotoxic anti-cancer agent.

In another embodiment, the one or more moieties Z are each an anticancer agent. In a further embodiment, the one or more moieties Z are each a hydroxyl-containing anticancer agent.

In one embodiment, Z is an alkylating agent, preferably a DNA alkylating agent. An alkylation agent is a compound that can replace a hydrogen atom with an alkyl group under physiological conditions (e.g. pH 7.4, 37 C, aqueous solution). Alkylation reactions are typically described in terms of substitution reactions by N, O and S heteroatomic nucleophiles with the electrophilic alkylating agent, although Michael addition reactions are also important. Examples of alkylating agents include nitrogen and sulfur mustards, ethylenimines, methanosulfonates, CC-1065 and duocarmycins, nitrosoureas, platinum-containing agents, agents that effectuate Topoisomerase II-mediated site dependent alkylation of DNA (e.g. psorospermin and related bisfuranoxanthones), ecteinascidin and other or related DNA minor groove alkylation agents.

In one embodiment, Z is a DNA minor groove binding and/or alkylating agent, e.g., a pyrrolobenzodiazepine, a duocarmycin, or derivatives thereof.

In a further embodiment, the one or more moieties Z are each independently selected from the group consisting of taxanes, anthracyclines, camptothecins, epothilones, mytomycins, combretastatins, vinca alkaloids, nitrogen mustards, maytansinoids, calicheamycins, duocarmycins, tubulysins, dolastatins and auristatins, enediynes, amatoxins, pyrrolobenzodiazepines, ethylenimines, radioisotopes, therapeutic proteins and peptides, and toxins or fragments thereof.

In a further embodiment, the one or more moieties Z are each independently selected from cyclophosphamide, ifosfamide, chlorambucil, 4-(bis(2-chloroethyl)amino)phenol, 4-(bis(2-fluoroethyl)ammo)phenol, N,N-bis(2-chloroethyl)-p-phenylenediamine, N,N-bis(2-fluoro-ethyl)-p-phenylenediamine, carmustine, lomustine, treosulfan, dacarbazine, cisplatin, carboplatin, vincristine, vinblastine, vindesine, vinorelbine, paclitaxel, docetaxel, etoposide, teniposide, topotecan, inirotecan, 9-aminocamptothecin, 9-nitrocamptothecin, 10-hydroxycamptothecin, lurtotecan, camptothecin, crisnatol, mitomycin C, mitomycin A, methotrexate, trimetrexate, mycophenolic acid, tiazofurin, ribavirin, hydroxyurea, deferoxamine, 5-fluorouracil, floxuridine, doxifluridine, raltitrexed, cytarabine, cytosine arabinoside, fludarabine, 6-mercaptopurine, thioguanine, raloxifen, megestrol, goserelin, leuprolide acetate, flutamide, bicalutamide, vertoporfin, phthalocyanine, photosensitizer Pc4, demethoxy-hypocrellin A, interferon-alpha, interferon-gamma, tumor necrosis factor, lovastatin, staurosporine, actinomycin D, bleomycin A2, bleomycin B2, peplomycin, daunorubicin, doxorubicin, N-(5,5-diacetoxypentyl)doxorubicin, morpholino doxorubicin, idarubicin, epirubicin, pirarubicin, zorubicin, mitoxantrone, thapsigargin, $N^8$-acetyl-spermidine, tallysomycin, esperamycin, butyric acid, retinoic acid, 1,8-dihydroxybicyclo[7.3.1]trideca-4-ene-2,6-diyne-13-one, anguidine, podophyllotoxin, combretastatin A-4, pancratistatin, tubulysin A, tubulysin D, carminomycin, streptonigrin, elliptmium acetate, maytansine, maytansinol, calicheamycin, mertansine (DM1), N-acetyl-$\gamma_1^1$-calicheamycin, calicheamycin-$\gamma_1^1$, calicheamycin-$\alpha_2^1$, calicheamycin-$\alpha_3^1$, duocarmycin SA, duocarmycin A, CC-1065, CB1-TMI, duocarmycin C2, duocarmycin B2, centanamycin, dolastatin, auristatin E, monomethylauristatin E (MMAE), monomethylauristatin F (MMAF), α-amanitin, β-amanitin, γ-amanitin, ϵ-amanitin, amanin, amaninamide, amanullin, and amanullinic acid and derivatives thereof.

Exemplary auristatin embodiments include the N-terminus linked monomethylauristatin drug moieties comprising a structure of any of Formulas V and VI below:

Formula V

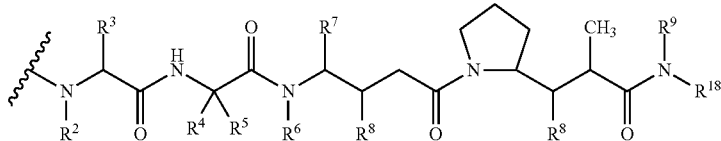

Formula VI

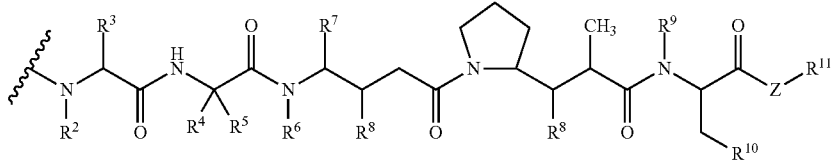

wherein the wavy line of V and VI indicates the covalent attachment site to a L, L', V, V', Y, Y', (RR'), R' or (C)$_n$ group of a compound (e.g. a compound of Formula I, II or IV), and independently at each location:

$R^2$ is selected from H and $C_1$-$C_8$ alkyl;

$R^3$ is selected from H, $C_1$-$C_8$ alkyl, $C_1$-$C_8$ carbocycle, aryl, $C_1$-$C_8$ alkyl-aryl, $C_1$-$C_8$ alkyl-($C_3$-$C_8$carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle. aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$ wherein $R^{12}$ is $C_1$-$C_8$ alkyl;

$R^{11}$ is selected from H, $C_1$-$C_{20}$ alkyl, aryl, C3-C8 heterocycle, —$(R^{13}O)_m$—$R^{14}$, or —$(R^{13}O)_m$—$CH(R^{15})_2$; m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_m$—$N(R^{16})_2$, —$(CH_2)_n$—$SO_3$—$C_1$-$C_8$ alkyl;

each occurrence of $R^{16}$ is independently H, $C_1$-$C_8$ alkyl, or —$(CH_2)_m$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment. $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, is —H, methyl or t-butyl.

In one embodiment, when Z is —NH, $R^{11}$ is —$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH.

In another embodiment, when Z is —NH, $R^{11}$ is —$CH(R^{15})_2$, wherein $R^{15}$ is —$(CH_2)_n$—$SO_3H$.

One exemplary auristatin embodiment of formula V is MMAE, wherein the wavy line indicates the covalent attachment to a L, L', V, V', Y, Y', (RR'), R' or (C)$_n$ group of a compound (e.g. a compound of Formula I, II or IV):

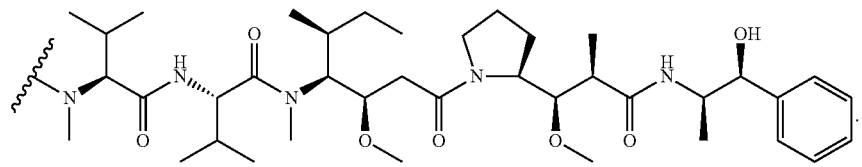

MMAE

An exemplary auristatin embodiment of formula VI is MMAF, wherein the wavy line indicates the covalent attachment to a linker (L) of an antibody-drug conjugate (see US 2005/0238649 and Doronina et al. (2006) Bioconjugate Cfiem. 17: 1 14-124):

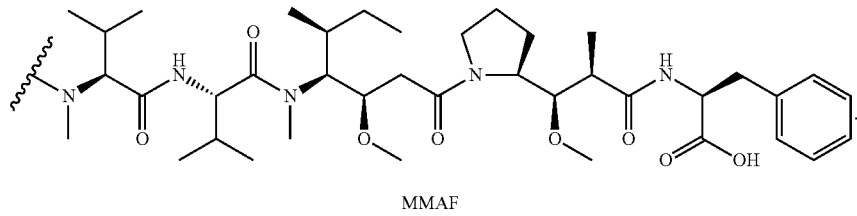

MMAF

Other exemplary Z embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Other drug moieties include the following MMAF derivatives, wherein the wavy line indicates the covalent attachment to a L, L', V, V', Y, Y', (RR'), R' or (C)$_n$ group of a compound (e.g. a compound of Formula I, II or IV):

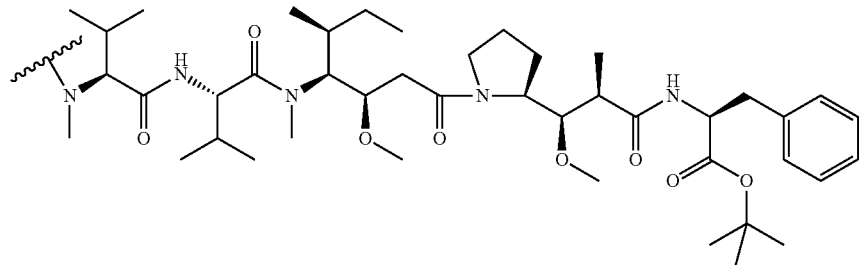

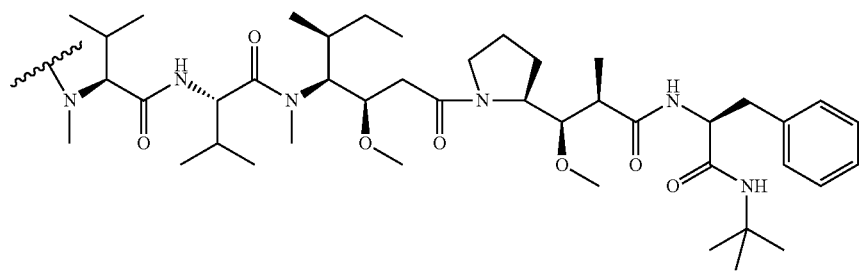

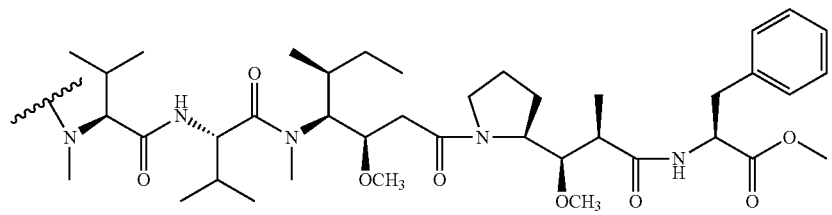

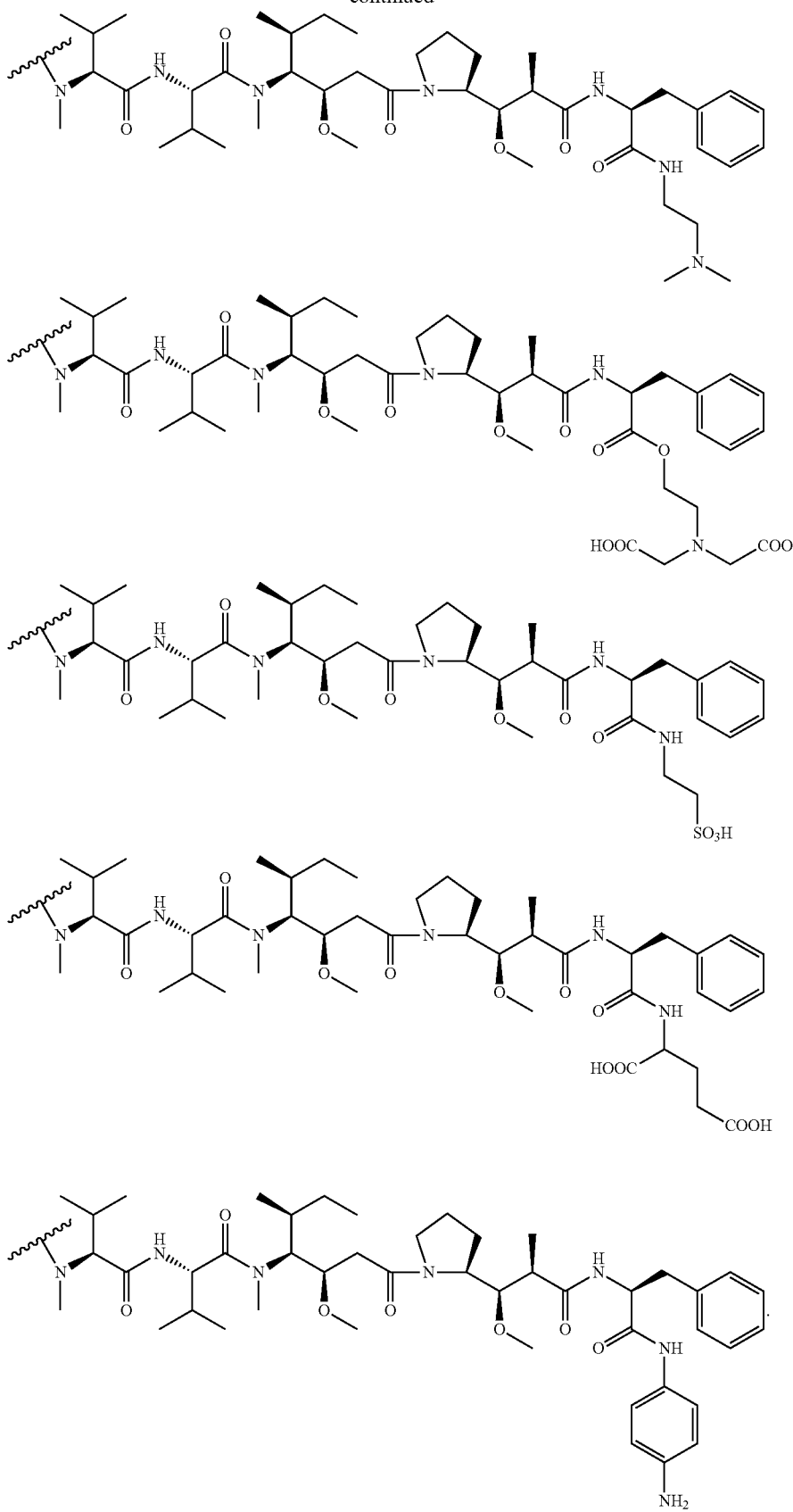

An example of a linker comprising a lysine residue as $(C)_n$ moiety, a valine-citrulline as the (V) moiety, a PAB as the (Y) moiety together with a MMAF as the (Z) moiety is shown below (corresponding to compound Ia-1):

[1,4]benzodiazepine. In one aspect of the any of the embodiments herein, a pyrrolobenzodiazepine dimer is a C8/C8'-linked pyrrolo[2,1-c][1,4]benzodiazepine dimer.

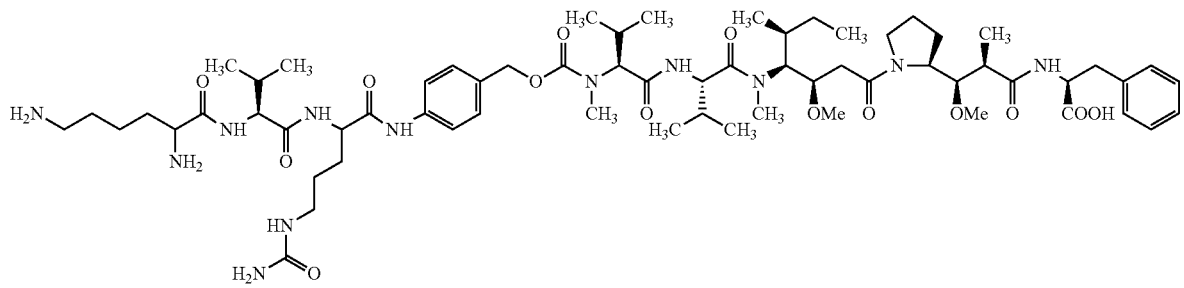 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)OCc1ccc(NC(=O)C(CCCNC(N)=O)NC(=O)[C@@H](NC(=O)C(N)CCCCN)C(C)C)cc1)C(C)C]

In one embodiment, the Z moiety comprises a pyrrolobenzodiazepine (PBD). In one embodiment, Z is a pyrrolobenzodiazepine monomer. In one embodiment, Z is a pyrrolobenzodiazepine dimer comprising two pyrrolobenzodiazepine units. In one embodiment, Z is a pyrrolobenzodiazepine trimer comprising three pyrrolobenzodiazepine units. In one embodiment, Z is a pyrrolobenzodiazepinemultimer comprising more than three pyrrolobenzodiazepine units. Structures of PBDs, as well as formulas and methods of producing them are described for example in PCT publications Nos: WO 2013/177481, WO 2011/130616, WO 2004/043880, WO 2005/085251, WO2012/112687 and WO 2011/023883, the disclosures of each of which are incorporated herein by reference.

The pyrrolo[2,1-c][1,4]benzodiazepines are a family of sequence-selective, minor-groove binding DNA-interactive agents that covalently attach to guanine residues. It has been reported that the (S)-chirality at the C11a-position of PBDs provides them with the appropriate 3-dimensional shape to fit perfectly into the DNA minor groove. PBDs can have different effects and modes of action. PBDs can be DNA-binders or DNA-alkylators that do not cause crosslinking of DNA, or PBDs can be DNA cross-linkers.

The pyrrolobenzodiazepine unit or monomer can have a general structure as follows:

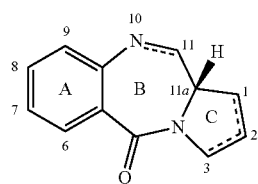

wherein the PBD can have different number, type and position of substituents, in both the aromatic A rings and pyrrolo C rings, and can vary in the degree of saturation of the C ring. In the B-ring there is either an imine (N=C), a carbinolamine (NH—CH(OH)), or a carbinolamine methyl ether (NH—CH(OMe)) at the $N^{10}$—$C^{11}$ position which is the electrophilic centre responsible for alkylating DNA.

The biological activity of PBDs can be potentiated by joining two PBD monomers or units together, typically through their C8/C8'-hydroxyl functionalities via a flexible alkylene linker.

In one aspect of the any of the embodiments herein, a pyrrolobenzodiazepine monomer or unit is a pyrrolo[2,1-c]

A PBD can be attached to a compound comprising a reactive group R' through any suitable position, thereby yielding a compound of Formula III which comprises the PBD and a reactive group R'. For example, in the compound of Formula III, the PBD can be connected to Y' or to V', or, when absent, to L' in a compound of Formula III, via any of the positions in a PBD unit indicated below.

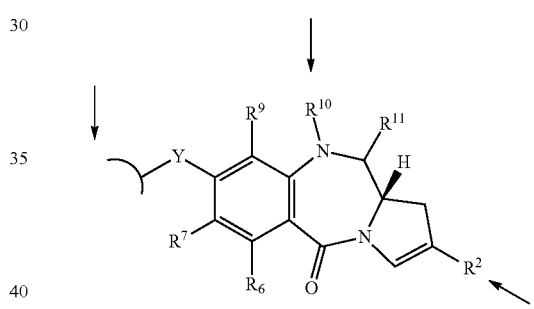

In one embodiment, a PBD dimer comprises the structure of the general formula below, with exemplary attachments points to other substituents or functionalities within a compound of Formula III indicated by arrows:

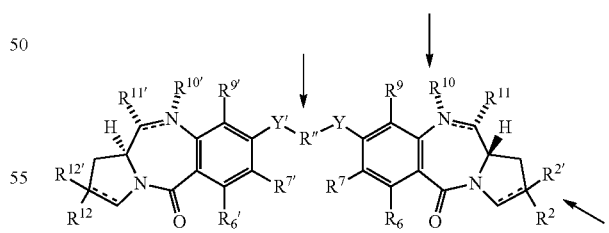

wherein:

$R^{12}$ and $R^{12'}$, and/or $R^2$ and $R^{2'}$ together respectively form a double bond =$CH_2$ or =CH—$CH_3$; or $R^{2'}$ and $R^{12'}$ are absent and $R^2$ and $R^{12}$ are independently selected from:

(iia) $C_{1-5}$ saturated aliphatic alkyl;

(iiib) $C_{3-6}$ saturated cycloalkyl;

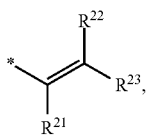

(iic)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(iid)

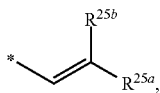

wherein one of $R^{25a}$ and $R^{25b}$ is H and the other is selected from:
phenyl, which phenyl is optionally substituted by a group selected from halo, methyl, meth xy; pyridyl; and thiophenyl; and

(iie)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

$R^6$ and $R^9$ are independently selected from H, R, OH, OR, SH, SR, $NH_2$, NHR, NRR', nitro, $Me_3Sn$ and halo; where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, $NH_2$, NHR, NHRR', nitro, $Me_3Sn$ and halo; either:

(a) $R^{10}$ is H, and $R^{11}$ is OH, $OR^A$, where $R^A$ is alkyl;

(b) $R^{10}$ and $R^{11}$ form a nitrogen-carbon double bond between the nitrogen and carbon atoms to which they are bound; or (c) $R^{10}$ is H and $R^{11}$ is $SO_zM$, where z is 2 or 3 and M is a monovalent pharmaceutically acceptable cation;

R" is a $C_{3-12}$ alkylene group, which chain may be interrupted by one or more heteroatoms, e.g. O, S, $NR^{N2}$ (where $R^{N2}$ is H or $C_{14}$ alkyl), and/or aromatic rings, e.g. benzene or pyridine;

Y and Y' are selected from O, S, or NH; and $R^{6'}$, $R^{7'}$, $R^{9'}$ are selected from the same groups as $R^6$, $R^7$ and $R^9$ respectively and $R^{10'}$ and $R^{11'}$ are the same as $R^{10}$ and $R^{11}$, wherein if $R^{11}$ and $R^{11'}$ are $SO_zM$, M may represent a divalent pharmaceutically acceptable cation.

In anther example, a PBD dimer comprises the structure of the general formula below:

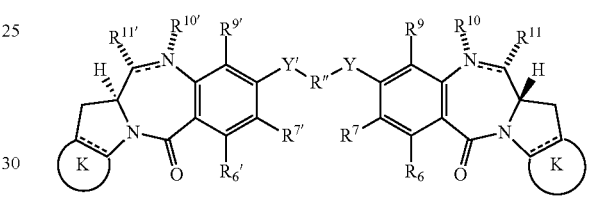

wherein $R^6$, $R^7$, $R^9$, $R^{6'}$, $R^{7'}$, $R^{9'}$, $R^{10'}$, and $R^{11'}$ are as defined above, and wherein the "K" ring is a substituted or unsubstituted aromatic or non-aromatic ring, optionally a 6-member ring, optionally a phenyl.

Examples of PBD dimers

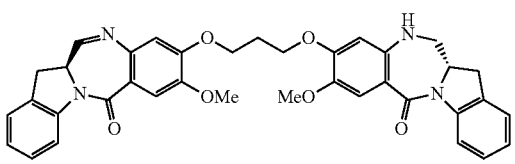

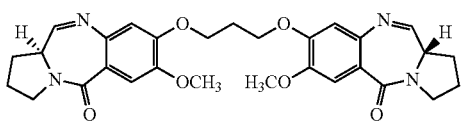

31 DSB-120

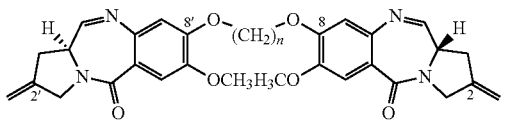

32 n = 3
33 n = 5

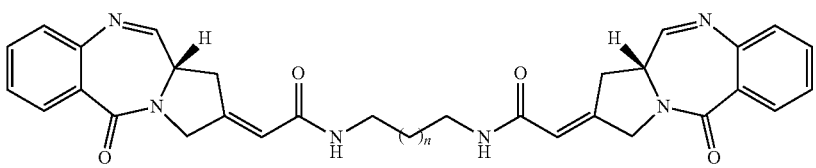

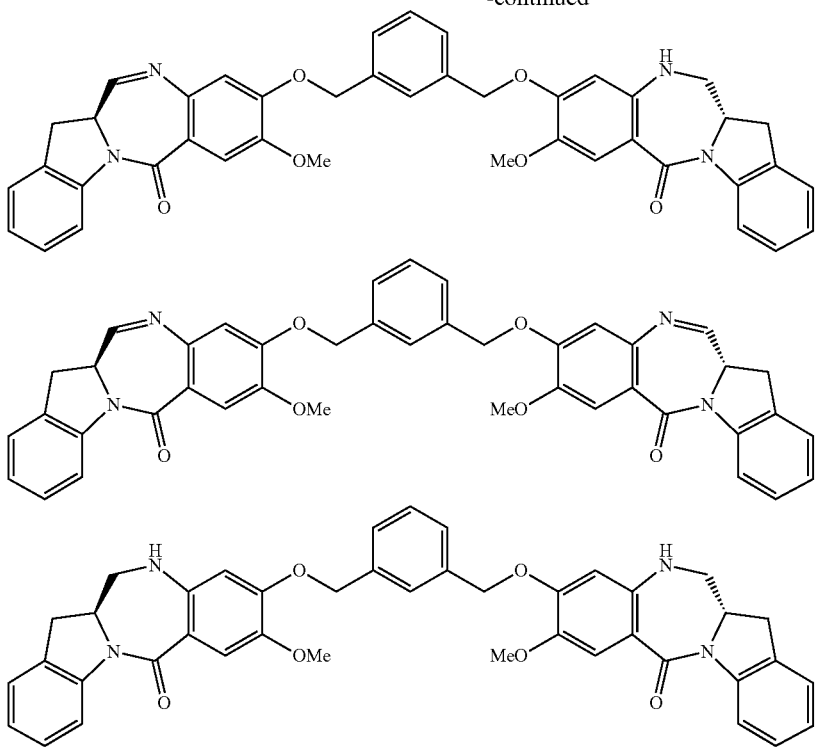

include:

In one embodiment, the Z moiety is an epothilone or epothilone derivative. An epothilone is a cyclic molecule with a 16-membered ring and variable substituents and pharmaceutical activity as a cytostatic agent that binds to tubulin. Various epothilone derivatives are known, including variants with 14-, 15- or 18-membered rings have also been developed (e.g. WO2011085523; WO2009105969). Examples of epothilones or epothilone analogs or derivatives include epothilone A, epothilone B, epothilone C, 13-alkyl-epothilone C derivatives, epothilone D, trans-epothilone D, epothilone E, epothilone F, an effector conjugate of epothilone, Sagopilone, or any of the epothilones referred to in the literature as ixabepilone (BMS-247550), BMS-310705, EPO-906, Patupilone, Kos-862, Kos-1584, Kos-1803 and ABJ 879, and pharmaceutically active salts thereof. The production of epothilones, their precursors and derivatives is generally carried out according to the methods known to one skilled in the art. Suitable methods are, for example, described in DE 19907588, WO 98/25929, WO 99/58534, WO 99/2514, WO 99/67252, WO 99/67253, WO 99/7692, EP 99/4915, WO 00/485, WO 00/1333, WO 00/66589, WO 00/49019, WO 00/49020, WO 00/49021, WO 00/71521, WO 00/37473, WO 00/57874, WO 01/92255, WO 01/81342, WO 01/73103, WO 01/64650, WO 01/70716, U.S. Pat. No. 6,204,388, U.S. Pat. No. 6,387,927, U.S. Pat. No. 6,380,394, US 02/52028, US 02/58286, US 02/62030, WO 02/32844, WO 02/30356, WO 02/32844, WO 02/14323, and WO 02/8440. Further epothilones are described in WO 93/10102, WO 98/25929, WO 99/02514, WO 99/07692, WO 99/02514, WO 99/67252, WO 00/49021, WO 00/66589, WO 00/71521, WO 01/027308, WO 02/080846, WO 03/074053, WO 2004/014919.

Other useful therapeutics are set forth in the Physician's Desk Reference and in the Orange Book maintained by the US Food and Drug Administration (FDA). New drugs are continually being discovered and developed which may also be incorporated into a compound herein.

Chelated metals include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$Au, $^{110}$Ag, $^{206}$Bi, $^{207}$Bi, $^{207}$Bi, $^{111}$In, $^{67}$Ga, $^{68}$Ga, $^{88}$Y, $^{90}$Y $^{160}$Tb, $^{153}$Gd and $^{47}$Sc.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in PCT publication no. WO 92/22583); and polyamides, especially desferriox-amine and derivatives thereof.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerytbrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Synthetic or naturally occurring polymers for use as effector molecules include, for example optionally substituted straight or branched chain polyalkylene, polyalkenylene, or polyoxyalkylene polymers or branched or unbranched polysaccharides, e.g. a homo- or hetero-polysaccharide such as lactose, amylose, dextran or glycogen.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol), poly(vinylalcohol) or derivatives thereof, especially optionally substituted poly(ethyleneglycol) such as methoxypoly(ethyleneglycol) or derivatives thereof. Such compounds, when used as a moiety Z can be employed as a moiety that improves the pharmacokinetic properties of the antibody.

The size of the polymer may be varied as desired, but will generally be in an average molecular weight range from 500 Da to 50,000 Da, preferably from 5,000 to 40,000 Da and more preferably from 10,000 to 40,000 Da and 20,000 to 40,000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5,000 Da. For applications where the product remains in the circulation, it may be advantageous to use a higher molecular weight polymer, for example having a molecular weight in the range from 20,000 Da to 40,000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 10,000 Da to about 40,000 Da.

In another embodiment, z' equals 1, each V, Y or V—Y (including whether any V and Y is a V' or Y') moiety contains a single attachment site for a functional group of Z.

In another embodiment, a one V (or V'), Y, (or Y') or V—Y (or V'—Y', V—Y') moiety is attached to more than one Z moiety via multiple functional groups R on the said V, Y or V—Y moiety. Optionally, the one or more V (or V') moieties comprise a polymer, optionally an oligoethylene glycol or a polyethylene glycol or a derivative thereof.

Any one of the Z moieties disclosed herein can be utilized in Formula Ia, IIII, and IVa. Any one of the Z moieties described herein can be used in combination with any of the $(C)_n$, X, L, V, R, Y, Z, M, z, q, and r groups described herein.

Any one of the Z moieties described herein can be used in combination with any of the R', L', V', Y', z', q', and r' groups described herein.

Antibody-Z Conjugates

In one embodiment, a linking reagent (e.g. of Formula Ia) is directly conjugated to an antibody or antibody fragment, without requirement for a step of reaction involving reactive groups R and R'. In one aspect, an antibody or antibody fragment comprises a functionalized glutamine residue of Formula IVa, below,

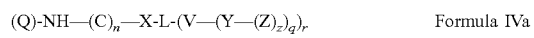

$$(Q)\text{-NH}—(C)_n—X\text{-}L\text{-}(V—(Y—(Z)_z)_q)_r \qquad \text{Formula IVa}$$

or a pharmaceutically acceptable salt thereof;
wherein:
Q is glutamine residue present in an antibody or antibody fragment;
$(C)_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide (e.g. a O, N or S atom of an ether, ester, thioether, thioester, amine, alkylamine, amide, or alkylamide);
n is an integer selected from among the range of 2 to 20;
X is NH, O, S, or absent;
L is a bond or a carbon comprising framework, preferably of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;
r is an integer selected among 1, 2, 3 or 4;
q is an integer selected among 1, 2, 3 or 4;
z is an integer selected among 1, 2, 3 or 4; and
V is independently absent, a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";
Y is independently absent or a spacer (e.g., a self-eliminating spacer system or a non-self-elimination spacer system) which is comprised of 1 or more spacers; and
Z is a moiety-of-interest, optionally a moiety that improves the pharmacokinetic properties, or a therapeutic moiety or a diagnostic moiety. Preferably, Z is a cytotoxic anti-cancer agent, e.g. a compound selected from the group consisting of taxanes, anthracyclines, camptothecins, epothilones, mytomycins, combretastatins, vinca alkaloids, nitrogen mustards, maytansinoids, calicheamycins, duocarmycins, tubulysins, amatoxins, dolastatins and auristatins, enediynes, radioisotopes, therapeutic proteins and peptides, and toxins or fragments thereof.

Generally, each Z is directly coupled to either Y or V when Y is absent, or L when both Y and V are absent.

In some embodiments, Z is selected from the group consisting of taxanes, anthracyclines, camptothecins, epothilones, mytomycins, combretastatins, vinca alkaloids, nitrogen mustards, maytansinoids, calicheamycins, duocarmycins, tubulysins, amatoxins, dolastatins and auristatins, enediynes, pyrrolobenzodiazepines, and ethylenimines It will be appreciated that Formula IVa can for convenience also be expressed as (Ab)-NH—(C)$_n$—X-L-(V—(Y—(Z)$_z$)$_q$)$_r$ (Formula IVa), where (Ab) is an immunoglobulin (Ab) is conjugated via a glutamine (Q) residue to an NH of the linking reagent (e.g the compound of Formula Ia).

Examples of antibodies or antibody fragments of Formula IVa include but are not limited to antibodies and fragments attached via an amide bond (e.g. through an acceptor glutamine residue in the primary sequence of the antibody or antibody fragment) to a compound selected from the group consisting of compounds Ia-1 to Ia-23 (wherein the terminal NH$_2$— of each of said compound Ia-1 to Ia-23 is replaced by a moiety ((Q)-NH—) when attached to the antibody or fragment, wherein Q is glutamine residue present in an antibody or antibody fragment.

The antibody conjugates resulting from the reaction of the compounds of Formula Ib or III with an antibody conjugated to a lysine-based linker will yield an antibody conjugate in which a moiety Z is connected to linker L (or L') when Y (or Y') and V (or V') are absent, to the spacer system Y (or Y') or, when Y (or Y') is absent, to V (or V). Optionally said connections are via linking group (RR') of M.

The conjugates resulting from the reaction yield an antibody (Ab) which is conjugated (i.e., covalently attached) via an acceptor glutamine residue (Q) present on the antibody to a NH group of a lysine-based linker, and one or more moieties (Z) through optional linking group (RR'), optional linker (V or V') and/or optional spacer (Y or Y').

In one embodiment, the (RR') remains present in a conjugated antibody or antibody fragment, in which case a Formula IV will comprise an (M) moiety. Such an antibody or antibody fragment comprises a functionalized glutamine residue of Formula IVb, below, (Q)-NH—(C)$_n$—X-L-(V—(Y-(M)$_z$)$_q$)$_r$      Formula IVb or a pharmaceutically acceptable salt or solvate thereof; wherein:

Q is glutamine residue present in an antibody or antibody fragment;

(C)$_n$ is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide;

n is an integer selected from among the range of 2 to 20;

X is NH, O, S, or absent;

L is a bond or a carbon comprising framework, preferably of 1 to 200 atoms substituted at one or more atoms, optionally wherein the carbon comprising framework is a linear hydrocarbon, a symmetrically or asymmetrically branched hydrocarbon monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected among 1, 2, 3 or 4;

q is an integer selected among 1, 2, 3 or 4;

z is an integer selected among 1, 2, 3 or 4; and

V is independently absent, a non-cleavable moiety or a conditionally-cleavable moiety that can optionally be cleaved or transformed by a chemical, photochemical, physical, biological, or enzymatic process (e.g. cleavage of V ultimately leading to release of one or more moieties subsequently or ultimately linked to V, for example a Z moiety). In some embodiments, V is, preferably, a di-, tri-, tetra-, or oligopeptide as described below in the section entitled "The V Moiety";

Y is independently absent or a spacer (e.g., a self-eliminating spacer system or a non-self-elimination spacer system) which is comprised of 1 or more spacers; and M is independently: R or (RR')-L'-(V'—(Y'—(Z)$_{z'}$)$_{q'}$)$_{r'}$, wherein each of L', V', Y', z', q', and r' are as defined in Formula III (or are defined as L, V, Y, z, q and r, respectively, Z is a moiety-of-interest, optionally a moiety that improves the pharmacokinetic properties, or a therapeutic moiety or a diagnostic moiety, R is as defined in Formula I and wherein each (RR') is an addition product between an R of Formula I and its complementary R' of Formula III (see, for example, FIG. 1 and FIG. 2).

Thus, RR' can be for example an addition product of a thio-maleimide (or haloacetamide) addition, for example, a N,S-disubstituted-3-thio-pyrrolidine-2,5-dione; Staudinger ligation, for example, a N,3- or N,4-substituted-5-dipenyl-phosphinoxide-benzoic amide; Huisgen 1,3-cycloaddition (click reaction), for example, a N,S-disubstituted-3-thio-pyrrolidine-2,5-dione, 1,4-disubstituted-1,2,3-triazole, 3,5-disubstituted-isooxazole, or 3,5-disubstituted-tetrazole; Diels-Alder cycloaddition adduct, for example the 2,4-cycloaddition product between an O or N-substituted-5-norbornene-2-carboxylic ester or amide, N-substituted-5-norbornene-2,3-dicarboxylic imide, O or N-substituted-7-oxonorbornene-5-carboxylic ester or amide, or N-substituted-7-oxonorbornene-5,6-dicarboxylic imide and a 9-substituted anthracene or 3-substituted 1,2,4,5-tetrazine; or any high yield selective amidation or imidization reaction. Some reactions and the corresponding RR' reaction products are illustrated in FIGS. 1 and 2.

Examples of RR' include:

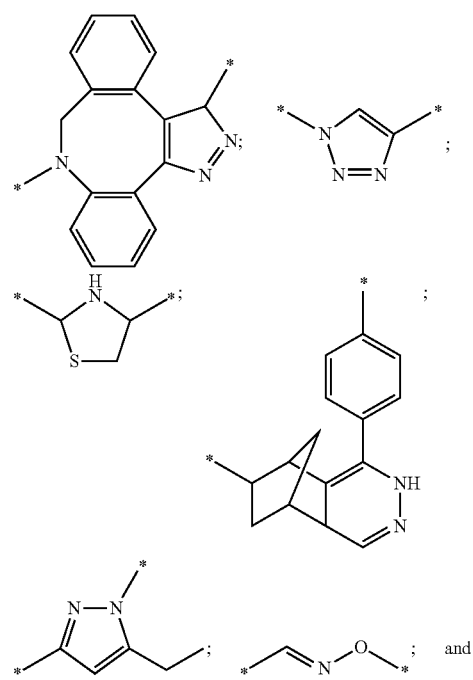

-continued

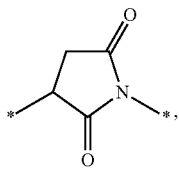

wherein (*) indicates the site of attachment of —(C)$_n$, X, L, L', V, V', Y, Y' or Z. RR' can be in either orientation with respect to their attachment to —(C)$_n$, X, L, L', V, V', Y, Y' or Z).

Optionally, the antibody conjugate comprises a group (RR') representing the remainder of a reactive moiety R when R has reacted with a reactive moiety R', wherein the group (RR') connects (a) an L to a Z, a V or a Y, (b) a V to a Z or a Y, or (c) a Y to a Z. For example, any V, Y and/or Z may be characterized as comprising a (RR') group. Any L, V, Y may be an L', V' or Y', respectively.

It will be appreciated that Formula IVb can for convenience also be expressed as (Ab)-NH—(C)$_n$—X-L-(V—(Y-(M)$_z$)$_q$)$_r$ where (Ab) is an immunoglobulin (Ab) is conjugated via a glutamine (Q) residue to an NH of the linking reagent (e.g the compound of Formula Ib or Ic).

Examples of antibodies or antibody fragments of Formula IVb include but are not limited to:

Compound IVb-1

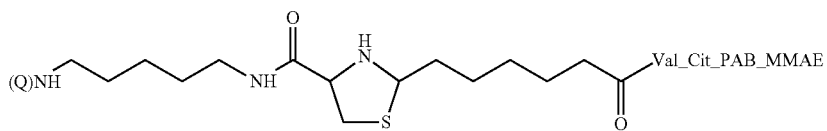

Compound IVb-2

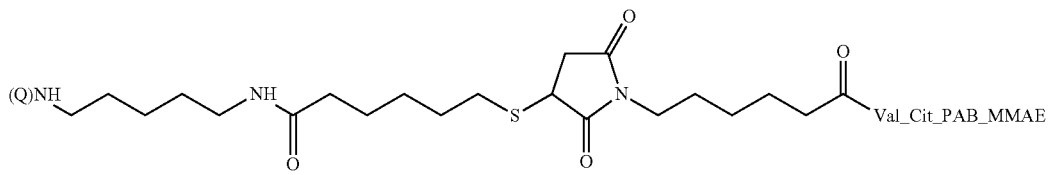

Compound IVb-3

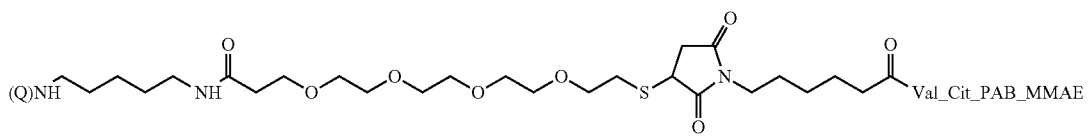

Compound IVb-4

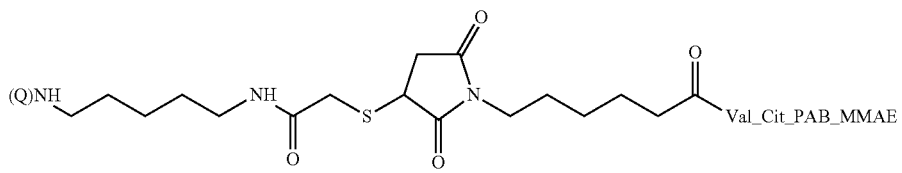

Compound IVb-5

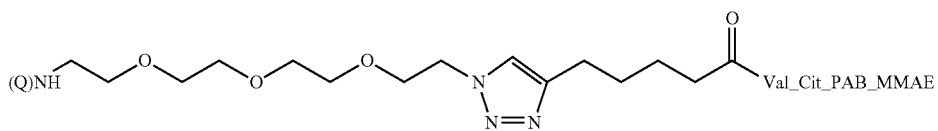

Compound IVb-6

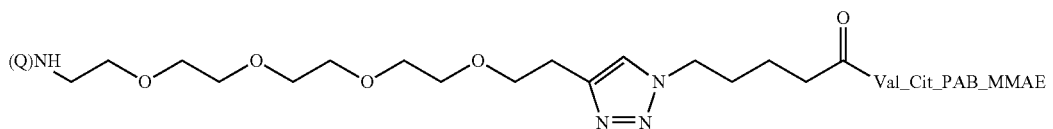

-continued

Compound IVb-7

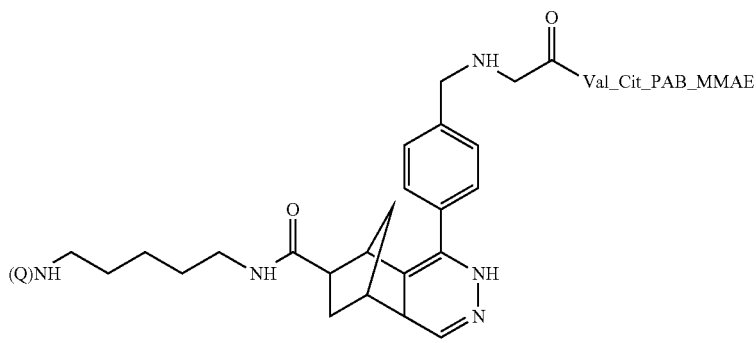

Compound IVb-8

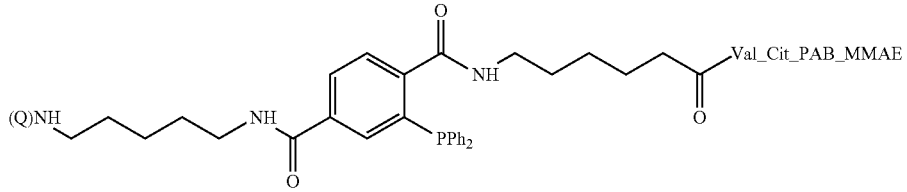

Compound IVb-8

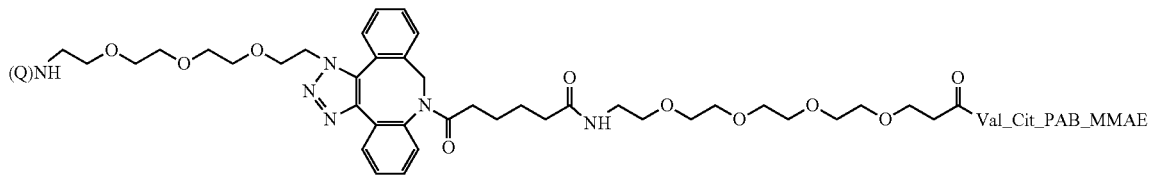

Compound IVb-9

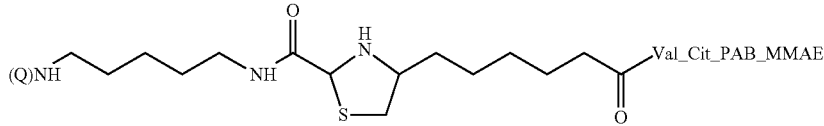

Compound IVb-9

Compound IVb-9

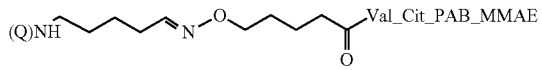

In one embodiment, the glutamine (Q) is present in the constant region of an antibody heavy chain. In one embodiment, the glutamine (Q) is at position 295. In one embodiment, an acceptor glutamine (Q) is at position 297 (e.g., a N297Q substitution). In one embodiment, the antibody comprises a substitution of an asparagine at position 297 with a non-asparagine, non-aspartic acid, non-glutamine, residue.

In one embodiment, a single surface exposed acceptor glutamine (Q) is present in the constant region of an antibody heavy chain. Optionally the antibody optionally comprises two heavy chains; such an antibody will comprise two functionalized acceptor glutamines of Formula IV per antibody molecule. Optionally said single acceptor glutamine (Q) is located at position 295. In one embodiment, the antibody comprises a N297Q substitution such that said single glutamine (Q) is located at position 295. In one embodiment, the antibody comprises a Q295 substitution (the glutamine at residue 295 is substituted by a non-glutamine residue) and a N297Q substitution, and said single glutamine (Q) is located at position 297.

In one embodiment, two surface exposed acceptor glutamines (Q) are present in the constant region of an antibody heavy chain. Optionally the antibody optionally comprises two heavy chains; such an antibody will comprise four functionalized acceptor glutamines of Formula IV per antibody molecule. Optionally the first glutamine (Q) is located at position 295 and the second glutamine (Q) is located at position 297 (e.g, a N297Q substitution).

Uses of Compounds

In one aspect, the disclosure provides the use of a compound of Formula I for the preparation of an antibody conjugate of Formula II.

In another aspect, the disclosure provides the use of a compound of Formula III and/or an antibody conjugate of Formula II, for the preparation of an antibody conjugate of Formula IV.

In yet another aspect, the disclosure provides the use of any of the compounds disclosed herein for the manufacture of a diagnostic product, a kit and/or a pharmaceutical preparation for the treatment or diagnosis of a mammal in need thereof. In one embodiment, the disclosure relates to the use of any of the compounds defined above for the manufacture of a pharmaceutical composition for the treatment of a tumor or infectious disease in a mammal.

Also the disclosure provides use of any of the compounds defined above as a medicament or an active component or active substance in a medicament. In a further aspect the disclosure relates to a method for preparing a pharmaceutical composition containing a compound as defined above, to provide a solid or a liquid formulation for administration orally, topically, or by injection. Such a method or process at least comprises the step of mixing the compound with a pharmaceutically acceptable carrier.

In one aspect, provided is a method to affect or prevent a predefined condition by exerting a certain effect, or detect a certain condition using a compound of the present disclosure, or a (pharmaceutical) composition comprising a compound disclosed herein.

In one embodiment, provided is a method of detecting the presence of a certain condition, e.g., the presence of an enzyme, the presence of a certain pH, the presence of a (bio)molecule, the presence of a substrate, or the presence of a certain oxygen concentration, with a compound disclosed herein, either in vivo or ex vivo.

In one embodiment, provided is a method of determining an enzyme ex vivo, e.g., in a diagnostic assay, using a compound disclosed herein by incubating a sample (possibly) containing said enzyme with a compound disclosed herein containing one or more diagnostic moieties Z and a substrate for said (proteolytic) enzyme, and observing release of said Z moieties. The phrase "determining an enzyme" means both qualitative analysis, i.e., detecting the presence of the enzyme, determining whether it is present, and quantitative analysis, i.e., quantifying the enzyme, determining the enzyme activity present in the sample. An enzyme can also be indirectly determined via its pro-enzyme containing a recognition site, e.g., an activation site, cleavable by said enzyme to be determined. Cleavage of the pro-enzyme can in such case be detected by observing the resulting activity using a suitable compound disclosed herein.

In one embodiment provided is a diagnostic assay method (in vivo or ex vivo) in which a compound disclosed herein is used.

In a further embodiment provided is a method in which the presence or amount of an enzyme is determined by using a compound disclosed herein.

In one embodiment, provided is a method to affect or prevent a predefined condition, e.g., a disease such as an autoimmune disease, a microbial disease, or cancer, by exerting an effect using a compound disclosed herein.

In a further embodiment, provided is a method of treating a mammal being in need thereof, whereby the method comprises the administration of a pharmaceutical composition to the mammal in a therapeutically effective dose.

In a further embodiment, provided is a method of treating a mammal having an illness characterized by undesired (cell) proliferation with a compound disclosed herein. In another embodiment the disclosure relates to a method of treating a mammal carrying a tumor with a compound of the disclosure. In yet another embodiment the disclosure relates to a method of treating a mammal having an inflammatory disease with a compound of the disclosure. In yet another embodiment the disclosure relates to a method of treating a mammal having an autoimmune disease with a compound of the disclosure. In yet another embodiment the disclosure relates to a method of treating a mammal having a bacterial or microbial infection with a compound of the disclosure.

In one embodiment, provided is a method of treating cancer in a mammal, whereby the method comprises the administration of a pharmaceutical composition to the mammal in a therapeutically effective dose.

In one embodiment, a compound is used to treat an illness characterized by undesired proliferation. In another embodiment, a compound of the disclosure is used to treat an illness characterized by undesired (cell) proliferation. In another embodiment, a compound of the disclosure is used to treat a tumor. In yet another embodiment, a compound of the disclosure is used to treat an inflammatory disease. In yet another embodiment a compound of the disclosure is used to treat an autoimmune disease. In yet another embodiment a compound of the disclosure is used to treat a bacterial or microbial infection.

In one embodiment, the antibodies are capable of being internalized into cells that express an antigen to which the antibody binds (e.g. a tumor or viral antigen) and/or induces internalization of the antigen on said antigen-expressing cells. In one embodiment, the compound of the disclosure is toxic to a cell upon internalization (i.e. the compound comprises a moiety Z that is toxic to a cell). Preferably such compounds can be used in methods of killing or eliminating cells, preferably wherein said cells are tumor cells.

In one embodiment of any aspect herein, the tumor is a solid tumor, e.g., a carcinoma, including a cancer or carcinoma of the bladder, breast, colon, kidney, liver, lung, ovary, prostate, pancreas, stomach, cervix, thyroid and skin. In one embodiment of any aspect herein, the tumor is a hematological tumor.

Provided are also pharmaceutical compositions comprising the compounds of the disclosure as defined above. A compound of the disclosure may be administered in purified form together with a pharmaceutical carrier as a pharmaceutical composition. The preferred form depends on the intended mode of administration and therapeutic or diagnostic application. The pharmaceutical carrier can be any compatible, nontoxic substance suitable to deliver the compounds of the disclosure to the patient. Pharmaceutically acceptable carriers are well known m the art and include, for example, aqueous solutions such as (sterile) water or physiologically buffered saline or other solvents or vehicles such as glycols, glycerol, oils such as olive oil or injectable organic esters, alcohol, fats, waxes, and inert solids. A pharmaceutically acceptable carrier may further contain physiologically acceptable compounds that act for example to stabilize or to increase the absorption of the compounds of the disclosure. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. Pharmaceutically acceptable adjuvants, buffering agents, dispersing agents, and the like, may also be incorporated into the pharmaceutical compositions.

For oral administration, the active ingredient can be administered in solid dosage forms, such as capsules, tablets, and powders, or m liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours Compressed tablets can be sugar-coated or film-coated to mask any unpleasant taste and protect the tablet from the atmosphere, or enteric-coated for selective disintegration in the gastrointestinal tract Liquid dosage forms for oral administration can contain coloring and flavoring to increase patient acceptance.

The compounds of the disclosure are however preferably administered parenterally. Preparations of the compounds of the disclosure for parenteral administration must be sterile Sterilization is readily accomplished by filtration through sterile filtration membranes, optionally prior to or following lyophilization and reconstitution. The parenteral route for administration of compounds of the disclosure is in accord with known methods, e.g. injection or infusion by intravenous, intraperitoneal, intramuscular, intraarterial, or intralesional routes. The compounds of the disclosure may be administered continuously by infusion or by bolus injection.

EXAMPLES

Materials and Methods

Antibodies chADC1 (or chimADC1) is an antibody specific for a human tumor antigen, chimADC1 (or chADC1), a chimeric antibody generated in mice and converted to human IgG1 isotype. chCE7 is specific for human L1-CAM and is composed of murine VL and murine VH fused to the Fc part of human IgG1 (see, e.g., Jeger et al., (2010) Angew. Chem. Int., 49, 9995-9997 and Knogler et al, (2007) Clin Cancer res., 13, 603-611). SGN-35 is specific for human CD30 and is described in Maeda et al. 2010 Cancer Sci. 101(1):224-230 and U.S. Pat. No. 7,090,843. ChADC1, SGN-35 and chCE7 are full length tetrameric antibodies with one acceptor glutamine per heavy chain at amino acid residue 295 (Kabat EU), i.e. a total of two acceptor glutamines. Unless otherwise indicated, chADC1, SGN-35 and chCE7 antibodies without the Fc mutations used in BTG coupling reaction were deglycosylated with PNGase F.

Fc Mutant Antibodies.

Variants of antibodies chimADC1 and SGN-35 were constructed that contained a N297S mutation; this antibody thus had one acceptor glutamine per heavy chain at amino acid residues 295 (Kabat EU), i.e. a total of two acceptor glutamines per tetrameric antibody, and were aglycosylated.

Variants of antibodies chimADC1, SGN-35 and chCE7 were also constructed that contained a N297Q mutation; these antibodies thus had two acceptor glutamine per heavy chain at amino acid residues 295 and 297 (Kabat EU), i.e. a total of four acceptor glutamines, and were aglycosylated. A further variant of chCE7 contained both Q295N and N297Q mutations.

For chimADC1 and SGN-35, two different sequences having the N297S or N297Q mutations in the human constant region of γ1 antibodies were synthesized by MWG-Biotech. These two mutated sequences were designed respectively N297S and N297Q.

The nucleic acid and amino acid sequences synthesized for the N297S construct (the mutation is underlined) is shown below:

(SEQ ID NO: 5)
GGGCCCAAGCGTGTTCCCCCTGGCCCCCAGCAGCAAGAGCACCAGCGGCGGCACAGCCGCCCTGGGCTGCCT

GGTGAAGGACTACTTCCCCGAGCCCGTGACCGTGTCCTGGAACAGCGGAGCCCTGACCTCCGGCGTGCACAC

CTTCCCCGCCGTGCTGCAGAGCAGCGGCCTGTACAGCCTGAGCAGCGTGGTGACCGTGCCCAGCAGCAGCCT

GGGCACCCAGACCTACATCTGTAACGTGAACCACAAGCCCAGCAACACCAAGGTGGACAAGAGAGTGGAGCC

CAAGAGCTGTGACAAGACCCACACCTGCCCCCCCTGCCCAGCCCCCGAGCTGCTGGGCGGACCCAGCGTGTT

CCTGTTCCCCCCCAAGCCCAAGGACACCCTGATGATCAGCAGAACCCCCGAGGTGACCTGTGTGGTGGTGGA

CGTGTCCCACGAGGACCCAGAGGTGAAGTTCAACTGGTACGTGGACGGCGTGGAGGTGCACAACGCCAAGAC

CAAGCCCAGAGAGGAGCAGTACAGCAGCACCTACAGGGTGGTGTCCGTGCTGACCGTGCTGCACCAGGACTG

GCTGAACGGCAAGGAGTACAAGTGTAAGGTGTCCAACAAGGCCCTGCCAGCCCCAATCGAAAAGACCATCAG

CAAGGCCAAGGGCCAGCCAAGAGAGCCCCAGGTGTACACCCTGCCACCCAGCAGGGAGGAGATGACCAAGAA

CCAGGTGTCCCTGACCTGTCTGGTGAAGGGCTTCTACCCAAGCGACATCGCCGTGGAGTGGGAGAGCAACGG

CCAGCCCGAGAACAACTACAAGACCACCCCCCCAGTGCTGGACAGCGACGGCAGCTTCTTCCTGTACAGCAA

GCTGACCGTGGACAAGAGCAGATGGCAGCAGGGCAACGTGTTCAGCTGCTCCGTGATGCACGAGGCCCTGCA

CAACCACTACACCCAGAAGAGCCTGAGCCTGTCCCCAGGCAAGTGATGAATTC (SEQ ID NO: 6)
G P S V F P L A P S S K S T S G G T A A L G C L V K D Y F P E P V T V S

W N S G A L T S G V H T F P A V L Q S S G L Y S L S S V V T V P S S S L

G T Q T Y I C N V N H K P S N T K V D K R V E P K S C D K T H T C P P C

P A P E L L G G P S V F L F P P K P K D T L M I S R T P E V T C V V V D

V S H E D P E V K F N W Y V D G V E V H N A K T K P R E E Q Y S S T Y R

```
V V S V L T V L H Q D W L N G K E Y K C K V S N K A L P A P I E K T I S

K A K G Q P R E P Q V Y T L P P S R E E M T K N Q V S L T C L V K G F Y

P S D I A V E W E S N G Q P E N N Y K T T P P V L D S D G S F F L Y S K

L T V D K S R W Q Q G N V F S C S V M H E A L H N H Y T Q K S L S L S P

G K
```

The nucleic acid and amino acid sequences synthesized for the N297Q construct (the mutation is underlined) is shown below:

SGN-30 N297S and N297Q and cells were grown in rolling bottle to produce large quantities of antibodies that were purified from the harvested supernatant.

```
                                                        (SEQ ID NO: 7)
GGGCCCAAGCGTGTTCCCCCTGGCCCCCAGCAGCAAGAGCACCAGCGGCGGCACAGCCGCCCTGGGCTGCCT

GGTGAAGGACTACTTCCCCGAGCCCGTGACCGTGTCCTGGAACAGCGGAGCCCTGACCTCCGGCGTGCACAC

CTTCCCCGCCGTGCTGCAGAGCAGCGGCCTGTACAGCCTGAGCAGCGTGGTGACCGTGCCCAGCAGCAGCCT

GGGCACCCAGACCTACATCTGTAACGTGAACCACAAGCCCAGCAACACCAAGGTGGACAAGAGAGTGGAGCC

CAAGAGCTGTGACAAGACCCACACCTGCCCCCCCTGCCCAGCCCCCGAGCTGCTGGGCGGACCCAGCGTGTT

CCTGTTCCCCCCCAAGCCCAAGGACACCCTGATGATCAGCAGAACCCCCGAGGTGACCTGTGTGGTGGTGGA

CGTGTCCCACGAGGACCCAGAGGTGAAGTTCAACTGGTACGTGGACGGCGTGGAGGTGCACAACGCCAAGAC

CAAGCCCAGAGAGGAGCAGTACCAAAGCACCTACAGGGTGGTGTCCGTGCTGACCGTGCTGCACCAGGACTG

GCTGAACGGCAAGGAGTACAAGTGTAAGGTGTCCAACAAGGCCCTGCCAGCCCCAATCGAAAAGACCATCAG

CAAGGCCAAGGGCCAGCCAAGAGAGCCCCAGGTGTACACCCTGCCACCCAGCAGGGAGGAGATGACCAAGAA

CCAGGTGTCCCTGACCTGTCTGGTGAAGGGCTTCTACCCAAGCGACATCGCCGTGGAGTGGGAGAGCAACGG

CCAGCCCGAGAACAACTACAAGACCACCCCCCCAGTGCTGGACAGCGACGGCAGCTTCTTCCTGTACAGCAA

GCTGACCGTGGACAAGAGCAGATGGCAGCAGGGCAACGTGTTCAGCTGCTCCGTGATGCACGAGGCCCTGCA

CAACCACTACACCCAGAAGAGCCTGAGCCTGTCCCCAGGCAAGTGATGAATTC
```

```
                                                        (SEQ ID NO: 8)
G P S V F P L A P S S K S T S G G T A A L G C L V K D Y F P E P V T V S

W N S G A L T S G V H T F P A V L Q S S G L Y S L S S V V T V P S S S L

G T Q T Y I C N V N H K P S N T K V D K R V E P K S C D K T H T C P P C

P A P E L L G G P S V F L F P P K P K D T L M I S R T P E V T C V V V D

V S H E D P E V K F N W Y V D G V E V H N A K T K P R E E Q Y Q S T Y R

V V S V L T V L H Q D W L N G K E Y K C K V S N K A L P A P I E K T I S

K A K G Q P R E P Q V Y T L P P S R E E M T K N Q V S L T C L V K G F Y

P S D I A V E W E S N G Q P E N N Y K T T P P V L D S D G S F F L Y S K

L T V D K S R W Q Q G N V F S C S V M H E A L H N H Y T Q K S L S L S P

G K
```

These sequences were then digested from the MWG-Biotech cloning vector with the ApaI and EcoRI restriction enzymes and cloned into the vector B digested with the same restriction enzymes (B N297S and B N297Q). Light chain and heavy chain of the variable domains of the chADC1 antibody were amplified by PCR and the purified products of the PCR were cloned together into the vectors B N297S and N297Q using the InFusion cloning system (Ozyme) to create bicistronic vectors. The bicistronic vectors generated were then sequenced and validated prior to cell transfection. CHO cells were transfected with the vectors encoding chADC1 or For chCE7 (anti-L1-CAM antibody), cDNAs from heavy and light chain were cloned separately into the HindIII/BamHI site of the mammalian expression vector pcDNA3.1+ (Invitrogen, Basel, Switzerland). The specific mutation N297Q was introduced into the CH2 domain of chCE7 heavy chain using overlapping PCR and standard molecular biology techniques. The nucleic acid and amino acid sequences for the N297Q construct are shown below (the mutation is underlined):

(SEQ ID NO: 9)
GTTTGTAAGCTTGCTAGCACCAAGGGCCCATCGGTCTTCCCCCTGGCACCCTCCTCCAAGAGCACCTCTGGG

GGCACAGCGGCCCTGGGCTGCCTGGTCAAGGACTACTTCCCCGAACCGGTGACGGTGTCGTGGAACTCAGGC

GCCCTGACCAGCGGCGTGCACACCTTCCCGGCTGTCCTACAGTCCTCAGGACTCTACTCCCTCAGCAGCGTG

GTGACCGTGCCCTCCAGCAGCTTGGGCACCCAGACCTACATCTGCAACGTGAATCACAAGCCCAGCAACACC

AAGGTGGACAAGAAAGTTGAGCCCAAATCTTGTGACAAAACTCACACATGCCCACCGTGCCCAGCACCTGAA

CTCCTGGGGGGACCGTCAGTCTTCCTCTTCCCCCCAAAACCCAAGGACACCCTCATGATCTCCCGGACCCCT

GAGGTCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACCAAAGCACGTACCGGGTGGTCAGCGTC

CTCACCGTCCTGCACCAGGACTGGCTGAATGGCAAGGAGTACAAGTGCAAGGTCTCCAACAAAGCCCTCCCA

GCCCCCATCGAGAAAACCATCTCCAAAGCCAAAGGGCAGCCCCGAGAACCACAGGTGTACACCCTGCCCCCA

TCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGAC

GGCTCCTTCTTCCTCTACAGCAAGCTCACCGTGGACAAGAGCAGGTGGCAGCAGGGGAACGTCTTCTCATGC

TCCGTGATGCATGAGGCTCTGCACAACCACTACACGCAGAAGAGCCTCTCCCTGTCTCCGGGTAAATGAGGA

TCCACACAC (SEQ ID NO: 10)
GPSVFPLAPSSKSTSGGTAALGCLVKDYFPEPVTVSWNSGALTSGVHTFPAVLQSSGLYS

LSSVVTVPSSSLGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTKPREEQYQSTYR

VVSVLTVLHQDWLNGKEYKCKVSNKALPAPIEKTISKAKGQPREPQVYTLPPSRDELTKN

QVSLTCLVKGFYPSDIAVEWESNGQPENNYKTTPPVLDSGSFFLYSKLTVDKSRWQQGN

VFSCSVMHEALHNHYTQKSLSLSPGK

Additionally, a further modified variant of aglycosylated N297Q variant was made containing a Q295N mutation (i.e. containing Q295N, N297Q). The antibodies were produced in HEK293 cells. HEK293 cells were co-transfected with heavy and light chain containing plasmids. chCE7 was produced in culture dishes and purified from the harvested supernatant on a protein A sepharose column.

Lysine-Based Linkers

Cadaverin-dansyl, cadaverin-biotin and cadaverin-TAMRA were purchased from Zedira (Darmstadt, Germany). C2-SAc, C6-SAc, PEG-4-SAc were prepared as described in Example 1. 5-FAM cadaverin (fluorescein-5-carboxamide) was purchased from Tebu-Bio (Le Perray en Yveline, France). DBCO-amine, DBCO-PEG4-NH$_2$, Azide-PEG4-NH$_2$ and Alkyne-PEG4-NH$_2$ were purchased from Click Chemistry Tools (Scottsdale, Ariz.). C2-SH and C6-SH thiol linkers were synthesized by reduction of their corresponding disulfides as described in Example 1. PEG-4-SH was synthesized by cleavage of the acetate group of PEG-4-SAc with sodium methoxide. MMAF linkers were prepared by reacting C6-SH with maleimide-valine-citrullin-PAB-MMAF and subsequent Boc-deprotection. C2-DOTA and C6-DOTA linkers (thiol linkers coupled to maleimide-DOTA) were prepared by reacting C2-SH or C6-SH with DOTA-maleimide followed by Boc deprotection. C2-fluorescein (C2-thiol linker coupled to fluorescein maleimide) was prepared with a similar procedure. C2-N$_3$ and C6-N$_3$ linkers were synthesized as mentioned in Example 1.

Deglycosylation of Antibodies

To antibody in PBS buffer (PBS (10×): Weight 2.1 g KH$_2$PO$_4$, 90 g NaCl, 4.8 g Na$_2$HPO$_4$×2H$_2$O and transfered to a 1 L glass bottle, was added water to a volume of 1 L. To get PBS 1X, use 100 mL PBS (10×) and add water to a volume of 900 mL. pH was adjusted to 7.2 and filled to 1 L with water), and was incubated with 6 Units/mg protein of N-glycosidase F (PNGase F) from *Flavobacterium meningosepticum* (Roche, Switzerland) overnight at 37° C. The enzyme was then removed by centrifugation-dialysis (Vivaspin MWCO 50 kDa, Vivascience, Winkel, Switzerland).

Enzymatic Modification of Antibodies 1 mg/mL deglycosylated antibody in PBS was incubated with 80 equivalents of ligand and 1 U/mL or >1 U/mL bacterial transglutaminase (BTGase, Zedira, Darmstadt, Germany) overnight at 37° C. Excess of ligand and the BTGase were removed by centrifugation-dialysis (Vivaspin MWCO 50 kDa, Vivascience, Winkel, Switzerland).

Deprotection of Protected Thiol Linkers

The method for deacetylation of the protected thiol linker is adapted from published procedures (Thermo Scientific). 0.5M hydroxylamine, 25 mM EDTA is prepared in phosphate buffered saline (PBS), pH 7.2-8.5. 1 mL of antibody-linker conjugate is combined with 100-200 µL of prepared 0.5M hydroxylamine. The mixture is incubated for 2 h at room temperature. The reaction mixture is then be purified into PBS containing 10 mM EDTA by using a desalting column (HiTrap Desalting column, 5 mL, GE Healthcare).

Coupling Deprotected Antibody-Linker Conjugate with Maleimide Functionalized Moiety of Interest (Z)

Coupling of deprotected antibody-linker conjugate with maleimide functionalized toxin is carried out as in J. R. Junutula et al., (2008) Nat Biotechnol 26, 925. 5 equivalents per SH group of the maleimide functionalized ligand is combined with the deprotected antibody-linker conjugate. The reaction is incubated at RT for 1.5 h before desalting into PBS.

Coupling Antibody-Linker Conjugate with Azide Group with Alkyne Functionalized Moiety of Interest (Z)

Conjugation reactions were performed by adding amine-DBCO (50 µM, final concentration for 2 site-mutants; 1000/1 final concentration) to the antibody-linker conjugate with azide group (20 µM) and incubating the reaction mixture for 0.5 h at room temperature. The mixture was directly analyzed by LC-MS.

LC-MS Analysis

LC-MS analysis was performed on a Waters LCT Premier mass spectrometer. Samples were chromatographed on an Aeris WIDEPORE XB-C18 column (3.6 µm, 100 mm×2.1 mm; Phenomenex) heated to 65° C. using a linear gradient from 22 to 55% A in 15 min plus 5% solvent C (solvent A: acetonitrile+0.1% formic acid, solvent B: water+0.1% formic acid, solvent C: 2-propanol) at a flow rate of 0.5 mL/min. The eluent was ionized using an electrospray source. Data were collected with MassLynx 4.1 and deconvolution was performed using MaxEnt1. Before the LC-MS analysis, 10 µg of antibody were mixed with DTT (final concentration should be 20 mM). Guan-buffer (7.5M Guan-HCl, 0.1M Tris-HCl, 1 mM EDTA buffer pH 8.5 (adjusted by addition of concentrated $NH_4OH$ (28% aqueous solution) was added to a final volume of 50 µL. Finally, 5 µL of the mixture were injected.

HIC Analysis

Hydrophobic interaction chromatography (HIC) analysis was conducted on Agilent Technologies 1200 series UPLC system using a TSKgel Butyl-NPR column, 4.6×35 mm, 2.5 mm particle size (Tosoh Bioscience) with a linear gradient of 100% mobile phase A (1.5 M $(NH_4)_2SO_4$ in 25 mM potassium phosphate) to 70% mobile phase B (25 mM potassium phosphate, pH 7.0, 25% isopropanol) in 14 min. The flow rate was set at 1 mL/min and the column temperature was maintained at 30° C. HIC analysis of chADC1dg1 coupled to a Dansyl cadaverine substrate (see Example 3) was performed using double detection by UV (280 nm) and fluorescence (X excitation at 250 nm, X emission at 535 nm). The overall mean drug loading or DAR (Drug Antibody Ratio) is calculated as the weighted average using the integrated areas of the constituent peaks and the drug loading of each peak as the weighting factor.

Western Blot Analysis

Western blot analysis: Enzymatically modified antibodies were subjected to SDS-PAGE (12.5%) and were transferred to polyvinylidene difluoride (PVDF) membranes (Immobilon P, Millipore). After blocking with 2% bovine serum albumin (BSA) in TBST (20 mM Tris-HCl, pH 7.5, 140 mM NaCl, 0.05% Tween-20) for 2 hours at room temperature (RT), membrane was incubated with Streptavidin-horseradish peroxidase conjugate (High Sensitivity Streptavidin-HRP diluted 1:20000; Beckman Coulter) for 30 min. Membrane was washed three times with TBST for 15 min and antibodies were detected with Immune-Star Western C Kit chemiluminescence substrate from Biorad.

Tryptic Digest $6.67*10^{-9}$ mol protein was incubated in 100 µl 50 mM ammonium bicarbonate pH 8.0 containing 0.1% Rapidgest SF (Waters) and 0.96 µl 1M DTT at 55° C. for 30 min. After the sample was cooled to RT. 1.92 µl 1 M iodoacetamide was added and the samples were incubated for 40 min at RT. The samples were then digested with 5 µg trypsin over night at 37° C. and diluted (1:1 v/v) with 1% formic acid in 10% acetonitrile and analysed by ESI-TOF LC-MS using an ACE 3 C18, 150×3 mm column.

Example 1

Synthesis of New Lysine-Based Linkers with and without Spacer Groups

Materials and Methods

All solvents used for reactions were purchased as anhydrous grade from Acros Organics (puriss., dried over molecular sieves, $H_2O<0.005\%$) and were used without further purification unless otherwise stated. Solvents for extractions, column chromatography and thin layer chromatography (TLC) were purchased as commercial grade. All non aqueous reactions were performed under an argon atmosphere using flame-dried glassware and standard syringe/septa techniques. Commercially available reagents were used without further purification. In general, reactions were magnetically stirred and monitored by TLC performed on Merck TLC glass sheets (silica gel 60 $F_{254}$). Spots were visualized with UV light (λ=254 nm) or by staining with anisaldehyde solution or $KMnO_4$ solution and subsequent heating. Chromatographic purification of products was performed using Fluka silica gel 60 for preparative column chromatography.

Nuclear magnetic resonance (NMR) spectra were recorded in $CDCl_3$, $CD_3OD$ or $D_2O$ either on a Bruker Av-400 or a Bruker Av-500 spectrometer at room temperature. The measured chemical shifts are reported in δ (ppm) and the residual signal of the solvent was used as the internal standard ($CDCl_3$ $^1H$: δ=7.26 ppm, $^{13}C$: δ=77.0 ppm, $CD_3OD$ $^1H$: δ=3.31 ppm, $^{13}C$: δ=49.1 ppm, $D_2O$ $^1H$: δ=4.81 ppm). All $^{13}C$ NMR spectra were measured with complete proton decoupling. Data of NMR spectra are reported as follows: s=singlet, d=doublet, t=triplet, m=multiplet, dd=doublet of doublets, dt=doublet of triplets, br=broad signal. The coupling constant J is reported in Hertz (Hz). High resolution mass spectrometry (HRMS) was performed on a Bruker Daltonics maxis ESI-QTOF or a Varian HiResMALDI instrument.

The analytical and preparative HPLC system used was a Merck-Hitachi D-7000 system. The columns used for chromatography were either an Ultimate XB-C18 (4.6×150 mm, 3 µm) or an Xbridge C18 (4.6×150 mm, 5 µm) for analytical separations operated with a flow of 1 ml/min. For preparative purifications, either an Ultimate XB-C18 (21.2×150 mm, 5 µm) or an Xbridge C18 (10×150 mm, 5 µm) column was used operated with a flow of 15 ml/min and 4 ml/min respectively.

Figure 15:
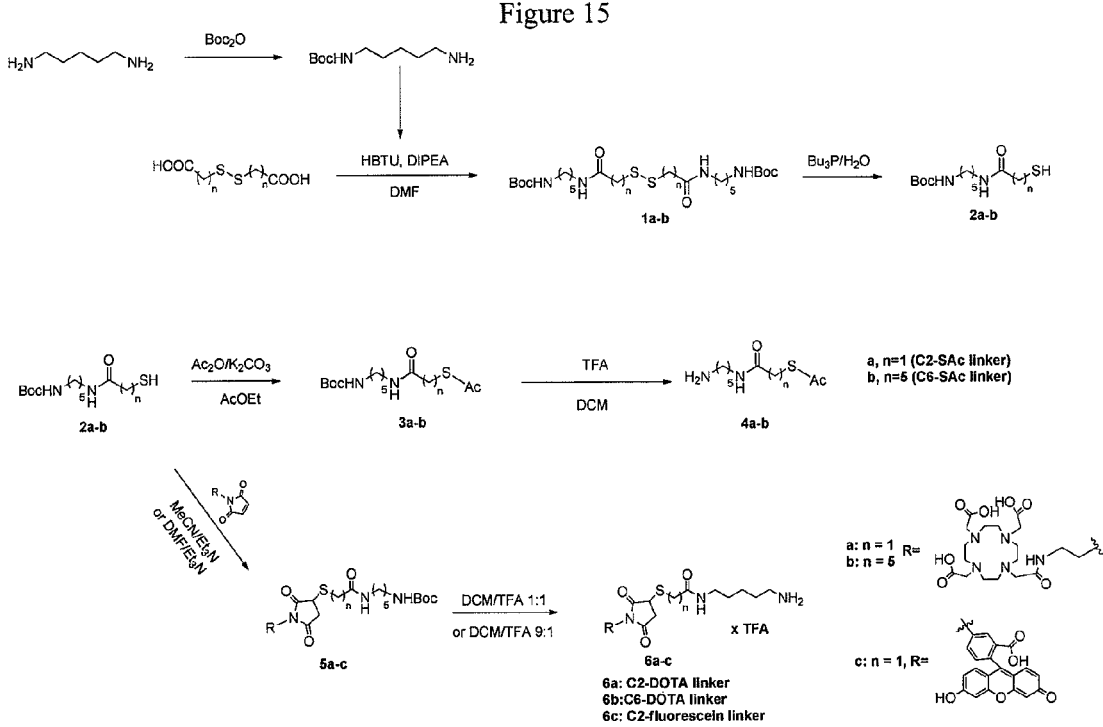
FIG. 15 shows a scheme for preparing S-acetyl-protected cadaverin linkers of different lengths (either n=1 or 5 carbons) as well as a short thiol linker coupled to maleimide-DOTA.
Figure 16A:
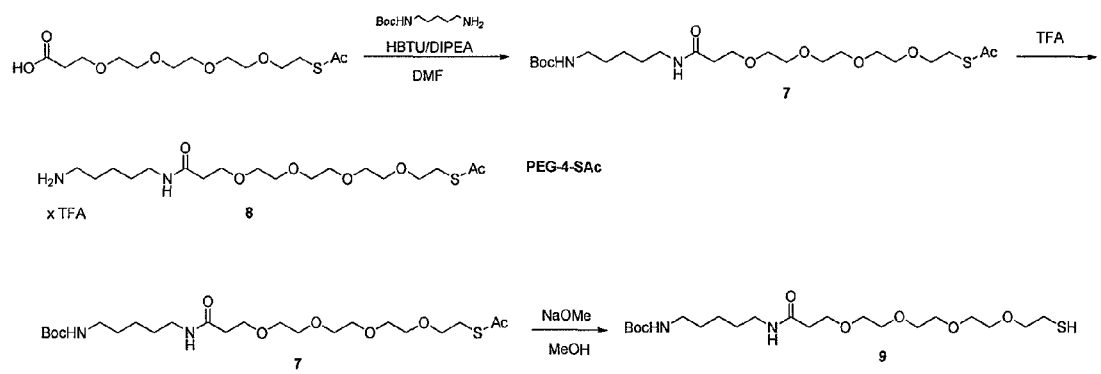
FIGS. 16A, 16B and 16C show schemes for preparing linkers.

Compounds 1-6 and reaction schemes are shown in FIG. 15. Compounds 7-9 and reaction schemes are shown in FIG. 16A. For Compounds 10-13 and reaction schemes, see FIG. 16B.

di-tert-butyl(((2,2'-disulfanediyibis(acetyl))bis (azanediyl))bis(pentane-5,1-diyl))dicarbamate (1a)

In a solution of 2,2'-disulfanediyldiacetic acid (160 mg, 0.878 mmol), tert-butyl(5-amino-pentyl)carbamate (391 mg, 1.932 mmol) and DIPEA (920 µl, 5.27 mmol) in DMF (4.9 ml), HBTU (1.33 g, 3.51 mmol) was added portionwise at room temperature. After stirring for 5 hours, the brownish solution was diluted with ethyl acetate (80 ml) and washed with water (3×30 ml) and brine (1×30 ml). The organic layer was dried under sodium sulfate, filtered and evaporated to dryness. The crude was purified by flash column chromatography on silica using CHCl$_3$/EtOH 95:5 to yield 420 mg (87%) of a yellow oil which solidified upon standing at room temperature. $^1$H NMR (400 MHz, CDCl$_3$): δ 6.91 (br, 2H), 4.68 (br, 2H), 3.44 (s, 4H), 3.29 (dt, J$_1$=7.2 Hz, J$_2$=6.8 Hz, 4H), 3.10 (dt, J$_1$=7.7 Hz, J$_2$=6.3 Hz, 4H), 1.64-1.31 (m, 30H). $^{13}$C NMR (100 MHz, CDCl$_3$): δ 168.5, 156.1, 79.1, 42.6, 40.2, 39.8, 29.7, 28.8, 28.4, 23.9. ESI-QTOF MS m/z calculated for C$_{24}$H$_{46}$N$_4$O$_6$S$_2$ [M+H]$^+$ 551.2932. measured 551.2921 di-tert-butyl(((6,6'-disulfanediylbis(hexanoyl))bis (azanediyl))bis(pentane-5,1-diyl))dicarbamate (1b)

In a solution of 6,6'-disulfanediyldihexanoic acid (250 mg, 0.849 mmol), tert-butyl(5-amino-pentyl)carbamate (412 mg, 2.038 mmol) and DIPEA (0.890 ml, 5.09 mmol) in DMF (4.7 ml), HBTU (1.29 g, 3.40 mmol) was added portionwise at room temperature. After stirring for 20 hours, the yellowish reaction mixture was diluted with ethyl acetate (70 ml) and washed with cold HCl 0.1N (3×50 ml), NaHCO$_3$ (sat) (1×50 ml) water (1×50 ml) and brine (1×50 ml). The organic layer was dried under sodium sulfate, filtered and evaporated to dryness. The crude was purified by flash column chromatography on silica using CHCl$_3$/EtOH 95:5 to yield 525 mg (93%) of compound as a yellow sticky solid. $^1$H NMR (400 MHz, CDCl$_3$): δ 5.87 (br, 2H), 4.64 (br, 2H), 3.22 (dt, J$_1$=7.3 Hz, J$_2$=6.8 Hz, 4H), 3.09 (dt, J$_1$=8.1 Hz, J$_2$=6.7 Hz, 4H), 2.65 (t, J=7.2 Hz, 4H), 2.16 (t, J=7.2 Hz, 4H), 1.73-1.59 (m, 8H), 1.55-1.45 (m, 8H), 1.42 (s, 18H), 1.37-1.28 (m, 4H). $^{13}$C NMR (100 MHz, CDCl$_3$): δ 172.9, 156.1, 79.0, 40.2, 39.2, 38.8, 36.5, 29.7, 29.1, 28.8, 28.4, 28.0, 25.3, 23.9. ESI-QTOF MS m/z calculated for C$_{32}$H$_{62}$N$_4$O$_6$S$_2$ [M+H]$^+$ 663.4184. measured 663.4185.

tert-butyl(5-(2-mercaptoacetamido)pentyl)carbamate (2a)

To a solution of Di-tert-butyl(((2,2'-disulfanediylbis (acetyl))bis(azanediyl))bis(pentane-5,1-diyl))di-carbamate (390 mg, 0.478 mmol) in a mixture of tetrahydrofuran (7 ml) and water (0.74 ml), tributylphosphine (528 mg, 2.48 mmol) was added dropwise at room temperature, within 1 min. The reaction mixture was stirred for 1 h and then the volatiles were removed under reduced pressure at 33° C. The crude was azeotroped once with 50 ml benzene to remove traces of water and the residue was purified with flash column chromatography on silica with CHCl$_3$/EtOH 95:5 to yield a slightly yellow clear oil. The product was re-purified with flash column chromatography with hexane/ethyl acetate 2:8 to remove oxidized tributylphosphine byproducts. Final yield was 180 mg (91%) of product as a colorless oil which solidified to a white solid after storage at −25° C. $^1$H NMR (400 MHz, CDCl$_3$): δ 6.73 (br, 1H), 4.57 (br, 1H), 3.28 (dt, J$_1$=7.6 Hz, J$_2$=6.9 Hz, 2H), 3.23 (d, J=9.0 Hz, 2H), 3.11 (dt, J$_1$=8.1 Hz, J$_2$=6.6 Hz, 2H), 1.87 (t, $^3$J=9.0 Hz, 1H), 1.61-1.47 (m, 4H), 1.43 (s, 9H), 1.40-1.30 (m, 2H). $^{13}$C NMR (100 MHz, CDCl$_3$): δ 169.1, 156.1, 79.1, 40.2, 39.7, 29.7, 29.0, 28.4, 28.3, 23.9. ESI-QTOF MS m/z calculated for C$_{12}$H$_{24}$N$_2$O$_3$S [M+Na]$^+$ 299.1400. measured 299.1408.

tert-butyl(5-(6-mercaptohexanamido)pentyl)carbamate (2b)

To a solution of di-tert-butyl(((6,6'-disulfanediylbis (hexanoyl))bis(azanediyl))bis(pentane-5,1-diyl))di-carbamate (196 mg, 0.296 mmol) in a mixture of tetrahydrofuran (3 ml) and water (0.31 ml, 17.21 mmol), tributylphosphine (272 ml, 1.035 mmol) was added dropwise at room temperature, within 1 min. The reaction mixture was stirred for 1 h and then the volatiles were removed under reduced pressure at 33° C. The crude was azeotroped once with 50 ml benzene to remove traces of water and the residue was purified with flash column chromatography on silica with chloroform/ethanol 95:5 to yield a slightly yellow clear oil. NMR revealed that the compound was contaminated with tributylphosphine oxidized byproducts so the crude was purified again with flash column chromatography with hexane/ethyl acetate 2:8 to yield 180 mg (91%) of product as a colorless oil which solidified after storage at −25° C. $^1$H NMR (400 MHz, CDCl$_3$): δ 5.88 (br, 1H), 4.57 (br, 1H), 3.23 (dt, J$_1$=7.3 Hz, J$_2$=6.9 Hz, 2H), 3.09 (dt, J$_1$=7.8 Hz, J$_2$=6.5 Hz, 2H), 2.52 (dt, J$_1$=8.0 Hz, J$_2$=7.6 Hz, 2H), 2.16 (t, J=7.5 Hz, 4H), 1.69-1.57 (m, 4H), 1.56-1.46 (m, 4H), 1.43 (s, 9H), 1.36-1.28 (m, 3H). $^{13}$C NMR (100 MHz, CDCl$_3$): δ 172.8, 156.1, 79.1, 40.2, 39.2, 36.5, 33.6, 29.7, 29.1, 28.4, 27.9, 25.1, 24.4, 23.9. ESI-QTOF MS m/z calculated for C$_{16}$H$_{32}$N$_2$O$_3$S [M+H]$^+$ 333.2206. measured 333.2198.

S-(2-((5-((tert-butoxycarbonyl)amino)pentyl)amino)-2-oxoethyl) ethanethioate (3a)

To a mixture of tert-butyl(5-(2-mercaptoacetamido)pentyl)carbamate (189 mg, 0.684 mmol) and dry potassium carbonate (189 mg, 1.368 mmol) in degassed (freeze-pump-thaw) ethyl acetate (2.7 ml), acetic anhydride (77 mg, 0.821 mmol) was added and the reaction was stirred for 16 h. The reaction was then diluted with ethyl acetate (30 ml), filtered and washed with cold water (1×15 ml) and brine (1×15 ml), dried under sodium sulfate and evaporated to dryness. The crude was purified by flash column chromatography on silica with CHC$_3$/EtOH 96:4 to yield 192 mg (88%) of product as a white solid. $^1$H NMR (400 MHz, CDCl$_3$): δ 6.22 (br, 1H), 4.56 (br, 1H), 3.51 (s, 2H), 3.21 (dt, J$_2$=7.1 Hz, J$_2$=6.9 Hz, 2H), 3.09 (dt, J$_1$=7.6 Hz, J$_2$=6.6 Hz, 2H), 2.40 (s, 3H), 1.54-1.45 (m, 4H), 1.43 (s, 9H), 1.35-1.26 (m, 2H). $^{13}$C NMR (100 MHz, CDCl$_3$): δ 190.5, 168.0, 156.0, 79.1, 40.3, 39.6, 33.1, 30.3, 29.6, 29.0, 28.4, 23.8. ESI-QTOF MS m/z calculated for C$_{14}$H$_{26}$N$_2$O$_4$S [M+Na]$^+$ 341.1505. measured 341.1506.

S-(6-((5-((tert-butoxycarbonyl)amino)pentyl)amino)-6-oxohexyl) ethanethioate (3b)

To a solution of tert-butyl(5-(6-mercaptohexanamido) pentyl)carbamate (180 mg, 0.541 mmol) and dry potassium carbonate (150 mg, 1.083 mmol) in degassed (freeze-pump-thaw) ethyl acetate (2.2 ml), acetic anhydride (61 μl, 0.650 mmol) was added and the reaction was stirred for 16 h. The reaction was then diluted with ethyl acetate (20 ml), filtered and washed with cold water (1×10 ml) and brine (1×10 ml), dried under sodium sulfate and evaporated to dryness. The crude was purified by flash column chromatography using chloroform/ethanol 96:4 to yield 182 mg (90%) of a white solid. $^1$H NMR (400 MHz, CDCl$_3$): δ 5.68 (br, 1H), 4.61 (br, 1H), 3.21 (dt, =7.3 Hz, J$_2$=6.9 Hz, 2H), 3.09 (dt, J$_1$=7.7 Hz, J$_2$=6.4 Hz, 2H), 2.83 (t, J=7.2 Hz, 2H), 2.30 (s, 1H), 2.14 (t, J=7.2 Hz, 2H), 1.67-1.44 (m, 8H), 1.42 (s, 9H), 1.40-1.27 (m, 4H). $^{13}$C NMR (100 MHz, CDCl$_3$): δ 196.0, 172.8, 156.1, 79.3, 40.2, 39.2, 36.4, 30.6, 29.7, 29.2, 29.1, 28.8, 28.4, 28.3, 25.1, 23.9. ESI-QTOF MS m/z calculated for C$_{18}$H$_{34}$N$_2$O$_4$S [M+H]$^+$ 375.2312, measured 375.2312

S-(2-((5-aminopentyl)amino)-2-oxoethyl) ethanethioate (4a) (C2-SAc Linker)

To a solution of S-(2-((5-((tert-butoxycarbonyl)amino)pentyl)amino)-2-oxoethyl)ethanethioate (189 mg, 0.594 mmol) in dichloromethane (7.9 ml), trifluoroacetic acid (0.92 ml, 11.87 mmol) was added dropwise at 0° C. After stirring for 10 min, the reaction mixture was allowed to reach room temperature where it was stirred for 1 h. Toluene was then added (20 ml), volatiles were removed under reduced pressure and the residue was dried under high vacuum for 30 min to yield quantitatively a slightly yellow oil which was sufficiently pure when analyzed by NMR. The oil was dissolved in water and lyophilized to give a white solid. $^1$H NMR (400 MHz, CD$_3$OD): 3.60 (s, 2H), 3.20 (t, J=6.9 Hz, 2H), 2.91 (t, J=7.6 Hz, 2H), 2.37 (s, 3H), 1.72-1.61 (m, 2H), 1.59-1.50 (m, 2H), 1.45-1.35 (m, 2H). $^{13}$C NMR (100 MHz, CDCl$_3$): δ 196.3, 170.8, 40.7, 40.4, 33.9, 30.1, 29.9, 28.2, 24.6. ESI-QTOF MS m/z calculated for C$_9$H$_{18}$N$_2$O$_2$S [M+H]$^+$ 219.1162. measured 219.1171.

S-(6-((5-aminopentyl)amino)-6-oxohexyl) ethanethioate (4b) (C6-SAc linker)

To a solution of S-(6-((5-((tert-butoxycarbonyl)amino)pentyl)amino)-6-oxohexyl) ethanethioate (187 mg, 0.5 mmol) in dichloromethane (6.6 ml), trifluoroacetic acid (0.77 ml, 5.34 mmol) was added dropwise at 0° C. After stirring for 10 min, the reaction mixture was allowed to reach room temperature where it was stirred for 1 h. The volatiles were removed under reduced pressure at 30° C. and the residue was azeotroped with toluene and dried under high vacuum for 30 min. Lyophilization yielded a white solid (185 mg) which was sufficiently pure by NMR. $^1$H NMR (400 MHz, CD$_3$OD): δ 3.18 (t, J=7.0 Hz, 2H), 2.92 (t, J=7.8 Hz, 2H), 2.86 (t, J=7.3 Hz, 2H), 2.30 (s, 3H), 2.17 (t, J=7.3 Hz, 2H), 1.72-1.50 (m, 8H), 1.45-1.33 (m, 4H). $^{13}$C NMR (100 MHz, CD$_3$OD): 197.7, 176.2, 40.7, 40.0, 37.0, 30.64, 30.61, 30.0, 29.8, 29.4, 28.3, 26.6, 24.8. ESI-QTOF MS m/z calculated for C$_{13}$H$_{26}$N$_2$O$_2$S [M+H]$^+$ 275.1788. measured 275.1785.

2,2',2''-(10-(2-((2-(3-((2-((5-((tert-butoxycarbonyl)amino)pentyl)amino)-2-oxoethyl)thio)-2,5-dioxopyrrolidin-1-yl)ethyl)amino)-2-oxoethyl)-1,4,7,10-tetraazacyclododecane-1,4,7-triyl)triacetic acid (5a)

DOTA-maleimide (25 mg, 0.032 mmol) was suspended in acetonitrile (1 ml) and triethylamine was added (22.59 μl, 0.162 mmol) and after 5 min of stirring, a clear colorless solution was formed. A solution of tert-butyl(5-(2-mercaptoacetamido)pentyl)-carbamate (10.54 mg, 0.038 mmol) in 0.5 ml acetonitrile was then added and the reaction was stirred for 1 h at which point HPLC confirmed complete consumption of starting material. The solvent system used for reaction monitoring is as follows: water/0.1% TFA (solvent A), acetonitrile (solvent B); 0-5 min: 0% B, 5-20 min: 0-50% B, 20-25 min: 50% B, 25-30 min 50-0% B; UV=214 nm; t$_R$=18.3 min. The reaction was then diluted with 3 ml water and was purified by preparative HPLC with the following solvent system: water/0.1% TFA (solvent A), acetonitrile (solvent B); 0-5 min: 0% B, 5-20 min: 0-50% B. The product eluted approximately at 17 min; XB-C18 column; UV=214 nm. The product was obtained as a white solid after lyophilization (19.7 mg, 77% yield). ESI-MS m/z calculated for C$_{34}$H$_{58}$N$_8$O$_{12}$S [M+H]$^+$ 803.39. measured 803.40.

2,2',2''-(10-(2-((2-(3-((6-((5-((tert-butoxycarbonyl)amino)pentyl)amino)-6-oxohexyl)thio)-2,5-dioxopyrrolidin-1-yl)ethyl)amino)-2-oxoethyl)-tetraazacyclododecane-1,4,7-triyl)triacetic acid (5b)

To a solution of DOTA-maleimide (80 mg, 0.102 mmol) and triethylamine (52.5 mg, 0.519 mmol) in acetonitrile (3.5 ml) was added a solution of tert-butyl(5-(6-mercaptohexanamido)pentyl)carbamate (40.6 mg, 0.122 mmol) in acetonitrile (1.5 ml) and the reaction mixture was stirred for 6 h at room temperature. Approximately half of the solvent was then removed under reduced pressure, water was added (3 ml) and the mixture was purified with preparative RP HPLC with the following solvent system: water/0.1% TFA (solvent A), acetonitrile (solvent B); 0-5 min: 0% B, 5-20 min: 0-50% B; t$_R$=17.4 min; UV=214 nm; XB-C18 column. The product was obtained as a white solid after lyophilization (58 mg, 57% yield). ESI-MS m/z calculated for C$_{38}$H$_{66}$N$_8$O$_{12}$S [M+H]$^+$ 859.46. measured 859.39.

5-(3-((2-((5-((tert-butoxycarbonyl)amino)pentyl)amino)-2-oxoethyl)thio)-2,5-dioxopyrrolidin-1-yl)-2-(6-hydroxy-3-oxo-3H-xanthen-9-yl)benzoic acid (5c)

A solution of tert-butyl(5-(2-mercaptoacetamido)pentyl) carbamate (14.22 mg, 0.051 mmol) in DMF (0.3 ml) was added to a solution of 5-(2,5-dioxo-2,5-dihydro-1H-pyrrol-1-yl)-2-(6-hydroxy-3-oxo-3H-xanthen-9-yl)benzoic acid (18.32 mg, 0.043 mmol) and triethylamine (4.29 μmol) and the clear yellow solution was stirred for 3 h at room temperature. After this time, the reaction was diluted with water (3 ml) and purified with preparative RP HPLC with the following solvent system: water/0.1% HCOOH (solvent A), acetonitrile (solvent B); 0-5 min: 30% B, 5-20 min: 30-80% B; UV=254 nm; t$_R$=15.4 min; XB-C18 column. The product was obtained as a bright yellow solid after lyophilization (22 mg, 73% yield). ESI-MS m/z calculated for C$_{36}$H$_{37}$N$_3$O$_{10}$S [M+H]$^+$ 704.23. measured 704.05.

2,2',2''-(10-(2-((2-(3-((2-((5-(aminopentyl)amino)-2-oxoethyl)thio)-2,5-dioxopyrrolidin-1-yl)ethyl)-amino)-2-oxoethyl)-1,4,7,10-tetraazacyclododecane-1,4,7-triyl)triacetic acid (6a) (C2-DOTA linker)

2,2',2''-(10-(2-((2-(3-((2-((5-((tert-butoxycarbonyl)amino)pentyl)amino)-2-oxoethyl)thio)-2,5-dioxo-pyrrolidin-1-yl)ethyl)amino)-2-oxoethyl)-1,4,7,10-tetraazacyclododecane-1,4,7-triyl)triaceticacid (18 mg, 0.022 mmol) was dissolved in a mixture of dichloromethane/TFA 1:1 (2.7 ml) at 0° C. The reaction mixture was stirred for 10 min at this temperature and was then allowed to reach room temperature where it was stirred for 1 h at which point HPLC confirmed complete consumption of the starting material. The volatiles were removed under reduced pressure at 20° C. and the crude was dried under high vacuum for 30 min. The residue was dissolved in 1 ml water and was purified with preparative HPLC to provide 12.7 mg (81%) of a white solid after lyophilization. The solvent systems that were used were the same as in the case of 5a (t$_R$=12.8 min and t$_R$=11.6 min for analytical and preparative HPLC respectively). $^1$H NMR (500 MHz, D$_2$O): δ 4.26-2.89 (br, 28H), 4.07 (dd, J$_1$=9.1 Hz, J$_2$=4.1 Hz, 1H), 3.58 (d, J=15.3 Hz, 1H), 3.42 (d, J=15.3 Hz, 1H), 3.31 (dd, J$_1$=19.1 Hz, J$_2$=9.1 Hz, 1H), 3.22, (t, J=7.1 Hz, 2H), 2.99 (t, J=7.5 Hz, 2H), 2.74 (dd, J$_1$=19.1 Hz, J$_2$=4.1 Hz, 1H), 1.72-1.64 (m, 2H), 1.60-1.52 (m, 2H), 1.44-1.36 (m, 2H). $^{13}$C NMR (100 MHz, D$_2$O): δ 178.8, 178.1, 171.3, 163.0, 162.7, 117.4, 115.1, 54.7, 40.3, 39.4, 39.3, 38.3, 37.1, 35.5, 34.5, 27.7, 27.6, 26.3, 22.9 ESI-MS m/z calculated for $C_{29}H_{51}N_8O_{10}S$ [M+H]$^+$ 703.34. measured 703.32.

2,2',2''-(10-(2-((2-(3-((6-((5-aminopentyl)amino)-6-oxohexyl)thio)-2,5-dioxopyrrolidin-1-yl)ethyl)-amino)-2-oxoethyl)-1,4,7,10-tetraazacyclododecane-1,4,7-triyl)triacetic acid (6b) (C6-DOTA linker)

Compound 5b (45 mg, 0.045 mmol) was dissolved in a mixture of dichloromethane/TFA 1:1 (5.4 ml) at 0° C. and after stirring for 10 min at this temperature, the reaction mixture was allowed to reach room temperature where it was stirred for 2 h. The volatiles when then removed under reduced pressure at 30° C. and traces of TFA were removed with drying under high vacuum for 30 min. The residue was dissolved in water (4 ml) and was purified with preparative RP HPLC using the method described for 5b; $t_R$=13.5 min. ESI-MS m/z calculated for $C_{33}H_{58}N_8O_{10}S$ [M+H]$^+$ 759.41. measured 759.40.

5-(3-((2-((5-aminopentyl)amino)-2-oxoethyl)thio)-2,5-dioxopyrrolidin-1-yl)-2-(6-hydroxy-3-oxo-3H-xanthen-9-yl)benzoic acid (6c) (C2-fluorescein linker)

To an ice cold suspension of 5c (10 mg, 0.014 mmol) in dichloromethane (2 ml), TFA (200 µl, 2.60 mmol) was added dropwise and the clear bright yellow solution was stirred for 10 min at 0° C. for 10 min before allowing it to reach room temperature where it was stirred for 40 min. Toluene was then added and the volatiles were removed under reduced pressure. The crude was purified with semi-preparative RP HPLC with the following system: water/0.1% TFA (solvent A), acetonitrile (solvent B); 0-3 min: 5% B, 3-10 min: 5-25% B, 10-20 min: 25% B; UV=254 nm; $t_R$=15.3 min; Xbridge column. The product was obtained as a bright yellow solid after lyophilization (6.7 mg, 78% yield). ESI-MS m/z calculated for $C_{31}H_{29}N_3O_8S$ [M+H]$^+$ 604.18. measured 604.04.

Synthesis of PEG Linkers

For Compounds 7-9 and reaction schemes, see FIG. 16A.

S-(2,2-dimethyl-4,12-dioxo-3,15,18,21,24-pentaoxa-5,11-diazahexacosan-26-yl) ethanethioate (7)

HBTU (421 mg, 1.11 mmol) was slowly added to a solution of 2-oxo-6,9,12,15-tetraoxa-3-thiaocta-decan-18-oic acid (300 mg, 0.925 mmol) and DIPEA (0.32 ml, 1.85 mmol) in DMF (4.5 ml) and the resulting solution was stirred for 15 min. A solution of tert-butyl(5-aminopentyl)carbamate (225 mg, 1.11 mmol) in DMF (0.6 ml) was then added dropwise and the reaction was stirred for 14 h. The reaction was then diluted with 60 ml ethyl acetate and was washed with water (2×25 ml) and brine (1×25 ml). The organic layer was dried under sodium sulfate, filtered and evaporated under reduced pressure. The crude was purified by flash column chromatography on silica using chloroform/ethanol 95:5 to afford 380 mg (81%) of product as a slight yellow oil. $^1$H NMR (400 MHz, CDCl$_3$): δ 6.51 (br, 1H), 4.66 (br, 1H), 3.70 (t, J=5.8 Hz, 2H), 3.65-3.59 (m, 12H), 3.57 (t, J=6.6 Hz, 2H), 3.21 (dt, J$_2$=7.3 Hz, J$_2$=6.9 Hz, 2H), 3.12-3.02 (m, 4H), 2.44 (t, J=5.8, 2H), 2.31 (s, 3H), 1.53-1.43 (m, 4H), 1.41 (s, 9H), 1.36-1.27 (m, 2H). $^{13}$C NMR (100 MHz, CDCl$_3$): δ 195.4, 171.5, 156.0, 78.9, 70.6, 70.5, 70.3, 70.2, 70.1, 69.7, 67.3, 40.3, 39.0, 36.9, 30.5, 29.6, 29.2, 28.7, 28.4, 24.0. ESI-QTOF MS m/z calculated for $C_{23}H_{44}N_2O_8S$ [M+H]$^+$ 509.2891. measured 509.2884

S-(21-amino-15-oxo-3,6,9,12-tetraoxa-16-azahenicosyl)ethanethioate (8) (PEG-4-SAc linker)

To an ice cold solution of S-(2,2-dimethyl-4,12-dioxo-3,15,18,21,24-pentaoxa-5,11-diazahexacosan-26-yl) ethanethioate (370 mg, 0.73 mmol) in dichloromethane (9.7 ml) was added trifluoroacetic acid (1.1 ml, 14.55 mmol). After stirring for 10 min, the reaction mixture was allowed to reach room temperature and stirred for 2 h. The volatiles were then removed under reduced pressure, followed by drying under high vacuum. A light yellow oil resulted which was sufficiently pure as revealed by NMR (quantitative yield). $^1$H NMR (400 MHz, CDCl$_3$): δ 7.79 (br, 1H), 7.23 (br, 3H), 2.33 (t, J=5.3 Hz, 2H), 3.69-3.56 (m, 14H), 3.31 (dt, J$_1$=7.5 Hz, J$_2$=6.1 Hz, 2H), 3.06 (t, J=6.7 Hz, 2H), 3.03-2.92 (m, 2H), 2.58 (t, J=5.3 Hz, 2H), 2.32 (s, 3H), 1.77-1.65 (m, 2H), 1.64-1.51 (m, 2H), 1.49-1.38 (m, 2H). $^{13}$C NMR (100 MHz, CDCl$_3$): δ 195.7, 174.0, 70.2, 69.99, 69.97, 69.9, 69.8, 69.6, 67.2, 40.0, 38.8, 35.8, 30.4, 28.1, 27.2, 26.0, 22.5. ESI-QTOF MS m/z calculated for $C_{18}H_{36}N_2O_6S$ [M+H]$^+$ 409.2367. measured 409.2381

Tert-butyl(1-mercapto-15-oxo-3,6,9,12-tetraoxa-16-azahenicosan-21-yl)carbamate (9)

A solution of sodium methoxide 0.5 M in methanol (1.8 ml, 0.904 mmol) was added dropwise to a solution of 7 (92 mg, 0.181 mmol) in degassed (freeze-pump-thaw) methanol and the reaction was stirred at room temperature for 3 h. After neutralization with Amberlite 120, the solution was filtered and evaporated to dryness. The crude was purified by flash column chromatography on silica using chloroform/ethanol 95:5 to yield a clear colorless oil (75 mg, 89%). $^1$H NMR (400 MHz, CDCl$_3$): δ 6.48 (br, 1H), 4.64 (br, 1H), 3.71 (t, J=5.7 Hz, 2H), 3.66-3.61 (m, 12H), 3.60 (t, J=6.4 Hz, 2H, partially overlapped by the previous multiplet), 3.22 (q, J$_1$≈J$_2$=7.0, 2H), 3.09 (dt, J$_1$=6.4 Hz, J$_2$=7.8 Hz, 2H), 2.68 (td, J$_1$=6.4 Hz, J$_2$=8.2 Hz, 2H), 2.45 (t, J=5.7 Hz, 2H), 1.59 (t, J=8.2 Hz, 1H), 1.55-1.46 (m, 4H), 1.43 (s, 9H), 1.37-1.30 (m, 2H). $^{13}$C NMR (100 MHz, CDCl$_3$): δ 171.5, 156.0, 79.0, 72.8, 70.6, 70.5, 70.3, 70.2, 67.3, 40.3, 39.1, 37.0, 29.6, 29.2, 28.4, 24.2, 24.0

Synthesis of Azide Linkers

Figure 16B:
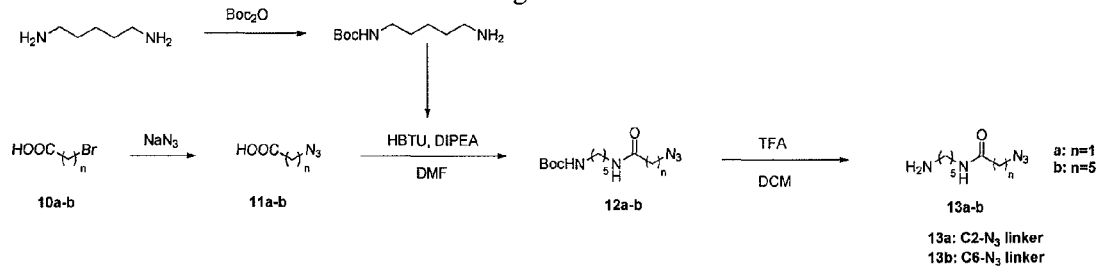

For Compounds 10-13 and reaction schemes, see FIG. 16B. Compounds 11a and 11b were synthesized by following procedures already published in the literature (Brabez N. et al, Journal of Medicinal Chemistry, 2011, 54(20), 7375-7384 for 11a and Kuil J. et al, Organic and Biomolecular Chemistry, 2009, 7, 4088-4094 for 11b)

tert-butyl(5-(2-azidoacetamido)pentyl)carbamate (12a)

In a solution of 2-azidoacetic acid (50 mg, 0.495 mmol), tert-butyl(5-amino-pentyl)carbamate (120 mg, 0.594 mmol) and DIPEA (128 mg, 0.989 mmol) in DMF (2.7 ml), HBTU (225 mg, 0.594 mmol) was added slowly at room temperature. After stirring for 3 hours, the slight yellow solution was diluted with ethyl acetate (30 ml) and was washed with HCl 0.5 M (3×15 ml) and sat. NaHCO$_3$ (1×15 ml) solutions, water (1×15 ml) and brine (1×15 ml). The organic layer was dried under sodium sulfate, filtered and evaporated to dryness. The crude was purified by flash column chromatography on silica using chloroform/EtOH 95:5 to yield a clear colorless oil (128 mg, 91%). $^1$H NMR (400 MHz, CDCl$_3$): δ 6.35 (br, 1H), 4.55 (br, 1H), 3.97 (s, 2H), 3.28 (dt, J$_1$=7.2 Hz, J$_2$=6.9 Hz, 2H), 3.11 (dt, J$_1$=7.8 Hz, J$_2$=6.5 Hz, 2H), 1.61-1.47 (m, 4H), 1.43 (s, 9H), 1.40-1.31 (m, 2H). $^{13}$C NMR (100 MHz, CDCl$_3$): δ 166.5, 156.0, 79.1, 52.7, 40.2, 39.2, 29.7, 29.0, 28.4, 23.9.

Tert-butyl(5-(6-azidohexanamido)pentyl)carbamate (12b)

HBTU (290 mg, 0.764 mmol) was slowly added to a solution of 6-azidohexanoic acid (100 mg, 0.636 mmol) and DIPEA (164 mg, 1.273 mmol) in DMF (3 ml) and the resulting solution was stirred for 15 min. A solution of tert-butyl(5-aminopentyl)carbamate (154 mg, 0.764 mmol) in DMF (0.5 ml) was then added dropwise and the reaction was stirred for 3 h. After this time, the reaction mixture was diluted with ethyl acetate (40 ml) and washed with HCl 0.5 M (3×20 ml) and sat. NaHCO$_3$ (1×20 ml) solutions, water (1×20 ml) and brine (1×20 ml). The organic layer was dried under sodium sulfate, filtered and evaporated to dryness. The crude was purified by flash column chromatography on silica using chloroform/EtOH 95:5 to yield a clear colorless oil (189 mg, 87%). $^1$H NMR (400 MHz, CDCl$_3$): δ 5.61 (br, 1H), 4.58 (br, 1H), 3.30-3.20 (m, 4H), 3.10 (dt, J$_1$=8.0 Hz, J$_2$=6.8 Hz, 2H), 2.16 (t, J=7.4 Hz, 2H), 1.56-1.45 (m, 4H), 1.56-1.45 (m, 4H), 1.43 (s, 9H), 1.41-1.29 (m, 4H). $^{13}$C NMR (100 MHz, CDCl$_3$): δ 172.7, 156.1, 79.1, 51.3, 40.2, 39.3, 36.5, 29.8, 29.2, 28.6, 28.4, 26.4, 25.2, 23.9.

N-(5-aminopentyl)-2-azidoacetamide (13a) (C2-N$_3$ Linker)

To an ice cold solution of 12a (19.2 mg, 0.067 mmol) in dichloromethane (0.9 ml) was added trifluoroacetic acid (153 mg, 1.346 mmol). After stirring for 10 min, the reaction mixture was allowed to reach room temperature and stirred for 2 h. Toluene (4 ml) was then added and the volatiles were removed under reduced pressure. The crude was azeotroped again with toluene to remove traces of TFA and was then dried under HVP for 3 hours to yield a light yellow oil (quantitative yield) which was sufficiently pure for further use, as revealed by NMR. $^1$H NMR (400 MHz, CD$_3$OD): δ 3.87 (s, 2H), 3.24 (t, J=7.1 Hz, 2H), 2.92 (t, J=7.5 Hz, 2H), 1.72-1.63 (m, 2H), 1.62-1.53 (m, 2H), 1.46-1.36 (m, 2H). $^{13}$C NMR (100 MHz, CD$_3$OD): δ 170.3, 53.1, 40.7, 40.1, 30.0, 28.3, 24.7.

N-(5-aminopentyl)-6-azidohexanamide (13b) (C6-N$_3$ Linker)

Compound 13b was synthesized by following a similar procedure as described above for 13a (starting with 22.8 mg, 0.067 mmol of 12b). $^1$H NMR (400 MHz, CD$_3$OD): δ 3.29 (t, J=6.8 Hz, 2H), 3.19 (t, J=7 Hz, 2H), 2.92 (t, J=7.7 Hz, 2H), 2.20 (t, J=7.3 Hz, 2H), 1.73-1.51 (m, 8H), 1.46-1.35 (m, 4H). $^{13}$C NMR (100 MHz, CD$_3$OD): δ 176.2, 52.5, 40.7, 40.0, 37.0, 30.1, 29.8, 28.3, 27.5, 26.7, 24.8.

MMAF-6Cthiol Linker Synthesis

Figure 16C:
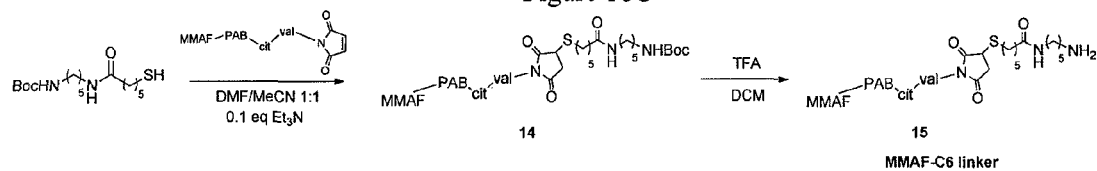

Compounds 14-15 and reaction schemes are shown in FIG. 16C.

maleimide-valine-citrullin-PAB-MMAF+6C thiol linker (Boc protected) (14)

To a solution of maleimide-valine-citrullin-PAB-MMAF (8.8 mg, 6.61 μmol) in DMF (0.6 ml) was added 6.6 μl of a 0.1 M solution of triethylamine in DMF (0.66 μmol Et$_3$N), followed by the dropwise addition of a solution of tert-butyl (5-(6-mercaptohexanamido)pentyl)carbamate (3 mg, 9.02 μmol) in acetonitrile (0.3 ml). The reaction was stirred for 3 h, diluted with water (2 ml) and purified with semi-preparative RP HPLC with the following system: water/50 mM NH$_4$HCO$_3$ (solvent A), acetonitrile (solvent B); 0-5 min: 40% B, 5-20 min: 40-80% B; UV=254 nm; t$_R$=10.3 min; Xbridge column. The product was obtained as a white solid after lyophilization (8.7 mg, 79% yield).

maleimide-valine-citrullin-PAB-MMAF+6C thiol linker (MMAF-6C linker) (15)

Compound 14 (8 mg, 4.81 μm) was dissolved in an ice cold solution of dichloromethane/TFA 95:5 (8 ml). The reaction mixture was allowed to reach room temperature and stirred for 40 min after which time the volatiles were removed under reduced pressure with the addition of toluene. Traces of solvents were removed under high vacuum and the residue was purified by semi-preparative HPLC with the following system: water/50 mM NH$_4$HCO$_3$ (solvent A), acetonitrile (solvent B); 0-5 min: 30% B, 5-20 min: 30-70% B; UV=254 nm; t$_R$=11.7 min; Xbridge column. The product was obtained as a white solid after lyophilization (4.86 mg, 65% yield). ESI-QTOF MS m/z calculated for C$_{79}$H$_{127}$N$_{13}$O$_{17}$S [M+2H]$^{2+}$ 781.9670. measured 781.9667.

Example 2

BTG is Unable to Couple Linkers with Large, Hydrophobic and/or Charged Payloads in Quantitative Fashion to Antibodies 1. Coupling of Dansyl and Biotin Linkers The structures of biotin-cadaverin and dansyl cadaverin are shown below.

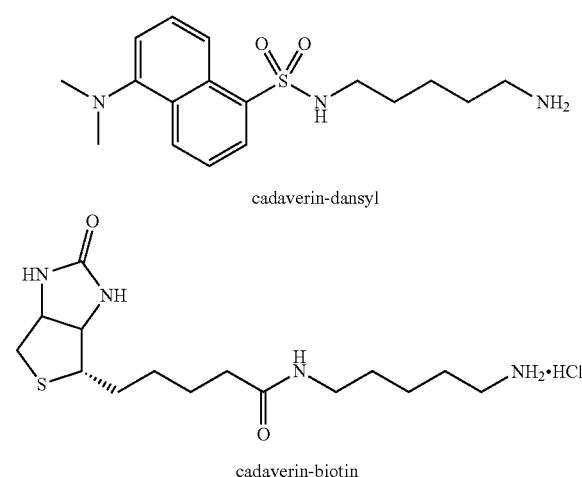

cadaverin-dansyl cadaverin-biotin

Antibody chADC1 having one potential acceptor glutamine on each heavy chain was degycolsylated by PNGaseF treatment and a mass of 48945 Da for unmodified, deglycosylated heavy chain was determined. The light chain remained unaffected (23341 Da found). The coupling reaction (using standard conditions with 1 U/mL BTG) for biotin-cadaverin and dansyl cadaverin was successful however it did not go to completion In view of the only partial coupling of biotin-cadaverin and dansyl cadaverin, reaction conditions were explored in an initial step of testing factors influencing reaction conditions. It was found that using 6 U/mL BTG permitted the modification of all heavy chains of PNGaseF-deglycosylated antibody chADC1 was achieved with either exactly one biotin-cadaverin (MW: 328 g/mol; 328−17=311 Da; 48945+311=49256 Da, 49257 Da found) or one dansyl-cadaverin (MW: 335 g/mol; 335−17=318 Da; 48945+318=49263 Da, 49264 Da found) per heavy chain.

2. Coupling of Linkers with DOTA Payload is Unsuccessful

The chemical structure of a thiol linker coupled to maleimide-DOTA (1,4,7,10-tetraazacyclododecane-1,4,7,10-tetraacetic acid) is shown below (for preparation see Example 1). The molecular weight is indicated below the structure.

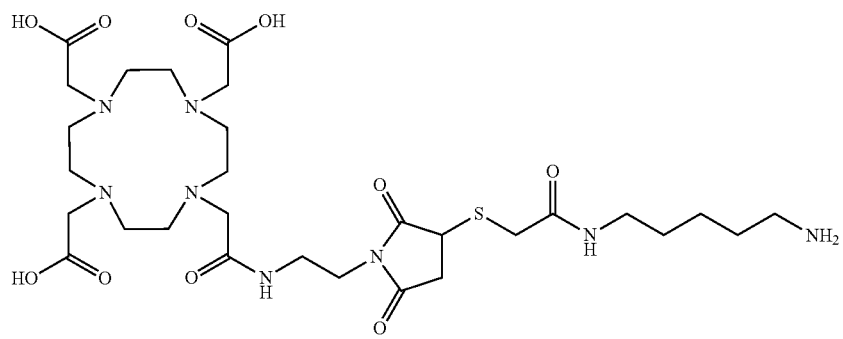

Molecular Weight: 702.82, 5

Figure 17A:
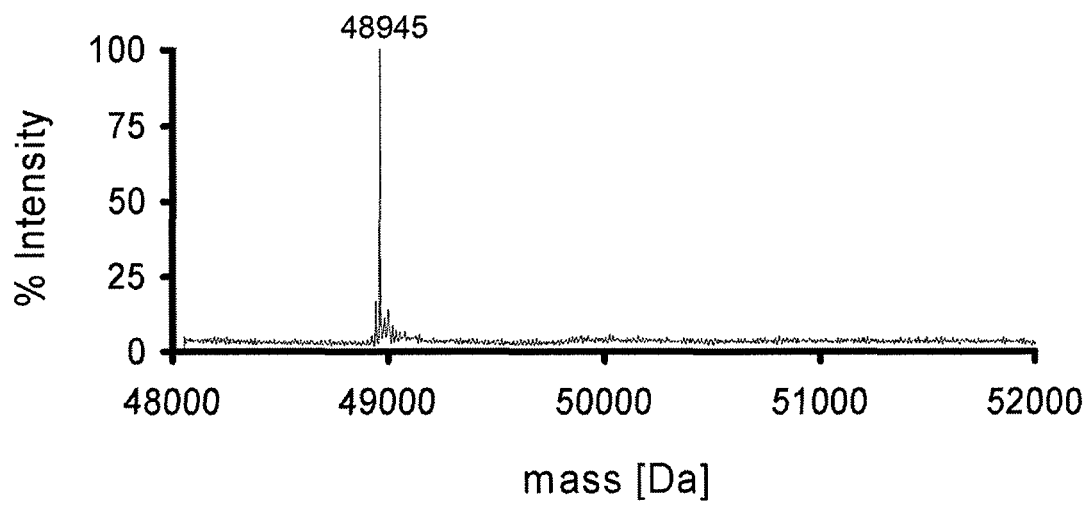
FIGS. 17A and 17B show the deconvoluted mass spectra of chADC1 heavy chain coupled to DOTA thiol linker 5 using either IU/mL (left) or 6 U/mL BTG.
Figure 17B:
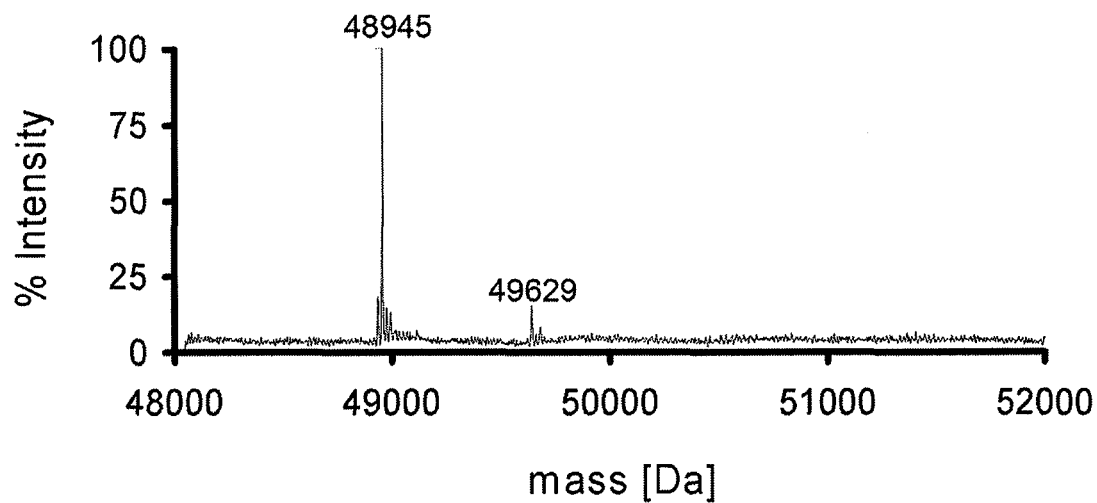

ChADC1 antibodies and DOTA linker were reacted in the presence of BTG to modify antibodies. Quantitative enzymatic modification of chimADC1 heavy chain with short DOTA thiol linker (compound 5) by BTG could not be accomplished (see FIG. 17A: 1 U/mL BTG, only unmodified chADC1 heavy chain, 48945 Da, was found. FIG. 17B: 6 U/mL BTG, minor peak modified chADC1 heavy chain with one DOTA thiol linker per heavy chain, MW 702 g/mol, 702−17=685 Da, 48945+685=49630 Da, 49629 Da found). Reaction conditions were explored but neither by using 1 U/mL (expected) nor by using 6 U/mL BTG could significantly complete coupling be achieved. Prolonged incubation time could not influence the efficiency or completion of coupling. Compared to biotin and dansyl, DOTA has a higher molecular weight, has a more rigid structure (containing a macrocycle), and in particular is electronically negatively charged that may interfere with BTG activity.

3. Coupling of Linker with Fluorescein Payload is Unsuccessful

The chemical structure of lysine-based linker (cadaverin) coupled to fluorescein is shown below.

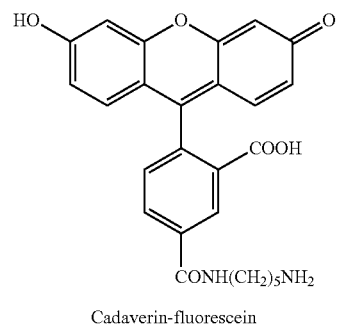

Cadaverin-fluorescein

ChADC1 antibodies and cadaverin-fluorescein linker were reacted in the presence of BTG to modify antibodies. The light chain remained unaffected. Quantitative enzymatic modification of chADC1 heavy chain with short fluorescein-containing linker by BTG could not be accomplished, only unmodified chADC1 heavy chain was found. Following exploration of reaction conditions (see Example 3), optimized conditions were tested (80 eq ligand, 6 U/ml BTG, 1 mg/ml mAb, 18H at 37° C.) but coupling could not be achieved. Compared to biotin and dansyl, fluorescein has a higher molecular weight, has a possibly more rigid and hydrophobic structure, notably containing a polycycle, notably a tri-cycle and a further cyclic group in proximity to the site of BTG activity.

4. Coupling of Linker with DBCO Payload is Unsuccessful

The chemical structure of the dibenzylcyclooctyne (DBCO) lysine-based linker (DBCO-amine) used is shown below.

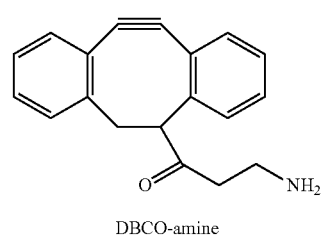 [SMILES: NCCC(=O)C1Cc2ccccc2C#Cc2ccccc21]

DBCO-amine

ChADC1 antibodies and the DBCO lysine-based linker were reacted in the presence of BTG to modify antibodies.

The light chain remained unaffected. Quantitative enzymatic modification of chADC1 heavy chain with short DBCO lysine-based linker by BTG could not be accomplished, only unmodified chADC1 heavy chain was found. Following exploration of reaction conditions (see Example 3), optimized conditions were tested (80 eq ligand, 6 U/ml BTG, 1 mg/ml mAb, 37° C.) but coupling could not be achieved. Compared to biotin and dansyl linkers, the DBCO has a possibly more rigid structure, notably containing a polycycle, notably a tri-cycle group in proximity to the site of BTG activity.

5. Coupling of Linker with TAMRA Payload is Unsuccessful

The chemical structure of a TAMRA lysine-based linker is shown below.

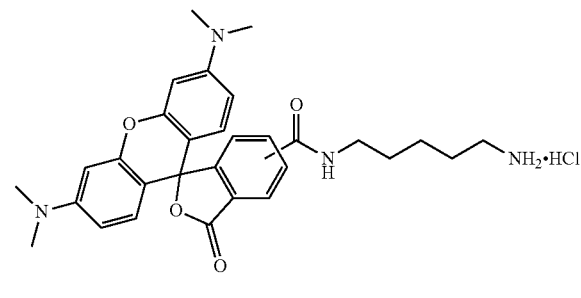

Cadaverin-TAMRA

ChADC1 antibodies and TAMRA lysine-based linker were reacted in the presence of BTG to modify antibodies. The light chain remained unaffected. Quantitative enzymatic modification of chimADC1 heavy chain with short TAMRA lysine-based linker by BTG could not be accomplished, only unmodified chADC1 heavy chain was found. Following exploration of reaction conditions (see Example 3), optimized conditions were tested (80 eq ligand, 6 U/ml BTG, 1 mg/ml mAb, 18 h at 37° C.) but at best only partial coupling could be achieved, with about 50% of all heavy chains having a linker coupled thereto. Compared to biotin and dansyl, TAMRA has a higher molecular weight, has a possibly more rigid and hydrophobic structure, notably containing a polycycle, notable a tri-cycle and a cyclic group in proximity to the site of BTG activity.

6. Coupling of Linker with Auristatin Payload is Unsuccessful

A linker comprising the monomethyl auristatin F (MMAF), as well as a valine-citrulline dipeptide spacer, a 6-carbon spacer and a PAB self-elimination spacer (MW 1562, C6-MMAF linker) were reacted in the presence of BTG to modify chADC1 or chCE7 antibodies using optimized reaction conditions (80 eq ligand, 6 U/ml BTG, 1 mg/ml mAb, 37° C.). Quantitative enzymatic modification of heavy chains with MMAF linker by BTG could not be accomplished.

Primarily unmodified chADC1 or chCE7 heavy chain was found, with a major peak corresponding to unmodified heavy chain (70%) and a minor peak to heavy chain with one MMAF linker (30%) for chADC1 and a major peak corresponding to unmodified heavy chain (81%) and a minor peak to heavy chain with one MMAF linker (19%) for chCE7.

Example 3

Discovery of Optimized Reaction Conditions for BTG

Despite improvement with spacers, large and/or hydrophobic organic molecules representative of cytotoxic drugs are not able to be coupled by BTG onto acceptor glutamines quantitatively (complete coupling). To explore the possibility that optimized reactions might permit quantitative coupling reaction parameters were explored.

All the experiments were performed on chADC1 deglycosylated with PNGase F. Antibody concentration was to 1 mg/mL for all experiments. All the experiments were performed using 6 U/mL of BTG. All reactions were monitored by HIC analysis and LC-MS. Samples for HIC analysis were taken after time periods and directly injected in HIC. Samples for MS analysis were frozen to stop the reaction.

Figure 18A:
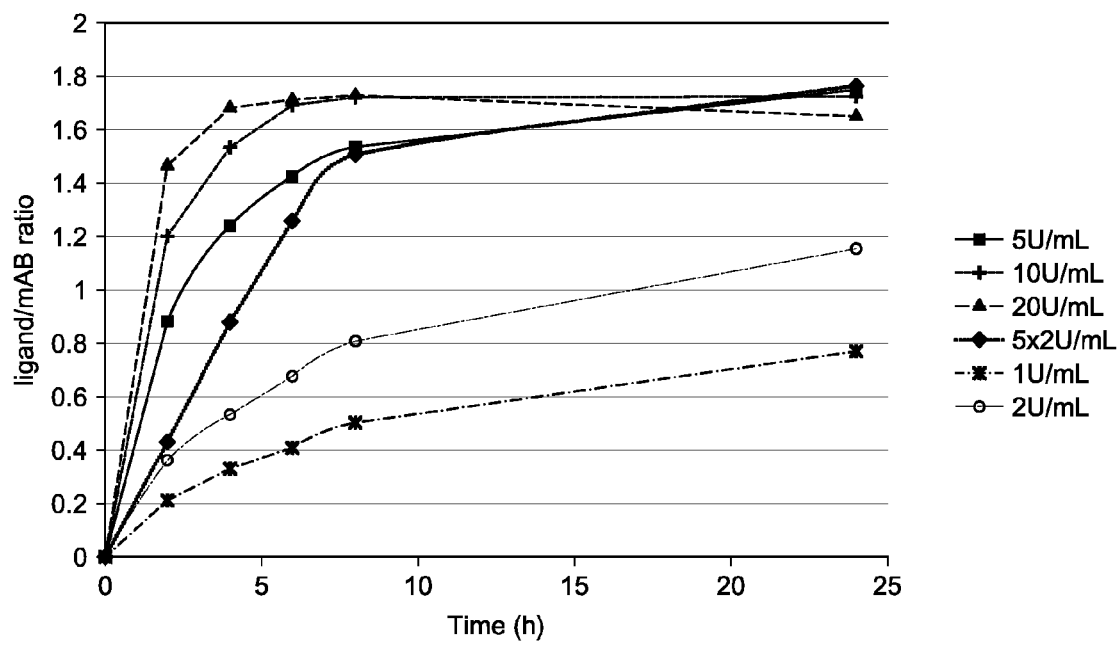
FIGS. 18A-18G shows optimized conditions for BTG coupling, including BTG concentrations (18A), pH (18B and 18C), temperature (18D and 18E), and substrate stoichiometry (18F and 18G).

First, the effect of enzyme concentrations was investigated. FIG. 18A depicts the labeling of chADC1 at different concentrations of BTGase. Higher labeling yields were achieved with increasing enzyme concentrations for BTGase. The following exploration of reaction conditions then used optimized conditions (6 U/ml BTG, 1 mg/ml mAb, 18 h) at which a plateau was reached for conjugation.

Figure 18B:
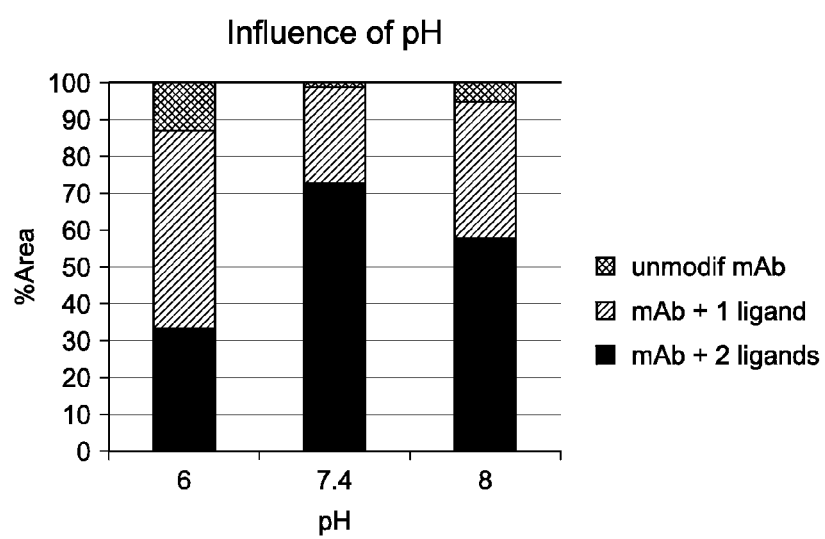
Figure 18C:
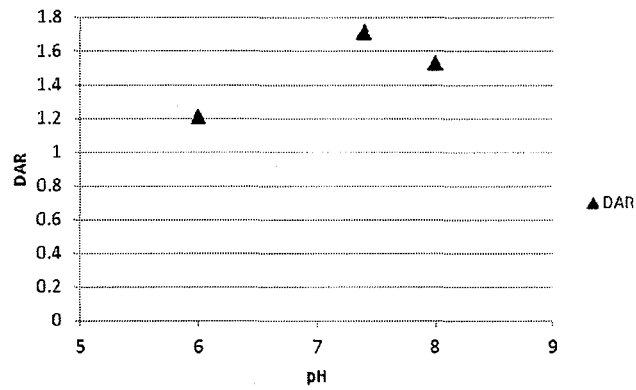

We then investigated the effect of the pH of the reaction media on the enzymatic labeling. FIGS. 18B and 18C show the labeling degrees achieved at different pH values by the BTG-mediated modification of the antibody. The most efficient labeling was detected at neutral reaction conditions (pH 7.4).

Figure 18D:
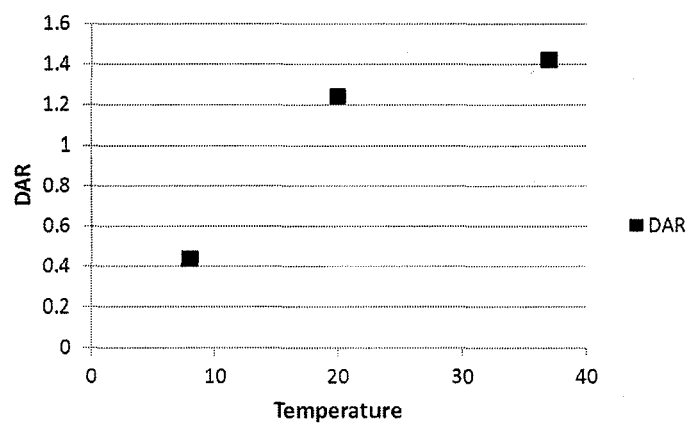
Figure 18E:
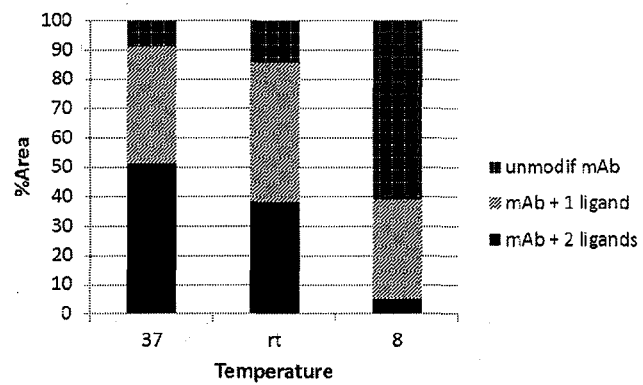

Next, the effect of temperature was investigated. FIGS. 18D and 18E depict the labeling of chADC1 at different temperatures. Higher labeling yields were achieved at 37° C.

Figure 18F:
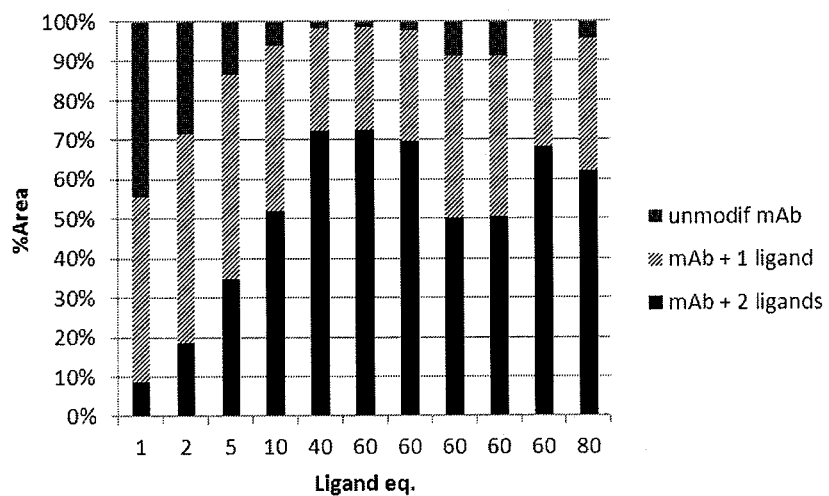
Figure 18G:
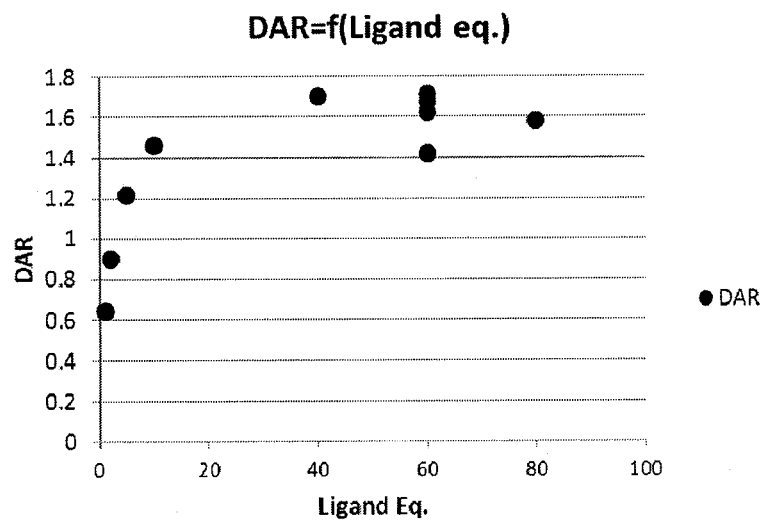

As a further parameter for optimization, we examined the effect of the substrate stoechiometry. FIGS. 18F and 18G show the labeling of chADC1 with BTG employing varying amount of dansyl-cadaverin substrate. Increasing amount of the substrate resulted in a higher labeling yield. The best labeling of the antibody was achieved with dansyl-cadaverin substrate above 40 eq/mAb. Because of the limited solubility of the dansyl-cadaverin in aqueous buffer (containing a maximum of 10% DMSO), higher concentrations could not be investigated. Further experiments then used 80 equivalents of linker (molar excess based on molarity of the mAb), 6 U/ml BTG, 1 mg/ml mAb, 37° C. unless indicated otherwise. While equivalents (eq) are expressed as molar excess based on molarity of the mAb in the Examples herein, equivalents can also be expressed as a function of the number of acceptor glutamines in an antibody, e.g, the eq figure is divided by two for a mAb having two acceptor glutamines (e.g., one on each heavy chain) or by four for a mAb having four acceptor glutamines (e.g, two on each heavy chain)

Example 4

Improved Lysine-Based Linkers for BTG-Mediated Direct Coupling

To explore the possibility that large, charged or hydrophobic groups close to the site of BTG coupling (i.e. the primary amine) influences and inhibits BTG coupling efficiency, linkers having linear carbon-containing frameworks acting as spacers were tested.

1. Coupling of DOTA Linkers with Spacer Group

The chemical structure of a spacer-containing thiol linker coupled to maleimide-DOTA (1,4,7,10-tetraazacyclododecane-1,4,7,10-tetraacetic acid) and a short linker were compared (for preparation see Example 1). The molecular weights are indicated below the structures.

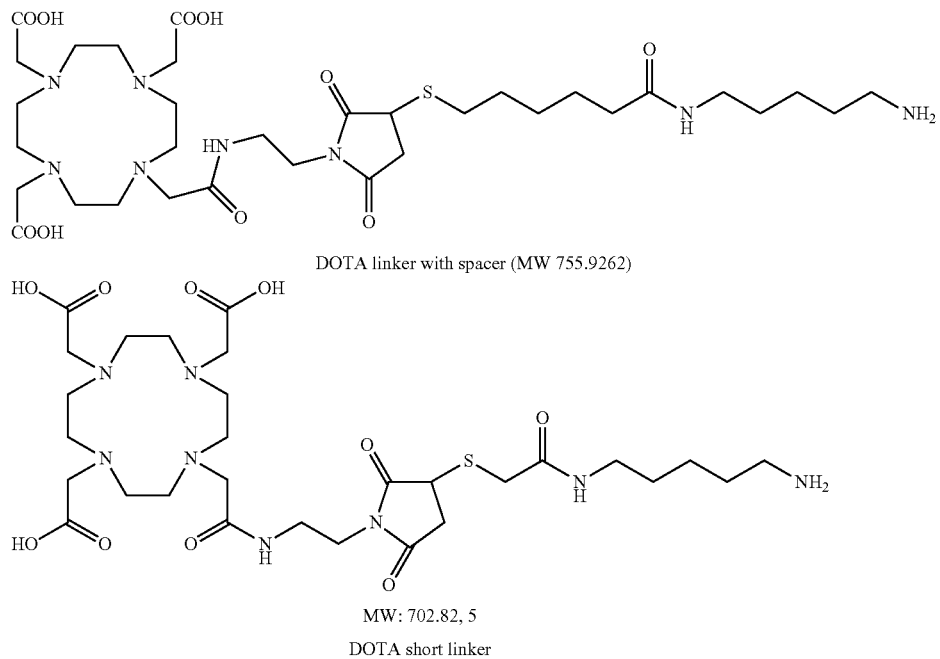

DOTA linker with spacer (MW 755.9262)

MW: 702.82, 5
DOTA short linker

ChADC1 antibodies and short DOTA linker (see Example 2, part 3, referred to as C2-DOTA) or DOTA linker comprising a 6-carbon spacer (referred to as C6-DOTA) were reacted in the presence of BTG to modify antibodies. Following exploration of reaction conditions (see Example 3), optimized conditions were used (80 eq ligand, 6 U/ml BTG, 1 mg/ml mAb, 18 h at 37° C.).

Figure 19A:
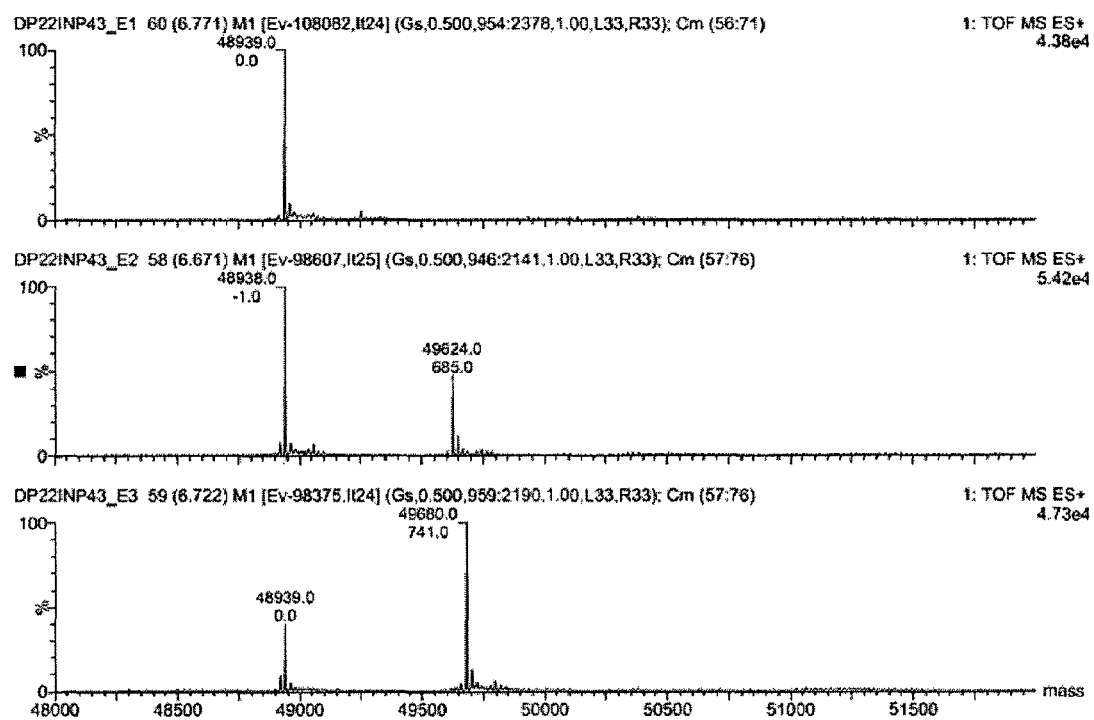
FIG. 19A shows improved enzymatic modification of deglycosylated chimeric antibody heavy chain C6-DOTA linker by BTG, compared to C2-DOTA linker.

Quantitative enzymatic modification of chADC1 heavy chain with C2-DOTA linker by BTG could not be accomplished and primarily unmodified chADC1 heavy chain was found, with a major peak corresponding to unmodified heavy chain (70%) and a minor peak to heavy chain with one C2-DOTA (30%). C6-DOTA linker comprising a 6-carbon spacer however achieved significantly improved coupling, with a major peak corresponding to heavy chain with one C6-DOTA (70%) and a minor peak corresponding to unmodified heavy chain (30%). Results are shown in FIG. 19A.

Example 5

PNGaseF Treatment Causes Deamidation of N297 to Generate N297D

Monoclonal antibodies treated with PNGaseF are known to efficiently remove N297-linked glycosylation. According to the literature (Suzuki et al, Glycoconjugate Journal (1995) 12:183-193) the hydrolysis of the asparaginyl amide bond by PNGase can result in the formation of an aspartic acid containing polypeptide chain. As a consequence, it is possible that the catalytic action of PNGaseF generates a deamidated N297 residue in the close proximity of the Q295 coupling site of BTG.

In order to investigate the extent of the deamidation reaction induced by PNGaseF, a purified sample of PNGaseF deglycosylated chADC1 enzymatically conjugated to a cadaverin-biotin linker following the procedure of Example 3 was characterized by tryptic peptide map analysis. The tryptic peptides of chADC1 were generated using a standard digestion/alkylation protocol and analyzed by nano-LC coupled to electrospray ionization (ESI) tandem mass spectrometry. The analyses were conducted at the PIT2 proteomic platform (Faculté de Pharmacie de la Timone, Marseille, France) on a LTQ Orbitrap Velos (Thermo Electron, San Jose, Calif.) coupled with the nanomate 3000 from Dionex. The method chosen for the bottom-up Orbitrap analysis consisted of one full MS at 30,000 of resolution in the Orbitrap cell and 10 dependant MS/MS scan in the LTQ Velos linear trap simultaneously. The data were analyzed with Proteome Discoverer (Thermo Scientific) using the Sequest software that allows querying Database.

Figure 19B:
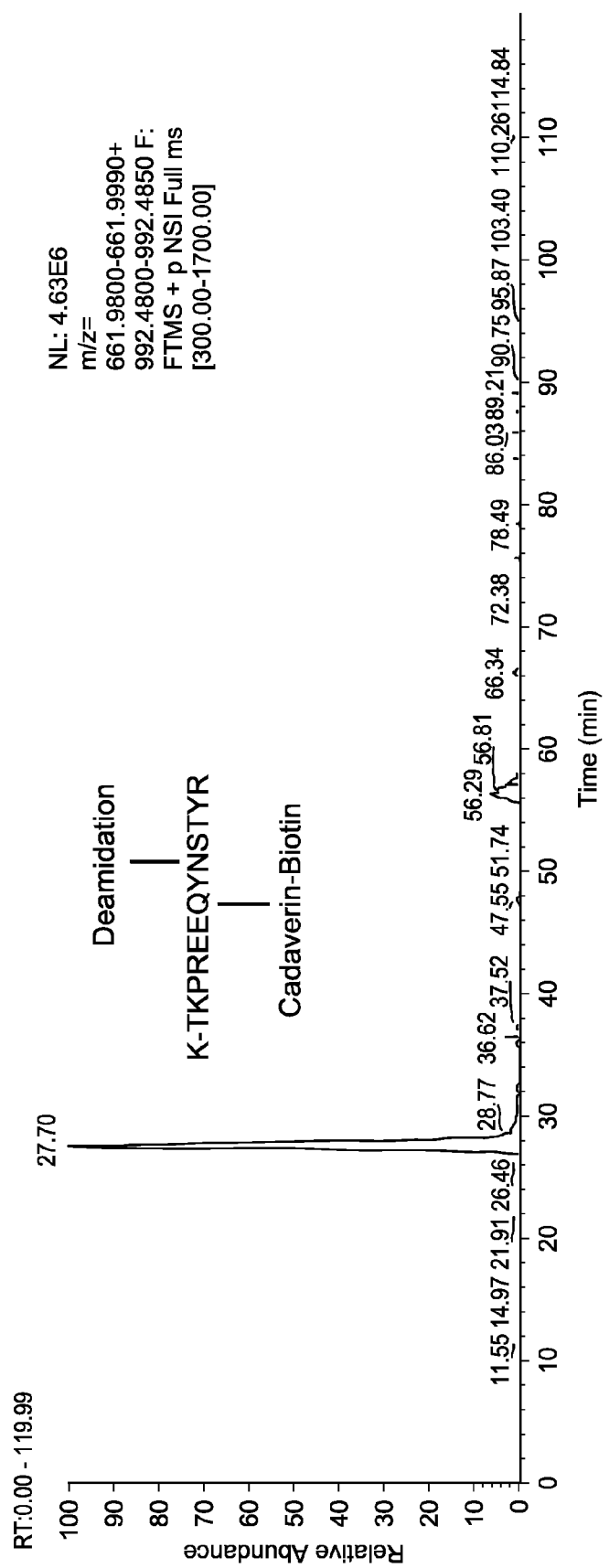
FIG. 19B shows an ion chromatogram extract showing, after tryptic digest, a deamidated peptide including the biotin-modified glutamine at position 295.

The full scan LC-MS analysis performed in the positive ion mode revealed the presence of a specific N297-deamidated tryptic peptide (TKPREEQ$_{295}$YN$_{297}$STYR) including the biotin-modified glutamine at position 295 [m/z=1983.9592 (z=1); m/z=992.4832 (z=2) and m/z=661.9912 (z=3)]. The extracted ion chromatogram corresponding to the di- and tri-charged pseudo-molecular ions of the specific deamidated tryptic peptide (EIC peak at 27.70 min) is shown in FIG. 19B. The non-deamidated peptide [m/z=1982.9752 (z=1); m/z=991.9912 (z=2) and m/z=661.6632 (z=3)] was not detected, thus confirming that the deamidation of N297 following PNGase F treatment was quantitative.

Figure 19C:
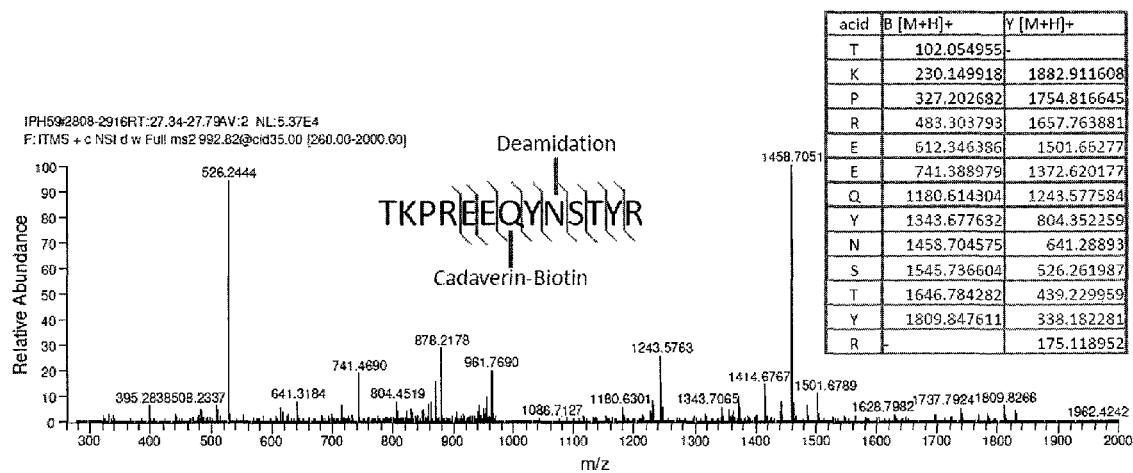
FIG. 19C shows the MS/MS spectrum and sequence confirmation of the specific N297-deamidated tryptic peptide including the biotin-modified glutamine at position 295.

Full sequencing of the specific N297-deamidated tryptic peptide (TKPREEQ$_{295}$YN$_{297}$STYR) was obtained by MS/MS analysis. The MS/MS spectrum of the double-charged pseudo molecular ion is presented in FIG. 19C with the associated fragmentation pattern (b and y ions types resulting from fragmentation at the amide bond with charge retention on the N or C terminus respectively).

The peptide map analysis of PNGase F deglycosylated ChADC1 conjugated to a cadaverin-biotin linker revealed a quantitative deamidation of Asparagin 297 in the CH2 domain (the +2 position relative to acceptor glutamine Q295).

Example 6

The Environment of the Acceptor Glutamine in the Heavy Chain Influences BTG Coupling Despite improvement with spacers, large and/or hydrophobic organic molecules representative of cytotoxic drugs could not be coupled by BTG onto acceptor glutamines of deglycosylated chADC1 quantitatively (complete coupling). To explore the possibility that the environment, in terms of amino acids of the antibody, at the site of BTG-mediated coupling influences and inhibits BTG coupling efficiency, modified antibodies having amino acid substitutions were tested. Antibodies treated with PNGaseF to remove N297-linked glcoyslation will have an aspartic acid at residue 297 as a result of PNGaseF-induced deamidation at the asparagine. Three antibodies having N297S substitutions were generated which avoided N297-linked glycosylation and in turn avoided an aspartic acid or other negatively charged residue: chADC1, SGN-35 (anti-CD30) and chCE7.

Unmodified (N297), PNGaseF-deglycosylated chADC1 antibodies were reacted with the cadaverin-fluorescein linker in the presence of BTG to modify antibodies using optimized reaction conditions (80 eq ligand, 6 U/ml BTG, 1 mg/ml mAb, 37° C.). Quantitative enzymatic modification of chADC1 heavy chain with cadaverin-fluorescein linker by BTG could not be accomplished. Only partial modification of chADC1 heavy chains was found, with a substantial peak corresponding to unmodified heavy chains. However, when N297S chADC1 mutant antibodies were reacted with the cadaverin-fluorescein linker in the presence of BTG, high levels of coupling was observed, with a major peak corresponding to heavy chain with one cadaverin-fluorescein linker (80%) and a minor peak to unmodified heavy chains (20%).

In another experiment, unmodified (N297), PNGaseF-deglycosylated chADC1 antibodies were reacted with the cadaverin-TAMRA linker in the presence of BTG to modify antibodies using optimized reaction conditions (80 eq ligand, 6 U/ml BTG, 1 mg/ml mAb, 37° C.). Quantitative enzymatic modification of chADC1 heavy chain with cadaverin-TAMRA linker by BTG could not be accomplished. Partly modified chADC1 heavy chain was found, with a substantial peak corresponding to unmodified heavy chain. However, when modified N297S chADC1 antibodies were reacted with the cadaverin-TAMRA linker in the presence of BTG, quantitative coupling was achieved, with a peak corresponding to heavy chains with one cadaverin-TAMRA linker and no uncoupled heavy chains.

PNGaseF treatment modifies the side chain of the asparagine at position 297 such that an aspartic acid is present at position 297 following PNGaseF treatment. It is believed that BTG activity is inhibited by negative electrical charges. One possible explanation is therefore that a negative electrical charge at the amino acid residue at the +2 position relative to the acceptor glutamine inhibits BTG's ability to couple onto the glutamine within the particular context of the Fc domain of the antibody. The findings therefore open the possibility to use modified antibodies where aspartic acids are no longer present at the +2 position for the coupling of large and/or hydrophobic molecules to antibodies, or more generally to modify antibodies to avoid negative electrical charges adjacent to the acceptor glutamine, notably at the +2 position.

Example 7

Combining Spacers and Modified Antibody Constant Regions for Direct Coupling

To explore the ability of the combination of modified environment at the substrate (implemented by use of spacer groups in the linker) and modified environment at the site of BTG coupling (implemented by use Fc domain mutants) to further improve BTG coupling, linkers comprising a different cyclic groups with and without spacers were tested using both unmodified or modified chimeric antibodies. The modified antibodies contained mutations at residue N297 to avoid formation of the negatively charged aspartic acid caused by PNGase deglysosylation. Antibodies were also modified as Q295 in combination with N297 to form N295, Q297 antibodies.

1. DOTA (Negatively Charged Payload)

ChADC1 N297S antibodies and short DOTA linker (see Example 2, part 3, referred to as C2-DOTA) or DOTA linker comprising a 6-carbon spacer (referred to as C6-DOTA) were reacted in the presence of BTG to modify antibodies using optimized reaction conditions (80 eq ligand, 6 U/ml BTG, 1 mg/ml mAb, 37° C.). See Example 3 for optimized reaction conditions.

Figure 21A:
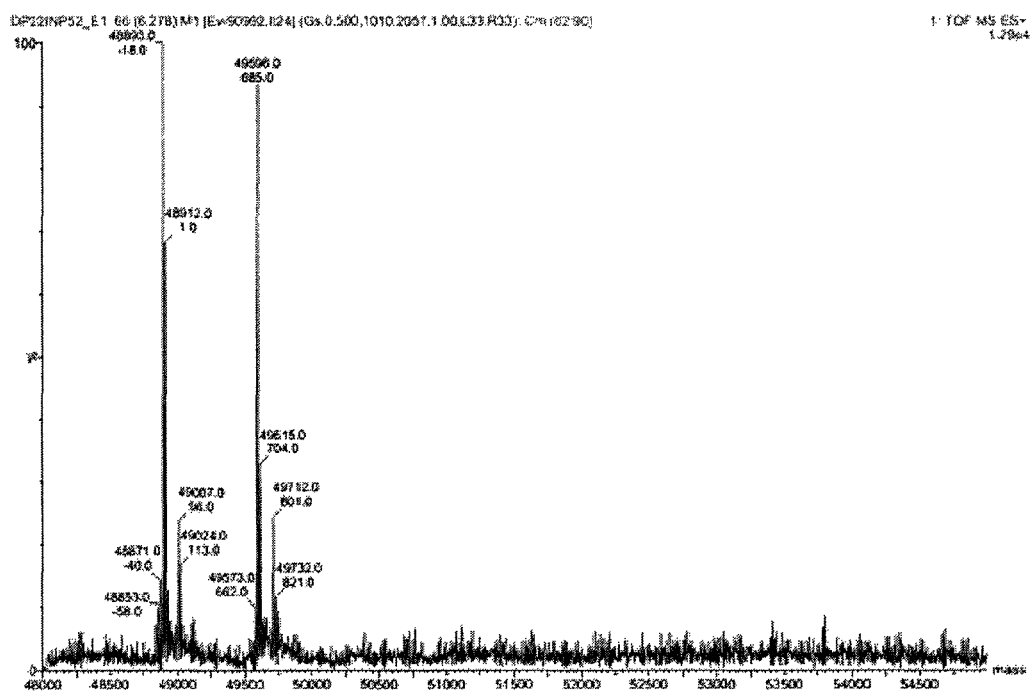
FIGS. 21A and 21B show improved enzymatic modification of N297S chimeric antibody heavy chain with C6-DOTA linker by BTG, compared to C6-DOTA linker on PNGaseF-deglycosylated antibody.
Figure 21B:
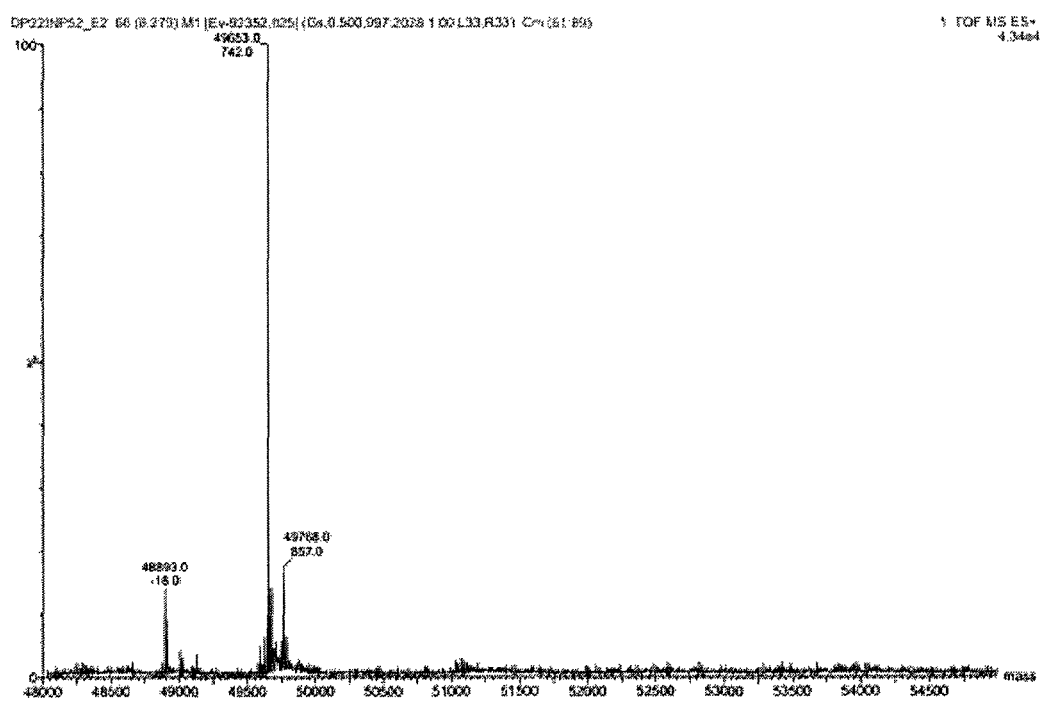

While enzymatic modification of chADC1 N297S heavy chain with C2-DOTA by BTG was more complete than that observed for C2-DOTA on chADC1 (PNGaseF deglycosylated) (see Example 4), quantitative coupling could not be accomplished and some unmodified chimADC1 heavy chain remained (see FIG. 21A). However, reacting C6-DOTA linker with chADC1 N297S achieved near quantitative coupling of all heavy chains with one C6-DOTA (see FIG. 21B). The combination of improved linker and protein environment therefore improved the coupling observed for C6-DOTA on chADC1 (PNGaseF deglycosylated) (see Example 4 and FIG. 21A) in which only about 70% coupling was observed.

The experiments were repeated using chCE7 Q295N, N197Q antibodies and the C6-DOTA linker using optimized reaction conditions (80 eq ligand, 6 U/ml BTG, 1 mg/ml mAb, 37° C.). The reaction achieved high levels coupling of all heavy chains with one C6-DOTA, with a major peak corresponding to heavy chain modified with one one C6-DOTA (greater than 80%).

2. DBCO (Polycycle/Rigid Payload)

In another experiment, the chemical structure of a dibenzylcyclooctyne (DBCO) lysine-based linker comprising a "PEG" spacer and short DBCO linkers were compared (structures shown below).

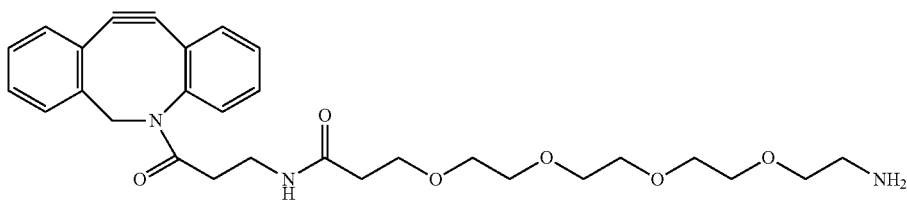
DBCO linker with PEG spacer

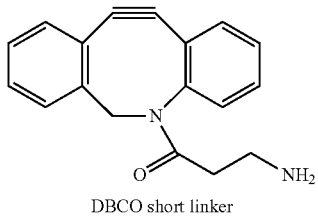
DBCO short linker

ChADC1 N297S antibodies and short DBCO linker or DBCO linker comprising a 15-atom PEG spacer were reacted in the presence of BTG to modify antibodies using optimized reaction conditions (80 eq ligand, 6 U/ml BTG, 1 mg/ml mAb, 37° C.). See Example 3 for optimized reaction conditions.

Quantitative enzymatic modification of chADC1 N297S heavy chain with short DBCO linker by BTG could not be accomplished and primarily unmodified chADC1 heavy chain was found, with a major peak corresponding to unmodified heavy chain (70%) and a minor peak to heavy chain with one short DBCO linker (30%). However, reacting DBCO linker with spacer comprising a 15-carbon PEG spacer achieved substantially quantitiative (complete) coupling of all heavy chains with one DBCO linker with spacer.

3. Cytotoxic Agent (Large, Hydrophobic Payload)

The linker tested comprised the monomethyl auristatin F (MMAF) as a representative large cytotoxic drug used in antibody drug conjugates, as well as a valine-citrulline dipeptide spacer, a 6-carbon spacer and a PAB self-elimination spacer. The structure is shown below. The molecular weight is indicated below the structure.

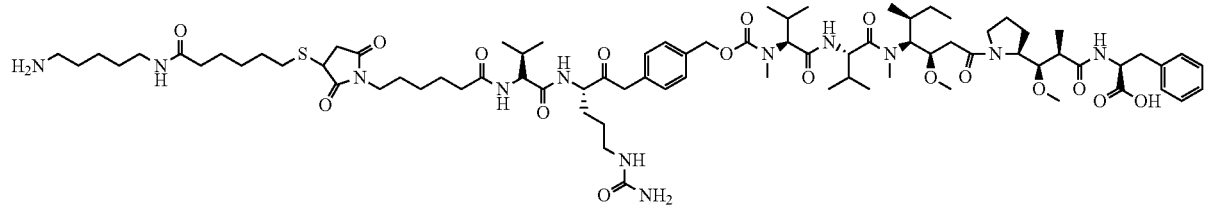

Unmodified (N297), PNGaseF deglycosylated chADC1 and chCE7 antibodies were reacted with the MMAF linker in the presence of BTG to modify antibodies using optimized reaction conditions (80 eq ligand, 6 U/ml BTG, 1 mg/ml mAb, 37° C.). Quantitative enzymatic modification of chADC1 heavy chain with MMAF linker by BTG could not be accomplished. Primarily unmodified chADC1 or chCE7 heavy chain was found, with a major peak corresponding to unmodified heavy chain (70%) and a minor peak to heavy chain with one MMAF linker (30%) for chADC1 and a major peak corresponding to unmodified heavy chain (81%) and a minor peak to heavy chain with one MMAF linker (19%) for chCE7.

Figure 20A:
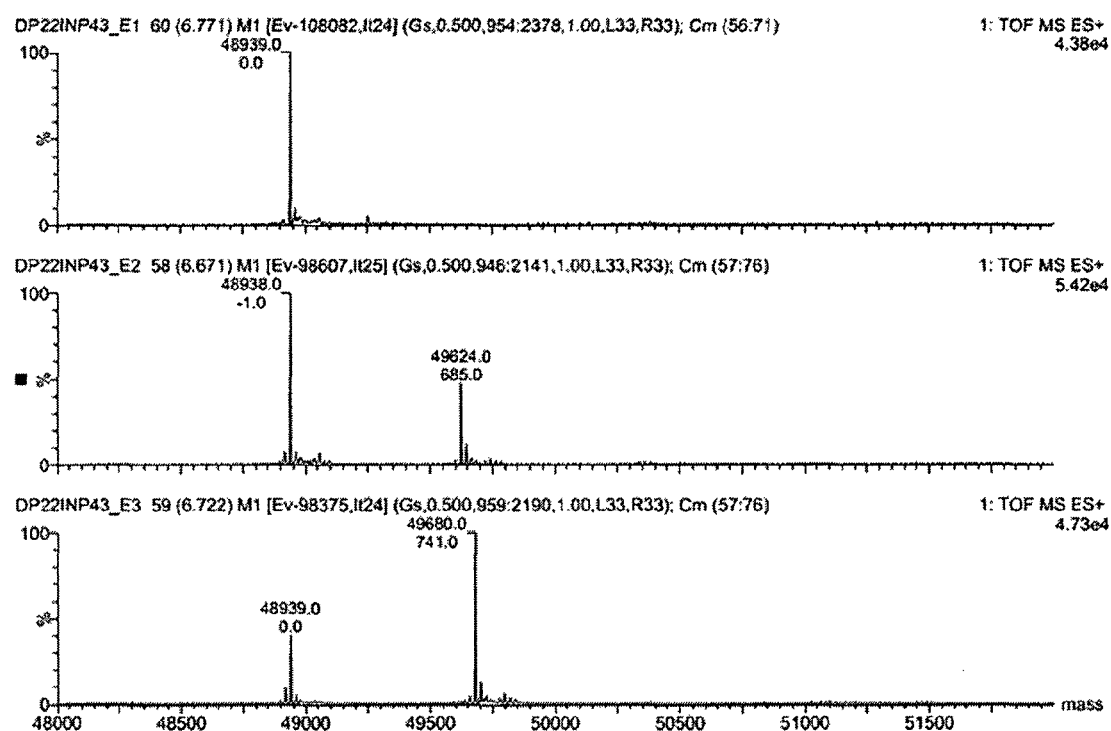
FIG. 20A shows the MS spectrum of chADC1dgl coupled to C6-Maleimide-vc-PAB-MMAF.
Figure 20B:
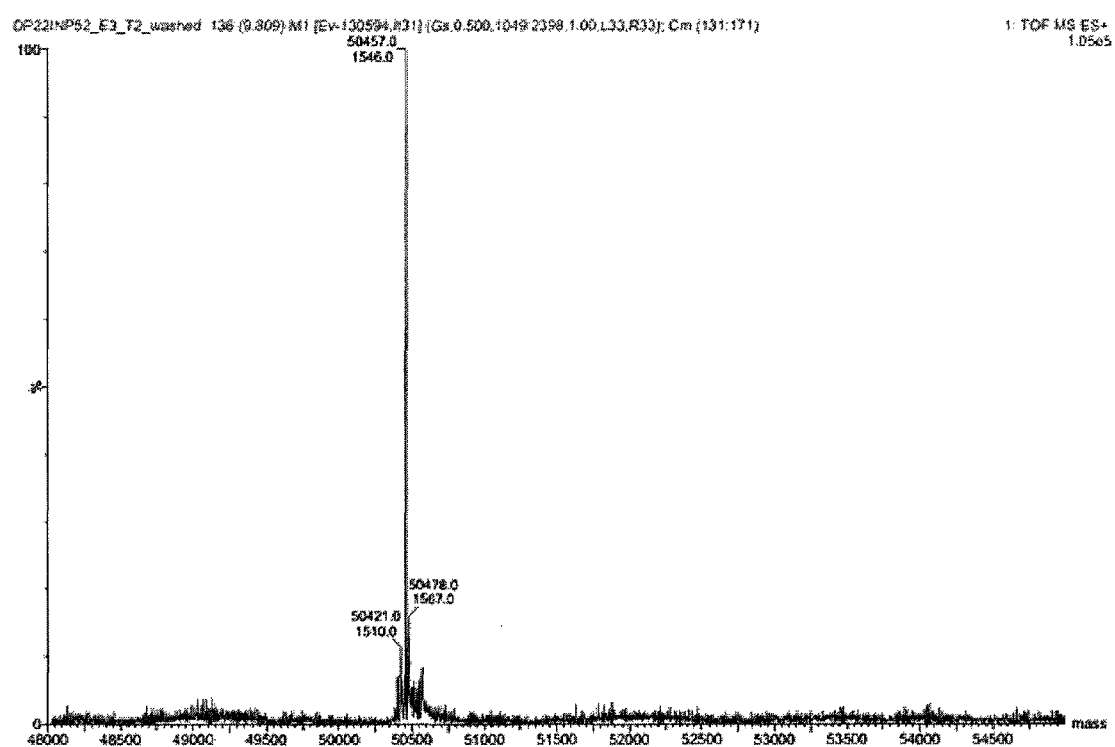
FIG. 20B shows the MS spectrum of chADC1N297S coupled to C6-Maleimide-vc-PAB-MMAF.

However, when modified N297S chADC1 antibodies were reacted with the MMAF linker in the presence of BTG achieved, quantitative coupling was achieved, with a major peak corresponding to heavy chains with one MMAF linker (greater than 90%). The MS spectrum of chADC1 coupled to C6-Maleimide-vc-PAB-MMAF is shown in FIG. 20A and the MS spectrum of chADC1N297S coupled to C6-Maleimide-vc-PAB-MMAF is shown in FIG. 20B.

The experiments were repeated using chCE7 Q295N, N297Q antibodies and the MMAF linker using optimized reaction conditions (80 eq ligand, 6 U/ml BTG, 1 mg/ml mAb, 37° C.). The reaction achieved high levels coupling of all heavy chains with one MMAF linker, with a major peak corresponding to heavy chain modified with one C6-DOTA (between 86% and 91%) and a minor peak corresponding to 9%-14% unmodified heavy chains.

Highly favorable reaction conditions were investigated to test whether direct coupling of C6-MMAF linker onto a PNGaseF-deglycosylated mAb could be pushed to completion. Conditions tested were: mAb (1 mg/ml), 160 equivalent excess of 20 mM substrate in DMSO (molar excess based on molarity of the mAb), 6 U/mL BTGase, 200 uL reaction vol., at two incubation durations, either T1 of 40 hours or T2 of 110 hours, in each case at 37° C. Amount of HC+2×C6-MMAF could be observed compared to 16 h incubation time. No difference between T1 and T2 were observed for chADC1 N297Q, and only a small difference between T1 and T2 for chCE7agl. Increasing the incubation time does not push the reaction to completion for PNGaseF-deglycosylated antibodies.

Example 8

Improved Processes for Direct Coupling of Auristatin

A range of processes involving different quantities of BTG and/or linkers were tested in order to develop a process involving lower amounts of cytotoxic drug substrate for direct coupling to antibodies. Briefly, antibody-linker conjugates were formed by quantitative BTG-mediated coupling of the C6-MMAF linker onto chADC1 N297S and chSGN35 N297S (two glutamines per antibody) different conditions: mAb (1 mg/ml), 80 eq., 40 eq., 20 eq., 10 eq. excess of 20 mM linker substrate in DMSO, 4 U/mL, 2 U/mL BTG, 200 uL reaction vol., 18.5 h incubation time at 37° C. Equivalents (eq) are indicated as molar excess based on molarity of the mAb, thus for N297S antibodies having two acceptor glutamines, 80 eq corresponds to 40 times molar excess per acceptor glutamine.

The resulting antibodies were functionalized with C6-MMAF, with only minimal unfunctionalized linker remaining, for all concentrations of BTG when 40 eq C6-MMAF were used (i.e. 20 eq of C6-MMAF per acceptor glutamine), while below 40 eq C6-MMAF coupling was no longer quantitative. Additionally, 80 equivalents of C6-MMAF yields close to complete functionalization when 4 U/ml or 2 U/ml of BTG are used.

Example 9

Improved Linkers for a Multi-Step Process

To explore the ability of a multi-step process to improve BTG coupling, various lysine-based linker comprising a reactive group were generated. The lysine-based linker can be conjugated to an antibody via BTG, followed by reaction of the conjugated antibody with a reagent comprising a reactive group capable of reacting with the reactive group on the lysine-based linker. Various lysine-based linkers were designed to be capable of quantitiative coupling onto an antibody by BTG. The linkers lacked cyclic groups, notably polycyclic or macrocyclic groups proximal to the primary amine (site of BTG uptake and coupling).

A first linker C2-SAc (see Example 1) comprises a lysine based moiety and a protected thiol as reactive group, having the structure as follows.

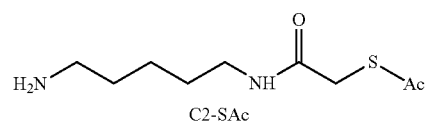 [SMILES: CC(=O)SCC(=O)NCCCCCN]
C2-SAc

A further linker C6-SAc (see Example 1) comprises a lysine based moiety, a protected thiol as reactive group and an additional linear carbon-comprising framework that acts as a spacer group, and has the structure as follows.

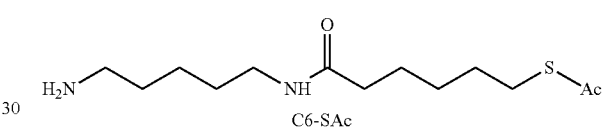
C6-SAc

A further linker PEG-SAc (see Example 1) comprises a lysine based moiety, a protected thiol as reactive group and an additional linear carbon-comprising PEG framework that acts as a spacer group, and has the structure as follows.

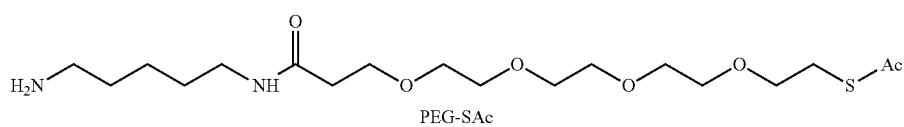 [SMILES: CC(=O)SCCOCCOCCOCCOCCC(=O)NCCCCCN]
PEG-SAc

A further linker Azide-PEG4-NH$_2$ comprises a lysine based moiety and spacer group together embodied as a linear carbon-comprising PEG framework, and an azide as reactive group, and has the structure as follows.

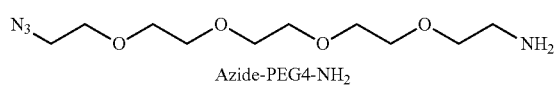
Azide-PEG4-NH$_2$

A further linker Alkyne-PEG4-NH$_2$ comprises a lysine based moiety and spacer group together embodied as a linear carbon-comprising PEG framework, and an alkene as reactive group, and has the structure as follows.

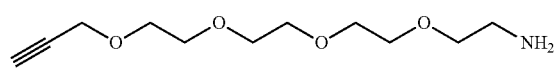
Alkyne-PEG4-NH$_2$

A further linker DBCO-PEG4-NH$_2$ comprises a lysine based moiety and spacer group together embodied as a linear carbon-comprising PEG framework, and as alkyne a dibenzylcyclooctyne (DBCO) as the reactive group, and has the structure as follows.

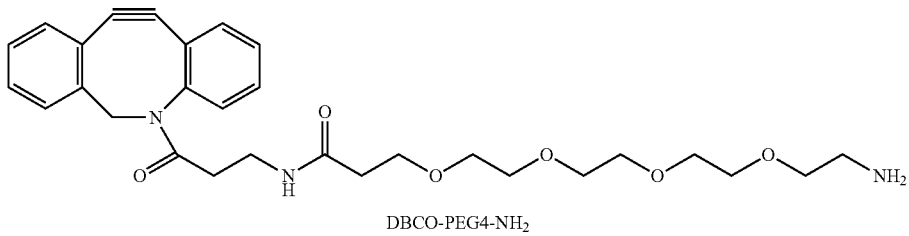 [SMILES: NCCOCCOCCOCCOCCC(=O)NCCC(=O)N1Cc2ccccc2C#Cc2ccccc21]

DBCO-PEG4-NH$_2$

Unmodified chADC1 and chADC1 N297S antibodies and the various reactive-group-comprising linkers were reacted in the presence of BTG to modify antibodies using optimized reaction conditions (80 eq ligand, 6 U/ml BTG, 1 mg/ml mAb, 37° C.). See Example 3 for optimized reaction conditions.

Quantitative enzymatic modification chADC1 and chADC1 N297S heavy chains with each linker by BTG could was observed. Using 6 U/mL BTG in reaction conditions it was possible to couple the different tested thiol linkers quantitatively and stoichiometrically uniform to the heavy chain of chADC1. The preparation for analysis is shown in the scheme below. It is likely that two peaks are appearing in the MS spectra (FIG. 21) as the basic pH during the sample preparation for the MS measurement (see "LC-MS analysis") can promote deacetylation of the protected thiol group. Partial deprotection occurred for the short thiol linker (n=1) whereas complete deprotection was observed for the long thiol linker (n=5).

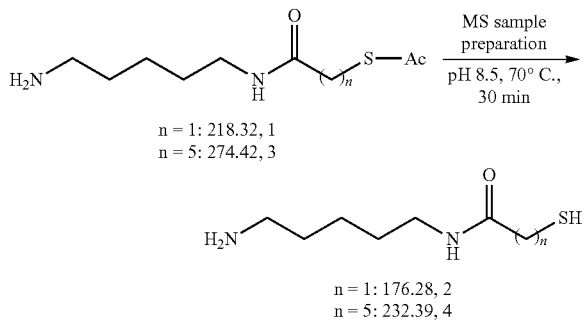

Scheme (above): Deacetylation of protected thiol linkers 1 and 3 during sample preparation for mass spectrometry. Molecular weights for both short (n=1) and long (n=5) protected thiol linker as well as for the corresponding deprotected linkers 2 and 4 are indicated below the structures.

Figure 22A:
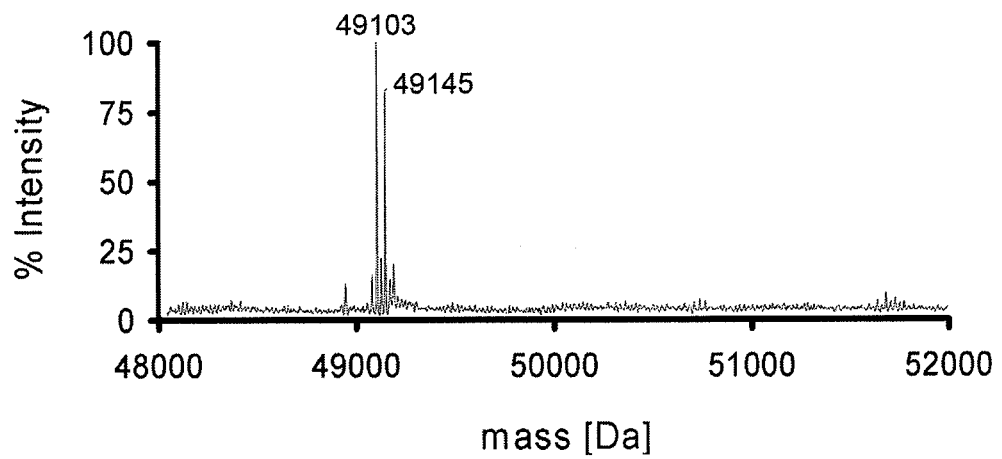
FIGS. 22A and 22B show the deconvoluted mass spectra of chADC1 heavy chain coupled to the short (left) and long (right) thiol linker, compounds 4a and 4b. The FIG. 22A spectrum shows the protected short linker compound 4a and the FIG. 22B spectrum shows deprotected long linker 4b.
Figure 22B:
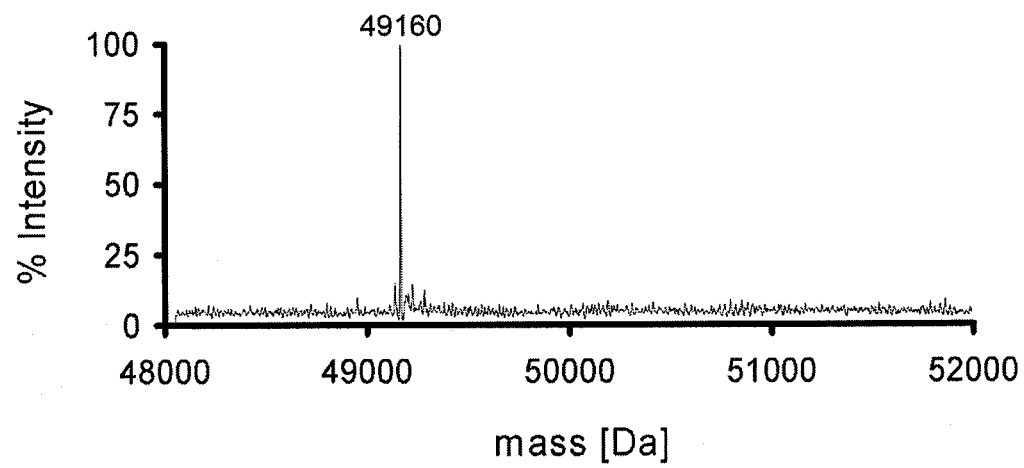

The results in FIGS. 22A and 22B show the deconvoluted mass spectra of chADC1 heavy chain coupled to the short (1A) and long (2B) thiol linker. FIG. 22A spectrum: Protected short linker 1: 218 g/mol, 218-17=201 Da, 48945+201=49146 Da, 49145 Da found; deprotected short linker 2: 176 g/mol, 176-17=159 Da, 48945+159=49104, 49103 found. FIG. 22B spectrum: Deprotected long linker 4: 232 g/mol, 232-17=215 Da, 48945+215=49160 Da, 49160 Da found.

Various antibody-bound linkers were then reacted with reaction partners to obtain final compounds. In one series of experiments, antibody-linker conjugates were formed by quantitative BTG-mediated coupling of S-acetyl protected linker C6-SAc onto chADC1, followed by deprotection and reaction with maleimide functionalized toxin. The resulting antibodies were successfully functionalized with toxin, accompanied by a fraction of linkers that were not functionalized.

In another series of experiments, antibody-linker conjugates were formed by quantitative BTG-mediated coupling of the Azide-PEG4-NH$_2$ linker onto chADC1 N297S, followed by reaction with DBCO-amine. The resulting antibodies were completely/quantitatively functionalized with DBCO-amine, with no unfunctionalized linkers remaining.

Example 10

A Multiple Step Process Achieves Quantitative Coupling onto Two Glutamines Per Heavy Chain We explored the ability of a multi-step process to improve BTG coupling so as to increase the number of glutamines coupled on each antibody heavy chain. Lysine-based linkers were conjugated to antibodies modified to have two potential acceptor glutamines at both positions 295 and 297 in a one-step or a multi-step process.

Different antibodies having N297Q substitutions were generated, chADC1 N297Q, SGN-35 N297Q and chCE7 N297Q. The modified antibodies comprise one acceptor glutamine at position Q295 on each heavy chain and one acceptor glutamine at position 297 on each heavy chain, and furthermore do not require PNGaseF treatment to remove N297-linked glycans prior to coupling with BTG.

Combinations of linkers C2-SAc, C6-SAc and PEG-SAc (see Example 8) and chADC1 N297Q, SGN-35 N297Q and chCE7 N297Q were reacted in the presence of BTG to modify antibodies using optimized reaction conditions (80 eq ligand, 6 U/ml BTG, 1 mg/ml mAb, 37° C.).

Quantitative (substantially complete) enzymatic modification of unmodified chADC1 N297Q and SGN-35 N297Q heavy chains with each linker by BTG could was observed. Each of linkers C2-SAc, C6-SAc and PEG-SAc provided complete coupling to two glutamines on all heavy chains. Likewise, Azide-PEG4-NH$_2$ linker also provided complete coupling to two glutamines on all heavy chains of chADC1 N297Q.

For comparison, MMAF linker (see Example 6) was reacted with PNGaseF-deglycosylated antibodies chADC1 N297Q in the presence of BTG using optimized reaction conditions (80 eq ligand, 6 U/ml BTG, 1 mg/ml mAb, 37° C.). However, quantitative enzymatic modification of both glutamines on each heavy chain with MMAF linker by BTG could not be accomplished. Primarily chADC1 heavy chain modified with a single MMAF linker was found, with a major peak corresponding to modified heavy chain with one MMAF linker (75%) and a minor peak to heavy chain with two MMAF linkers (25%) for chADC1.

Use of linkers with reactive groups capable of quantitative coupling onto two acceptor glutamines per antibody heavy chain, together with modified antibodies having two glutamines per antibody heavy chain, provides a strategy to couple moieties of interest onto four acceptor glutamines per full antibody.

Example 11

Improved Processes for Click-Chemistry Functionalization

Equivalents of reaction partners for antibodies functionalized with Azide-PEG4-$NH_2$ linker were decreased in order to develop a process involving lower amounts of cytotoxic drug substrate. Briefly, antibody-linker conjugates were formed by quantitative BTG-mediated coupling of the Azide-PEG4-$NH_2$ linker onto chADC1 N297S (two glutamines per antibody) and chADC1 N297Q (four glutamines per antibody), followed by incubation with reaction partners having complementary reactive groups and a cytotoxic moiety.

DBCO-PEG4-vc-PAB-MMAE (structure shown below) 1.5 equivalents per acceptor glutamine was reacted with antibody chADC1 N297S or N297Q conjugated to the azide-PEG4-$NH_2$ linker at room temperature for three hours, followed by purification by size exclusion chromatography. The drug antibody ratio (DAR) obtained was 2.0 on chADC1 N297S and 4.0 for chADC1 N297Q.

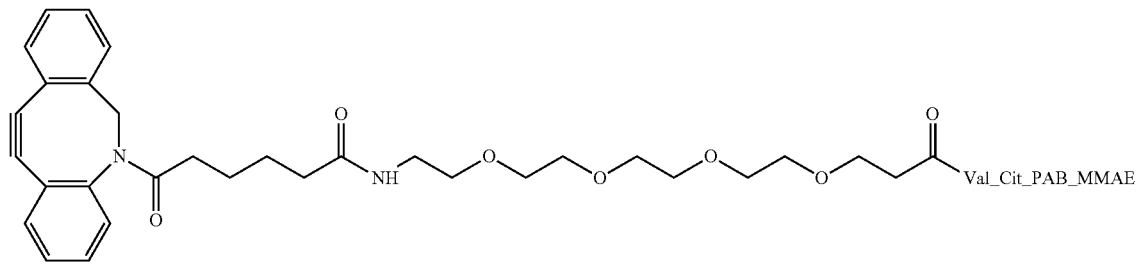

DBCO-PEG4-vc-PAB-MMAE

Example 12

Improved Stability Linkers for Click-Chemistry

The effect of different linkers on aggregation propensity of antibodies was evaluated using a thermal shift stability assay designed to measure the aggregation temperature of peptides and proteins in aqueous solutions. The "ProteoStat® Thermal Shift Stability Assay" kit (TSSA), available from Enzo Life Sciences Inc. (NY) was used according to the manufacturer's instructions. Briefly, the sample to analyse is heated from 0 to 100° C. and the fluorescence is read along the temperature increases. A high increase of sample fluorescence is detected when the aggregation temperature is reached. This fluorescent measurement uses a 480 nm excitable molecular rotor probe. It is compatible with a wide pH range (4-10) and tolerant to surfactants such as Polysorbate 80 present at normal concentrations.

Antibodies SGN-35 N297Q or SGN-35 N297S were reacted with linkers having either an S-acetyl (on either a C6 or PEG linker), an azide (on a PEG linker) or the cycloalkyne DBCO (on a PEG linker were evaluated. The linkers are shown below.

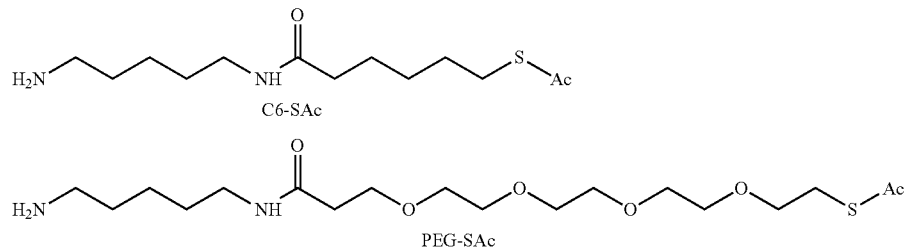

-continued

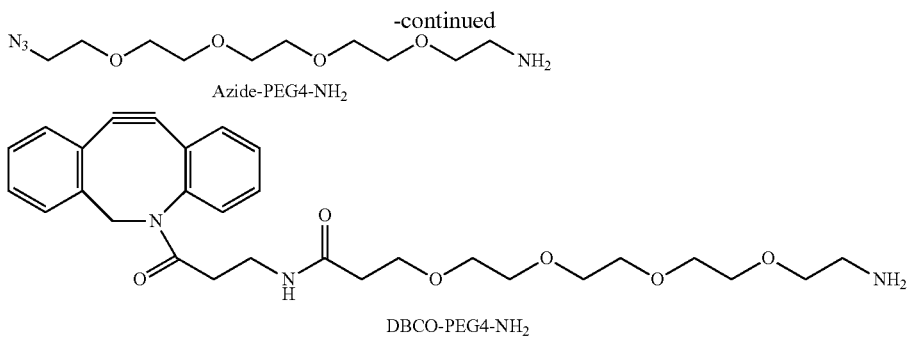

Results of stability studies of antibody conjugates in aqueous solution are shown in Table 6A.

TABLE 6

Aggregation Propensity

| Product | TSSA: $T_{Agg}$ (° C.) |
|---|---|
| SGN35 N297Q | 70.9 |
| SGN35 N297S | 70.7 |
| SGN35 N297S-PEG-N3- | 70.0 |
| SGN35 N297Q-PEG-N3- | 69.7 |
| SGN35 N297S-PEG-SAc | 69.7 |
| SGN35 N297S-C6-SAc | 69.5 |
| SGN35 N297Q-C6-SAc | 68.8 |
| SGN35 N297S-PEG-DBCO | 67.8 |
| SGN35 N297Q- PEG-DBCO | 66.3 |

While linkers showed acceptable stability, it can be seen that the SGN-35 antibodies (both N297S and N297Q, having an aggregation temperature of almost 71° C. (70.7° C. and 70.9° C. respectively) have particularly low propensity to aggregate, in comparison to other conjugates. At the opposite end of the range, linkers with hydrophobic DBCO groups had lower stability, with aggregation temperatures of 66.3° C. and 67.8° C. for N297Q and N297S respectively. Azide and thiol linkers (i.e. no hydrophobic groups) all had better stability than DBCO linkers. The stability between C6 and PEG linkers for thiol linkers on the same antibody was comparable. Additionally, N297Q antibodies with four glutamines did not show significant differences in aggregation temperature when azide linkers were used. However, for DBCO linkers, a full degree decrease in aggregation temperature was observed for antibodies with four acceptor glutamines indicating that two closely spaced linkers with hydrophobic groups may have a negative effect on stability of the antibody.

Example 13

Linker with Spacers and Cleavable Peptide (V) Moieties are Stable and Effective

The effect of different antibodies conjugated to linkers having a payload of peptide linker and cytotoxic drug were evaluated for stability and efficacy on tumor models in vitro.

Aggregation propensity was evaluated with a thermal shift stability assay (TSSA), using the ProteoStat® Thermal Shift Stability Assay as in Example 12.

Physical stability was measured after a Freeze/Thaw (F/T) cycle in which ADC products are frozen at least 2 hours at −20° C. and thawed at least 1 hour at room temperature three times and tested 24 h after the last Freeze/Thaw cycle, and after shaking in which ADC products samples are shaken with a "vortex" 3 min at 3000 rpm and tested 24 h after this shaking stress application. Measurements were made using an aggregation assay (AA) indicating percentage of soluble aggregates following physical stress. The AA assay was carried out using the ProteoStat® Protein aggregation assay available from Enzo Life Sciences Inc. (NY), according to the manufacturer's instructions. ProteoStat® reagent is an example of a molecular rotor-type fluorophore. In solution, the dye is a poor fluorophore as excited states relax through heat generation into the surrounding solution caused by the ability of the fluorophore to rotate around a central axis in its molecular structure. In the case of ProteoStat® dye, in the presence of protein aggregates, the dye can slip into cavities produced by the quaternary structure of the aggregate. In this state, rotation is constrained, resulting in a significant increase in fluorescence quantum yield. Measurements were also made by SE-HPLC, performed with the Acquity UPLC from WATERS® with a BEH200 SEC 1.7 μm column. SE-HPLC is used to evaluate soluble and covalent/non-covalent aggregates levels and the proteic fragments that could be generated.

A chemical stability study monitored the molecular integrity of the ADC products that could be impacted following 3 months storage at +40° C. (thermal stress accelerated degradation storage conditions). Samples stored at +40° C. were compared to samples stored at +5° C., as assessed by SE-HPLC, performed with the Acquity UPLC from WATERS® with a BEH200 SEC 1.7 μm column.

The antibodies were compared to the gold standard antibody-drug conjugate, Adcetris™ anti-CD30 antibody based on SGN-35 to which is conjugated maleimidocaproyl-vc-PAB-MMAE linkers.

Adcetris™, however has sites for conjugation of linkers at cysteines that are in areas of the antibody that may be relatively shielded, in turn possibly decreasing propensity to aggregate. Conjugation to glutamines at residue 295 or 297 within the CH2 region of non-glycosylated antibodies, on the other hand, is expected to yield highly exposed linkers, which in turn may lead to aggregation.

Antibodies SGN-35 N297Q or SGN-35 N297S were reacted with (1) C6 or PEG linkers having either a C6 or PEG linker, the product of a N3-DBCO reaction, a valine-citrulline cleavable linker, a PAB spacer, and an auristatin cytotoxic drug, or (2) linkers having a PEG linker, a valine-citrulline cleavable linker, a PAB spacer, and an auristatin cytotoxic drug (NH2-PEG-vc-PAB-MMAE, shown below).

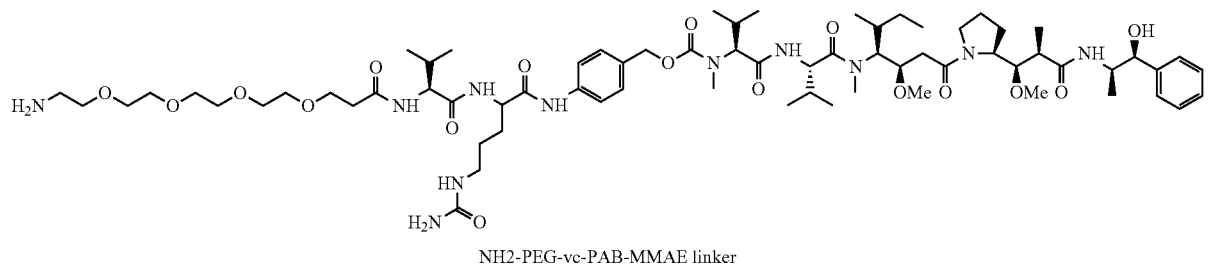 [SMILES: CCC(C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)C(CCCNC(N)=O)NC(=O)[C@@H](NC(=O)CCOCCOCCOCCOCCN)C(C)C)cc1)C(C)C]

NH2-PEG-vc-PAB-MMAE linker

All ADC products were formulated identically, as shown in Table 7 below.

TABLE 7

ADCETRIS ®/ADC Product Formulation

| Ingredients | Function | Quantity/ Concentration |
|---|---|---|
| ADCETRIS ®/ADC products | Active | 5.00 mg/mL |
| Sodium citrate (dihydrate) | Buffer | 5.60 mg/mL |
| Citric acid (monohydrate) | Buffer | 0.21 mg/mL |
| Trehalose (dihydrate) | Isotonic agent | 70.00 mg/mL |
| Polysorbate 80 | Surfactant | 1 mg/mL |
| Water for injection | Diluent | Qs. |

Results of the TSSA study are shown in Table 8. It can be seen that the SGN-35 antibodies (both N297S and N297Q show aggregation propensity that is at worst comparable to Adcetris™. Antibodies with a single acceptor glutamine per heavy chain showed improved thermal stability compared to Adcetris™, with aggregation temperatures of almost 68° C. for N297S variants when azide-DBCO linkers were used, and over 69° C. for the NH2-PEG-vc-PAB-MMAE conjugate.

TABLE 8

| Aggregation Propensity | |
|---|---|
| Product | TSSA: $T_{Agg}$ (° C.) |
| SGN35 N297Q-C6-N3-DBCO-NH-PEG4-vc-PAB-MMAE | 64.82 |
| SGN35 N297Q-NH-PEG4-vc-PAB-MMAE | 65.68 |
| SGN35 N297Q-PEG-N3-DBCO-NH-PEG4-vc-PAB-MMAE | 65.85 |
| ADCETRIS ® | 66.10 |
| SGN35 N297S-PEG-N3-DBCO-NH-PEG4-vc-PAB-MMAE | 67.93 |
| SGN35 N297S-C6-N3-DBCO-NH-PEG4-vc-PAB-MMAE | 67.97 |
| SGN35 N297S-NH-PEG4-vc-PAB-MMAE | 69.38 |

Results of the physical stability study are shown in Table 9. All SGN-35 N297S or N297Q conjugated antibodies, including N297Q variants with two acceptor glutamine per heavy chain showed lower percentages of soluble aggregates compared to Adcetris™. N297S variants in particular showed very low levels of soluble aggregates at all timepoints and conditions. Additionally, no fragments were observed for any of the SGN-35 N297S or N297Q conjugated antibodies, although significant levels of fragments were observed for Adcetris™.

TABLE 9

| | | | Stress Conditions | | |
|---|---|---|---|---|---|
| Products | Assay | Study Parameter | T0 | 3F/T | Shaken |
| SGN35 N297S-C6-N3-DBCO-NH-PEG4-vc-PAB-MMAE | AA | Aggregates % | 0.45% | 0.38% | 0.37% |
| | SE-HPLC | Soluble Aggregates % | 1.77 | 2.08 | 1.94 |
| | | Fragments % | 0.00 | 0.00 | 0.00 |
| SGN35 N297Q-C6-N3-DBCO-NH-PEG4-vc-PAB-MMAE | AA | Aggregates % | 0.82% | 0.76% | 0.85% |
| | SE-HPLC | Soluble Aggregates % | 2.43 | 2.50 | 2.47 |
| | | Fragments % | 0.00 | 0.00 | 0.00 |
| SGN35 N297S-PEG-N3-DBCO-NH-PEG4-vc-PAB-MMAE | AA | Aggregates % | 0.28% | 0.24% | 0.27% |
| | SE-HPLC | Soluble Aggregates % | 0.81 | 0.88 | 0.79 |
| | | Fragments % | 0.00 | 0.00 | 0.00 |
| SGN35 N297Q-PEG-N3-DBCO-NH-PEG4-vc-PAB-MMAE | AA | Aggregates % | 0.68% | 0.59% | 0.56% |
| | SE-HPLC | Soluble Aggregates % | 0.56 | 0.58 | 0.58 |
| | | Fragments % | 0.00 | 0.00 | 0.00 |
| SGN35 N297S-NH-PEG4-vc-PAB-MMAE | AA | Aggregates % | NT | NT | NT |
| | SE-HPLC | Soluble Aggregates % | 0.57 | 0.60 | 0.57 |
| | | Fragments % | 0.00 | 0.00 | 0.00 |
| SGN35 N297Q-NH-PEG4-vc-PAB-MMAE | AA | Aggregates % | 0.50% | 0.55% | 0.57% |
| | SE-HPLC | Soluble Aggregates % | 0.46 | 0.51 | 0.48 |
| | | Fragments % | 0.00 | 0.00 | 0.00 |
| ADCETRIS ® | AA | Aggregates % | 1.08% | 1.12% | 0.90% |
| | SE-HPLC | Soluble Aggregates % | 2.53 | 2.20 | 2.21 |
| | | Fragments % | 1.31 | 1.49 | 1.67 |

NT = Not Tested

Results of the chemical stability at 5° C. are shown in Table 10. All SGN-35 N297S or N297Q conjugated antibodies, including N297Q variants with two acceptor glutamine per heavy chain showed similar or lower percentages of soluble aggregates compared to Adcetris™. N297S variants in particular showed very low levels of soluble aggregates at all timepoints and conditions. Additionally, no fragments were observed for any of the SGN-35 N297S or N297Q conjugated antibodies, although significant levels of fragments were observed for Adcetris™

TABLE 10

| Product | Study Parameter | T0 | T1 W |
|---|---|---|---|
| SGN35 N297S-C6-N3-DBCO-NH-PEG4-vc-PAB-MMAE | Soluble Aggregates % | 1.77 | 1.81 |
| | Fragments % | 0.00 | 0.00 |
| SGN35 N297Q-C6-N3-DBCO-NH-PEG4-vc-PAB-MMAE | Soluble Aggregates % | 2.43 | 2.33 |
| | Fragments % | 0.00 | 0.00 |
| SGN35 N297S-PEG-N3-DBCO-NH-PEG4-vc-PAB-MMAE | Soluble Aggregates % | 0.81 | 0.71 |
| | Fragments % | 0.00 | 0.00 |
| SGN35 N297Q-PEG-N3-DBCO-NH-PEG4-vc-PAB-MMAE | Soluble Aggregates % | 0.56 | 0.48 |
| | Fragments % | 0.00 | 0.00 |
| SGN35 N297S-NH-PEG4-vc-PAB-MMAE | Soluble Aggregates % | 0.57 | 0.44 |
| | Fragments % | 0.00 | 0.00 |
| SGN35 N297Q-NH-PEG4-vc-PAB-MMAE | Soluble Aggregates % | 0.46 | 0.38 |
| | Fragments % | 0.00 | 0.00 |
| Adcetris ™ | Soluble Aggregates % | 2.53 | 2.31 |
| | Fragments % | 1.31 | 1.77 |

Efficacy of antibodies was evaluated by measuring cytotoxicity on the CD30-expressing KARPASS-299 cell line. All antibody drug conjugates were effective in inhibiting cell proliferation of CD30-expressing KARPASS-299 cells, while negative controls SGN-35 N297S and SGN-35 N297Q without toxin have no effect. At 10 µg/ml, all SGN-35 N297S or N297Q conjugated antibodies had an effect equivalent to ADCETRIS.

Example 14

BTG-Mediated Coupling of Substrates Sequence Tags on Single Chain mAbs

Recombinant proteins used included scFv (myc-tagged); affibody (dimeric, myc-tagged); nanobody (myc-tagged; non-tagged). Ligands used included: biotin-cadaverin (Zedira); desferrioxamine (Sigma Aldrich). Enzyme: MTGase (Zedira). Myc-Tag sequence: EQKLISEEDL 1. Modification of a Nanobody with Biotin-Cadaverin.

Figure 23A:
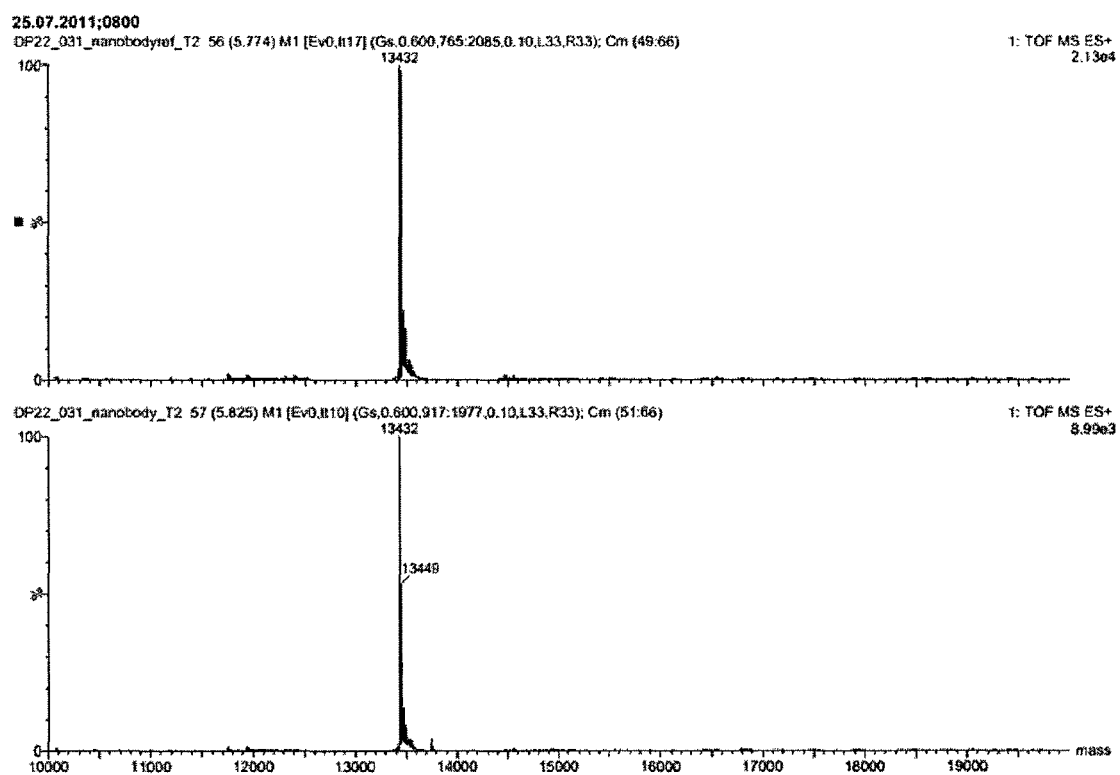
FIG. 23A shows LC-MS analysis of untagged nanobody incubated with BTG (top) or BTG and biotin-cadaverin (bottom).

In order to assess potential acceptor glutamines, a recombinant nanobody (camelid-derived single VH domain) was incubated with MTGase and biotin-cadaverin, and results were analysed by LC-MS. Analysis of the conjugates revealed lack of substantial labeling of the untagged nanobody (FIG. 23A). Thus, MTG does not functionalize glutamines present within the backbone of the nanobody.

Figure 23B:
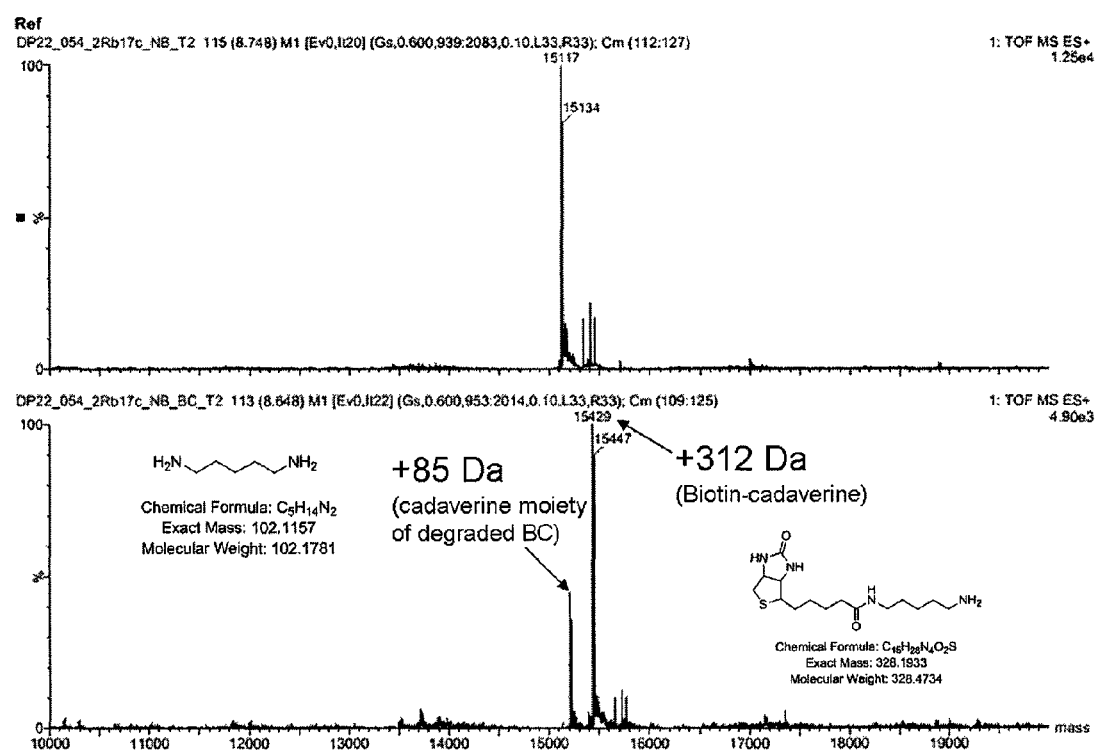
FIG. 23B shows LC-MS analysis of myc-tagged nanobody incubated with BTG (top) or BTG and biotin-cadaverin (bottom).

In contrast, LC-MS analysis revealed that the enzymatic reaction resulted in modification of the same nanobody carrying a C-terminal myc-tag (FIG. 23B). The mass peak at 15429 has the correct mass shift of 312 Da. Thus, MTG functionalizes the unique glutamine present within the myc-tag sequence. After tryptic digest, a peptide with the correct mass including the biotin-modified glutamine could be identified (Table 6B).

1. Modification of a Single Chain Variable Fragment (scFv) with Biotin-Cadaverin.

A myc-tagged scFv was incubated with MTGase and biotin-cadaverin, and results were analysed by SDS-PAGE/western blotting. The biotinylated scFv could be detected with streptavidin-HRP (MW 28 kDa). A degradation product with lower molecular weight was also detected. The modified peptide could be identified after tryptic digest (Table 6B).

2. Modification of a Dimeric, Myc-Tagged Affibody with Biotin-Cadaverin and Dansyl-Cadaverin.

Figure 23C:
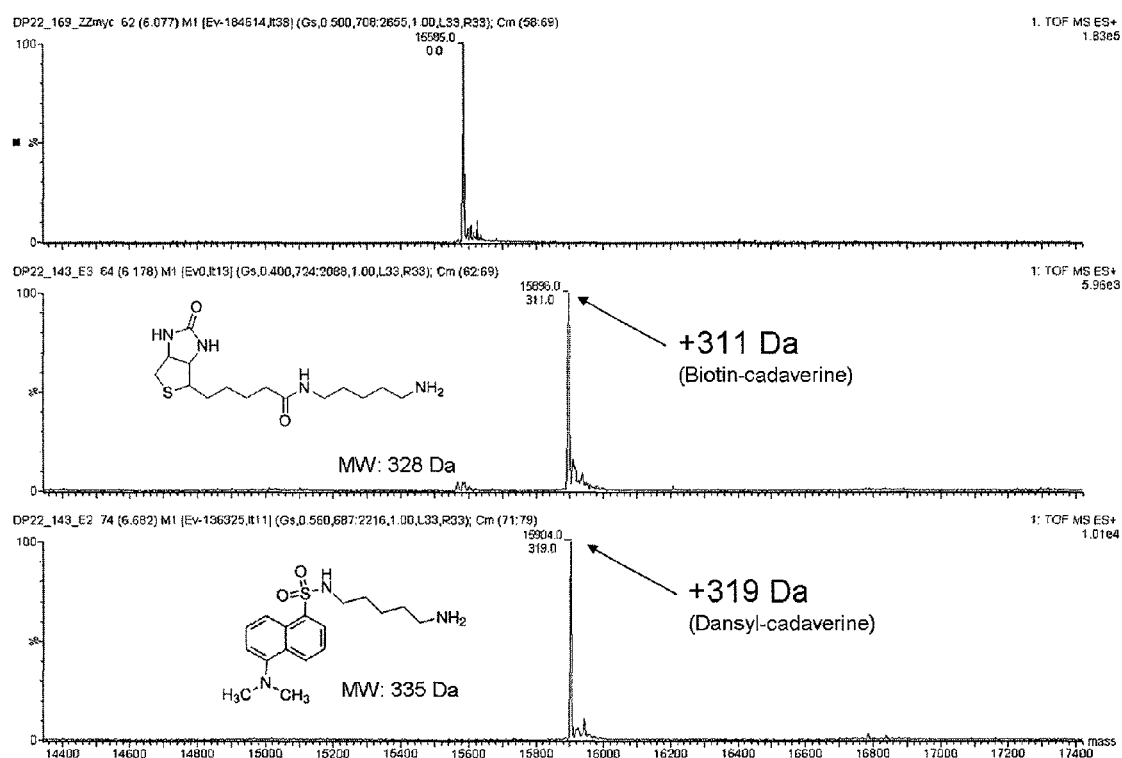
FIG. 23C shows LC-MS analysis of myc-tagged dimeric affibody incubated with BTG only (top) or BTG and biotin-cadaverin (middle) or BTG and dansyl-cadaverin (bottom).

LC-MS analysis showed quantitative modification of myc-tagged dimeric affibody with the substrates biotin-cadaverin and dansyl-cadaverin (FIG. 23C). The modified biotinylated peptide was identified by mass spectrometry after tryptic digest (Table 6B).

3. Modification of a Dimeric, Myc-Tagged Affibody with Biotin-Cadaverin and Dansyl-Cadaverin.

LC-MS analysis showed quantitative modification of myc-tagged dimeric affibody with the substrates biotin-cadaverin and dansyl-cadaverin (FIG. 23C). The modified biotinylated peptide was identified by mass spectrometry after tryptic digest (Table 6).

TABLE 6

| identified peptides of scFv, Nanobody and Affibody. | | | |
|---|---|---|---|
| Protein | Peptide | Mass (calc) | Mass (found) |
| scFv | LTVLGAAAEQ*K | 1410.7904 | 1410.7996 |
| Nanobody | TPTGQGTQVTVSSAAAEQ*K | 2171.0891 | 2171.0613 |
| Affibody | VDANSEQ*K | 1200.5808 | 1200.5671 |

Biotin-cadaverin modified Q residues are indicated by asterisks.

Example 15

Engineered-Constant Regions for Small Reactive Linkers

Variants of antibodies chimADC1 were constructed that contained various mutations in the CH2 domain to assess the impact of different residues at the +2 position on coupling of substrates by BTG. The chimADC1 mutants were produced using the same general methods for N297S mutants described above. Single and double mutants included the following: T299A, T299Q, N297D, N297A, N297H, N297R, Q295N+N297Q, Q295S+N297Q. These, along with N297S variant, were compared for effect on BTG coupling of a relatively small, non-hydrophobic substrate, dansyl-cadaverin. The coupling conditions used were: mAb: 0.5 mg/mL; linker: dansyl-cadaverin: 20 equivalents/acceptor glutamine; BTG: 1 U/mL; at a temperature of 37° C. with timepoints evaluated over a duration of 72 hours.

Figure 24A:
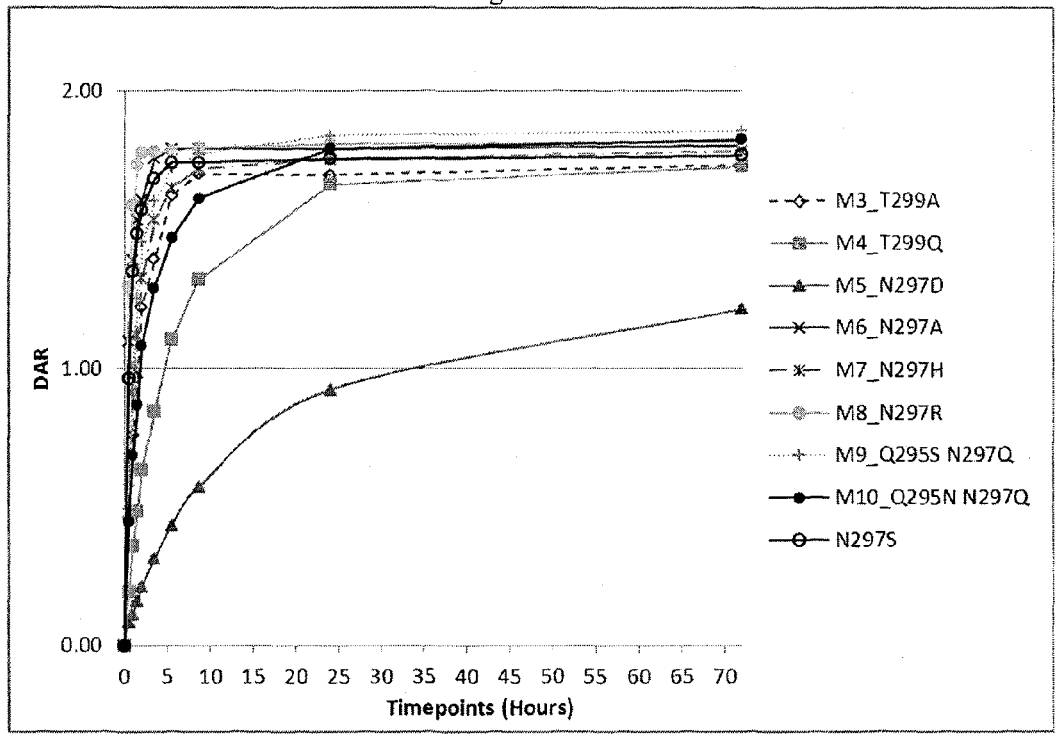
FIG. 24A shows good coupling of Q295 variants for reactive linkers, with the exception of the N297D variant in which the acceptor glutamine in flanked at the +2 position by an amino acid having a negative electrical charge. The 297D variant, despite extended reaction times, did not reach a DAR near that of the other variants.

Results are shown in FIG. 24. FIG. 24A shows good coupling of the different mutants, with the exception of the N297D variant in which the acceptor glutamine in flanked at the +2 position by an amino acid having a negative electrical charge. The 297D variant, despite extended reaction times, did not reach a DAR near that of the other variants.

Figure 24B:
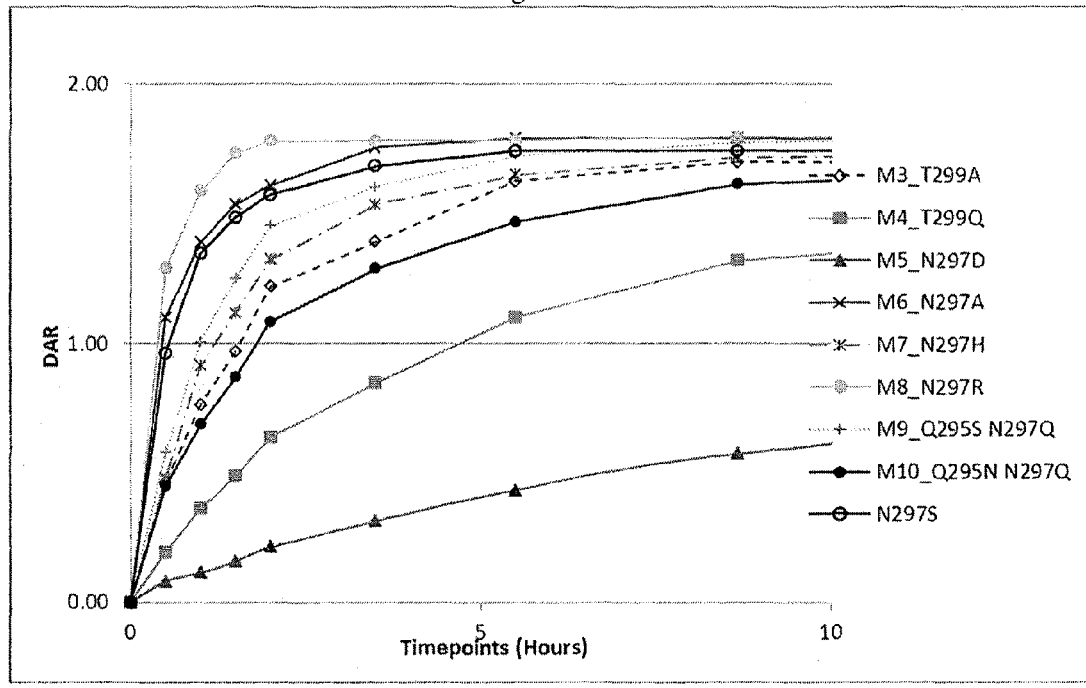
FIG. 24B shows the kinetics of coupling of the different mutants, where the amino acid (arginine) having a positive electrical charge was coupled faster than any other variant.

FIG. 24B shows the kinetics of coupling of the different mutants. Surprisingly, not only did small differences emerge in the absolute DAR after extended reaction times, but significant differences in reaction kinetics were observed. In particular, the amino acid (arginine) having a positive electrical charge was coupled faster than any other variant.

The results show that amino acids having a negative electrical charge at the +2 position relative to an acceptor glutamine should be avoided, particularly within the context of the CH2 domain. Interestingly, a positively charged amino acid at the +2 position can improve reaction kinetics.

While negative charge at the +2 position negatively influences coupling, negative charges at the −1 to −6 positions do not, and may on the contrary create a favorable coupling environment, possibly even more so when a positively charged residue is downstream (e.g. at the +2 position). In particular, the experiments were conducted using antibodies (the N297S, N297H, N297R, N297A variants) in which the residues at the −1 and −2 positions relative to the acceptor glutamine in the CH2 domain are negatively charged (glutamic acid), in which the residues at the −3 and −4 positions relative to the acceptor glutamine in the CH2 domain are negatively charged (the Q295N+N297Q and the Q295S+N297Q double mutants). Similarly, tags containing TGase recognition sequences (see Example 14) also contain negatively charged (glutamic acid) residues at the −1 position relative to the acceptor glutamine. It will therefore be possible to include negative charged residues (e.g. glutamic acid, aspartic acid) in the −1 to −4 positions relative to an acceptor glutamine in combination with absence of negative charged residues (e.g. glutamic acid, aspartic acid) at the +2 position. Furthermore, the positively charged residue arginine can be placed at the +2 position relative to an acceptor glutamine.

Example 16

Engineered-Constant Regions for Large Hydrophobic Linkers

Single and double mutants of chimADC1 of Example 15 were tested for conjugation of the large hydrophobic NH2-PEG-vc-PAB-MMAE linker, including mutants: N297S, T299A, T299Q, N297D, N297A, N297H, N297R, Q295N+N297Q, Q295S+N297Q. The coupling conditions used were: mAb: 0.5 mg/mL; linker: dansyl-cadaverin: 10 equivalents/acceptor glutamine; BTG: 1 U/mL; at a temperature of 37° C. with timepoints evaluated over a duration of 72 hours.

Figure 25:
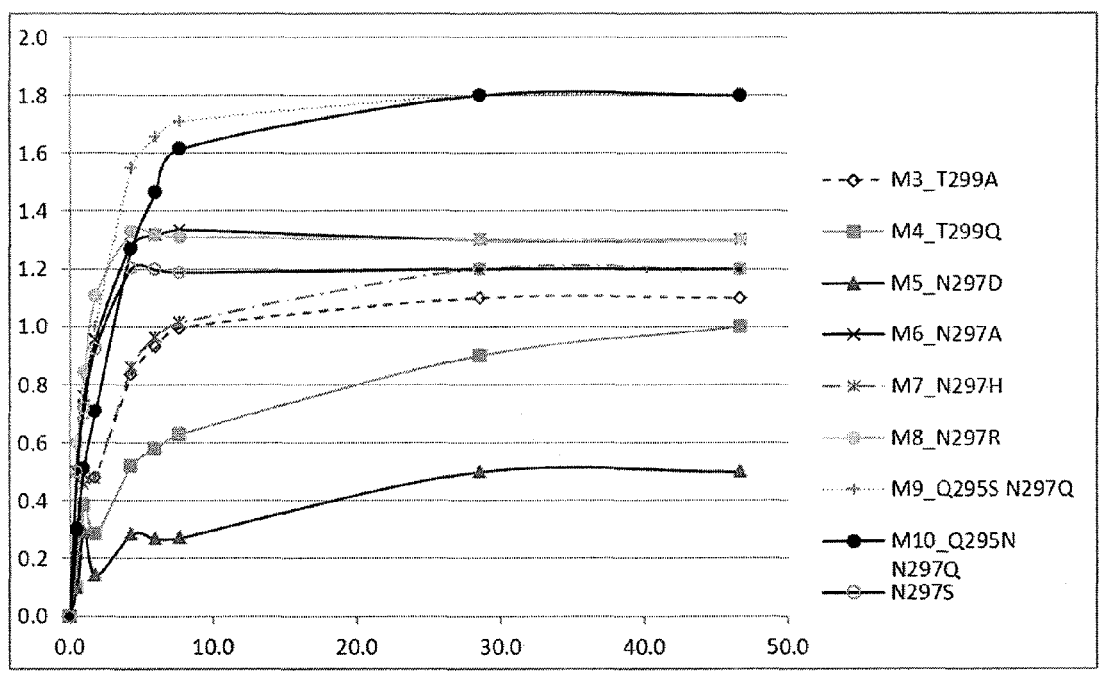
FIG. 25 shows single and double mutants tested for conjugation of the large hydrophobic NH2-PEG-vc-PAB-MMAE linker at 10 equivalents of linker per acceptor glutamine. Both double mutants Q295N+N297Q and Q295S+N297Q reach a plateau for completion of conjugation that is higher than any of the other variants (the last two timepoints tested for Q295N+N297Q and Q295S+N297Q are the same and thus not appear on the figure.

Results are shown in FIG. 25. Surprisingly, different coupling plateau were observed. With small linkers, differences in reaction kinetics can be observed between mutants, however coupling of small linkers reaches a plateau at similar levels (even if differences can exist). However, for large hydrophobic linkers, both double mutants Q295N+N297Q and Q295S+N297Q reach a plateau for completion of conjugation that is higher than any of the other variants (the last two timepoints tested for Q295N+N297Q and Q295S+N297Q are the same and thus not appear on the figure). Q295N+N297Q and Q295S+N297Q reached a DAR of 1.8 compared to 1.0 to 1.4 for other variants, and less than 0.6 for N297D.

It should be noted that these results were obtained using reaction conditions with a suboptimal number of equivalents of linker-toxin substrate (10 eq/acceptor glutamine). The Q295X+N297Q variants are therefore advantageous in that they permit decreases in the equivalents of toxin used to functionalize antibodies. Both asparagine and serine are used to replace the glutamine at residue 295 in these experiments, however other residues can be substituted at Q295, for example conservative substitutions (e.g. glycine, threonine) or alanine. For cytotoxic drugs which are hydrophobic and often poorly soluble and therefore cannot be used at high concentrations or that require organic solvents that are not compatible with BTG coupling, this opens avenues for obtaining highly homogenous antibody compositions.

Example 17

Effect of Organic Solvents on Conjugation of Hydrophobic Drugs

A range of processes involving different quantities of solvent (DMSO or 1,2-propanediol) were tested in order to study the impact of solvent on BTG. Briefly, antibody-linker conjugates were formed by BTG-mediated coupling of a cyclooctyne-C5NH2 linker onto chimADC1 N297S (two glutamines per antibody) in different conditions: mAb (5 mg/mL), 20 eq. excess of linker substrate in DMSO or 1,2-propanediol (1.4-30% of reaction volume), 2 U/mL BTG, 100 µL reaction vol., 4 days incubation time at 37° C. The reaction was monitored by LC/MS. Equivalents (eq) are indicated as molar excess based on molarity of the mAb, thus for N297S antibodies having two acceptor glutamines, 20 equivalents corresponds to 20 times molar excess per acceptor glutamine.

Figure 26A:
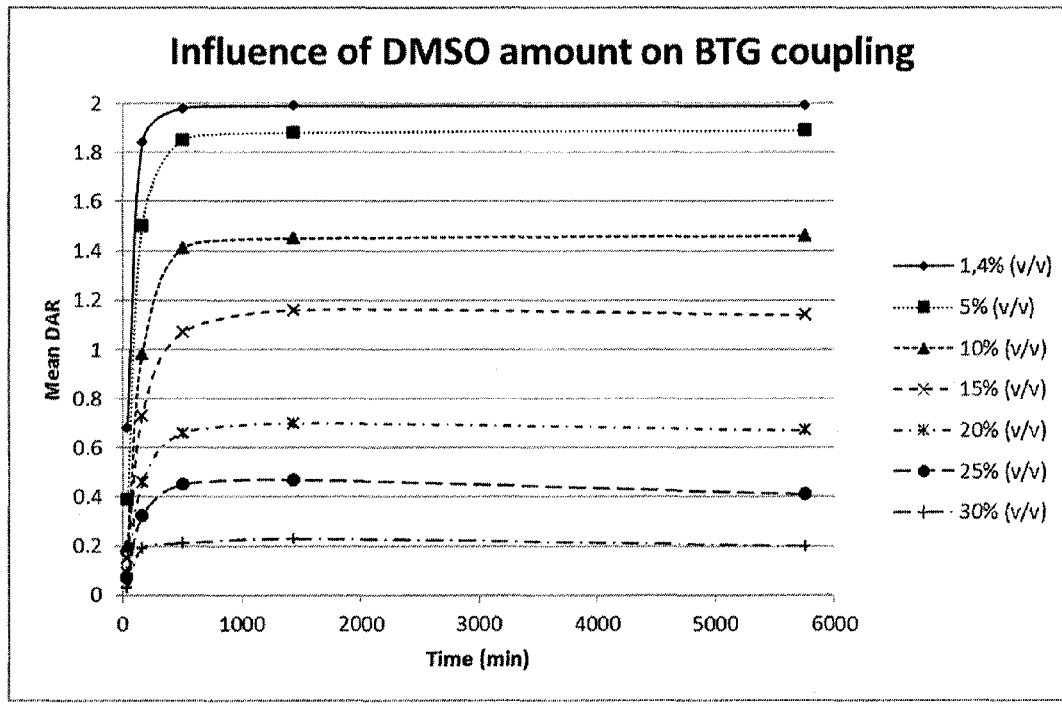
FIGS. 26A and 26B show the effect of increasing concentrations of organic solvent 1,2-propanediol solvent on BTG-mediated coupling of a linker onto antibody ADC1 N297S (two glutamines per antibody).
Figure 26B:
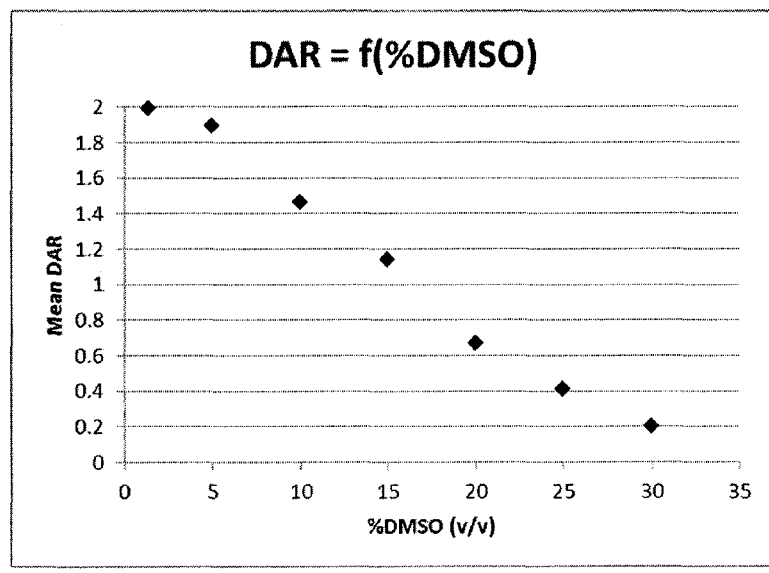
Figure 27A:
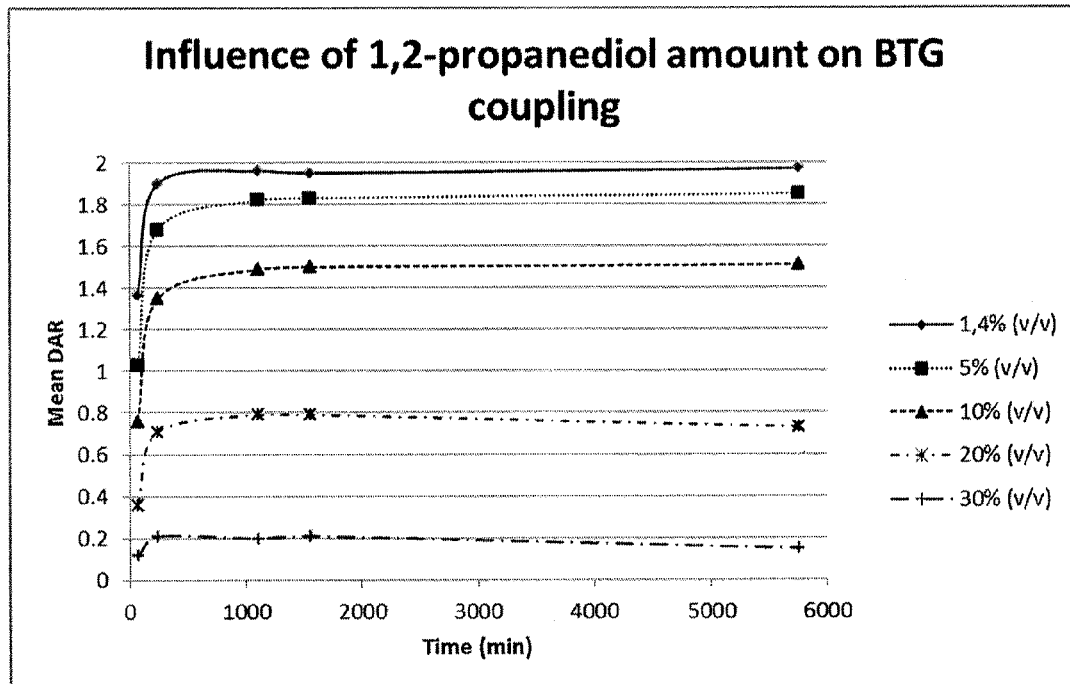
FIGS. 27A and 27B show the effect of increasing concentrations of organic solvent 1,2-propanediol solvent on BTG-mediated coupling of a linker onto antibody ADC1 N297S (two glutamines per antibody).
Figure 27B:
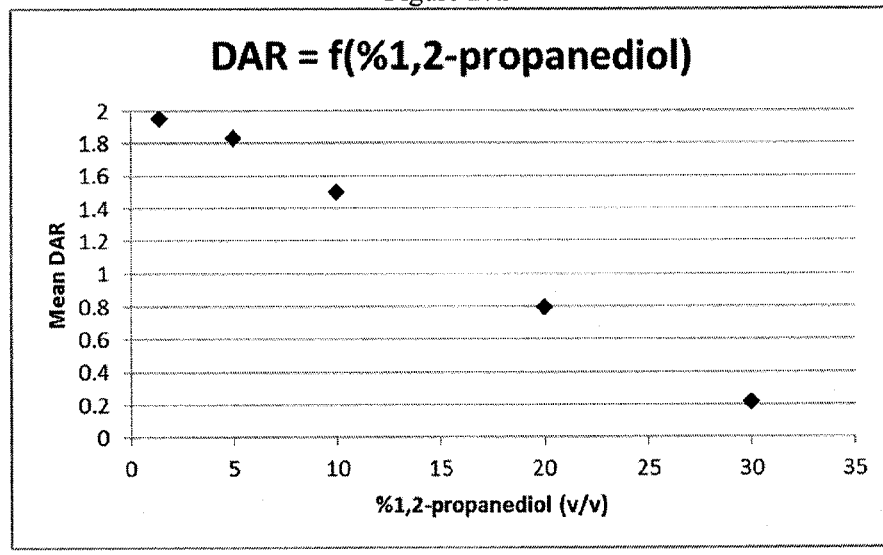

The results are shown in FIGS. 26A and 26B for the 1,2-propanediol solvent and in FIGS. 27A and 27B for DMSO. 1.4% (v/v) of either solvent led to complete coupling to acceptor glutamines. 5% (v/v) of either solvent led to high coupling to acceptor glutamines (DAR about 1.9 or about 95% complete coupling to acceptor glutamines). However 10% (v/v) of either solvent led to complete coupling to acceptor glutamines drastically lowered coupling, with a DAR of no more than 1.5. Hydrophobic drugs such as several cytotoxic drugs are difficult to couple to antibodies via TGase. This may be due in part because these drugs require organic solvents to maintain in solutions that in turn have an effect on TGase. Auristatins, or particularly hydrophobic such as pyrrolobenzodiazepines typically require organic solvents. Our results provide for modified coupling reactions for the direct coupling of drugs to antibodies, in which organic solvents are used at less than 10%, preferably no more than 5% or even less where possible. We have coupled auristatins in this way with as low as 1% DMSO at substantially complete coupling. An alternative, e.g., when it is not possible to reduce the concentration of solvent, is to use a two-step approach with a reactive group, where the TGase coupling is carried out in the absence of organic solvent, and the subsequent functionalization with drug is carried out in the presence of solvent.

Example 18

Influence of 1,2-propanediol on N3-DBCO Click Coupling of DBCO-PBD

A range of experiments involving different quantities of solvent (1,2-propanediol) were tested in order to study the impact of solvent on click coupling of DBCO-PBD with mAb derivatized with azide moiety. Briefly, DBCO-PBD was reacted with chimADC1 N297S (two glutamines per antibody) having the reactive azide in different conditions: mAb (2 mg/mL), 1.25 eq. excess of linker substrate in 1,2-propanediol (10-50% of reaction volume), 3-16 h incubation time at rt. The reaction was monitored by LC/MS.

Equivalents (eq) are indicated as molar excess based on molarity of the mAb, thus for N297S antibodies having two acceptor glutamines, 1.25 equivalents corresponds to 1.25 times molar excess per acceptor glutamine. Results are shown in the Table below. Neither 10% v/v nor 25% v/v solvent permitted click coupling to approach a DAR of 2.

| % of 1,2-propanediol | DAR achieved |
|---|---|
| 10% v/v | DAR = 0.95 |
| 25% v/v | DAR = 1.1 |

Example 19

Two-Step Procedure for Synthesis of PBD-ADC

In order to permit coupling of a PBD at higher DAR and greater homogeneity, a method was tested in which reactive linker (NH2-PEG-N3 spacer, having the structure shown below) was coupled onto an antibody having two acceptor glutamines (one per heavy chain) without organic solvent, followed by functionalization with a compound having a complementary reactive group, cleavable linker and a PBD (DBCO-val-ala-PBD, having the structure shown below). The resulting functionalized acceptor glutamine in the antibody had the structure shown below (mAb-PEG-DBCO-PBD), wherein "mAb" indicates the acceptor glutamine-NH.

NH2-PEG-N3 spacer:

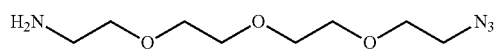 [SMILES: [N-]=[N+]=NCCOCCOCCOCCN]

DBCO-val-ala-PBD:

Briefly, 5 mg/mL mAb-N297S (mAb) was incubated with 10 equivalents of amino-PEG-azide per site of coupling and 2 U/mL BTG 5 h at 37° C. in PBS. mAb-spacer was purified by affinity chromatography on protA.

Functionalized antibody (2 mg/mL in PBS/1,2-propanediol 50/50 v/v) was incubated with 1.25 molar equivalent of derivatized-PBD per site of coupling (i.e. 2.5 equivalents for mAb-N297S). The mixture was incubated for 2-6 h at RT with gentle agitation. Excess of derivatized-PBD was removed by filtration on ZEBA spin desalting column (MWCO=7 kDa).

Figure 28:
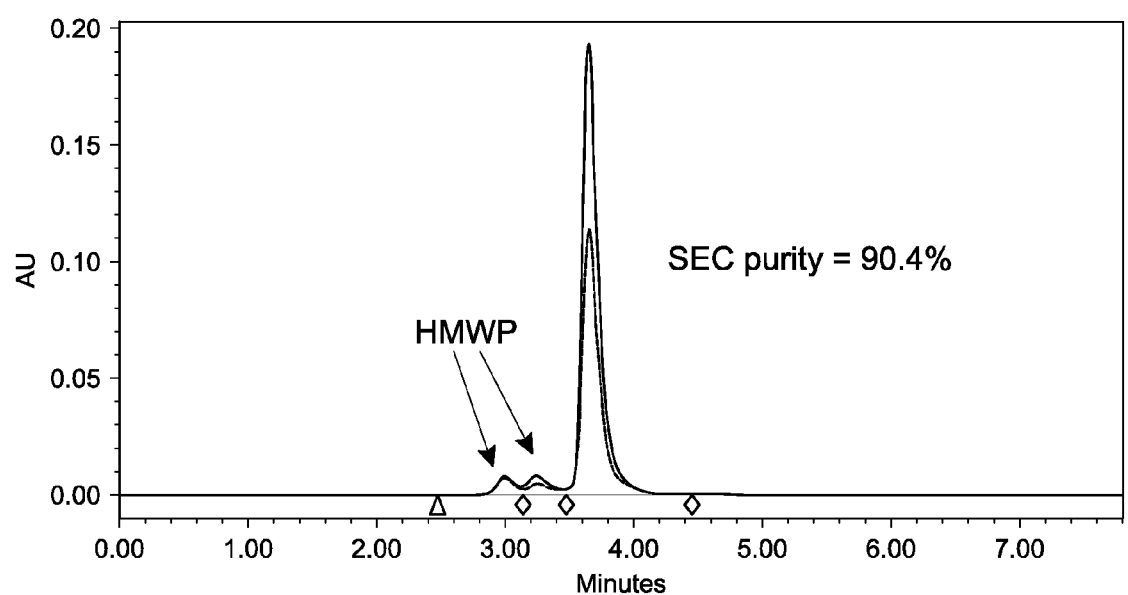
FIG. 28 shows an SEC analysis upon functionalization of an azide-linker tagged antibody with 1.25 molar equivalent of derivatized-PBD per site of coupling (i.e. 2.5 equivalents for mAb-N297S) in PBS/1,2-propane-diol 50/50 v/v).

LC/MS analysis results are shown in FIG. 28A. The BTG-mediated coupling of the reactive PEGN3 linker was substantially completely coupled (DAR>1.9). The functionalization with DBCO-val-ala-PBD was also substantially complete, with the final DAR of greater than 1.9 for the antibody-drug conjugate. SEC results are shown in FIG. 28B; the compound exhibited purity of 90.4%, with a small amount of high molecular weight product.

| Molecule | DAR |
|---|---|
| mAb-PEGN3 | DAR > 1.9 |
| mAb-PEGN3-DBCO-PBD | DAR > 1.9 |

Example 20

In Vitro Efficacy of PBD Conjugates mAbs-PBD of Example 19 were tested at 4 concentrations: 10, 1, 0.1 and 0.01 μg/ml+medium on HCT116 colorectal carcinoma cells (ATCC CCL247®) cells) expressing antigen recognized by the mAb.

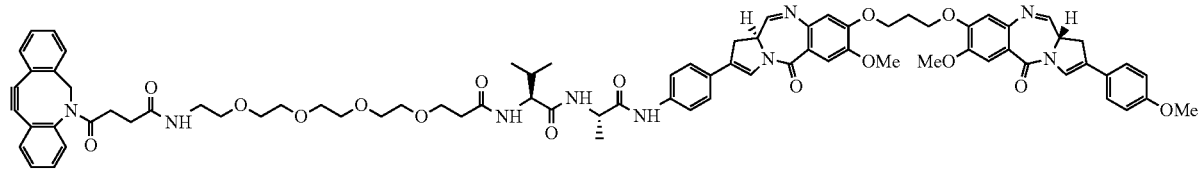 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCOCCOCCOCCOCCNC(=O)CCC(=O)N8Cc9ccccc9C#Cc9ccccc98)C(C)C)cc7)C[C@H]5C=N6)cc4N=C[C@@H]3C2)cc1]

mAb-PEG-DBCO-PBD:

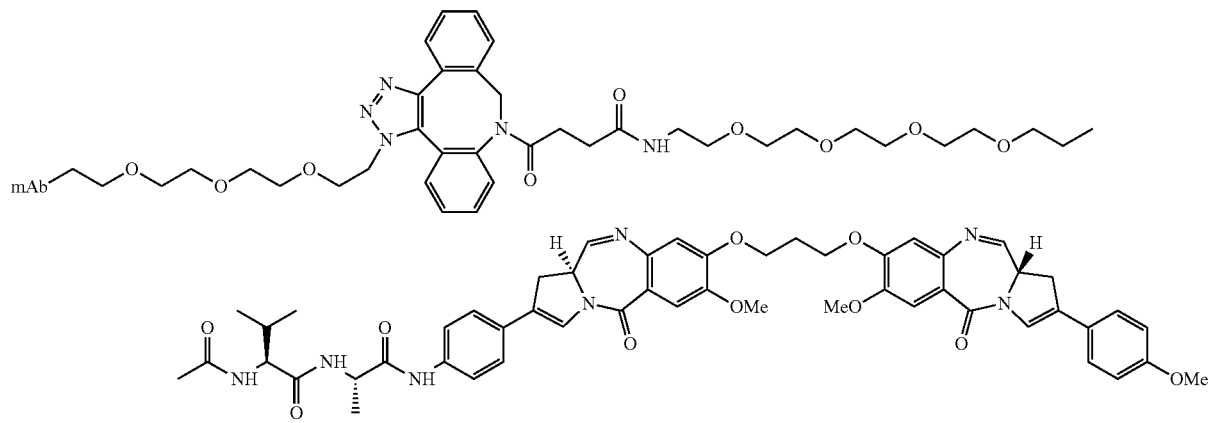

Figure 29A:
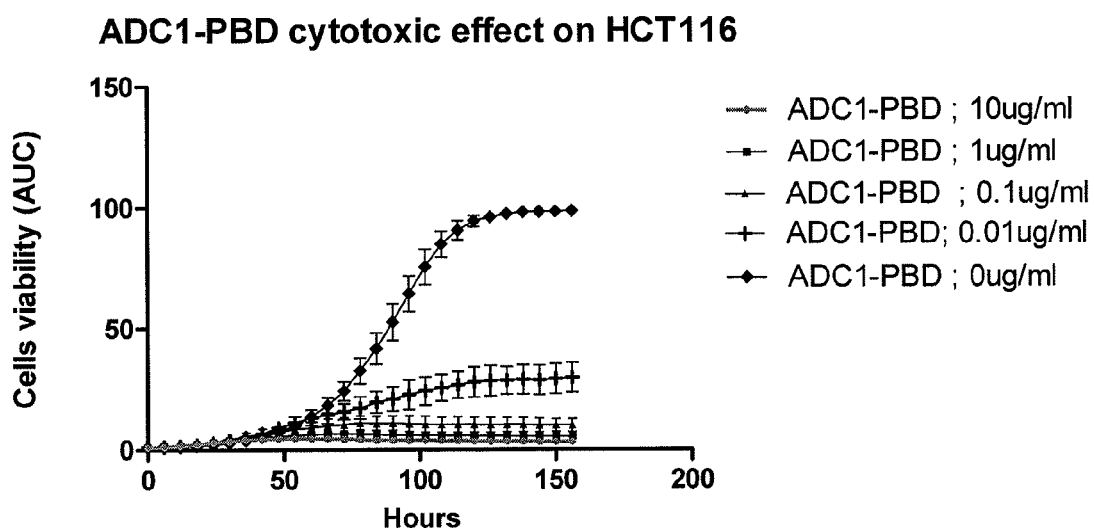
FIG. 29A shows that the mAb-PEGN3-DBCO-PBD caused decrease in cell viability at all concentrations tested (except at the µg/ml concentration).
Figure 29B:
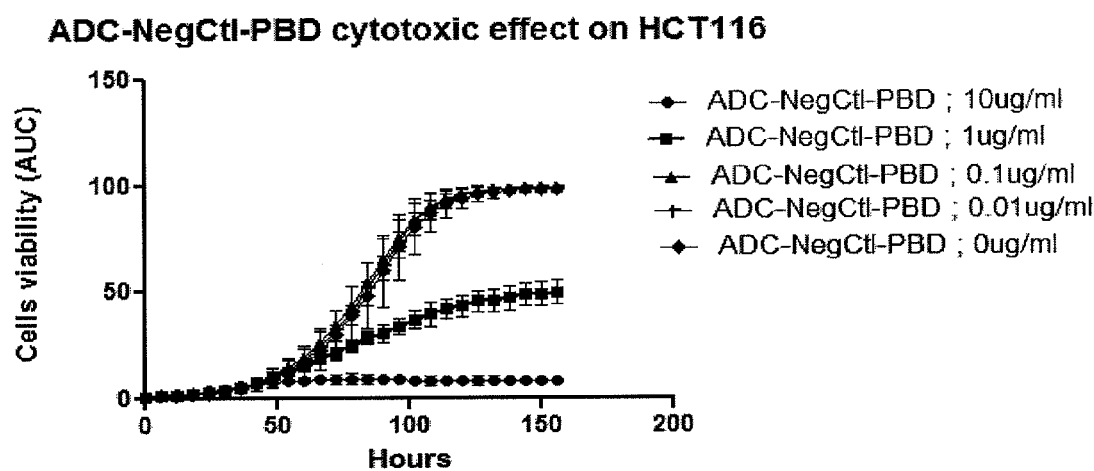
FIG. 29B shows that the negative control mAb, an irrelevant mAb not binding targets on the HCT116 cells functionalized with the same PEGN3-DBCO-PBD, caused a decrease in cell viability only at the highest dose tested (10 µg/ml) and 50% reduction in viability at 1 µg/ml, with no effect at any lower concentrations.

The mAb-PBD (mAb-PEGN3-DBCO-PBD) was functionalized at one acceptor glutamine on each of the two heavy chains at residue Q295 with the structure shown in Example 19:

Target antigen expression on cells was confirmed by flow cytometry at the time of the cell viability experiment. For efficacy, 100 µl of cells/well were distributed in triplicate in flat-bottom 96-well plates (the HCT116 cells density was estimated at 2.5K/wells) and incubated at 37° C. After 3-4 h, mAb-PBDs were added to the cells. The plates were incubated at +37° C. into Incucyte over 7 days. Cell viability was assessed, with results shown in FIGS. 29A and 29B. FIG. 29A shows that the mAb-PEGN3-DBCO-PBD caused decrease in cell viability at all concentrations tested (except at the µg/ml concentration). In contrast, as shown in FIG. 29B, the negative control mAb, an irrelevant mAb not binding targets on the HCT116 cells functionalized with the same PEGN3-DBCO-PBD, caused a decrease in cell viability only at the highest dose tested (10 µg/ml) and 50% reduction in viability at 1 µg/ml, with no effect at any lower concentrations.

TABLE 2

| (C)$_n$ | X | L | V | Y | Z |
|---|---|---|---|---|---|
| (CH$_2$)$_5$ | NH | —(C=O)—CH$_2$— | — | — | Charged compound |
| (CH$_2$)$_5$ | NH | —(C=O)—(CH$_2$)$_5$— | — | Spacer system | Large, charged or hydrophobic compound; toxin; auristatin; MMAE |
| (CH$_2$)$_5$ | NH | —(C=O)—(CH$_2$)$_5$— | Cleavable or non-cleavable linker; di- or tri- or oligo peptide; val-cit | Spacer system | Large, charged or hydrophobic compound; toxin; auristatin; MMAE |
| (CH$_2$)$_5$ | NH | —(C=O)—(CH$_2$)$_5$— | Cleavable or non-cleavable linker; di- or tri- or oligo peptide; val-cit; or absent | Spacer system | Large, charged or hydrophobic compound; toxin; auristatin; MMAE |
| (CH$_2$)$_{10}$ | NH | —(C=O)—(CH$_2$)$_5$— | Cleavable or non-cleavable linker; di- or tri- or oligo peptide; val-cit; or absent | Spacer system | Large, charged or hydrophobic compound; toxin; auristatin; MMAE |
| (CH$_2$)$_{15}$ | NH | —(C=O)—(CH$_2$)$_5$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | NH | —CH$_2$—(CH$_2$—O—CH$_2$)$_4$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | NH | —CH$_2$—(CH$_2$—O—CH$_2$)$_{12}$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | NH | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_{10}$ | NH | —CH$_2$—(CH$_2$—O—CH$_2$)$_4$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_{15}$ | NH | —CH$_2$—(CH$_2$—O—CH$_2$)$_4$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | NH | —(C=O)—CH$_2$—(CH$_2$—O—CH$_2$)$_4$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_{10}$ | NH | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_{15}$ | NH | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | NH | —(C=O)—(CH$_2$)$_{10-20}$— | Cleavable or non-cleavable linker; di- or tri- or oligo peptide; val-cit; or absent | Spacer system | Large, charged or hydrophobic compound; toxin; auristatin; MMAE |
| (CH$_2$)$_{10}$ | NH | —(C=O)—(CH$_2$)$_{10-20}$— | Cleavable or non-cleavable linker; di- or tri- or oligo peptide; val-cit; or absent | Spacer system | Large, charged or hydrophobic compound; toxin; auristatin; MMAE |
| (CH$_2$)$_{15}$ | NH | —(C=O)—(CH$_2$)$_{10-20}$— | Cleavable or non-cleavable linker; di- or tri- or oligo peptide; val-cit; or absent | Spacer system | Large, charged or hydrophobic compound; toxin; auristatin; MMAE |

TABLE 2-continued

| $(C)_n$ | X | L | V | Y | Z |
|---|---|---|---|---|---|
| $(CH_2)_5$ | NH | $—(CH_2)_{1-6}—$ | Cleavable or non-cleavable linker; di- or tri-or oligo peptide; val-cit; or absent | Spacer system | Large, charged or hydrophobic compound; toxin; auristatin; MMAE |
| $(CH_2)_{10}$ | NH | $—(CH_2)_{1-6}—$ | Cleavable or non-cleavable linker; di- or tri-or oligo peptide; val-cit; or absent | Spacer system | Large, charged or hydrophobic compound; toxin; auristatin; MMAE |
| $(CH_2)_{15}$ | NH | $—(CH_2)_{1-6}—$ | Cleavable or non-cleavable linker; di- or tri-or oligo peptide; val-cit; or absent | Spacer system | Large, charged or hydrophobic compound; toxin; auristatin; MMAE |
| $(CH_2)_5$ | NH | $—(CH_2)_{10-20}—$ | Cleavable or non-cleavable linker; di- or tri-or oligo peptide; val-cit; or absent | Spacer system | Large, charged or hydrophobic compound; toxin; auristatin; MMAE |
| $(CH_2)_{10}$ | NH | $—(CH_2)_{10-20}—$ | Cleavable or non-cleavable linker; di- or tri-or oligo peptide; val-cit; or absent | Spacer system | Large, charged or hydrophobic compound; toxin; auristatin; MMAE |
| $(CH_2)_{15}$ | NH | $—(CH_2)_{10-20}—$ | Cleavable or non-cleavable linker; di- or tri-or oligo peptide; val-cit; or absent | Spacer system | Large, charged or hydrophobic compound; toxin; auristatin; MMAE |
| $(CH_2)_5$ | NH | $—(C=O)—O—CH_2—$ | Cleavable or non-cleavable linker; di- or tri-or oligo peptide; val-cit; or absent | Spacer system | Large, charged or hydrophobic compound; toxin; auristatin; MMAE |
| $(CH_2)_{10}$ | NH | $—(C=O)—O—CH_2—$ | Cleavable or non-cleavable linker; di- or tri-or oligo peptide; val-cit; or absent | Spacer system | Large, charged or hydrophobic compound; toxin; auristatin; MMAE |
| $(CH_2)_{15}$ | NH | $—(C=O)—O—CH_2—$ | Cleavable or non-cleavable linker; di- or tri-or oligo peptide; val-cit; or absent | Spacer system | Large, charged or hydrophobic compound; toxin; auristatin; MMAE |
| $(CH_2)_5$ | NH | $—(C=O)—O—(CH_2)_{2-20}—$ | Cleavable or non-cleavable linker; di- or tri-or oligo peptide; val-cit; or absent | Spacer system | Large, charged or hydrophobic compound; toxin; auristatin; MMAE |
| $(CH_2)_{10}$ | NH | $—(C=O)—O—(CH_2)_{2-20}—$ | Cleavable or non-cleavable linker; di- or tri-or oligo peptide; val-cit; or absent | Spacer system | Large, charged or hydrophobic compound; toxin; auristatin; MMAE |
| $(CH_2)_{15}$ | NH | $—(C=O)—O—(CH_2)_{2-20}—$ | Cleavable or non-cleavable linker; di- or tri-or oligo peptide; val-cit; or absent | Spacer system | Large, charged or hydrophobic compound; toxin; auristatin; MMAE |
| $(CH_2)_5$ | NH | Amino acid, di- or tri-or oligo peptide | Cleavable or non-cleavable linker; di- or tri-or oligo peptide; val-cit; or absent | Spacer system | Large, charged or hydrophobic compound; toxin; auristatin; MMAE |
| $(CH_2)_{10}$ | NH | Amino acid, di- or tri-or oligo peptide | Cleavable or non-cleavable linker; di- or tri-or oligo peptide; val-cit; or absent | Spacer system | Large, charged or hydrophobic compound; toxin; auristatin; MMAE |
| $(CH_2)_{15}$ | NH | Amino acid, di- or tri-or oligo peptide | Cleavable or non-cleavable linker; di- or tri-or oligo peptide; val-cit; or absent | Spacer system | Large, charged or hydrophobic compound; toxin; auristatin; MMAE |

TABLE 2-continued

| $C_n$ | X | L | V | Y | Z |
|---|---|---|---|---|---|
| $(CH_2)_5$ | NH | —(C=O)—$CH_2$—S—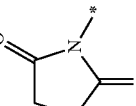 | Cleavable or non-cleavable linker; di- or tri- or oligo peptide; val-cit; or absent | Spacer system; $CH_2$—$(CH_2$—O—$CH_2)_4$—$CH_2$— | Large, charged or hydrophobic compound; toxin; auristatin; MMAE |
| $(CH_2)_5$ | NH | —(C=O)—$CH_5$—S—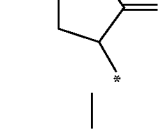 | Cleavable or non-cleavable linker; di- or tri- or oligo peptide; val-cit; or absent | Spacer system; $CH_2$—$(CH_2$—O—$CH_2)_4$—$CH_2$— | Large, charged or hydrophobic compound; toxin; auristatin; MMAE |
| $(CH_2)_5$ | NH | —$CH_2$—$(CH_2$—O—$CH_2)_{1-24}$—$CH_2$—S— | Cleavable or non-cleavable linker; di- or tri- or oligo peptide; val-cit; or absent | Spacer system; $CH_2$—$(CH_2$—O—$CH_2)_4$—$CH_2$— | Large, charged or hydrophobic compound; toxin; auristatin; MMAE |
| —$CH_2$—$(CH_2$—O—$CH_2)_3$—$CH_2$— | NH | — | Cleavable or non-cleavable linker; di- or tri- or oligo peptide; val-cit; or absent | Spacer system | Large, charged or hydrophobic compound; toxin; auristatin; MMAE |
| —$CH_2$—$(CH_2$—O—$CH_2)_3$—$CH_2$— | NH | —$CH_2$—$(CH_2$—O—$CH_2)_{1-24}$—$CH_2$— | Cleavable or non-cleavable linker; di- or tri- or oligo peptide; val-cit; or absent | Spacer system | Large, charged or hydrophobic compound; toxin; auristatin; MMAE |
| —$CH_2$—$(CH_2$—O—$CH_2)_3$—$CH_2$— | NH | —(C=O)—$CH_2$—$(CH_2$—O—$CH_2)_{1-24}$—$CH_2$— | Cleavable or non-cleavable linker; di- or tri- or oligo peptide; val-cit; or absent | Spacer system | Large, charged or hydrophobic compound; toxin; auristatin; MMAE |
| —O—$(CH_2)_{1-5}$ | NH | — | Cleavable or non-cleavable linker; di- or tri- or oligo peptide; val-cit; or absent | Spacer system | Large, charged or hydrophobic compound; toxin; auristatin; MMAE |
| —O—$CH_2$—$(CH_2$—O—$CH_2)_3$—$CH_2$— | NH | —$CH_2$—$(CH_2$—O—$CH_2)_{1-24}$—$CH_2$— | Cleavable or non-cleavable linker; di- or tri- or oligo peptide; val-cit; or absent | Spacer system | Large, charged or hydrophobic compound; toxin; auristatin; MMAE |
| —O—$CH_2$—$(CH_2$—O—$CH_2)_3$—$CH_2$— | NH | —(C=O)—$CH_2$—$(CH_2$—O—$CH_2)_{1-24}$—$CH_2$— | Cleavable or non-cleavable linker; di- or tri- or oligo peptide; val-cit; or absent | Spacer system | Large, charged or hydrophobic compound; toxin; auristatin; MMAE |
| $(CH_2)_4$—$CH(NH_2)$—(C=O)— | NH | — | — | — | Charged compound |
| $(CH_2)_4$—$CH(NH_2)$—(C=O)— | NH | — | di- or tri- or oligo peptide; val-cit | Spacer system | Large, charged or hydrophobic compound; toxin; auristatin; MMAE |

TABLE 2-continued

| $(C)_n$ | X | L | V | Y | Z |
|---|---|---|---|---|---|
| $(CH_2)_4$—CH(NH$_2$)—(C=O)— | NH | —(CH$_2$)$_{1-6}$— | Cleavable or non-cleavable linker; di- or tri-or oligo peptide; val-cit; or absent | Spacer system | Large, charged or hydrophobic compound; toxin; auristatin; MMAE |
| $(CH_2)_4$—CH(NH$_2$)—(C=O)— | NH | —(CH$_2$)$_5$— | Cleavable or non-cleavable linker; di- or tri-or oligo peptide; val-cit; or absent | Spacer system | Large, charged or hydrophobic compound; toxin; auristatin; MMAE |
| $(CH_2)_4$—CH(NH$_2$)—(C=O)— | NH | —CH$_2$—(CH$_2$—O—CH$_2$)$_{1-24}$—CH$_2$— | Cleavable or non-cleavable linker; di- or tri-or oligo peptide; val-cit; or absent | Spacer system | Large, charged or hydrophobic compound; toxin; auristatin; MMAE |
| $(CH_2)_5$ | NH | — | — | Spacer system; (CH$_2$)$_5$ | Large, charged or hydrophobic compound; toxin; auristatin; MMAF |
| $(CH_2)_{6-10}$ | NH | — | — | Spacer system; (CH$_2$)$_5$ | Large, charged or hydrophobic compound; toxin; auristatin; MMAF |
| $(CH_2)_{15}$ | NH | — | — | Spacer system; (CH$_2$)$_5$ | Large, charged or hydrophobic compound; toxin; auristatin; MMAF |
| —CH$_2$—(CH$_2$—O—CH$_2$)$_3$—CH$_2$— | NH | — | — | Spacer system; (CH$_2$)$_5$ | Large, charged or hydrophobic compound; toxin; auristatin; MMAF |
| —(CH$_2$)$_{1-5}$ | NH | —(C=O)—CH$_2$— | — | Spacer system; (CH$_2$)$_5$ | Large, charged or hydrophobic compound; toxin; auristatin; MMAF |
| $(CH_2)_5$ | NH | —(C=O)—(CH$_2$)$_5$— | — | Spacer system; (CH$_2$)$_5$ | Large, charged or hydrophobic compound; toxin; auristatin; MMAF |
| $(CH_2)_5$ | NH | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | NH | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | NH | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | NH | —(C=O)—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | NH | —(C=O)—(CH$_2$)$_5$— | — | Spacer system; (CH$_2$)$_5$ | Large, charged or hydrophobic compound; toxin; auristatin; MMAF |
| —CH$_2$—(CH$_2$—O—CH$_2$)$_3$—CH$_2$— | NH | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| $(CH_2)_5$ | NH | — | Non-cleavable linker; (CH$_2$)$_5$ | — | Large, charged or hydrophobic compound; toxin; auristatin; MMAF |
| $(CH_2)_{6-10}$ | NH | — | Non-cleavable linker; (CH$_2$)$_5$ | — | Large, charged or hydrophobic compound; toxin; auristatin; MMAF |

TABLE 2-continued

| $(C)_n$ | X | L | V | Y | Z |
|---|---|---|---|---|---|
| $(CH_2)_{15}$ | NH | — | Non-cleavable linker; $(CH_2)_5$ | — | Large, charged or hydrophobic compound; toxin; auristatin; MMAF |
| $-CH_2-(CH_2-O-CH_2)_3-CH_2-$ | NH | — | Non-cleavable linker; $(CH_2)_5$ | — | Large, charged or hydrophobic compound; toxin; auristatin; MMAF |
| $(CH_2)_5$ | NH | $-(C=O)-CH_2-$ | Non-cleavable linker; $(CH_2)_5$ | — | Large, charged or hydrophobic compound; toxin; auristatin; MMAF |
| $(CH_2)_5$ | NH | $-(C=O)-(CH_2)_5-$ | Non-cleavable linker; $(CH_2)_5$ | — | Large, charged or hydrophobic compound; toxin; auristatin; MMAF |
| $(CH_2)_5$ | NH | $-(C=O)-(CH_2)_5-$ | Non-cleavable linker; $(CH_2)_5$ | — | Large, charged or hydrophobic compound; toxin; auristatin; MMAF |
| $(CH_2)_5$ | NH | $-(C=O)-(CH_2)_5-$ | Non-cleavable linker; $(CH_2)_5$ | — | Large, charged or hydrophobic compound; toxin; auristatin; MMAF |
| $(CH_2)_5$ | NH | $-CH_2-(CH_2-O-CH_2)_{1-24}-CH_2-$ | Non-cleavable linker; $(CH_2)_5$ | — | Large, charged or hydrophobic compound; toxin; auristatin; MMAF |
| $-O-(CH_2)_{1-5}$ | NH | $-CH_2-(CH_2-O-CH_2)_{1-24}-CH_2-$ | Non-cleavable linker; $(CH_2)_5$ | — | Large, charged or hydrophobic compound; toxin; auristatin; MMAF |
| $-O-CH_2-(CH_2-O-CH_2)_3-CH_2-$ | NH | $-CH_2-(CH_2-O-CH_2)_{1-24}-CH_2-$ | Non-cleavable linker; $(CH_2)_5$ | — | Large, charged or hydrophobic compound; toxin; auristatin; MMAF |
| $-O-CH_2-(CH_2-O-CH_2)_3-CH_2-$ | NH | $-(C=O)-CH_2-$ | Non-cleavable linker; $(CH_2)_5$ | — | Large, charged or hydrophobic compound; toxin; auristatin; MMAF |
| $-O-CH_2-(CH_2-O-CH_2)_3-CH_2-$ | NH | $-(C=O)-(CH_2)_5-$ | Non-cleavable linker; $(CH_2)_5$ | — | Large, charged or hydrophobic compound; toxin; auristatin; MMAF |
| $-CH_2-(CH_2-O-CH_2)_3-CH_2-$ | NH | $-CH_2-(CH_2-O-CH_2)_{1-24}-CH_2-$ | Non-cleavable linker; $(CH_2)_5$ | — | Large, charged or hydrophobic compound; toxin; auristatin; MMAF |
| $(CH_2)_5$ | O | $-(C=O)-CH_2-$ | | | Charged compound |
| $(CH_2)_5$ | O | $-(C=O)-(CH_2)_5-$ | | Spacer system | Large, charged or hydrophobic compound; toxin; auristatin; MMAE |
| $(CH_2)_5$ | O | $-(C=O)-(CH_2)_5-$ | Cleavable or non-cleavable linker; di- or tri- or oligo peptide; val-cit | Spacer system | Large, charged or hydrophobic compound; toxin; auristatin; MMAE |
| $(CH_2)_5$ | O | $-(C=O)-(CH_2)_5-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | O | $-(C=O)-(CH_2)_5-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | O | $-(C=O)-(CH_2)_5-$ | Cleavable or non-cleavable linker; di- or tri- or oligo | | Large, charged or hydrophobic compound; toxin; auristatin; MMAE |

TABLE 2-continued

| $(C)_n$ | X | L | V | Y | Z |
|---|---|---|---|---|---|
| $(CH_2)_5$ | O | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | O | $-CH_2-(CH_2-O-CH_2)_{12}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | O | $-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | O | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | O | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | O | $-(C=O)-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | O | $-(C=O)-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | O | $-(C=O)-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | O | $-(C=O)-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | O | $-(C=O)-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | O | $-(C=O)-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | O | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | O | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | O | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | O | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | O | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | O | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |

TABLE 2-continued

| $(C)_n$ | X | L | V | Y | Z |
|---|---|---|---|---|---|
| $(CH_2)_5$ | O | —(C=O)—O—CH$_2$— | peptide; val-cit; or absent | Spacer system | MMAE |
| $(CH_2)_{10}$ | O | —(C=O)—O—CH$_2$— | Cleavable or non-cleavable linker; di- or tri-or oligo peptide; val-cit; or absent | Spacer system | Large, charged or hydrophobic compound; toxin; auristatin; MMAE |
| $(CH_2)_{15}$ | O | —(C=O)—O—CH$_2$— | Cleavable or non-cleavable linker; di- or tri-or oligo peptide; val-cit; or absent | Spacer system | Large, charged or hydrophobic compound; toxin; auristatin; MMAE |
| $(CH_2)_5$ | O | —(C=O)—O—(CH$_2$)$_{2-20}$— | Cleavable or non-cleavable linker; di- or tri-or oligo peptide; val-cit; or absent | Spacer system | Large, charged or hydrophobic compound; toxin; auristatin; MMAE |
| $(CH_2)_{10}$ | O | —(C=O)—O—(CH$_2$)$_{2-20}$— | Cleavable or non-cleavable linker; di- or tri-or oligo peptide; val-cit; or absent | Spacer system | Large, charged or hydrophobic compound; toxin; auristatin; MMAE |
| $(CH_2)_{15}$ | O | —(C=O)—O—(CH$_2$)$_{2-20}$— | Cleavable or non-cleavable linker; di- or tri-or oligo peptide; val-cit; or absent | Spacer system | Large, charged or hydrophobic compound; toxin; auristatin; MMAE |
| $(CH_2)_5$ | O | Amino acid, di- or tri-or oligo peptide | Cleavable or non-cleavable linker; di- or tri-or oligo peptide; val-cit; or absent | Spacer system | Large, charged or hydrophobic compound; toxin; auristatin; MMAE |
| $(CH_2)_{10}$ | O | Amino acid, di- or tri-or oligo peptide | Cleavable or non-cleavable linker; di- or tri-or oligo peptide; val-cit; or absent | Spacer system | Large, charged or hydrophobic compound; toxin; auristatin; MMAE |
| $(CH_2)_{15}$ | O | Amino acid, di- or tri-or oligo peptide | Cleavable or non-cleavable linker; di- or tri-or oligo peptide; val-cit; or absent | Spacer system | Large, charged or hydrophobic compound; toxin; auristatin; MMAE |
| $(CH_2)_5$ | O | —(C=O)—CH$_2$—S— (succinimide) | Cleavable or non-cleavable linker; di- or tri-or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| $(CH_2)_5$ | O | —(C=O)—CH$_2$—S— (succinimide) | Cleavable or non-cleavable linker; di- or tri-or oligo peptide; val-cit; or absent | Spacer system; CH$_2$—(CH$_2$—O—CH$_2$)$_4$—CH$_2$— | Large, charged or hydrophobic compound; toxin; auristatin; MMAE |

TABLE 2-continued

| $(C)_n$ | X | L | V | Y | Z |
|---|---|---|---|---|---|
| $(CH_2)_5$ | O | $-CH_2-(CH_2-O-CH_2)_{1-24}-CH_2-S-$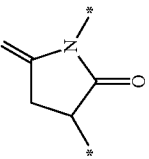 | Cleavable or non-cleavable linker; di- or tri-or oligo peptide; val-cit; or absent | Spacer system; $CH_2-(CH_2-O-CH_2)_4-CH_2-$ | Large, charged or hydrophobic compound; toxin; auristatin; MMAE |
| $-CH_2-(CH_2-O-CH_2)_3-CH_2-$ | O | — | Cleavable or non-cleavable linker; di- or tri-or oligo peptide; val-cit; or absent | Spacer system | Large, charged or hydrophobic compound; toxin; auristatin; MMAE |
| $-CH_2-(CH_2-O-CH_2)_3-CH_2-$ | O | $-CH_2-(CH_2-O-CH_2)_{1-24}-CH_2-$ | Cleavable or non-cleavable linker; di- or tri-or oligo peptide; val-cit; or absent | Spacer system | Large, charged or hydrophobic compound; toxin; auristatin; MMAE |
| $-CH_2-(CH_2-O-CH_2)_4-CH_2-$ | O | $-(C=O)-CH_2-(CH_2-O-CH_2)_{1-24}-CH_2-$ | Cleavable or non-cleavable linker; di- or tri-or oligo peptide; val-cit; or absent | Spacer system | Large, charged or hydrophobic compound; toxin; auristatin; MMAE |
| $-O-(CH_2)_{1-5}$ | O | — | Cleavable or non-cleavable linker; di- or tri-or oligo peptide; val-cit; or absent | Spacer system | Large, charged or hydrophobic compound; toxin; auristatin; MMAE |
| $-O-CH_2-(CH_2-O-CH_2)_3-CH_2-$ | O | $-CH_2-(CH_2-O-CH_2)_{1-24}-CH_2-$ | Cleavable or non-cleavable linker; di- or tri-or oligo peptide; val-cit; or absent | Spacer system | Large, charged or hydrophobic compound; toxin; auristatin; MMAE |
| $-O-CH_2-(CH_2-O-CH_2)_3-CH_2-$ | O | — | Cleavable or non-cleavable linker; di- or tri-or oligo peptide; val-cit; or absent | Spacer system | Large, charged or hydrophobic compound; toxin; auristatin; MMAE |
| $-O-CH_2-(CH_2-O-CH_2)_3-CH_2-$ | O | $-(C=O)-CH_2-(CH_2-O-CH_2)_{1-24}-CH_2-$ | Cleavable or non-cleavable linker; di- or tri-or oligo peptide; val-cit; or absent | Spacer system | Large, charged or hydrophobic compound; toxin; auristatin; MMAE |
| $-(CH_2)_4-CH(NH_2)-(C=O)-$ | O | — | — | Spacer system | Charged compound |
| $-(CH_2)_4-CH(NH_2)-(C=O)-$ | O | — | di- or tri-or oligo peptide; val-cit | Spacer system | Large, charged or hydrophobic compound; toxin; auristatin; MMAE |
| $-(CH_2)_4-CH(NH_2)-(C=O)-$ | O | $-(CH_2)_{1-6}-$ | Cleavable or non-cleavable linker; di- or tri-or oligo peptide; val-cit; or absent | Spacer system | Large, charged or hydrophobic compound; toxin; auristatin; MMAE |
| $-(CH_2)_4-CH(NH_2)-(C=O)-$ | O | $-(CH_2)_5-$ | Cleavable or non-cleavable linker; di- or tri-or oligo peptide; val-cit; or absent | Spacer system | Large, charged or hydrophobic compound; toxin; auristatin; MMAE |
| $-(CH_2)_4-CH(NH_2)-(C=O)-$ | O | $-CH_2-(CH_2-O-CH_2)_{1-24}-CH_2-$ | Cleavable or non-cleavable linker; di- or tri-or oligo peptide; val-cit; or absent | Spacer system | Large, charged or hydrophobic compound; toxin; auristatin; MMAE |
| $(CH_2)_5$ | O | — | — | Spacer system; $(CH_2)_5$ | Large, charged or hydrophobic compound; toxin; auristatin; MMAE |
| $(CH_2)_{6-10}$ | O | — | — | Spacer system; $(CH_2)_5$ | Large, charged or hydrophobic compound; toxin; auristatin; MMAF |
| $(CH_2)_{15}$ | O | — | — | Spacer system; $(CH_2)_5$ | Large, charged or hydrophobic compound; toxin; auristatin; MMAE |

TABLE 2-continued

| $(C)_n$ | X | L | V | Y | Z |
|---|---|---|---|---|---|
| —CH$_2$—(CH$_2$—O—CH$_2$)$_3$—CH$_2$— | O | — | — | Spacer system; (CH$_2$)$_5$ | Large, charged or hydrophobic compound; toxin; auristatin; MMAF |
| (CH$_2$)$_5$ | O | —(C=O)—CH$_2$— | — | Spacer system; (CH$_2$)$_5$ | Large, charged or hydrophobic compound; toxin; auristatin; MMAF |
| (CH$_2$)$_5$ | O | —(C=O)—(CH$_2$)$_5$— | — | Spacer system; (CH$_2$)$_5$ | Large, charged or hydrophobic compound; toxin; auristatin; MMAF |
| (CH$_2$)$_5$ | O | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—(CH$_2$)$_{1-5}$ | O | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | O | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | O | —(C=O)—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | O | —(C=O)—(CH$_2$)$_5$— | — | Spacer system; (CH$_2$)$_5$ | Large, charged or hydrophobic compound; toxin; auristatin; MMAF |
| —CH$_2$—(CH$_2$—O—CH$_2$)$_3$—CH$_2$— | O | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| (CH$_2$)$_5$ | O | — | Non-cleavable linker; (CH$_2$)$_5$ | — | Large, charged or hydrophobic compound; toxin; auristatin; MMAF |
| (CH$_2$)$_{6-10}$ | O | — | Non-cleavable linker; (CH$_2$)$_5$ | — | Large, charged or hydrophobic compound; toxin; auristatin; MMAF |
| (CH$_2$)$_{15}$ | O | — | Non-cleavable linker; (CH$_2$)$_5$ | — | Large, charged or hydrophobic compound; toxin; auristatin; MMAF |
| —CH$_2$—(CH$_2$—O—CH$_2$)$_3$—CH$_2$— | O | —(C=O)—CH$_2$— | Non-cleavable linker; (CH$_2$)$_5$ | — | Large, charged or hydrophobic compound; toxin; auristatin; MMAF |
| (CH$_2$)$_5$ | O | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | O | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | O | —(C=O)—(CH$_2$)$_5$— | Non-cleavable linker; (CH$_2$)$_5$ | — | Large, charged or hydrophobic compound; toxin; auristatin; MMAF |

TABLE 2-continued

| $(C)_n$ | X | L | V | Y | Z |
|---|---|---|---|---|---|
| $(CH_2)_5$ | O | $-CH_2-(CH_2-O-CH_2)_{1-24}-CH_2-$ | Non-cleavable linker; $(CH_2)_5$ | — | Large, charged or hydrophobic compound; toxin; auristatin; MMAF |
| $-O-(CH_2)_{1-5}$ | O | $-CH_2-(CH_2-O-CH_2)_{1-24}-CH_2-$ | Non-cleavable linker; $(CH_2)_5$ | — | Large, charged or hydrophobic compound; toxin; auristatin; MMAF |
| $-O-CH_2-(CH_2-O-CH_2)_3-CH_2-$ | O | $-CH_2-(CH_2-O-CH_2)_{1-24}-CH_2-$ | Non-cleavable linker; $(CH_2)_5$ | — | Large, charged or hydrophobic compound; toxin; auristatin; MMAF |
| $-O-CH_2-(CH_2-O-CH_2)_3-CH_2-$ | O | $-(C=O)-CH_2-$ | Non-cleavable linker; $(CH_2)_5$ | — | Large, charged or hydrophobic compound; toxin; auristatin; MMAF |
| $-O-CH_2-(CH_2-O-CH_2)_3-CH_2-$ | O | $-(C=O)-(CH_2)_5-$ | Non-cleavable linker; $(CH_2)_5$ | — | Large, charged or hydrophobic compound; toxin; auristatin; MMAF |
| $-CH_2-(CH_2-O-CH_2)_3-CH_2-$ | O | $-CH_2-(CH_2-O-CH_2)_{1-24}-CH_2-$ | Non-cleavable linker; $(CH_2)_5$ | — | Large, charged or hydrophobic compound; toxin; auristatin; MMAF |
| $(CH_2)_5$ | S | $-(C=O)-CH_2-$ | — | | Charged compound |
| $(CH_2)_5$ | S | $-(C=O)-(CH_2)_5-$ | — | Spacer system | Large, charged or hydrophobic compound; toxin; auristatin; MMAE |
| $(CH_2)_5$ | S | $-(C=O)-(CH_2)_5-$ | Cleavable or non-cleavable linker; di- or tri- or oligo peptide; val-cit | Spacer system | Large, charged or hydrophobic compound; toxin; auristatin; MMAE |
| $(CH_2)_5$ | S | $-(C=O)-(CH_2)_5-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-(C=O)-(CH_2)_5-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(C=O)-(CH_2)_5-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-CH_2-(CH_2-O-CH_2)_{12}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-CH_2-(CH_2-O-CH_2)_4-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-(C=O)-CH_2-(CH_2-O-CH_2)_4-CH_2-$ | Cleavable or non-cleavable | Spacer system | Large, charged or hydrophobic |

TABLE 2-continued

| $(C)_n$ | X | L | V | Y | Z |
|---|---|---|---|---|---|
| | | | Cleavable or non-cleavable linker; di- or tri- or oligo peptide; val-cit; or absent | | compound; toxin; auristatin; MMAE |
| $(CH_2)_{10}$ | S | $-(C=O)-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(C=O)-CH_2-(CH_2-O-CH_2)_{1-24}-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-(C=O)-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-(C=O)-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(C=O)-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(CH_2)_{1-6}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{16}$ | S | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(CH_2)_{10-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-(C=O)-O-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-(C=O)-O-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(C=O)-O-CH_2-$ | Cleavable or non-cleavable linker; di- or tri- or oligo peptide; val-cit; or absent | Spacer system | Large, charged or hydrophobic compound; toxin; auristatin; MMAE |
| $(CH_2)_5$ | S | $-(C=O)-O-(CH_2)_{2-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{10}$ | S | $-(C=O)-O-(CH_2)_{2-20}-$ | Cleavable or non-cleavable linker; di- or tri- or oligo peptide; val-cit; or absent | Spacer system | Large, charged or hydrophobic compound; toxin; auristatin; MMAE |
| $(CH_2)_{15}$ | S | $-(C=O)-O-(CH_2)_{2-20}-$ | Cleavable or non-cleavable linker; di- or tri- or oligo peptide; val-cit; or absent | Spacer system | Large, charged or hydrophobic compound; toxin; auristatin; MMAE |

TABLE 2-continued

| (C)$_n$ | X | L | V | Y | Z |
|---|---|---|---|---|---|
| | | | linker; di- or tri- or oligo peptide | | compound; toxin; auristatin; MMAE |
| (CH$_2$)$_5$ | S | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| (CH$_2$)$_{10}$ | S | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| (CH$_2$)$_{15}$ | S | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | S | —(C=O)—CH$_2$—S— 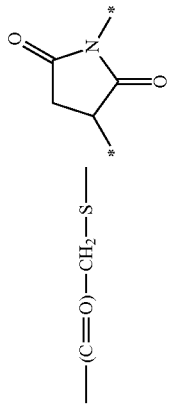 | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| (CH$_2$)$_5$ | S | —(C=O)—CH$_5$—S— | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| (CH$_2$)$_5$ | S | —CH$_2$—(CH$_2$—O—CH$_2$)$_{1-24}$—CH$_2$—S— | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| —CH$_2$—(CH$_2$—O—CH$_2$)$_3$—CH$_2$— | S | — | Cleavable or non-cleavable linker; di- or tri- or oligo peptide; val-cit; or absent | Spacer system | Large, charged or hydrophobic compound; toxin; auristatin; MMAE |
| —CH$_2$—(CH$_2$—O—CH$_2$)$_3$—CH$_2$— | S | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —CH$_2$—(CH$_2$—O—CH$_2$)$_3$—CH$_2$— | S | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —O—(CH$_2$)$_{1-5}$ | S | — | Cleavable or non-cleavable linker; di- or tri- or oligo peptide; val-cit; or absent | Spacer system | Large, charged or hydrophobic compound; toxin; auristatin; MMAE |
| —O—CH$_2$—(CH$_2$—O—CH$_2$)$_3$—CH$_2$— | S | — | Cleavable or non-cleavable | | Large, charged or hydrophobic |

TABLE 2-continued

| $C_n$ | X | L | V | Y | Z |
|---|---|---|---|---|---|
| —O—CH$_2$—(CH$_2$—O—CH$_2$)$_3$—CH$_2$— | S | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —O—CH$_2$—(CH$_2$—O—CH$_2$)$_3$—CH$_2$— | S | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_4$—CH(NH$_2$)—(C=O)— | S | — | — | | Charged compound |
| (CH$_2$)$_4$—CH(NH$_2$)—(C=O)— | S | — | di- or tri- or oligo peptide; val-cit | | Large, charged or hydrophobic compound; toxin; auristatin; MMAE |
| (CH$_2$)$_4$—CH(NH$_2$)—(C=O)— | S | —(CH$_2$)$_{1-6}$— | Cleavable or non-cleavable linker; di- or tri- or oligo peptide; val-cit; or absent | Spacer system | Large, charged or hydrophobic compound; toxin; auristatin; MMAE |
| (CH$_2$)$_4$—CH(NH$_2$)—(C=O)— | S | —(CH$_2$)$_5$— | Cleavable or non-cleavable linker; di- or tri- or oligo peptide; val-cit; or absent | Spacer system | Large, charged or hydrophobic compound; toxin; auristatin; MMAE |
| (CH$_2$)$_4$—CH(NH$_2$)—(C=O)— | S | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | S | — | — | Spacer system; (CH$_2$)$_5$ | Large, charged or hydrophobic compound; toxin; auristatin; MMAF |
| (CH$_2$)$_{6-10}$ | S | — | — | Spacer system; (CH$_2$)$_5$ | Large, charged or hydrophobic compound; toxin; auristatin; MMAF |
| (CH$_2$)$_{15}$ | S | — | — | Spacer system; (CH$_2$)$_5$ | Large, charged or hydrophobic compound; toxin; auristatin; MMAF |
| —CH$_2$—(CH$_2$—O—CH$_2$)$_3$—CH$_2$— | S | — | — | Spacer system; (CH$_2$)$_5$ | Large, charged or hydrophobic compound; toxin; auristatin; MMAF |
| (CH$_2$)$_5$ | S | —(C=O)—CH$_2$— | — | Spacer system; (CH$_2$)$_5$ | Large, charged or hydrophobic compound; toxin; auristatin; MMAF |
| (CH$_2$)$_5$ | S | —(C=O)—(CH$_2$)$_5$— | — | Spacer system; (CH$_2$)$_5$ | Large, charged or hydrophobic compound; toxin; auristatin; MMAF |
| (CH$_2$)$_5$ | S | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—(CH$_2$)$_{1-5}$ | S | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | S | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| —O—CH$_2$—(CH$_2$—O—CH$_2$)$_3$—CH$_2$— | S | —(C=O)—CH$_2$— | — | Spacer system; (CH$_2$)$_5$ | Large, charged or hydrophobic compound; toxin; auristatin; MMAF |

TABLE 2-continued

| $(C)_n$ | X | L | V | Y | Z |
|---|---|---|---|---|---|
| —O—CH$_2$—(CH$_2$—O—CH$_2$)$_3$—CH$_2$— | S | —(C=O)—(CH$_2$)$_5$— | — | Spacer system; (CH$_2$)$_5$ | Large, charged or hydrophobic compound; toxin; auristatin; MMAF |
| —CH$_2$—(CH$_2$—O—CH$_2$)$_3$—CH$_2$— | S | —CH$_2$—(CH$_2$—O—CH$_2$)$_{1-24}$—CH$_2$— | — | Spacer system; (CH$_2$)$_5$ | Large, charged or hydrophobic compound; toxin; auristatin; MMAF |
| (CH$_2$)$_5$ | S | — | Non-cleavable linker; (CH$_2$)$_5$ | — | Large, charged or hydrophobic compound; toxin; auristatin; MMAF |
| (CH$_2$)$_{6-10}$ | S | — | Non-cleavable linker; (CH$_2$)$_5$ | — | Large, charged or hydrophobic compound; toxin; auristatin; MMAF |
| (CH$_2$)$_{15}$ | S | — | Non-cleavable linker; (CH$_2$)$_5$ | — | Large, charged or hydrophobic compound; toxin; auristatin; MMAF |
| —CH$_2$—(CH$_2$—O—CH$_2$)$_3$—CH$_2$— | S | — | Non-cleavable linker; (CH$_2$)$_5$ | — | Large, charged or hydrophobic compound; toxin; auristatin; MMAF |
| (CH$_2$)$_5$ | S | —(C=O)—CH$_2$— | Non-cleavable linker; (CH$_2$)$_5$ | — | Large, charged or hydrophobic compound; toxin; auristatin; MMAF |
| (CH$_2$)$_5$ | S | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | S | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | S | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | S | —CH$_2$—(CH$_2$—O—CH$_2$)$_{1-24}$—CH$_2$— | Non-cleavable linker; (CH$_2$)$_5$ | — | Large, charged or hydrophobic compound; toxin; auristatin; MMAF |
| —O—(CH$_2$)$_{1-5}$— | S | —CH$_2$—(CH$_2$—O—CH$_2$)$_{1-24}$—CH$_2$— | Non-cleavable linker; (CH$_2$)$_5$ | — | Large, charged or hydrophobic compound; toxin; auristatin; MMAF |
| —O—CH$_2$—(CH$_2$—O—CH$_2$)$_3$—CH$_2$— | S | —(C=O)—CH$_2$— | Non-cleavable linker; (CH$_2$)$_5$ | — | Large, charged or hydrophobic compound; toxin; auristatin; MMAF |
| —O—CH$_2$—(CH$_2$—O—CH$_2$)$_3$—CH$_2$— | S | —(C=O)—(CH$_2$)$_5$— | Non-cleavable linker; (CH$_2$)$_5$ | — | Large, charged or hydrophobic compound; toxin; auristatin; MMAF |
| —O—CH$_2$—(CH$_2$—O—CH$_2$)$_3$—CH$_2$— | S | —(C=O)—(CH$_2$)$_5$— | Non-cleavable linker; (CH$_2$)$_5$ | — | Large, charged or hydrophobic compound; toxin; auristatin; MMAF |
| —CH$_2$—(CH$_2$—O—CH$_2$)$_3$—CH$_2$— | S | —CH$_2$—(CH$_2$—O—CH$_2$)$_{1-24}$—CH$_2$— | Non-cleavable linker; (CH$_2$)$_5$ | — | Large, charged or hydrophobic compound; toxin; auristatin; MMAF |
| (CH$_2$)$_5$ | — | —(C=O)—CH$_2$— | — | — | Charged compound |
| (CH$_2$)$_5$ | — | —(C=O)—(CH$_2$)$_5$— | — | Spacer system | Large, charged or hydrophobic compound; toxin; auristatin; MMAF |

TABLE 2-continued

| $(C)_n$ | X | L | V | Y | Z |
|---|---|---|---|---|---|
| $(CH_2)_5$ | — | —(C=O)—$(CH_2)_5$— | Cleavable or non-cleavable linker; di- or tri-or oligo peptide; val-cit | Spacer system | Large, charged or hydrophobic compound; toxin; auristatin; MMAE |
| $(CH_2)_5$ | — | —(C=O)—$(CH_2)_5$— | Cleavable or non-cleavable linker; di- or tri-or oligo peptide; val-cit; or absent | Spacer system | Large, charged or hydrophobic compound; toxin; auristatin; MMAE |
| $(CH_2)_{10}$ | — | —(C=O)—$(CH_2)_5$— | Cleavable or non-cleavable linker; di- or tri-or oligo peptide; val-cit; or absent | Spacer system | Large, charged or hydrophobic compound; toxin; auristatin; MMAE |
| $(CH_2)_{15}$ | — | —(C=O)—$(CH_2)_5$— | Cleavable or non-cleavable linker; di- or tri-or oligo peptide; val-cit; or absent | Spacer system | Large, charged or hydrophobic compound; toxin; auristatin; MMAE |
| $(CH_2)_5$ | — | —$CH_2$—$(CH_2$—O—$CH_2)_4$—$CH_2$— | Cleavable or non-cleavable linker; di- or tri-or oligo peptide; val-cit; or absent | Spacer system | Large, charged or hydrophobic compound; toxin; auristatin; MMAE |
| $(CH_2)_5$ | — | —$CH_2$—$(CH_2$—O—$CH_2)_{12}$—$CH_2$— | Cleavable or non-cleavable linker; di- or tri-or oligo peptide; val-cit; or absent | Spacer system | Large, charged or hydrophobic compound; toxin; auristatin; MMAE |
| $(CH_2)_5$ | — | —$CH_2$—$(CH_2$—O—$CH_2)_{1-24}$—$CH_2$— | Cleavable or non-cleavable linker; di- or tri-or oligo peptide; val-cit; or absent | Spacer system | Large, charged or hydrophobic compound; toxin; auristatin; MMAE |
| $(CH_2)_{10}$ | — | —$CH_2$—$(CH_2$—O—$CH_2)_4$—$CH_2$— | Cleavable or non-cleavable linker; di- or tri-or oligo peptide; val-cit; or absent | Spacer system | Large, charged or hydrophobic compound; toxin; auristatin; MMAE |
| $(CH_2)_{15}$ | — | —$CH_2$—$(CH_2$—O—$CH_2)_4$—$CH_2$— | Cleavable or non-cleavable linker; di- or tri-or oligo peptide; val-cit; or absent | Spacer system | Large, charged or hydrophobic compound; toxin; auristatin; MMAE |
| $(CH_2)_5$ | — | —(C=O)—$CH_2$—$(CH_2$—O—$CH_2)_4$—$CH_2$— | Cleavable or non-cleavable linker; di- or tri-or oligo peptide; val-cit; or absent | Spacer system | Large, charged or hydrophobic compound; toxin; auristatin; MMAE |
| $(CH_2)_{10}$ | — | —(C=O)—$CH_2$—$(CH_2$—O—$CH_2)_{1-24}$—$CH_2$— | Cleavable or non-cleavable linker; di- or tri-or oligo peptide; val-cit; or absent | Spacer system | Large, charged or hydrophobic compound; toxin; auristatin; MMAE |
| $(CH_2)_{15}$ | — | —(C=O)—$CH_2$—$(CH_2$—O—$CH_2)_{1-24}$—$CH_2$— | Cleavable or non-cleavable linker; di- or tri-or oligo peptide; val-cit; or absent | Spacer system | Large, charged or hydrophobic compound; toxin; auristatin; MMAE |
| $(CH_2)_5$ | — | —(C=O)—$(CH_2)_{10-20}$— | Cleavable or non-cleavable linker; di- or tri-or oligo peptide; val-cit; or absent | Spacer system | Large, charged or hydrophobic compound; toxin; auristatin; MMAE |
| $(CF_{12})_{10}$ | — | —(C=O)—$(CH_2)_{10-20}$— | Cleavable or non-cleavable linker; di- or tri-or oligo peptide; val-cit; or absent | Spacer system | Large, charged or hydrophobic compound; toxin; auristatin; MMAE |
| $(CH_2)_{15}$ | — | —(C=O)—$(CH_2)_{10-20}$— | Cleavable or non-cleavable linker; di- or tri-or oligo peptide; val-cit; or absent | Spacer system | Large, charged or hydrophobic compound; toxin; auristatin; MMAE |
| $(CH_2)_5$ | — | —$(CH_2)_{1-6}$— | Cleavable or non-cleavable linker; di- or tri-or oligo peptide; val-cit; or absent | Spacer system | Large, charged or hydrophobic compound; toxin; auristatin; MMAE |
| $(CH_2)_{10}$ | — | —$(CH_2)_{1-6}$— | Cleavable or non-cleavable linker; di- or tri-or oligo | Spacer system | Large, charged or hydrophobic compound; toxin; auristatin; MMAE |

TABLE 2-continued

| (C)n | X | L | V | Y | Z |
|---|---|---|---|---|---|
| (CH$_2$)$_{15}$ | — | —(CH$_2$)$_{1-6}$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | — | —(CH$_2$)$_{10-20}$— | Cleavable or non-cleavable linker; di- or tri- or oligo peptide; val-cit; or absent | Spacer system | Large, charged or hydrophobic compound; toxin; auristatin; MMAE |
| (CH$_2$)$_{10}$ | — | —(CH$_2$)$_{10-20}$— | Cleavable or non-cleavable linker; di- or tri- or oligo peptide; val-cit; or absent | Spacer system | Large, charged or hydrophobic compound; toxin; auristatin; MMAE |
| (CH$_2$)$_{15}$ | — | —(CH$_2$)$_{10-20}$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | — | —(C=O)—O—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_{10}$ | — | —(C=O)—O—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_{15}$ | — | —(C=O)—O—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | — | —(C=O)—O—(CH$_2$)$_{2-20}$— | Cleavable or non-cleavable linker; di- or tri- or oligo peptide; val-cit; or absent | Spacer system | Large, charged or hydrophobic compound; toxin; auristatin; MMAE |
| (CH$_2$)$_{10}$ | — | —(C=O)—O—(CH$_2$)$_{2-20}$— | Cleavable or non-cleavable linker; di- or tri- or oligo peptide; val-cit; or absent | Spacer system | Large, charged or hydrophobic compound; toxin; auristatin; MMAE |
| (CH$_2$)$_{15}$ | — | —(C=O)—O—(CH$_2$)$_{2-20}$— | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | — | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| (CH$_2$)$_{10}$ | — | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| (CH$_2$)$_{15}$ | — | Amino acid, di- or tri- or oligo peptide | Cleavable or non-cleavable linker; di- or tri- or oligo peptide; val-cit; or absent | Spacer system | Large, charged or hydrophobic compound; toxin; auristatin; MMAE |
| (CH$_2$)$_5$ | — | —(C=O)—CH$_2$—S— 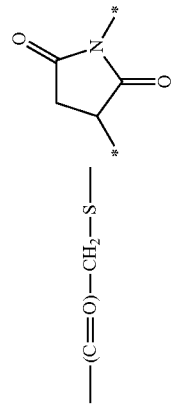 | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |

TABLE 2-continued

| $(C)_n$ | X | L | V | Y | Z |
|---|---|---|---|---|---|
| $(CH_2)_5$ | — | —(C=O)—CH$_5$—S—[succinimide structure]—* | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| $(CH_2)_5$ | — | —CH$_2$—(CH$_2$—O—CH$_2$)$_{1-24}$—CH$_2$—S—[succinimide structure]—* | Cleavable or non-cleavable linker; di- or tri- or oligo peptide; val-cit; or absent | Spacer system; CH$_2$—(CH$_2$—O—CH$_2$)$_4$—CH$_2$— | Large, charged or hydrophobic compound; toxin; auristatin; MMAE |
| —CH$_2$—(CH$_2$—O—CH$_2$)$_3$—CH$_2$— | — | — | Cleavable or non-cleavable linker; di- or tri- or oligo peptide; val-cit; or absent | Spacer system | Large, charged or hydrophobic compound; toxin; auristatin; MMAE |
| —CH$_2$—(CH$_2$—O—CH$_2$)$_3$—CH$_2$— | — | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —CH$_2$—(CH$_2$—O—CH$_2$)$_3$—CH$_2$— | — | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —O—(CH$_2$)$_{1-5}$— | — | — | Cleavable or non-cleavable linker; di- or tri- or oligo peptide; val-cit; or absent | Spacer system | Large, charged or hydrophobic compound; toxin; auristatin; MMAE |
| —O—CH$_2$—(CH$_2$—O—CH$_2$)$_3$—CH$_2$— | — | — | Cleavable or non-cleavable linker; di- or tri- or oligo peptide; val-cit; or absent | Spacer system | Large, charged or hydrophobic compound; toxin; auristatin; MMAE |
| —O—CH$_2$—(CH$_2$—O—CH$_2$)$_3$—CH$_2$— | — | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| —O—CH$_2$—(CH$_2$—O—CH$_2$)$_3$—CH$_2$— | — | —(C=O)—CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |
| (CH$_2$)$_4$—CH(NH$_2$)—(C=O)— | — | — | — | Spacer system | Charged compound |
| (CH$_2$)$_4$—CH(NH$_2$)—(C=O)— | — | — | di- or tri- or oligo peptide; val-cit | Spacer system | Large, charged or hydrophobic compound; toxin; auristatin; MMAE |
| (CH$_2$)$_4$—CH(NH$_2$)—(C=O)— | — | —(CH$_2$)$_{1-6}$— | Cleavable or non-cleavable linker; di- or tri- or oligo peptide; val-cit; or absent | Spacer system | Large, charged or hydrophobic compound; toxin; auristatin; MMAE |
| (CH$_2$)$_4$—CH(NH$_2$)—(C=O)— | — | —(CH$_2$)$_5$— | Cleavable or non-cleavable linker; di- or tri- or oligo peptide; val-cit; or absent | Spacer system | Large, charged or hydrophobic compound; toxin; auristatin; MMAE |
| (CH$_2$)$_4$—CH(NH$_2$)—(C=O)— | — | —CH$_2$—(CH$_2$—O—CH$_2$)$_{1-24}$—CH$_2$— | Cleavable or non-cleavable linker; di- or tri- or oligo peptide; val-cit; or absent | Spacer system | Large, charged or hydrophobic compound; toxin; auristatin; MMAE |

TABLE 2-continued

| $(C)_n$ | X | L | V | Y | Z |
|---|---|---|---|---|---|
| $(CH_2)_5$ | — | — | — | Spacer system; $(CH_2)_5$ | Large, charged or hydrophobic compound; toxin; auristatin; MMAF |
| $(CH_2)_{6-10}$ | — | — | — | Spacer system; $(CH_2)_5$ | Large, charged or hydrophobic compound; toxin; auristatin; MMAF |
| $(CH_2)_{15}$ | — | — | — | Spacer system; $(CH_2)_5$ | Large, charged or hydrophobic compound; toxin; auristatin; MMAF |
| $-CH_2-(CH_2-O-CH_2)_3-CH_2-$ | — | — | — | Spacer system; $(CH_2)_5$ | Large, charged or hydrophobic compound; toxin; auristatin; MMAF |
| $(CH_2)_5$ | — | $-(C=O)-CH_2-$ | — | Spacer system; $(CH_2)_5$ | Large, charged or hydrophobic compound; toxin; auristatin; MMAF |
| $(CH_2)_5$ | — | $-(C=O)-(CH_2)_5-$ | — | Spacer system; $(CH_2)_5$ | Large, charged or hydrophobic compound; toxin; auristatin; MMAF |
| $(CH_2)_5$ | — | $-CH_2-(CH_2-O-CH_2)_{1-24}-CH_2-$ | — | Spacer system; $(CH_2)_5$ | Large, charged or hydrophobic compound; toxin; auristatin; MMAF |
| $-O-(CH_2)_{1-5}$ | — | $-CH_2-(CH_2-O-CH_2)_{1-24}-CH_2-$ | — | Spacer system; $(CH_2)_5$ | Large, charged or hydrophobic compound; toxin; auristatin; MMAF |
| $-O-CH_2-(CH_2-O-CH_2)_3-CH_2-$ | — | $-CH_2-(CH_2-O-CH_2)_{1-24}-CH_2-$ | — | Spacer system; $(CH_2)_5$ | Large, charged or hydrophobic compound; toxin; auristatin; MMAF |
| $-O-CH_2-(CH_2-O-CH_2)_3-CH_2-$ | — | $-(C=O)-CH_2-$ | — | Spacer system; $(CH_2)_5$ | Large, charged or hydrophobic compound; toxin; auristatin; MMAF |
| $-O-CH_2-(CH_2-O-CH_2)_3-CH_2-$ | — | $-(C=O)-(CH_2)_5-$ | — | Spacer system; $(CH_2)_5$ | Large, charged or hydrophobic compound; toxin; auristatin; MMAF |
| $-CH_2-(CH_2-O-CH_2)_3-CH_2-$ | — | $-CH_2-(CH_2-O-CH_2)_{1-24}-CH_2-$ | — | Spacer system; $(CH_2)_5$ | Large, charged or hydrophobic compound; toxin; auristatin; MMAF |
| $(CH_2)_5$ | — | — | Non-cleavable linker; $(CH_2)_5$ | — | Large, charged or hydrophobic compound; toxin; auristatin; MMAF |
| $(CH_2)_{6-10}$ | — | — | Non-cleavable linker; $(CH_2)_5$ | — | Large, charged or hydrophobic compound; toxin; auristatin; MMAF |
| $(CH_2)_{15}$ | — | — | Non-cleavable linker; $(CH_2)_5$ | — | Large, charged or hydrophobic compound; toxin; auristatin; MMAF |
| $-CH_2-(CH_2-O-CH_2)_3-CH_2-$ | — | — | Non-cleavable linker; $(CH_2)_5$ | — | Large, charged or hydrophobic compound; toxin; auristatin; MMAF |
| $(CH_2)_5$ | — | $-(C=O)-CH_2-$ | — | — | Large, charged or hydrophobic compound; toxin; auristatin; MMAF |

TABLE 2-continued

| $(C)_n$ | X | L | V | Y | Z |
|---|---|---|---|---|---|
| (CH$_2$)$_5$ | — | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | — | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | — | —(C=O)—(CH$_2$)$_5$— | Non-cleavable linker; (CH$_2$)$_5$ | — | Large, charged or hydrophobic compound; toxin; auristatin; MMAF |
| (CH$_2$)$_5$ | — | —CH$_2$—(CH$_2$—O—CH$_2$)$_{1-24}$—CH$_2$— | Non-cleavable linker; (CH$_2$)$_5$ | — | Large, charged or hydrophobic compound; toxin; auristatin; MMAF |
| —O—(CH$_2$)$_{1-5}$ | — | —CH$_2$—(CH$_2$—O—CH$_2$)$_{1-24}$—CH$_2$— | Non-cleavable linker; (CH$_2$)$_5$ | — | Large, charged or hydrophobic compound; toxin; auristatin; MMAF |
| —O—CH$_2$—(CH$_2$—O—CH$_2$)$_3$—CH$_2$— | — | —CH$_2$—(CH$_2$—O—CH$_2$)$_{1-24}$—CH$_2$— | Non-cleavable linker; (CH$_2$)$_5$ | — | Large, charged or hydrophobic compound; toxin; auristatin; MMAF |
| —O—CH$_2$—(CH$_2$—O—CH$_2$)$_3$—CH$_2$— | — | —(C=O)—CH$_2$— | Non-cleavable linker; (CH$_2$)$_5$ | — | Large, charged or hydrophobic compound; toxin; auristatin; MMAF |
| —O—CH$_2$—(CH$_2$—O—CH$_2$)$_3$—CH$_2$— | — | —(C=O)—(CH$_2$)$_5$— | Non-cleavable linker; (CH$_2$)$_5$ | — | Large, charged or hydrophobic compound; toxin; auristatin; MMAF |
| —CH$_2$—(CH$_2$—O—CH$_2$)$_3$—CH$_2$— | — | —CH$_2$—(CH$_2$—O—CH$_2$)$_{1-24}$—CH$_2$— | Non-cleavable linker; (CH$_2$)$_5$ | — | Large, charged or hydrophobic compound; toxin; auristatin; MMAF |

TABLE 3

| Structure of Formula Ib | (C)$_n$ | X | L | V | Y | R |
|---|---|---|---|---|---|---|
| [H$_2$N-(CH$_2$)$_5$-NH-C(=O)-CH$_2$-SH] | (CH$_2$)$_5$ | NH | —(C=O)—CH$_2$— | — | — | SH |
| [H$_2$N-(CH$_2$)$_5$-NH-C(=O)-(CH$_2$)$_4$-CH(NH$_2$)-C(=O)-(CH$_2$)$_5$-SH] | (CH$_2$)$_4$—CH(NH$_2$)—(C=O)— | — | —CH$_2$— | — | — | SH |
| [H$_2$N-(CH$_2$)$_5$-NH-C(=O)-(CH$_2$)$_5$-SH] | (CH$_2$)$_5$ | NH | —(C=O)—(CH$_2$)$_5$— | — | — | SH |
|  | (CH$_2$)$_5$ | NH | —(CH$_2$)$_5$— | — | — | SH |
|  | (CH$_2$)$_4$—CH(NH$_2$)—(C=O)— | — | —(CH$_2$)$_5$— | — | — | SH |
|  | O—(CH$_2$)$_5$ | NH | —(C=O)—(CH$_2$)$_5$— | — | — | SH |
|  | O—(CH$_2$)$_5$ | NH | —(C=O)—(CH$_2$)$_{10}$— | — | — | SH |
| [H$_2$N-(CH$_2$)$_5$-NH-C(=O)-CH$_2$-(OCH$_2$CH$_2$)$_n$-O-CH$_2$-SH (PEG-thiol)] | (CH$_2$)$_5$ | NH | —(C=O)—CH$_2$—(CH$_2$—O—CH$_2$)$_4$—CH$_2$— | — | — | SH |
|  | (CH$_2$)$_5$ | NH | —(C=O)—CH$_2$—(CH$_2$—O—CH$_2$)$_{1-24}$—CH$_2$— | — | — | SH |
|  | (CH$_2$)$_5$ | — | —CH$_2$—(CH$_2$—O—CH$_2$)$_{1-24}$—CH$_2$— | — | — | SH |
|  | O—(CH$_2$)$_5$ | NH | —(C=O)—CH$_2$—(CH$_2$—O—CH$_2$)$_{1-24}$—CH$_2$— | — | — | SH |
| [H$_2$N-(CH$_2$)$_5$-NH-C(=O)-CH$_2$-(OCH$_2$CH$_2$)$_n$-N$_3$] | —CH$_2$—(CH$_2$—O—CH$_2$)$_3$—CH$_2$— | NH | —(C=O)—CH$_2$—(CH$_2$—O—CH$_2$)$_4$—CH$_2$— | — | — | N$_3$ |
|  | —CH$_2$—(CH$_2$—O—CH$_2$)$_{1-6}$—CH$_2$— | — | —(C=O)—CH$_2$—(CH$_2$—O—CH$_2$)$_{1-24}$—CH$_2$— | — | — | N$_3$ |
|  | (CH$_2$)$_5$ | NH | —(C=O)—CH$_2$—(CH$_2$—O—CH$_2$)$_{1-24}$—CH$_2$— | — | — | N$_3$ |
|  | (CH$_2$)$_5$ | NH | —(C=O)— | — | — | N$_3$ |
|  | O—(CH$_2$)$_5$ |  |  |  |  | N$_3$ |
| [H$_2$N-(CH$_2$)$_5$-NH-C(=O)-Ar(PPh$_2$)(CO$_2$Me)] | (CH$_2$)$_5$ | NH | —(C=O)— | — | — | [Ar(PPh$_2$)(CO$_2$Me)] |

TABLE 3-continued
| Structure of Formula Ib | (C)$_n$ | X | L | V | Y | R |
|---|---|---|---|---|---|---|
| | O—(CH$_2$)$_5$ | NH | (CH$_2$)$_5$ | — | — | 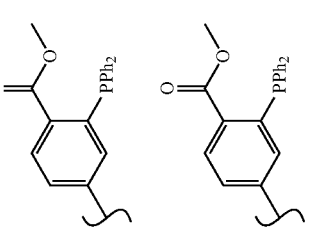 |
| | —CH$_2$—(CH$_2$—O—CH$_2$)$_6$—CH$_2$— | | | — | — | 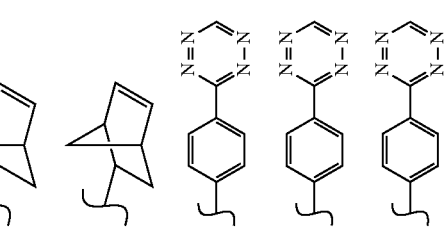 |
| 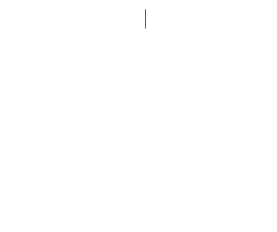 | (CH$_2$)$_5$ | NH | —(C=O)— | — | — | 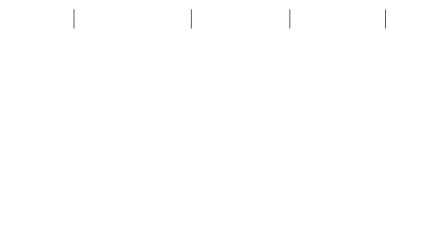 |
| | —CH$_2$—(CH$_2$—O—CH$_2$)$_6$—CH$_2$— | NH | — | — | — | 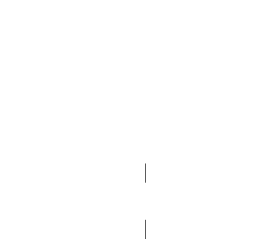 |
| | —O—(CH$_2$)$_5$ | NH | — | — | — | 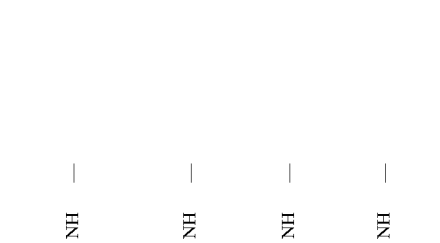 |
| 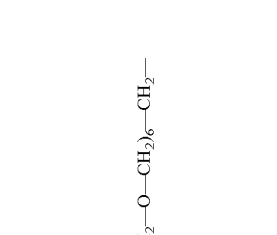 | (CH$_2$)$_5$ | NH | — | — | — |  |
| | —O—(CH$_2$)$_5$ | NH | — | — | — | 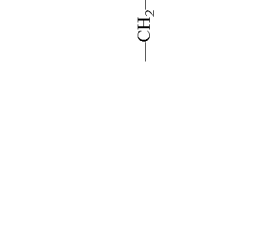 |
| | —CH$_2$—(CH$_2$—O—CH$_2$)$_6$—CH$_2$— | NH | — | — | — | 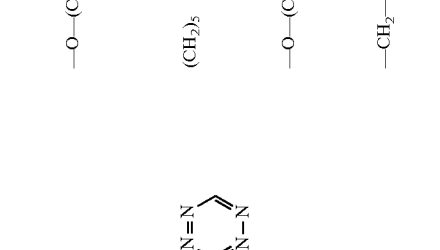 |

TABLE 3-continued

| Structure of Formula Ib | $(C)_n$ | X | L | V | Y | R |
|---|---|---|---|---|---|---|
| | $(CH_2)_5$ | NH | $-(C=O)-(CH_2)_5-$ | — | — | maleimide |
| | $(CH_2)_5$ | NH | $-(CH_2)_5-$ | — | — | maleimide |
| | $(CH_2)_4-CH(NH_2)-(C=O)-$ | — | $-CH_2-$ | — | — | maleimide |
| | $O-(CH_2)_5$ | NH | $-(C=O)-(CH_2)_5-$ | — | — | maleimide |
| | $(CH_2)_5$ | NH | $-(C=O)-(CH_2)_5-$ | — | — | DBCO |

TABLE 3-continued

| Structure of Formula Ib | (C)$_n$ | X | L | V | Y | R |
|---|---|---|---|---|---|---|
| | (CH$_2$)$_5$ | NH | —(CH$_2$)$_5$— | — | — | DBCO-C(=O)- |
| | (CH$_2$)$_4$—CH(NH$_2$)—(C=O)— | — | —CH$_2$— | — | — | DBCO-C(=O)- |
| | O—(CH$_2$)$_5$ | NH | —(C=O)—(CH$_2$)$_5$— | — | — | DBCO-C(=O)- |

TABLE 3-continued
| Structure of Formula Ib | $(C)_n$ | X | L | V | Y | R |
|---|---|---|---|---|---|---|
| 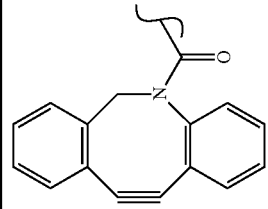 | —CH₂—(CH₂—O—CH₂)₄—CH₂— | — | — | — | — | — |
| | (CH₂)₅ | NH | —(CH₂)₂— | — | — | —C≡CH |
| | (CH₂)₅ | NH | —(C=O)—(CH₂)₅— | — | — | —C≡CH |
| | (CH₂)₅ | NH | —(CH₂)₅— | — | — | —C≡CH |
| | —(CH₂)₄—CH(NH₂)—(C=O)— | — | —CH₂— | — | — | —C≡CH |
| | O—(CH₂)₅ | NH | —(C=O)—CH₂— | — | — | —C≡CH |
| | —CH₂—(CH₂—O—CH₂)₃—CH₂— | — | — | — | — | —C≡CH |

TABLE 4

| of Formula III | R' |
|---|---|
| [maleimide-(CH2)5-C(O)-Val_Cit_PAB_MMAE] | [maleimide-N⟩] |
| | [maleimide-N⟩] |
| [DBCO-C(O)-CH2CH2-C(O)NH-(CH2CH2O)4-CH2CH2-C(O)-Val_Cit_PAB_MMAE] | [DBCO-N-C(O)-⟩] |
| | [DBCO-N-C(O)-⟩] |
| [HC≡C-(CH2)5-C(O)-Val_Cit_PAB_MMAE] | [HC≡C-⟩] |
| | [HC≡C-⟩] |
| | [HC≡C-⟩] |
| | $N_3$ |
| [N3-(CH2)5-C(O)-Val_Cit_PAB_MMAE] | |
| | $N_3$ |
| | $N_3$ |

| of Formula III | L' |
|---|---|
| | —(CH$_2$)$_5$—(C=O)— |
| [maleimide-(CH2)5-C(O)-Val_Cit_PAB_MMAE] | |
| | —CH$_2$—(CH$_2$—O—CH$_2$)$_4$—CH$_2$—(C=O)— |

TABLE 4-continued

| | |
|---|---|
| 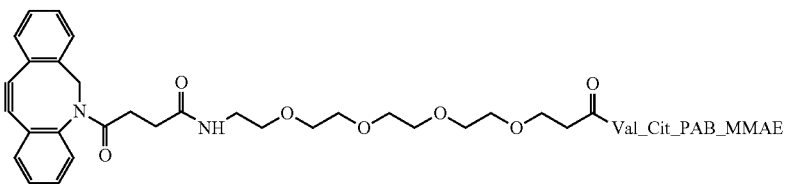 | —(C=O)—(CH₂)4—(C=O)—NH—CH₂—(CH₂—O—CH₂)₄—CH₂—(C=O)— |
| 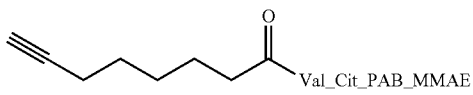 | —(C=O)—(CH₂)4—(C=O)—NH—CH₂—(CH₂—O—CH₂)₄—CH₂—(C=O)—<br>—(CH₂)₅—(C=O)— |
| | —CH₂—(CH₂—O—CH₂)₄—CH₂—(C=O)—<br>—CH₂—(CH₂—O—CH₂)₄—CH₂—(C=O)— |
| 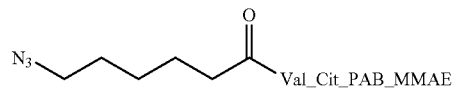 | —(CH₂)₅—(C=O)— |
| | —CH₂—(CH₂—O—CH₂)₄—CH₂—(C=O)—<br>—CH₂—(CH₂—O—CH₂)₄—CH₂—(C=O)— |

| of Formula III | V' | Y' | Z |
|---|---|---|---|
| 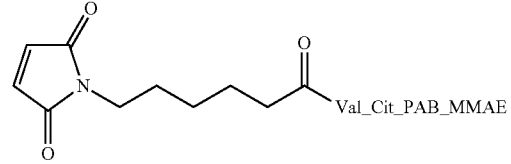 | Val-cit | PAB | MMAE |
| 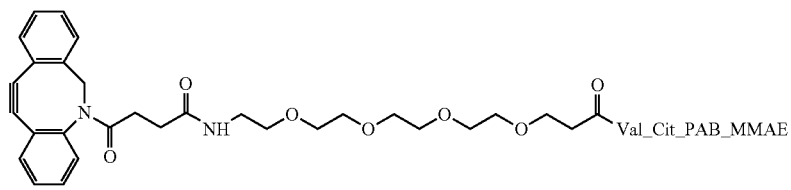 | Val-cit<br>Val-cit | PAB<br>PAB | MMAE<br>MMAE |
| 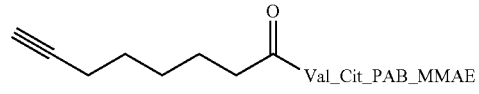 | —<br>Val-cit | —<br>PAB | MMAF<br>MMAE |
| 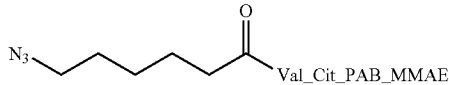 | Val-cit<br>—<br>Val-cit | PAB<br>—<br>PAB | MMAE<br>MMAF<br>MMAE |
| | Val-cit<br>— | PAB<br>— | MMAE<br>MMAF |

TABLE 5

Compound of Formula 1b

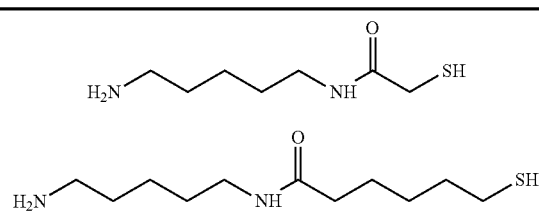

TABLE 5-continued
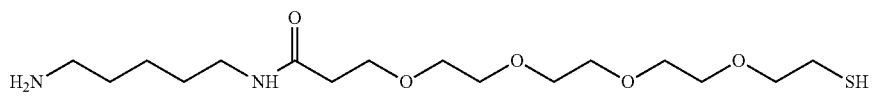 [SMILES: NCCCCCNC(=O)CCOCCOCCOCCOCCS]
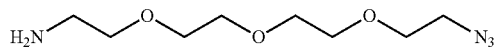
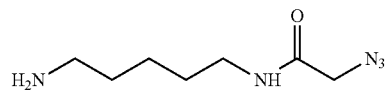
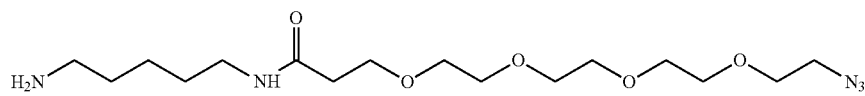 [SMILES: [N-]=[N+]=NCCOCCOCCOCCOCCC(=O)NCCCCCN]
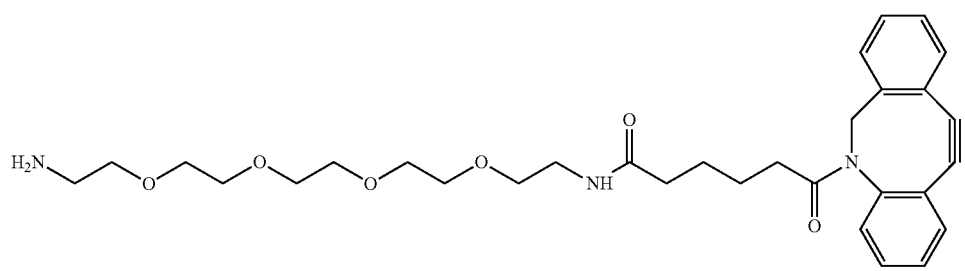 [SMILES: NCCOCCOCCOCCOCCNC(=O)CCCCC(=O)N1Cc2ccccc2C#Cc2ccccc21]
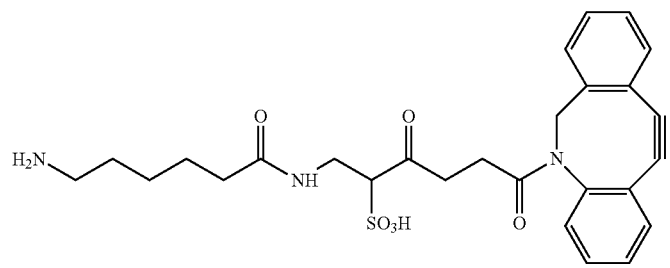 [SMILES: NCCCCCC(=O)NCC(C(=O)CCC(=O)N1Cc2ccccc2C#Cc2ccccc21)S(=O)(=O)O]
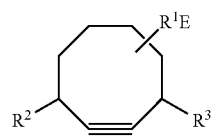
Formula B
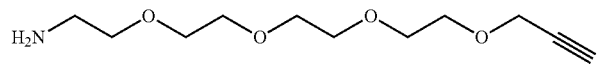 [SMILES: C#CCOCCOCCOCCOCCN]
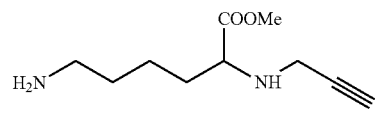
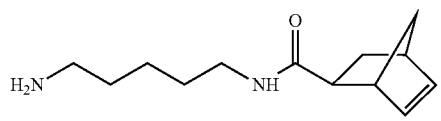 [SMILES: NCCCCCNC(=O)C1CC2C=CC1C2]
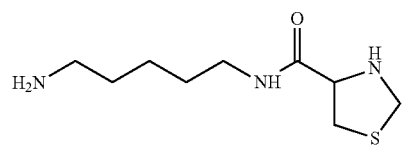 [SMILES: NCCCCCNC(=O)C1CSCN1]

TABLE 5-continued
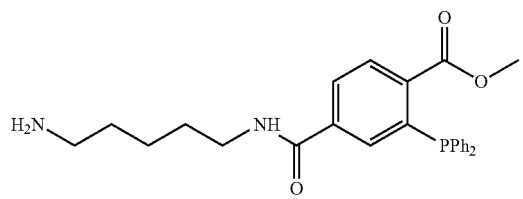
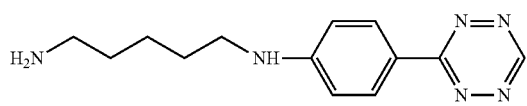
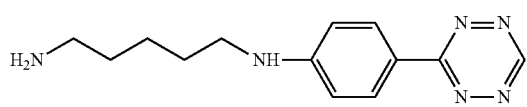
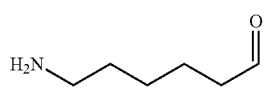
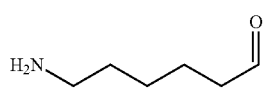
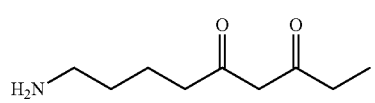
Compound of Formula III
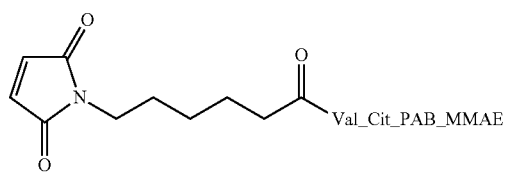
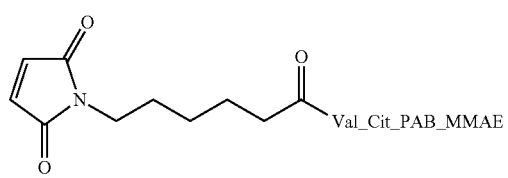
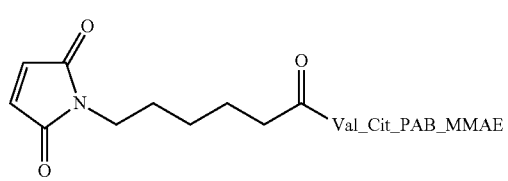
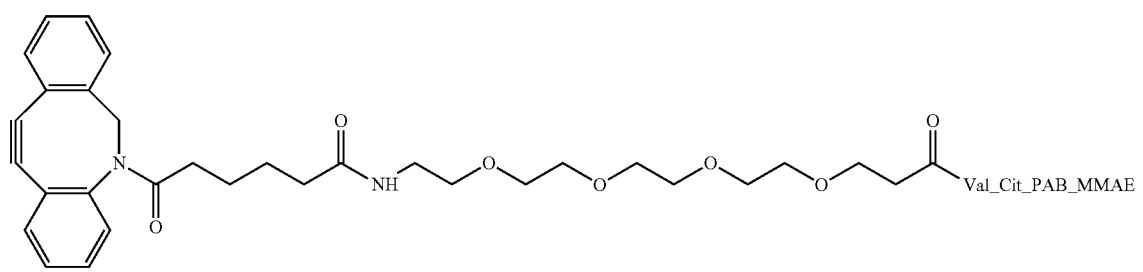

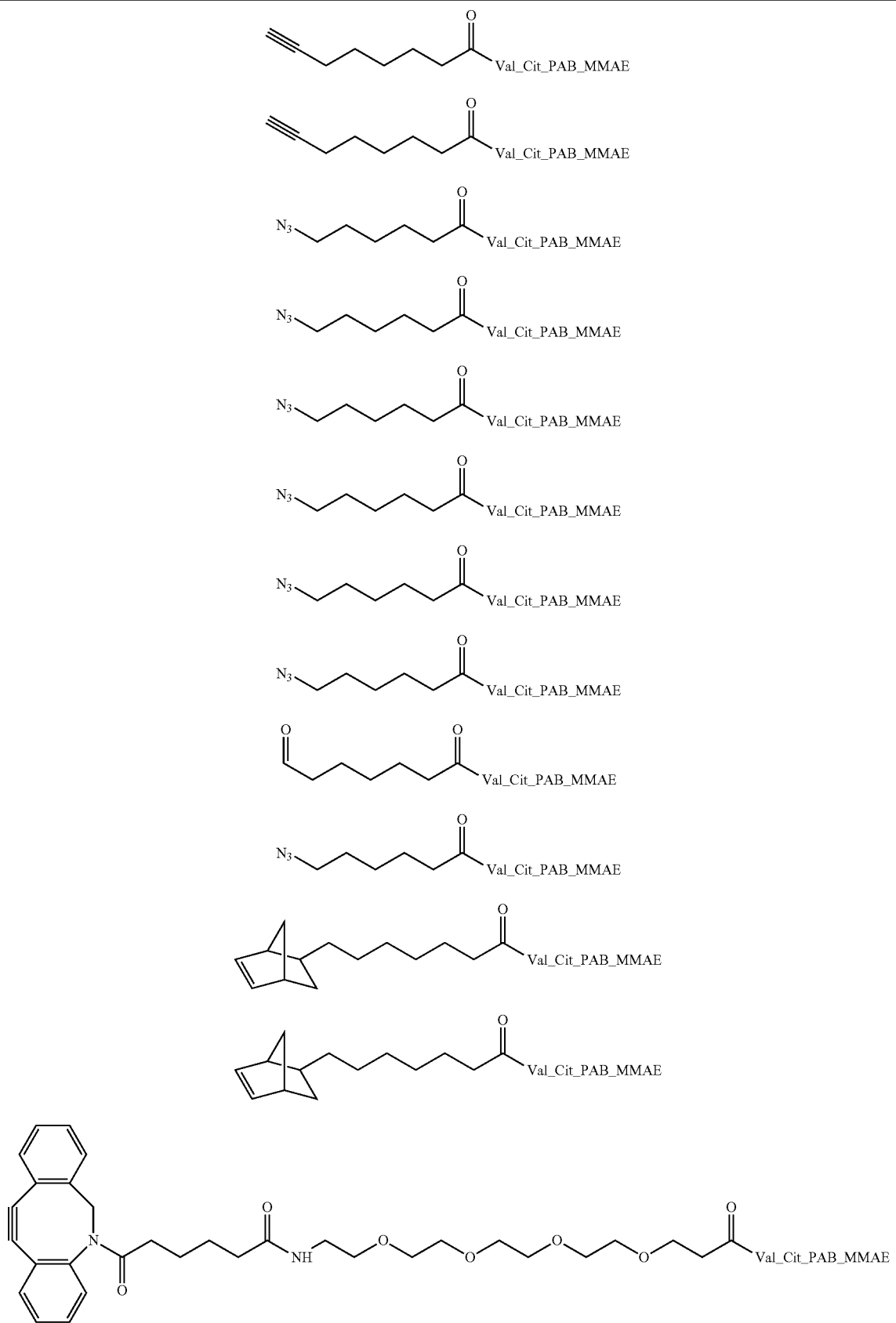

TABLE 5-continued

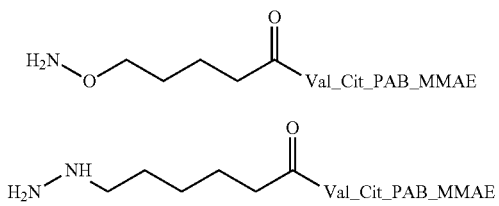

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents. The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e. g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. A composition comprising a plurality of antibodies or antibody fragments, wherein the plurality of antibodies or antibody fragments share the same heavy and/or light chain amino acid sequence, and wherein at least 90% of the antibodies or antibody fragments in said composition have (m) functionalized acceptor glutamine residues (Q) per antibody or fragment, wherein m is an integer selected from 2 or 4, and wherein each of the functionalized acceptor glutamine residues has the structure of Formula IVc, (Q)NHC-X-L-RR'-L'-V-Y-Z    Formula IVc or a pharmaceutically acceptable salt or solvate thereof, wherein:
Q is a glutamine residue present within or appended to a constant region of the antibodies or antibody fragments;
C is a substituted alkyl chain, an unsubstituted alkyl chain, a substituted heteroalkyl chain, or an unsubstituted heteroalkyl chain;
X is NH, O, S, absent, or a bond;
L is independently absent, a bond or a continuation of a bond, or a carbon comprising framework of 1 to 200 atoms substituted at one or more atoms;
(RR') is an addition product between a reactive moiety R and a complementary reactive moiety R';
L' is independently absent, a bond or a continuation of a bond, or a carbon comprising framework of 1 to 200 atoms substituted at one or more atoms;
V is independently absent, a bond or a continuation of a bond, a non-cleavable moiety or a conditionally-cleavable moiety;
Y is independently absent, a bond or a continuation of a bond, or a spacer system which is comprised of 1 or more spacers; and
Z is a pyrrolobenzodiazepine,
wherein the antibodies or antibody fragments specifically bind to a tumor antigen.

2. The composition of claim 1, wherein Z is a pyrrolobenzodiazepine dimer.

3. The composition of claim 1, wherein Z is a C8/C8'-linked pyrrolobenzodiazepine dimer.

4. The composition of claim 1, wherein said acceptor glutamine residue is flanked at position +2 by a non-aspartic acid residue.

5. The composition of claim 4, wherein said acceptor glutamine residue is flanked at position +2 by an arginine residue.

6. The composition of claim 1, wherein said antibodies comprise human heavy and light chain constant regions, wherein the heavy chain constant regions comprise a N297Q substitution and a Q295X substitution, wherein X is any amino acid other than glutamine.

7. The composition of claim 1, wherein R or R' is a moiety comprising a bioorthogonal-reaction compatible reactive group selected from the group consisting of an unprotected thiol, a protected thiol, an unprotected epoxide, a protected epoxide, an unprotected maleimide, a protected maleimide, an unprotected haloacetamide, a protected haloacetamide, an unprotected o-phoshenearomatic ester, a protected o-phoshenearomatic ester, an unprotected azide, a protected azide, an unprotected fulminate, a protected fulminate, an unprotected sulfonate ester, a protected sulfonate ester, an unprotected alkyne, a protected alkyne, an unprotected cyanide, a protected cyanide, an unprotected amino-thiol, a protected amino-thiol, an unprotected carbonyl, a protected carbonyl, an unprotected aldehyde, a protected aldehyde, a group capable of oxime formation, a group capable of hydrazine formation, a 1,2,4,5-tetrazine, a norbornene, a strained electronically activated alkene, an otherwise electronically activated alkene, a substituted cycloalkyne, an unsubstituted cycloalkyne, a reactive group which forms via bioorthogonal cycloaddition reaction a 1,3- or 1,5-disubstituted triazole, a diene or a strained alkene dienophile that can react via inverse electron demand Diels-Alder reaction, a protected amine, an unprotected amine, a carboxylic acid, an aldehyde, and an oxyamine.

8. The composition of claim 1, wherein R is an azide.

9. The composition claim 8, wherein R' comprises a strained alkene.

10. The composition of claim 8, wherein R' comprises a cyclooctyne.

11. The composition of claim 1, wherein less than 2% of the antibodies are present as soluble aggregates, as assessed using an aggregation assay.

12. The composition of claim 1, wherein the composition comprises less than 1% antibody fragments.

13. A pharmaceutical formulation comprising the composition of claim 1, and a pharmaceutically acceptable carrier.

14. The formulation of claim 13, wherein the formulation comprises trehalose and Polysorbate 80.

15. The composition of claim 1, wherein any carbon atom of the carbon chain of C is substituted with an alkoxy, hydroxyl, alkylcarbonyloxy, alkyl-S-, thiol, alkyl-C(O)S—, amine, alkylamine, amide, or alkylamide.

16. The composition of claim 1, wherein the carbon chain of C has a chain length of 2 to 20 carbon atoms.

17. The composition of claim 1, wherein L is a carbon comprising framework which comprises a linear framework of 3 to 30 carbon atoms optionally substituted at one or more atoms.

18. The composition of claim 1, wherein L is a carbon comprising framework which is a linear hydrocarbon, a symmetrically or asymmetrically branched hydrocarbon, monosaccharide, other natural linear or branched oligomers (asymmetrically branched or symmetrically branched), or a dimer, trimer, or higher oligomer (linear, asymmetrically branched or symmetrically branched) resulting from any chain-growth or step-growth polymerization process.

19. The composition of claim 1, wherein L' is a carbon comprising framework which comprises a linear framework of 3 to 30 carbon atoms optionally substituted at one or more atoms.

20. The composition of claim 1, wherein L' is a carbon comprising framework which is a linear hydrocarbon, a symmetrically or asymmetrically branched hydrocarbon, monosaccharide, other natural linear or branched oligomers (asymmetrically branched or symmetrically branched), or a dimer, trimer, or higher oligomer (linear, asymmetrically branched or symmetrically branched) resulting from any chain-growth or step-growth polymerization process.

21. A composition comprising a plurality of antibodies or antibody fragments wherein the plurality of antibodies or antibody fragments share the same heavy and/or light chain amino acid sequence, and wherein at least 90% of the antibodies or antibody fragments in said composition have (m) functionalized acceptor glutamine residues (Q) per antibody or fragment, wherein m is an integer selected from 2 or 4, wherein each of the functionalized acceptor glutamine residues has the structure:

(Q)-L"-RR'-Y-Z or a pharmaceutically acceptable salt or solvate thereof, wherein:
Q is a glutamine residue present within or appended to a constant region of the antibodies or antibody fragments;
L" is a lysine-based linker in which the nitrogen atom is covalently bonded to the y carbon of Q as a secondary amine;
(RR') is an addition product between a reactive moiety R and a complementary reactive moiety R';
Y is a spacer system; and
Z is a pyrrolobenzodiazepine,
wherein the antibodies or antibody fragments specifically bind to a tumor antigen.

* * * * *

SEQUENCE LISTING

```
<160> NUMBER OF SEQ ID NOS: 13

<210> SEQ ID NO 1
<211> LENGTH: 450
<212> TYPE: PRT
<213> ORGANISM: Artificial Sequence
<220> FEATURE:
<223> OTHER INFORMATION: Murine VH fused to human CH

<400> SEQUENCE: 1

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Gly Tyr
             20                  25                  30

Trp Met His Trp Val Lys Gln Arg Pro Gly His Gly Leu Glu Trp Ile
         35                  40                  45

Gly Glu Ile Asn Pro Ser Asn Gly Arg Thr Asn Tyr Asn Glu Arg Phe
     50                  55                  60

Lys Ser Lys Ala Thr Leu Thr Val Asp Lys Ser Ser Thr Thr Ala Phe
65                  70                  75                  80

Met Gln Leu Ser Gly Leu Thr Ser Glu Asp Ser Ala Val Tyr Phe Cys
```

```
                85                  90                  95
Ala Arg Asp Tyr Tyr Gly Thr Ser Tyr Asn Phe Asp Tyr Trp Gly Gln
                100                 105                 110

Gly Thr Thr Leu Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Murine VK fused to human Ck
```

-continued

```
<400> SEQUENCE: 2

Asp Ile Gln Met Thr Gln Ser Ser Ser Phe Ser Val Ser Leu Gly
 1               5                  10                  15

Asp Arg Val Thr Ile Thr Cys Lys Ala Asn Glu Asp Ile Asn Asn Arg
            20                  25                  30

Leu Ala Thr Tyr Gln Gln Thr Pro Gly Asn Ser Pro Arg Leu Leu Ile
        35                  40                  45

Ser Gly Ala Thr Asn Leu Val Thr Gly Val Pro Ser Arg Phe Ser Gly
    50                  55                  60

Ser Gly Ser Gly Lys Asp Tyr Thr Leu Thr Ile Thr Ser Leu Gln Ala
65                  70                  75                  80

Glu Asp Phe Ala Thr Tyr Tyr Cys Gln Gln Tyr Trp Ser Thr Pro Phe
                85                  90                  95

Thr Phe Gly Ser Gly Thr Glu Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 23
<212> TYPE: PRT
<213> ORGANISM: Homo sapiens
<220> FEATURE:
<221> NAME/KEY: VARIANT
<222> LOCATION: (12)...(12)
<223> OTHER INFORMATION: Xaa = Tyr or Phe
<220> FEATURE:
<221> NAME/KEY: VARIANT
<222> LOCATION: (13)...(13)
<223> OTHER INFORMATION: Xaa = any amino acid other than Asp

<400> SEQUENCE: 3

His Asn Ala Lys Thr Lys Pro Arg Glu Glu Gln Xaa Xaa Ser Thr Tyr
 1               5                  10                  15

Arg Val Val Ser Val Leu Thr
            20

<210> SEQ ID NO 4
<211> LENGTH: 23
<212> TYPE: PRT
<213> ORGANISM: Homo sapiens
<220> FEATURE:
<221> NAME/KEY: VARIANT
<222> LOCATION: (12)...(12)
<223> OTHER INFORMATION: Xaa = Tyr or Phe
<220> FEATURE:
<221> NAME/KEY: VARIANT
<222> LOCATION: (15)...(15)
<223> OTHER INFORMATION: Xaa = any amino acid other than Thr
```

<400> SEQUENCE: 4

His Asn Ala Lys Thr Lys Pro Arg Glu Glu Gln Xaa Asn Ser Xaa Tyr
1               5                   10                  15

Arg Val Val Ser Val Leu Thr
            20

<210> SEQ ID NO 5
<211> LENGTH: 989
<212> TYPE: DNA
<213> ORGANISM: Homo sapiens

<400> SEQUENCE: 5

```
gggcccaagc gtgttccccc tggcccccag cagcaagagc accagcggcg gcacagccgc    60
cctgggctgc ctggtgaagg actacttccc cgagcccgtg accgtgtcct ggaacagcgg   120
agccctgacc tccggcgtgc acaccttccc cgccgtgctg cagagcagcg gcctgtacag   180
cctgagcagc gtggtgaccg tgcccagcag cagcctgggc acccagacct acatctgtaa   240
cgtgaaccac aagcccagca caccaaggt ggacaagaga gtggagccca gagctgtga   300
caagacccac acctgccccc cctgcccagc ccccgagctg ctgggcggac ccagcgtgtt   360
cctgttcccc cccaagccca aggacaccct gatgatcagc agaacccccg aggtgacctg   420
tgtggtggtg gacgtgtccc acgaggaccc agaggtgaag ttcaactggt acgtggacgg   480
cgtggaggtg cacaacgcca agaccaagcc cagagaggag cagtacagca gcacctacag   540
ggtggtgtcc gtgctgaccg tgctgcacca ggactggctg aacggcaagg agtacaagtg   600
taaggtgtcc aacaaggccc tgccagcccc aatcgaaaag accatcagca ggccaagggg   660
ccagccaaga gagccccagg tgtacaccct gccacccagc aggggaggaga tgaccaagaa   720
ccaggtgtcc ctgacctgtc tggtgaaggg cttctaccca agcgacatcg ccgtggagtg   780
ggagagcaac ggccagcccg agaacaacta caagaccacc cccccagtgc tggacagcga   840
cggcagcttc ttcctgtaca gcaagctgac cgtggacaag agcagatggc agcagggcaa   900
cgtgttcagc tgctccgtga tgcacgaggc cctgcacaac cactacaccc agaagagcct   960
gagcctgtcc ccaggcaagt gatgaattc                                    989
```

<210> SEQ ID NO 6
<211> LENGTH: 326
<212> TYPE: PRT
<213> ORGANISM: Homo sapiens

<400> SEQUENCE: 6

Gly Pro Ser Val Phe Pro Leu Ala Pro Ser Ser Lys Ser Thr Ser Gly
1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

Phe Pro Ala Val Leu Gln Ser Ser Gly Leu Tyr Ser Leu Ser Ser Val
    50                  55                  60

Val Thr Val Pro Ser Ser Ser Leu Gly Thr Gln Thr Tyr Ile Cys Asn
65                  70                  75                  80

Val Asn His Lys Pro Ser Asn Thr Lys Val Asp Lys Arg Val Glu Pro
                85                  90                  95

Lys Ser Cys Asp Lys Thr His Thr Cys Pro Pro Cys Pro Ala Pro Glu
            100                 105                 110

```
Leu Leu Gly Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Ser
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
            195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 7
<211> LENGTH: 989
<212> TYPE: DNA
<213> ORGANISM: Homo sapiens

<400> SEQUENCE: 7
gggcccaagc gtgttccccc tggcccccag cagcaagagc accagcggcg gcacagccgc      60
cctgggctgc ctggtgaagg actacttccc cgagcccgtg accgtgtcct ggaacagcgg     120
agccctgacc tccggcgtgc acaccttccc cgccgtgctg cagagcagcg gcctgtacag     180
cctgagcagc gtggtgaccg tgcccagcag cagcctgggc acccagacct acatctgtaa     240
cgtgaaccac aagcccagca acaccaaggt ggacaagaga gtggagccca gagctgtga     300
caagacccac acctgccccc cctgcccagc ccccgagctg ctgggcggac ccagcgtgtt     360
cctgttcccc cccaagccca aggacaccct gatgatcagc agaacccccg aggtgacctg     420
tgtggtggtg gacgtgtccc acgaggaccc agaggtgaag ttcaactggt acgtggacgg     480
cgtggaggtg cacaacgcca agaccaagcc cagagaggag cagtaccaaa gcacctacag     540
ggtggtgtcc gtgctgaccg tgctgcacca ggactggctg aacggcaagg agtacaagtg     600
taaggtgtcc aacaaggccc tgccagcccc aatcgaaaag accatcagca ggccaagggg     660
ccagccaaga gagccccagg tgtacaccct gccacccagc agggaggaga tgaccaagaa     720
ccaggtgtcc ctgacctgtc tggtgaaggg cttctaccca agcgacatcg ccgtggagtg     780
ggagagcaac ggccagcccg agaacaacta caagaccacc cccccagtgc tggacagcga     840
```

```
cggcagcttc ttcctgtaca gcaagctgac cgtggacaag agcagatggc agcagggcaa    900
cgtgttcagc tgctccgtga tgcacgaggc cctgcacaac cactacaccc agaagagcct    960
gagcctgtcc ccaggcaagt gatgaattc                                      989
```

<210> SEQ ID NO 8
<211> LENGTH: 326
<212> TYPE: PRT
<213> ORGANISM: Homo sapiens

<400> SEQUENCE: 8

```
Gly Pro Ser Val Phe Pro Leu Ala Pro Ser Ser Lys Ser Thr Ser Gly
 1               5                  10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

Phe Pro Ala Val Leu Gln Ser Ser Gly Leu Tyr Ser Leu Ser Ser Val
    50                  55                  60

Val Thr Val Pro Ser Ser Ser Leu Gly Thr Gln Thr Tyr Ile Cys Asn
65                  70                  75                  80

Val Asn His Lys Pro Ser Asn Thr Lys Val Asp Lys Arg Val Glu Pro
                85                  90                  95

Lys Ser Cys Asp Lys Thr His Thr Cys Pro Pro Cys Pro Ala Pro Glu
           100                 105                 110

Leu Leu Gly Gly Pro Ser Val Phe Leu Phe Pro Pro Lys Pro Lys Asp
       115                 120                 125

Thr Leu Met Ile Ser Arg Thr Pro Glu Val Thr Cys Val Val Val Asp
   130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Gln
                165                 170                 175

Ser Thr Tyr Arg Val Val Ser Val Leu Thr Val Leu His Gln Asp Trp
           180                 185                 190

Leu Asn Gly Lys Glu Tyr Lys Cys Lys Val Ser Asn Lys Ala Leu Pro
       195                 200                 205

Ala Pro Ile Glu Lys Thr Ile Ser Lys Ala Lys Gly Gln Pro Arg Glu
   210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
           260                 265                 270

Thr Pro Pro Val Leu Asp Ser Asp Gly Ser Phe Phe Leu Tyr Ser Lys
       275                 280                 285

Leu Thr Val Asp Lys Ser Arg Trp Gln Gln Gly Asn Val Phe Ser Cys
   290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 9

<211> LENGTH: 1017
<212> TYPE: DNA
<213> ORGANISM: Homo sapiens

<400> SEQUENCE: 9

```
gtttgtaagc ttgctagcac caagggccca tcggtcttcc ccctggcacc ctcctccaag    60
agcacctctg ggggcacagc ggccctgggc tgcctggtca aggactactt ccccgaaccg   120
gtgacggtgt cgtggaactc aggcgccctg accagcggcg tgcacacctt cccggctgtc   180
ctacagtcct caggactcta ctccctcagc agcgtggtga ccgtgccctc agcagcttg    240
ggcacccaga cctacatctg caacgtgaat cacaagccca gcaacaccaa ggtggacaag   300
aaagttgagc ccaaatcttg tgacaaaact cacacatgcc caccgtgccc agcacctgaa   360
ctcctggggg gaccgtcagt cttcctcttc cccccaaaac ccaaggacac cctcatgatc   420
tcccggaccc ctgaggtcac atgcgtggtg gtggacgtga gccacgaaga ccctgaggtc   480
aagttcaact ggtacgtgga cggcgtggag gtgcataatg ccaagacaaa gccgcgggag   540
gagcagtacc aaagcacgta ccgggtggtc agcgtcctca ccgtcctgca ccaggactgg   600
ctgaatggca aggagtacaa gtgcaaggtc tccaacaaag cccteccage ccccatcgag   660
aaaaccatct ccaaagccaa agggcagccc cgagaaccac aggtgtacac cctgcccca   720
tcccgggatg agctgaccaa gaaccaggtc agcctgacct gcctggtcaa aggcttctat   780
cccagcgaca tcgccgtgga gtgggagagc aatgggcagc cggagaacaa ctacaagacc   840
acgcctcccg tgctggactc cgacggctcc ttcttcctct acagcaagct caccgtggac   900
aagagcaggt ggcagcaggg gaacgtcttc tcatgctccg tgatgcatga ggctctgcac   960
aaccactaca cgcagaagag cctctccctg tctccgggta aatgaggatc cacacac     1017
```

<210> SEQ ID NO 10
<211> LENGTH: 326
<212> TYPE: PRT
<213> ORGANISM: Homo sapiens

<400> SEQUENCE: 10

Gly Pro Ser Val Phe Pro Leu Ala Pro Ser Ser Lys Ser Thr Ser Gly
 1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

Phe Pro Ala Val Leu Gln Ser Ser Gly Leu Tyr Ser Leu Ser Ser Val
    50                  55                  60

Val Thr Val Pro Ser Ser Ser Leu Gly Thr Gln Thr Tyr Ile Cys Asn
65                  70                  75                  80

Val Asn His Lys Pro Ser Asn Thr Lys Val Asp Lys Val Glu Pro
                85                  90                  95

Lys Ser Cys Asp Lys Thr His Thr Cys Pro Pro Cys Pro Ala Pro Glu
            100                 105                 110

Leu Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Gln

```
                165                 170                 175
Ser Thr Tyr Arg Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 11
<211> LENGTH: 12
<212> TYPE: PRT
<213> ORGANISM: Artificial Sequence
<220> FEATURE:
<223> OTHER INFORMATION: Modified peptide of scFv
<220> FEATURE:
<221> NAME/KEY: VARIANT
<222> LOCATION: (11)...(11)
<223> OTHER INFORMATION: Xaa = Biotin-cadaverin modified glutamine

<400> SEQUENCE: 11

Leu Thr Val Leu Gly Ala Ala Ala Glu Gln Xaa Lys
1               5                   10

<210> SEQ ID NO 12
<211> LENGTH: 20
<212> TYPE: PRT
<213> ORGANISM: Artificial Sequence
<220> FEATURE:
<223> OTHER INFORMATION: Modified peptide of Nanobody
<220> FEATURE:
<221> NAME/KEY: VARIANT
<222> LOCATION: (19)...(19)
<223> OTHER INFORMATION: Xaa = Biotin-cadaverin modified glutamine

<400> SEQUENCE: 12

Thr Pro Thr Gly Gln Gly Thr Gln Val Thr Val Ser Ser Ala Ala Ala
1               5                   10                  15

Glu Gln Xaa Lys
            20

<210> SEQ ID NO 13
<211> LENGTH: 9
<212> TYPE: PRT
<213> ORGANISM: Artificial Sequence
<220> FEATURE:
<223> OTHER INFORMATION: Modified peptide of Affibody
<220> FEATURE:
<221> NAME/KEY: VARIANT
<222> LOCATION: (8)...(8)
```

```
<223> OTHER INFORMATION: Xaa = Biotin-cadaverin modified glutamine

<400> SEQUENCE: 13

Val Asp Ala Asn Ser Glu Gln Xaa Lys
1               5
```